United States Patent
Gaylord et al.

(10) Patent No.: US 10,365,285 B2
(45) Date of Patent: *Jul. 30, 2019

(54) REAGENTS FOR DIRECTED BIOMARKER SIGNAL AMPLIFICATION

(71) Applicant: SIRIGEN II LIMITED, Workingham (GB)

(72) Inventors: Brent S. Gaylord, San Diego, CA (US); Glenn P. Bartholomew, Escondido, CA (US); Russell A. Baldocchi, Encinitas, CA (US); Janice W. Hong, San Diego, CA (US); William H. Huisman, San Diego, CA (US); Yongchao Liang, Irvine, CA (US); Trung Nguyen, San Diego, CA (US); Lan T. Tran, Rosemead, CA (US); Jean M. Wheeler, San Diego, CA (US); Adrian Charles Vernon Palmer, Brighton (GB); Frank Peter Uckert, San Diego, CA (US)

(73) Assignee: Sirigen II Limited, Workingham, Berkshire (GB)

(*) Notice: Subject to any disclaimer, the term of this patent is extended or adjusted under 35 U.S.C. 154(b) by 10 days.

This patent is subject to a terminal disclaimer.

(21) Appl. No.: 15/717,580

(22) Filed: Sep. 27, 2017

(65) Prior Publication Data
US 2018/0074067 A1 Mar. 15, 2018

Related U.S. Application Data

(63) Continuation of application No. 15/239,713, filed on Aug. 17, 2016, now Pat. No. 10,094,838, which is a (Continued)

(51) Int. Cl.
*G01N 33/58* (2006.01)
*C08G 61/02* (2006.01)
(Continued)

(52) U.S. Cl.
CPC ......... *G01N 33/58* (2013.01); *C07K 16/2812* (2013.01); *C07K 16/2815* (2013.01);
(Continued)

(58) Field of Classification Search
CPC ...................................................... G01N 33/58
(Continued)

(56) References Cited

U.S. PATENT DOCUMENTS

| 4,486,530 A | 12/1984 | David et al. |
| 5,143,854 A | 9/1992 | Pirrung et al. |

(Continued)

FOREIGN PATENT DOCUMENTS

| CA | 2365814 | 6/2003 |
| CN | 101553579 A | 10/2009 |

(Continued)

OTHER PUBLICATIONS

U.S. Appl. No. 13/195,747, filed Aug. 1, 2011, Gaylord.
(Continued)

*Primary Examiner* — Duc Truong
(74) *Attorney, Agent, or Firm* — Bret E. Field; Bozicevic, Field & Francis LLP

(57) ABSTRACT

Described herein are methods, compositions and articles of manufacture involving neutral conjugated polymers including methods for synthesis of neutral conjugated water-soluble polymers with linkers along the polymer main chain structure and terminal end capping units. Such polymers may serve in the fabrication of novel optoelectronic devices and in the development of highly efficient biosensors. The invention further relates to the application of these polymers in assay methods.

20 Claims, 45 Drawing Sheets

Specification includes a Sequence Listing.

Related U.S. Application Data continuation of application No. 14/821,386, filed on Aug. 7, 2015, now Pat. No. 9,547,008, which is a continuation of application No. 14/018,985, filed on Sep. 5, 2013, now Pat. No. 9,139,869, which is a continuation of application No. 13/009,764, filed on Jan. 19, 2011, now Pat. No. 8,575,303.

(60) Provisional application No. 61/358,406, filed on Jun. 24, 2010, provisional application No. 61/296,379, filed on Jan. 19, 2010.

(51) Int. Cl.
| | | |
|---|---|---|
| *H01L 51/00* | (2006.01) | |
| *C12Q 1/6818* | (2018.01) | |
| *C12Q 1/682* | (2018.01) | |
| *C09B 67/00* | (2006.01) | |
| *C07K 16/28* | (2006.01) | |

(52) U.S. Cl.
CPC ............. *C08G 61/02* (2013.01); *C09B 68/41* (2013.01); *C12Q 1/682* (2013.01); *C12Q 1/6818* (2013.01); *G01N 33/582* (2013.01); *H01L 51/0043* (2013.01); *C08G 2261/1424* (2013.01); *C08G 2261/3142* (2013.01); *C08G 2261/411* (2013.01); *H01L 51/0039* (2013.01)

(58) Field of Classification Search
USPC .................................................. 528/371, 370
See application file for complete search history.

(56) References Cited

U.S. PATENT DOCUMENTS

| | | | |
|---|---|---|---|
| 5,288,514 A | 2/1994 | Ellman | |
| 5,384,261 A | 1/1995 | Winkler et al. | |
| 5,424,186 A | 6/1995 | Fodor et al. | |
| 5,677,195 A | 10/1997 | Winkler | |
| 5,807,974 A | 9/1998 | Kim | |
| 5,990,479 A | 10/1999 | Weiss et al. | |
| 6,263,286 B1 | 7/2001 | Gilmanshin et al. | |
| 6,280,933 B1 | 8/2001 | Glazer et al. | |
| 6,350,431 B1 | 2/2002 | Snow et al. | |
| 6,951,682 B1 | 10/2005 | Zebala | |
| 6,998,241 B2 | 2/2006 | Boga | |
| 7,141,437 B2 | 11/2006 | Dvornic et al. | |
| 7,144,950 B2 | 12/2006 | Bazan et al. | |
| 7,208,122 B2 | 4/2007 | Swager et al. | |
| 7,214,489 B2 | 5/2007 | Bazan | |
| 7,241,512 B2 | 7/2007 | Li et al. | |
| 7,270,956 B2 | 9/2007 | Bazan et al. | |
| 7,282,514 B1 | 10/2007 | Belfield et al. | |
| 7,629,448 B2 | 12/2009 | Bazan et al. | |
| 7,666,594 B2 | 2/2010 | Bazan | |
| 7,811,755 B2 | 10/2010 | Bazan et al. | |
| 7,897,684 B2 | 3/2011 | Bazan et al. | |
| 7,914,984 B2 | 3/2011 | Bazan et al. | |
| 8,101,416 B2 | 1/2012 | Bazan et al. | |
| 8,110,673 B2 | 2/2012 | Bazan et al. | |
| 8,158,444 B2 | 4/2012 | Gaylord et al. | |
| 8,227,187 B2 | 7/2012 | Bazan et al. | |
| 8,309,672 B2 | 11/2012 | Bazan et al. | |
| 8,338,532 B2 | 12/2012 | Bazan et al. | |
| 8,354,239 B2 | 1/2013 | Gaylord et al. | |
| 8,362,193 B2 | 1/2013 | Gaylord et al. | |
| 8,455,613 B2 | 6/2013 | Gaylord et al. | |
| 8,546,081 B2 | 10/2013 | Bazan et al. | |
| 8,575,303 B2 | 11/2013 | Gaylord et al. | |
| 8,617,814 B2 | 12/2013 | Bazan et al. | |
| 8,669,055 B2 | 3/2014 | Bazan et al. | |
| 8,759,444 B2 | 6/2014 | Bazan et al. | |
| 8,802,450 B2 | 8/2014 | Gaylord et al. | |
| 8,835,113 B2 | 9/2014 | Bazan et al. | |
| 8,841,072 B2 | 9/2014 | Bazan et al. | |
| 8,969,509 B2 | 3/2015 | Liu et al. | |
| 8,993,335 B2 | 3/2015 | Bazan et al. | |
| 9,085,799 B2 | 7/2015 | Bazan et al. | |
| 9,139,869 B2 | 9/2015 | Gaylord et al. | |
| 9,159,465 B2 | 10/2015 | Bazan et al. | |
| 9,371,559 B2 | 6/2016 | Bazan et al. | |
| 9,383,353 B2 | 7/2016 | Gaylord et al. | |
| 9,547,008 B2 | 1/2017 | Gaylord et al. | |
| 10,094,838 B2 * | 10/2018 | Gaylord | C08G 61/02 |
| 2003/0087311 A1 | 5/2003 | Wolf | |
| 2004/0009506 A1 | 1/2004 | Stephan et al. | |
| 2004/0023248 A1 | 2/2004 | O'Malley | |
| 2004/0023317 A1 | 2/2004 | Motamedi et al. | |
| 2004/0142344 A1 | 7/2004 | Bazan et al. | |
| 2004/0219556 A1 | 11/2004 | Bazan et al. | |
| 2005/0003386 A1 | 1/2005 | Bazan et al. | |
| 2005/0059168 A1 | 3/2005 | Bazan et al. | |
| 2005/0196775 A1 | 9/2005 | Swager et al. | |
| 2006/0073607 A1 | 4/2006 | Rose et al. | |
| 2006/0127929 A1 | 6/2006 | Swager et al. | |
| 2006/0175193 A1 | 8/2006 | Inganas et al. | |
| 2006/0183140 A1 | 8/2006 | Bazan et al. | |
| 2006/0204984 A1 | 9/2006 | Bazan et al. | |
| 2006/0216734 A1 | 9/2006 | Bazan et al. | |
| 2006/0216759 A1 | 9/2006 | Naasani | |
| 2007/0178470 A1 | 8/2007 | Bissonnette | |
| 2007/0281289 A1 | 12/2007 | Moon | |
| 2008/0038751 A1 | 2/2008 | Asberg et al. | |
| 2008/0064042 A1 | 3/2008 | Bazan et al. | |
| 2008/0293164 A1 | 11/2008 | Gaylord | |
| 2009/0230362 A1 | 9/2009 | Bazan et al. | |
| 2010/0136702 A1 | 6/2010 | Bazan et al. | |
| 2011/0256549 A1 | 10/2011 | Bartholomew et al. | |
| 2011/0256550 A1 | 10/2011 | Bartholomew et al. | |
| 2011/0257374 A1 | 10/2011 | Gaylord et al. | |
| 2012/0028828 A1 | 2/2012 | Gaylord et al. | |
| 2012/0029155 A1 | 2/2012 | Gaylord et al. | |
| 2012/0252986 A1 | 10/2012 | Liu et al. | |
| 2013/0190193 A1 | 7/2013 | Bazan et al. | |
| 2015/0226746 A1 | 8/2015 | Bazan et al. | |
| 2016/0266131 A1 | 9/2016 | Liang et al. | |
| 2016/0266132 A1 | 9/2016 | Gaylord et al. | |
| 2016/0341720 A1 | 11/2016 | Bazan et al. | |
| 2016/0349267 A1 | 12/2016 | Gaylord et al. | |
| 2017/0115298 A1 | 4/2017 | Gaylord et al. | |

FOREIGN PATENT DOCUMENTS

| | | |
|---|---|---|
| EP | 1281744 | 2/2003 |
| EP | 708837 | 3/2006 |
| EP | 1279023 | 2/2007 |
| JP | 2006-510389 | 3/2006 |
| JP | 2008-512523 A | 4/2008 |
| JP | 2009-139214 A | 6/2009 |
| JP | 2013-511700 A | 4/2013 |
| WO | WO 90/15070 | 12/1990 |
| WO | WO 92/10092 | 6/1992 |
| WO | WO 93/09668 | 5/1993 |
| WO | WO 93/10507 | 5/1993 |
| WO | WO 93/22684 | 11/1993 |
| WO | WO 94/09169 | 4/1994 |
| WO | WO 99/26299 | 5/1999 |
| WO | WO 00/66790 | 11/2000 |
| WO | WO 02/079268 A2 | 10/2002 |
| WO | WO 02/081735 A2 | 10/2002 |
| WO | WO 02/081735 A3 | 4/2003 |
| WO | WO 02/079268 A3 | 8/2003 |
| WO | WO 2004/001379 A2 | 12/2003 |
| WO | WO 2004/037886 | 5/2004 |
| WO | WO 2004/077014 A2 | 9/2004 |
| WO | WO 2004/092324 A2 | 10/2004 |
| WO | WO 2005/086617 A2 | 9/2005 |
| WO | WO 2006/029231 A1 | 3/2006 |
| WO | WO 2006/034081 A2 | 3/2006 |
| WO | WO 2006/034081 A3 | 5/2006 |
| WO | WO 2006/074471 A2 | 7/2006 |
| WO | WO 2006/074482 A2 | 7/2006 |
| WO | WO 2006/083932 A2 | 8/2006 |
| WO | WO 2006/092063 | 9/2006 |

(56) References Cited

FOREIGN PATENT DOCUMENTS

| WO | WO 2008/100344 | 8/2008 |
|---|---|---|
| WO | WO 2010/151807 | 12/2010 |
| WO | WO 2011/057295 A2 | 5/2011 |
| WO | WO 2011/091086 | 7/2011 |
| WO | WO 2016/144653 A1 | 9/2016 |

OTHER PUBLICATIONS

U.S. Appl. No. 13/195,736, filed Aug. 1, 2011, Gaylord.
U.S. Appl. No. 07/624,120, filed Dec. 6, 1990, Fodor.
U.S. Appl. No. 60/642,901, filed Jan. 10, 2005, Bazan.
An et al., "A fluorescence ratiometric protein asssay using light-harvesting conjugated polymers," Macromolecular Rapid Communications, 27(13):993-997 (2006).
Ausebel et al., eds., Current Protocols in Molecular Biology, vols. I, II, and III. 1997.
Ausubel et al., eds., Short Protocols in Molecular Biology: A Compendium of Methods from Current Protocols in Molecular Biology, $5^{th}$ ed., John Wiley & Sons, Inc., 2002.
Bailey et al., "Masked Micheal Acceptors in Poly(phenyleneethynylene)s for Facile Conjugation," Macromolecules, 39:2815-2818 (2006).
Bruchez et al., "Semiconductor nanocrystals as fluorescent biological labels," Science, 281:2013-2016 (1998).
Chen et al., "Highly sensitive biological and chemical sensors based on reversible fluorescence quenching in a conjugated polymer," PNAS USA, 96(220):12287-12292 (1999).
Delagrave et al., "Isolated mutants of cloned Aequorea victoria GFP that had red-shifted excitation spectra," Bio/Tech 13:151-154 (1995).
Fodor et al., "Light-directed, spatially addressable parallel chemical synthesis," Science 251(4995):767-773 (1991).
Gaylord et al., "DNA detection using water-soluble conjugated polymers and peptide nucleic acid probes," PNAS USA, 99(17):10954-10957 (2002).
Gaylord et al., "DNA hybridization detection with water-soluble conjugated polymers and chromophore-labeled single-stranded DNA" J Am Chem Soc, 124(4):896-900 (2003).
Gaylord et al., "SNP detection using peptide nucleic acid probes and conjugated polymers: application in neurodegenerative disease identification," PNAS USA, 102(1):34-39 (2005).
Geierstanger and Wemmer, "Complexes of the minor groove of DNA," Annu Rev Biophys Biomol Struct, 24:463-493 (1995).
Glumoff and Goldman, Nucleic Acids in Chemistry and Biology, $2^{nd}$ ed., Blackburn and Gait, eds., Oxford University Press, Oxford, 1996, pp. 375-441.
Heeger et al., "Making sense of polymer-based biosensors," PNAS USA, 96(22):12219-12221 (1999).
Heim et al., "Improved green fluorescence," Nature, 373:663-664 (1995).
Heim et al., "Wavelength mutations and post-translational autoxidation of green fluorescent protein," PNAS USA, 91:12501-12504 (1994).
Ho et al., "Colorimetric and fluorometric detection of nucleic acids using cationic polythiophene derivatives," Angewandte Chemie International Edition, 41(9):1548-1551 (2002).
Ho et al., "Direct molecular detection of nucleic acids by fluorescence signal amplification," J Am Chem Soc, 127(36):12673-12676 (2005).
Innis et al., eds., PCR Protocols: A Guide to Methods and Applications, Elsevier Science & Technology Books 1990.
Invitrogen—Molecular Probes, available at www.probes.com, accessed Dec. 19, 2007.
Invitrogen—available at www.invitrogen.com, accessed Dec. 19, 2007.
Kanehisa, "Use of statistical criteria for screening potential homologies in nucleic acid sequences," Nucleic Acids Research, 12(1 Pt 1):203-213 (1984).
Kreuzer et al., "LightCycler technology fo rthe quantitation of bcr/abl fusion transcripts," Cancer Research, 59(13):3171-3174 (1999).
Kreyenschmidt et al., "A New Soluble poly(p-phenylene) with Tetrahydropryrene Repeating Units," Macromolecules, 28:4577-4582 (1995).
Larson and Verdine, Bioorganic Chemistry: Nucleic Acids, Hecht ed., Oxford University Press: New York 1996 pp. 324-346.
Laurendeau et al., "Quantitation of MYC gene expression in sporadic breast tumors with a real-time reverse transcription PCR assay," Cancer Res, 59(12):2759-2765 (1999).
Laurendeau et al., "TaqMan PCR-based gene dosage assay for predictive testing in individuals from a cancer family with INK4 locus haploinsufficiency," Clin Chem, 45(7):982-986 (1999).
LeClerc, "Polyfluorenes: Twenty Years of Progress," Polym Sci Part A: Polym Chem, 39:2867-2873 (2001).
Lee, "Functionalized Conjugated Polymers for Signal Amplifying Biosensors and Sensor Arrays," Dissertation, The University of Michigan, 2008.
Lee et al., "Synthesis and Characterization of Oligo(9,9-dihyexyl-2,7-fluorene ethynylene)s: For Application as Blue Light-Emitting Diode," Org Lett, 3:2005-2007 (2001).
Liu et al., "Characterization of tectoRNA assembly with cationic conjugated polymers," J Am Chem Soc, 126(13):4076-4077 (2004).
Liu et al., "Interpolyelectrolyte complexes of conjugated copolymers and DNA: platforms for multicolor biosensors," J Am Chem Soc, 126(7):1942-1943 (2004).
Liu et al., "Methods for strand-specific DNA detection with cationic conjugated polymers suitable for incorporation into DNA chips and microarrays," PNAS USA, 102(3):589-593 (2005).
Liu et al., "Optimization of the molecular orbital energies of conjugated polymers for optical amplification of fluorescent sensors," J Am Chem Soc, 128:1188-1196 (2006).
Liu et al., "Shape-adaptable water-soluble conjugated polymers," J Am Chem Soc, 124(44):13306-13307 (2003).
Mikroyannidis et al., "Alternating copolyfluorenevinyles with polynuclear aromatic moieties: Synthesis, photophysics, and electroluminescence," J Polym Sci Part A:Polym Chem, 45:4661-4670 (2007).
Pei et al., "Efficient Photoluminescence and Electroluminescence from a Soluble Polyfluorene," J Am Chem Soc, 118:7416-7417 (1996).
Pierce, Biotechnology, available at www.piercenet.com, accessed Dec. 19, 2007.
Sambrook et al., Molecular Cloning: A Laboratory Manual, $3^{rd}$ ed., Cold Spring Harbor Laboratory Press, 2000.
Sekar et al., "Phycobiliproteins as a commodity: trends in applied research, patents and commercialization," J Appl Phycol, 20:113-136 (2008).
Sonogashira et al., "A convenient synthesis of acetylenes: catalytic substitutions of acetylenic hydrogen with bromoalkenes, iodoarenes and bromopyridines," Tetra Lett, 16:4467-4470 (1975).
Wang et al., "Biosensors from conjugated polyelectrolyte complexes," PNAS USA, 99(1):49-53 (2002).
Wang et al., "Collective optical behavior of cationic water-soluble dendrimers," Advanced Materials, 16(23-24):2127-2132 (2004).
Wang et al., "Fluorescein provides a resonance gate for FRET from conjugated polymers to DNA intercalated dyes," J Am Chem Soc, 126(17):5446-5451 (2004).
Wang, "From DNA biosensors to gene chips," Nucl Acids Res, 28(16):3011-3016 (2000).
Wang et al., "Optimally amplified RNA-protein detection methods using light-harvesting conjugated polymers," Advanced Materials, 15(17):1425-1428 (2003).
Wosnick et al., "Synthesis and application of poly(phenylen ethynylene)s for bioconjugation: a conjugated polymer-based fluorogenic proble for proteases," J Am Chm Soc, 127:3400-3405 (2005).
Xu et al., "Magnetically assisted DNA assays: high selectivity using conjugated polymers for amplified fluorescent transduction," Nucl Acids Res, 33(9):e83 (2005).
Yamamoto et al., "Preparation of π-Conjugated Poly(thiophene-2,5-diyl), Poly(p-phenylene), and Related Polymers Using Zerovalent Nickel Complexes. Linear Structure and Properties of the π-Conjugated Polymers," Macromolecules, 25:1214-1223 (1992).

(56) References Cited

OTHER PUBLICATIONS

Zhou et al., "Polyfluorenes with phosphonate groups in the side chains as chemosensors and electroluminescent materials," Macromolecules, 38:5416-5424 (2005).
EP 07873316 Supplemental Search Report dated Aug. 3, 2010.
JP 2009-531642 Office Action dated Mar. 22, 2012.
PCT/US2010/40051 International Search Report dated Sep. 30, 2010.
PCT/US11/21775 Search Report and Written Opinion dated May 19, 2011.

* cited by examiner

A

B

A

B

C

A  B  C

A

B

A

B

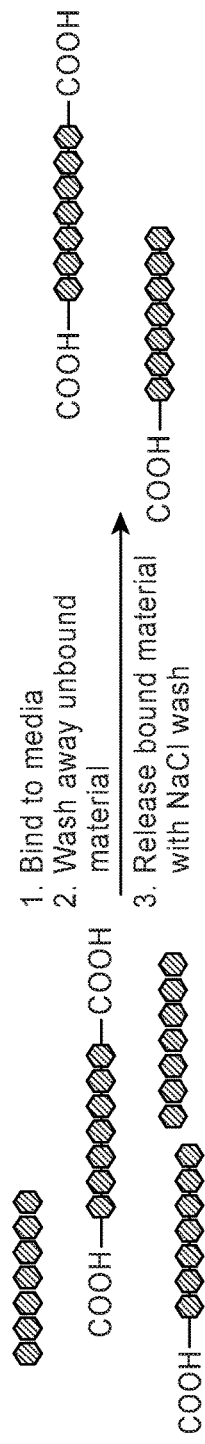
FIG. 39
1. Bind to media
2. Wash away unbound material
3. Release bound material with NaCl wash
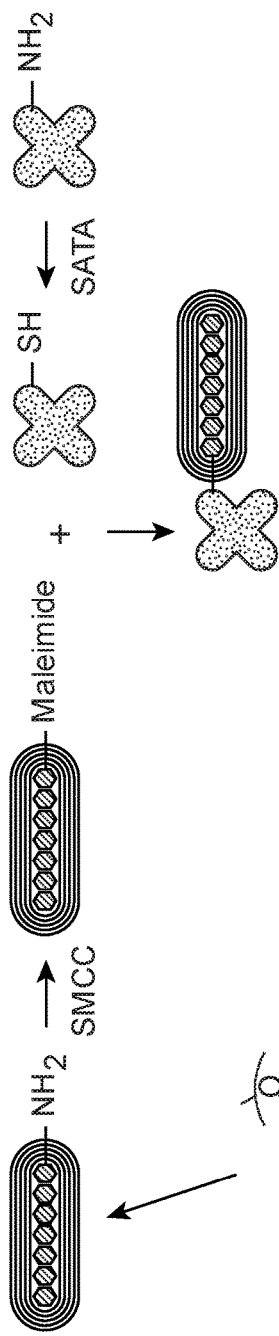
FIG. 40
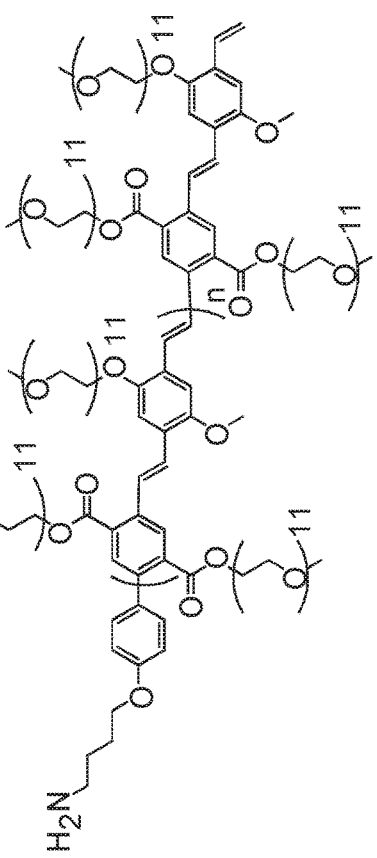

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
attttaccct ctgaaggctc c                                      21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
ggagccttca gagggtaaaa t                                      21

REAGENTS FOR DIRECTED BIOMARKER SIGNAL AMPLIFICATION

CROSS-REFERENCE

This application is a continuation of application Ser. No. 15/239,713, filed Aug. 17, 2016 and issued as U.S. patent Ser. No. 10/094,838; which application is a continuation of application Ser. No. 14/821,386, filed Aug. 7, 2015 and issued as U.S. Pat. No. 9,547,008; which application is a continuation of application Ser. No. 14/018,985, filed Sep. 5, 2013 and issued as U.S. Pat. No. 9,139,869; which application is a continuation of application Ser. No. 13/009,764, filed Jan. 19, 2011 and issued as U.S. Pat. No. 8,575,303, which claims the benefit of U.S. Provisional Application Ser. No. 61/296,379, filed Jan. 19, 2010 and U.S. Provisional Application Ser. No. 61/358,406, filed Jun. 24, 2010, which applications are incorporated herein by reference in their entireties.

BACKGROUND OF THE INVENTION

Fluorescent hybridization probes have developed into an important tool in the sequence-specific detection of DNA and RNA. The signals generated by the appended fluorescent labels (or dyes) can be monitored in real time and provide simple, rapid, and robust methods for the detection of biological targets and events. Utility has been seen in applications ranging from microarrays and real time PCR to fluorescence in situ hybridization (FISH).

Recent work in the area of multichromophores, particularly regarding conjugated polymers (CPs) has highlighted the potential these materials have in significantly improving the detection sensitivity of such methods (Liu and Bazan, Chem. Mater., 2004). The light harvesting structures of these materials can be made water soluble and adapted to amplify the fluorescent output of various probe labels (See U.S. patent application Ser. No. 10/600,286, filed Jun. 20, 2003 and Gaylord, Heeger, and Bazan, Proc. Natl. Acad. Sci., 2002, both of which are incorporated herein by reference in their entirety).

Results such as these indicate CPs to be highly promising in the field of nucleic acid diagnostics, particularly where sample quantities are scarce. However, there exist methods for the amplification (or replication) of nucleic acid targets, i.e., PCR. Comparatively, in the field of protein recognition, there are no such simple methods for amplifying the targeted materials. As such, signal enhancement arising from CP application is of high consequence in this area.

Dye-labeled antibodies are regularly used for the detection of protein targets in applications such as immunohistochemistry, protein arrays, ELISA tests, and flow cytometry. Integrating CP materials into such methodologies promises to provide a dramatic boost in the performance of such assays, enabling detection levels previously unattainable with conventional fluorescent reporters (e.g., dyes).

Beyond addition signal, one of the other key drivers in biological detection formats is the ability to detect multiple analytes in the same test or multiplexing. This is commonly achieved by using fluorescent reporters with operate at different, discernable wavelengths. CP materials are ideally suited to provide a platform for expanded multiplexing. This can be achieved by tuning the structure of different CPs to operate at different wavelengths or by incorporating a dye within the polymer-biomolecule conjugate.

The material and methods to produce higher sensitivity biological assays and increase multiplexing are highly desired in both molecular (nucleic acid) and immunoassay formats.

SUMMARY OF THE INVENTION

Provided herein are water soluble conjugated polymers of Formula (I):

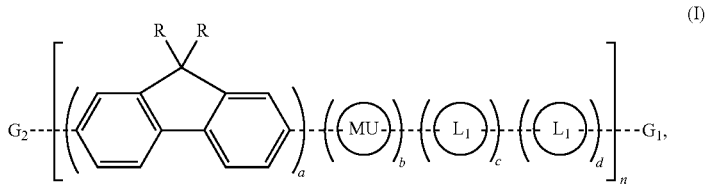

wherein:
each R is independently a non-ionic side group capable of imparting solubility in water in excess of 10 mg/mL;
MU is a polymer modifying unit or band gap modifying unit that is evenly or randomly distributed along the polymer main chain and is optionally substituted with one or more optionally substituted substituents selected from halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$(hetero)aryloxy, $C_2$-$C_{18}$(hetero)arylamino, $(CH_2)_{x'}(OCH_2CH_2)_{y'}OCH_3$ where each x' is independently an integer from 0-20, y' is independently an integer from 0 to 50, or a $C_2$-$C_{18}$(hetero)aryl group;
each optional linker $L_1$ and $L_2$ are aryl or heteroaryl groups evenly or randomly distributed along the polymer main chain and are substituted with one or more pendant chains terminated with a functional group for conjugation to another substrate, molecule or biomolecule selected from amine, carbamate, carboxylic acid, carboxylate, maleimide, activated esters, N-hydroxysuccinimidyl, hydrazines, hydrazides, hydrazones, azide, alkyne, aldehydes, thiols, and protected groups thereof;
$G_1$ and $G_2$ are each independently selected from hydrogen, halogen, amine, carbamate, carboxylic acid, maleimide, activated esters, N-hydroxysuccinimidyl, hydrazines, hydrazides, hydrazones, azide, alkyne, aldehydes, thiol, optionally substituted aryl, optionally substituted heteroaryl, halogen substituted aryl, boronic acid substituted aryl, boronic ester substituted aryl, boronic esters, boronic acids, optionally substituted fluorene and aryl or heteroaryl substituted with one or more pendant chains terminated with a functional group selected from amine, carbamate, carboxylic acid, carboxylate, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule;

wherein the polymer comprises at least 1 functional group selected from amine, carbamate, carboxylic acid, carboxylate, maleimide, activated esters, N-hydroxysuccinimidyl, hydrazines, hydrazides, hydrazones, azide, alkyne, aldehydes, and thiols within $G_1$, $G_2$, $L_1$ or $L_2$ that allows, for functional conjugation to another molecule, substrate or biomolecule;

each dashed bond, - - - - - -, is independently a single bond, triple bond or optionally substituted vinylene (—$CR^5$=$CR^5$—) wherein each $R^5$ is independently hydrogen, cyano, $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group, wherein each $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero) aryl group is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, or $C_1$-$C_{12}$ haloalkyl; and n is an integer from 1 to about 10,000; and a, b, c and d define the mol % of each unit within the structure which each can be evenly or randomly repeated and where a is a mol % from 10 to 100%, b is a mol % from 0 to 90%, and each c and d are mol % from 0 to 25%.

In one aspect, water soluble conjugated polymers of Formula (I) have the structure of Formula (Ia):

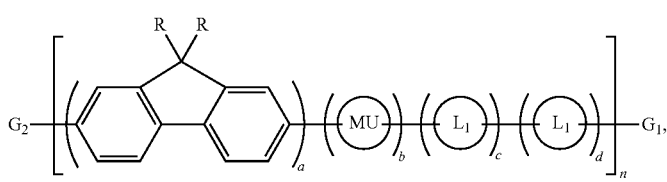

(Ia)

wherein R, $L_1$, $L_2$, $G_1$, $G_2$, MU, a, b, c, d and n are described previously for formula (I).

In some embodiments, each R is independently $(CH_2)_x$$(OCH_2CH_2)_y OCH_3$ where each x is independently an integer from 0-20, each y is independently an integer from 0 to 50, or a benzyl optionally substituted with one or more halogen, hydroxyl, $C_1$-$C_{12}$ alkoxy, or $(OCH_2CH_2)_z OCH_3$ where each z is independently an integer from 0 to 50. In some instances, each R is $(CH_2)_3(OCH_2CH_2)_{11}CH_3$.

In other embodiments, each R is a benzyl substituted with at least one $(OCH_2CH_2)_{10}OCH_3$ group. In some instances, the benzyl is substituted with two $(OCH_2CH_2)_{10}OCH_3$ groups. In other instances, the benzyl is substituted with three $(OCH_2CH_2)_{10}OCH_3$ groups.

In some embodiments, optional linkers $L_1$ or $L_2$ have the structure:

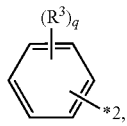

*=site for covalent attachment to unsaturated backbone; wherein $R^3$ is independently hydrogen, halogen, alkoxy($C_1$-$C_{12}$), $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group, wherein each $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, or $C_1$-$C_{12}$ haloalkyl; and q is an integer from 0 to 4.

In other embodiments, optional linkers $L_1$ or $L_2$ have the structure:

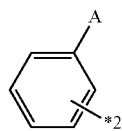

*=site for covalent attachment to unsaturated backbone wherein A is a site for conjugation, chain extension or crosslinking and is [O—$CH_2$—$CH_2$]$_q$—W, or ($C_1$-$C_{12}$) alkoxy-X or $C_2$-$C_{18}$(hetero)aryl, phenoxy, amido, amino, carbamate, carboxylate, carbonates, sulfide, disulfide, or imido groups terminated with a functional group selected from amine, carbamate, carboxylate, carboxylic acid, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule; W is —OH or —COOH; X is —$NH_2$, —NHCOOH, —NHCOOC($CH_3$)$_3$, —NHCO($C_3$-$C_{12}$)cycloalkyl($C_1$-$C_4$)alkyl-N-maleimide; or —NHCO[$CH_2$—$CH_2$—O]$_t$$NH_2$; q is an integer from 1 to 20; and t is an integer from 1 to 8.

In yet other embodiments, optional linkers $L_1$ or $L_2$ have the structure:

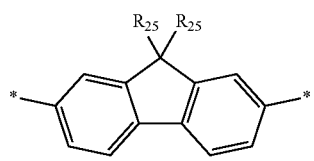

*=site for covalent attachment to backbone
wherein $R^{25}$ are each independently any one of or a combination of a bond, $C_1$-$C_{20}$ alkyl, $C_1$-$C_{20}$ alkoxy, $C_2$-$C_{20}$ alkene, $C_2$-$C_{20}$ alkyne, $C_3$-$C_{20}$ cycloalkyl, $C_1$-$C_{20}$ haloalkyl, $(CH_2)_x(OCH_2CH_2)_p(CH_2)_x$ where each x is independently an integer from 0-20, p is independently an integer from 0 to 50, aryl, $C_2$-$C_{18}$ (hetero)aryl, phenoxy, amido, amino, carbamate, carboxylate, carbonates, sulfide, disulfide, or imido groups;

wherein at least one $R^{25}$ is terminated with a functional group selected from amine, carbamate, carboxylate, carboxylic acid, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule.

In further embodiments, optional linkers $L_1$ or $L_2$ have the structure:

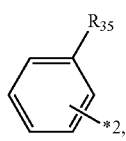

*=site for covalent attachment to unsaturated backbone; wherein R35 is any one of or a combination of a bond, C1-C20 alkyl, C1-C20 alkoxy, C2-C20 alkene, C2-C20 alkyne, C3-C20 cycloalkyl, C1-C20 haloalkyl, (CH2)x(OCH2CH2)p(CH2)x where each x is independently an integer from 0-20, p is independently an integer from 0 to 50, aryl, C2-C18(hetero)aryl, phenoxy, amido, amino, carbamate, carboxylate, carbonates, sulfide, disulfide, or imido groups terminated with a functional group selected from amine, carbamate, carboxylate, carboxylic acid, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule.

In further embodiments, optional linkers $L_1$ or $L_2$ are selected from the group consisting of a-h having the structures:

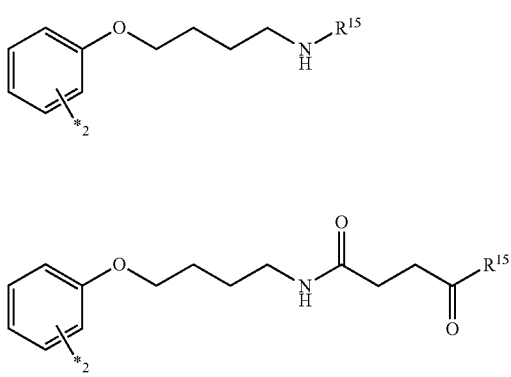

a b

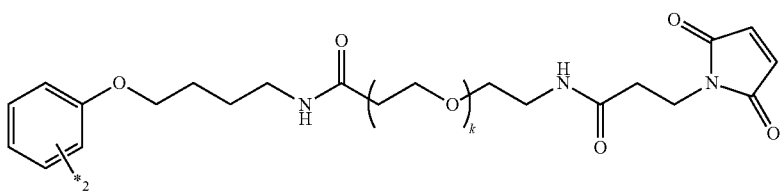

c

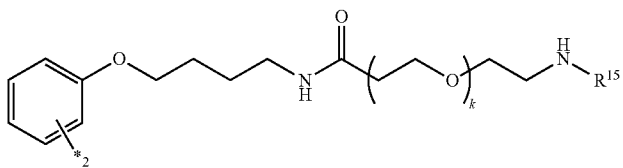

d e

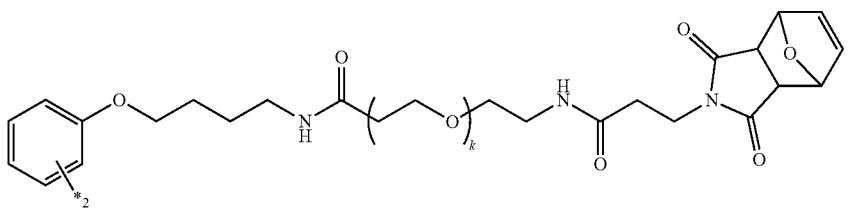

f

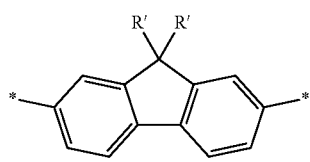

g

-continued

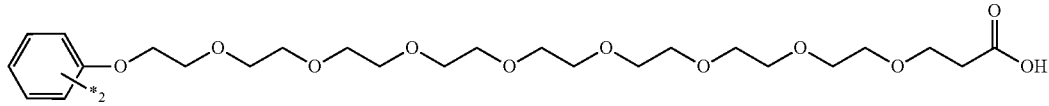
h

*=site for covalent attachment to unsaturated backbone;

wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$ cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$($OCH_2CH_2$)$_{x''}$$OCH_3$ where x'' is independently an integer from 0 to 50, or a benzyl optionally substituted with one or more halogen, hydroxyl, $C_1$-$C_{12}$ alkoxy, or ($OCH_2CH_2$)$_{y''}$—$OCH_3$ where each y'' is independently an integer from 0 to 50 and R' is different from R;

wherein k is 2, 4, 8, 12 or 24;

wherein $R^{15}$ is selected from the group consisting of l-t having the structure:

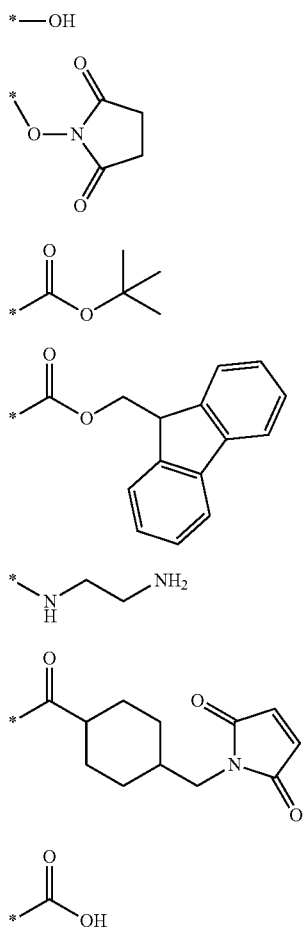

-continued s
*\
 $NH_2$ t
*\
 SH

*=site for covalent attachment to backbone.

In yet further embodiments, optional linkers $L_1$ or $L_2$ are

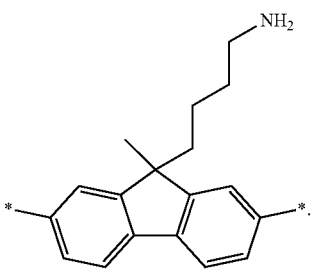

In some embodiments, $G_1$ and $G_2$ are each independently selected from hydrogen, halogen, alkyne, optionally substituted aryl, optionally substituted heteroaryl, halogen substituted aryl, boronic acid substituted aryl, boronic ester substituted aryl, boronic esters, boronic acids, optionally substituted fluorine and aryl or heteroaryl substituted with one or more pendant chains terminated with a functional group, molecule or biomolecule selected from amine, carbamate, carboxylic acid, carboxylate, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule.

In some embodiments, $G_1$ and $G_2$ each independently have the structure

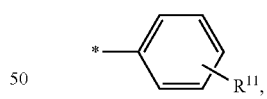

wherein $R^{11}$ is any one of or a combination of a bond, $C_1$-$C_{20}$ alkyl, $C_1$-$C_{20}$ alkoxy, $C_2$-$C_{20}$ alkene, $C_2$-$C_{20}$ alkyne, $C_3$-$C_{20}$ cycloalkyl, $C_1$-$C_{20}$ haloalkyl, ($CH_2$)$_x$($OCH_2CH_2$)$_p$($CH_2$)$_x$ where each x is independently an integer from 0-20, p is independently an integer from 0 to 50, aryl, $C_2$-$C_{18}$(hetero)aryl, phenoxy, amido, amino, carbamate, carboxylate, carbonates, sulfide, disulfide, or imido groups terminated with a functional group selected from amine, carbamate, carboxylate, carboxylic acid, maleimide, activated esters, N-hydroxysuccinimidyl, hydrazines, hydrazones, azide, alkyne, aldehydes, thiols, and protected groups thereof for conjugation to another substrate, molecule or biomolecule.

In other embodiments, $G_1$ and $G_2$ are each independently selected from the group consisting of 1-31 having the structures:

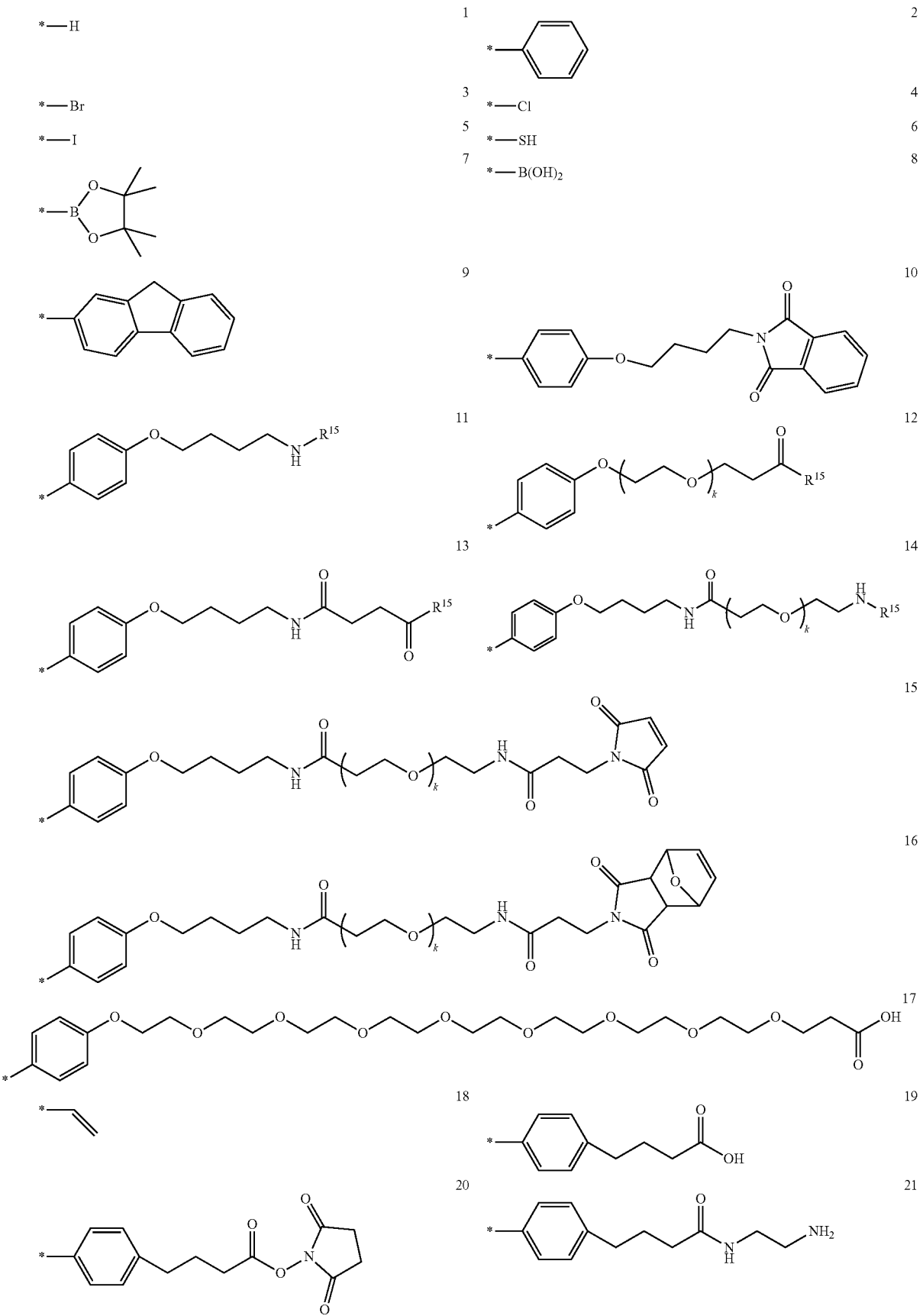

-continued
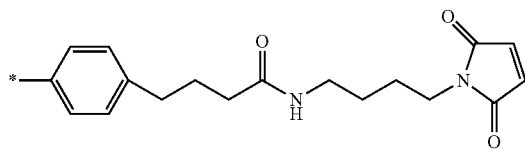
22
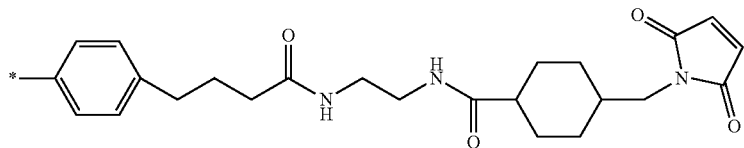
23
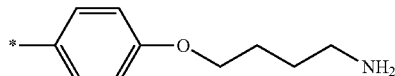
24
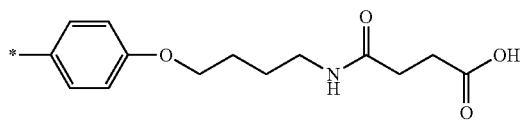
25
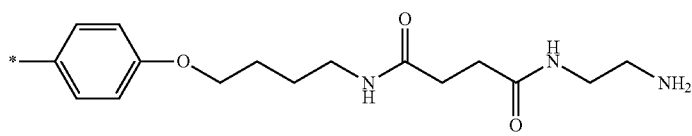
26
27
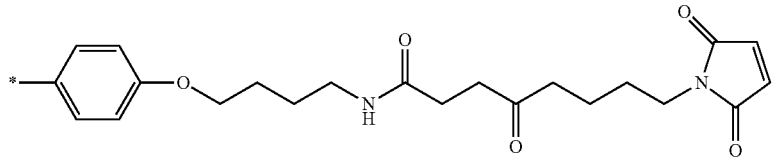
28
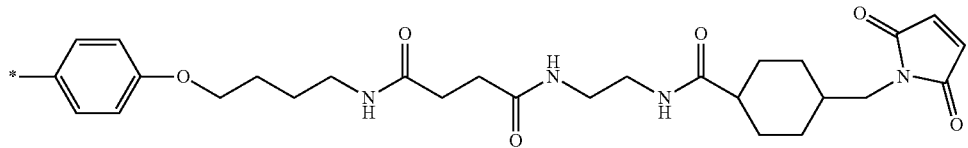
29
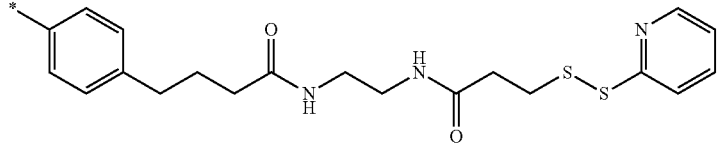
30
31
*=site for covalent attachment to backbone
wherein $R^{15}$ is selected from the group consisting of 1-t having the structure:
*—OH  l
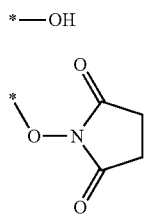 m
-continued
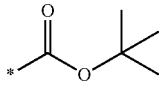 n
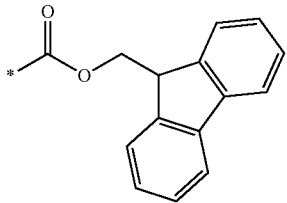 o

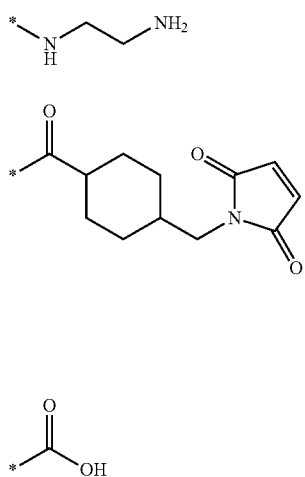

p q r s t and k is 2, 4, 8, 12 or 24.

In further embodiments, $G_1$ and $G_2$ are optionally substituted aryl or heteroaryl wherein the optional substituent is selected from halogen, amine, carbamate, carboxylic acid, maleimide, activated esters, N-hydroxysuccinimidyl, hydrazines, hydrazides, hydrazones, azide, alkyne, aldehydes, thiol, boronic acid, boronate radical, boronic esters and optionally substituted fluorene.

In some embodiments, $G_1$ and $G_2$ are the same. In other embodiments, $G_1$ and $G_2$ are different. In further embodiments, the polymer contains a single conjugation site at only one terminus of the polymer chain $G_1$ or $G_2$.

In yet further embodiments, $G_1$ and $G_2$ is

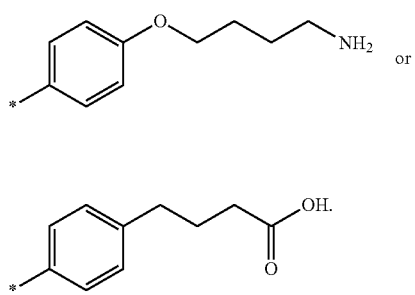

In some embodiments, MU is selected from the group consisting of a'-k' having the structure:

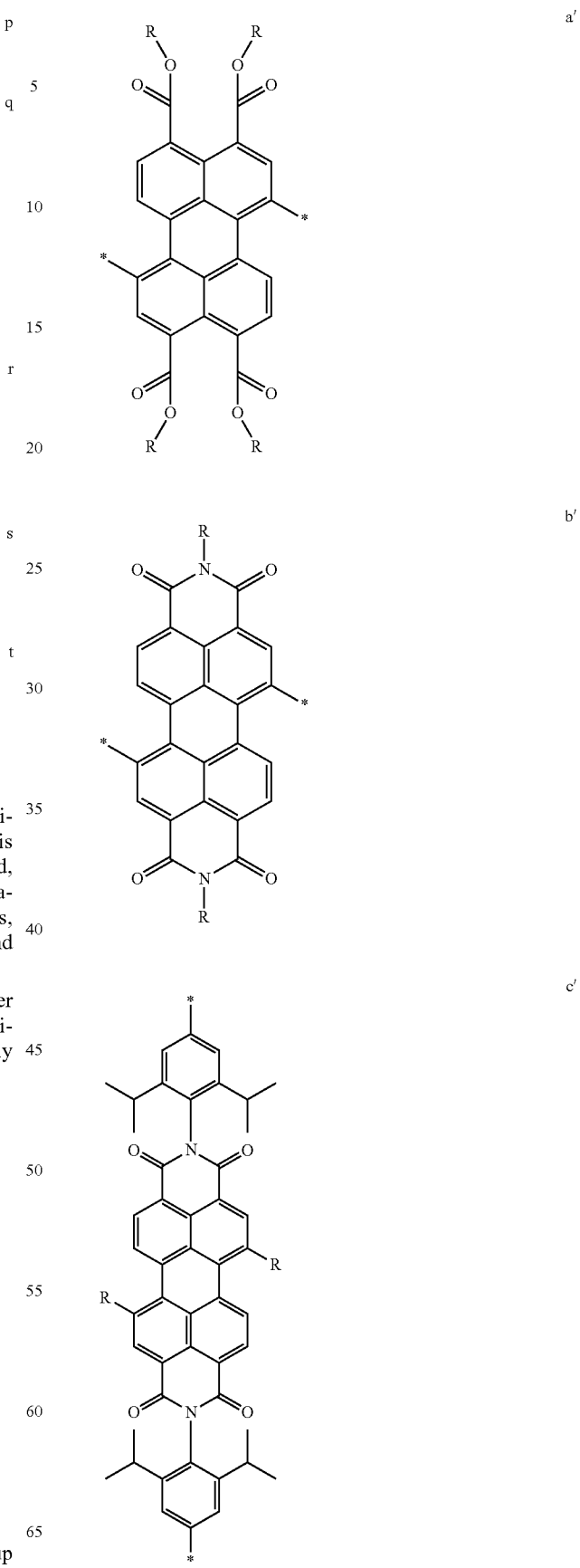

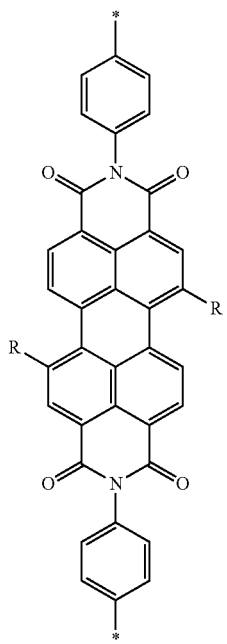

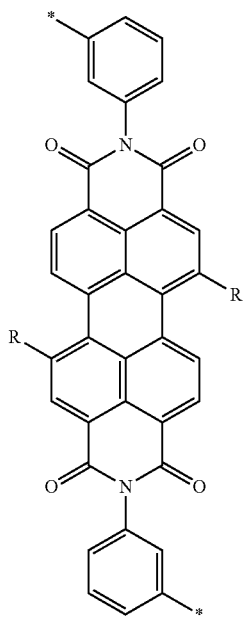

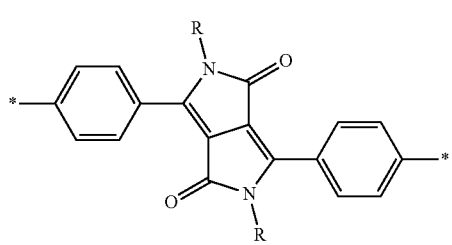

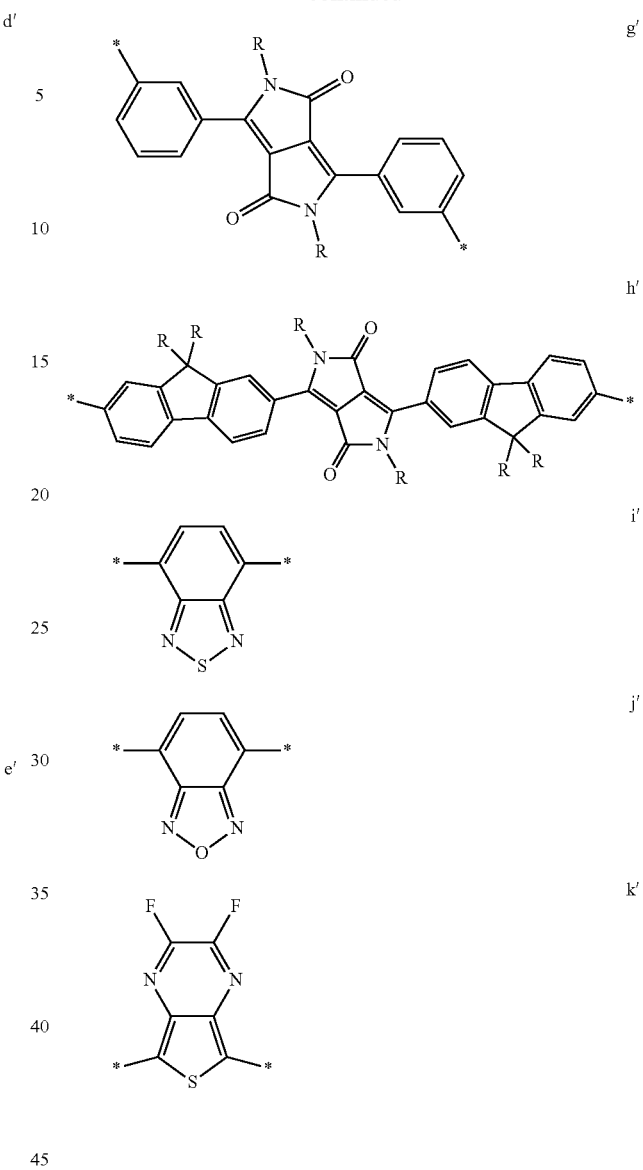

*=site for covalent attachment to unsaturated backbone wherein R is a non-ionic side group capable of imparting solubility in water in excess of 10 mg/mL.

In some embodiments, the water soluble conjugated polymer has the structure of formula:

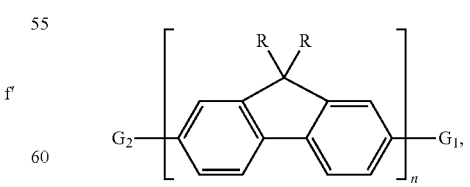

wherein at least one of $G_1$ or $G_2$ comprises a functional conjugation site.

In some embodiments, the water soluble conjugated polymer has the structure of formula:

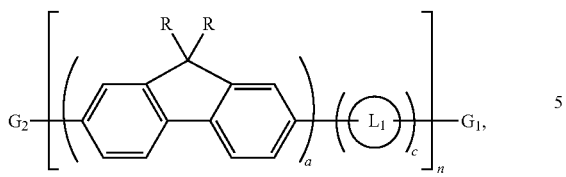

wherein $L_1$ comprises a functional conjugation site.

In some embodiments, the water soluble conjugated polymer has the structure of formula:

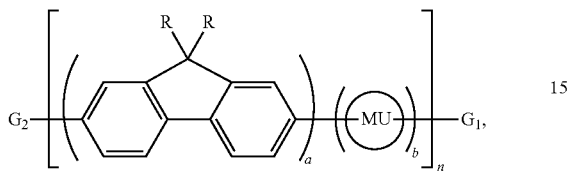

wherein at least one of $G_1$ or $G_2$ comprises a functional conjugation site.

In other embodiments, the polymer has the structure of formula:

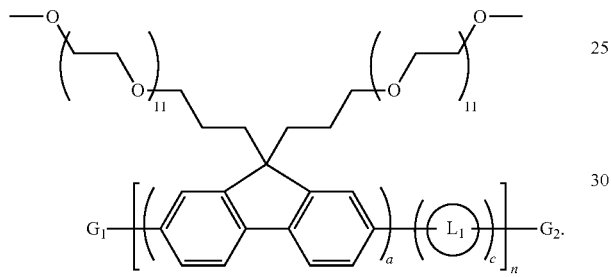

In other embodiments, the polymer has the structure of formula:

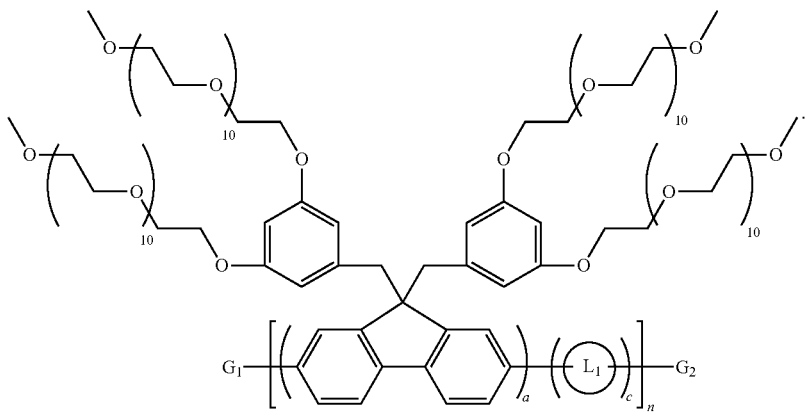

In other embodiments, the polymer has the structure of formula:

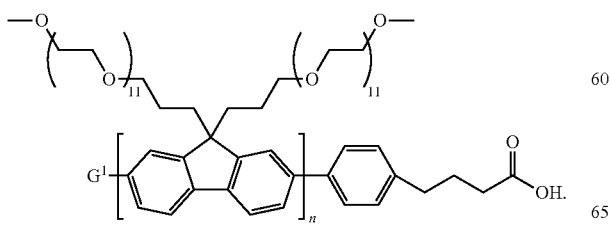

In other embodiments, the polymer has the structure of formula:
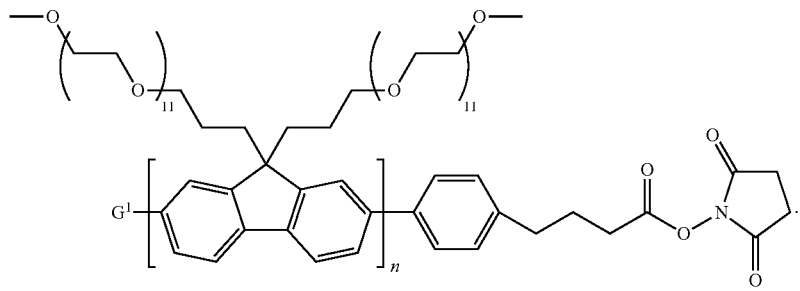
In other embodiments, the polymer has the structure of formula:
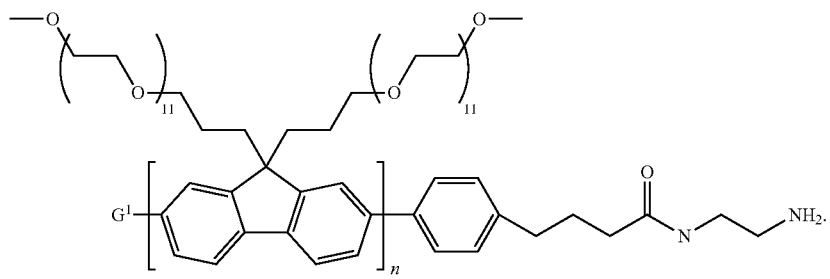
In other embodiments, the polymer has the structure of formula:
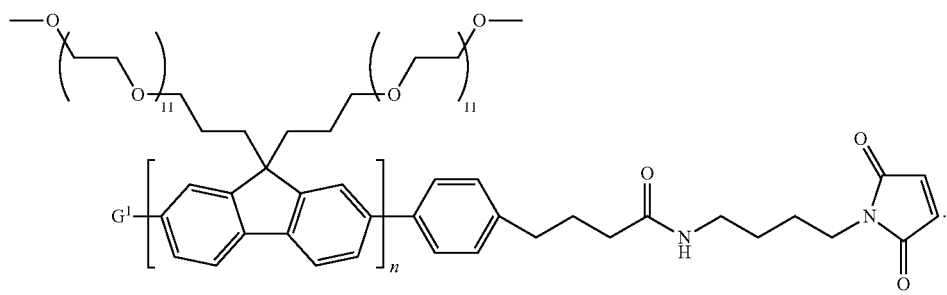
In other embodiments, the polymer has the structure of formula:
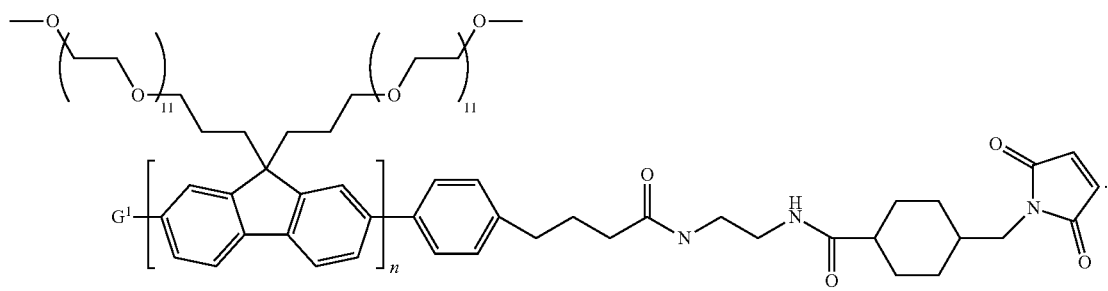
In other embodiments, the polymer has the structure of formula:

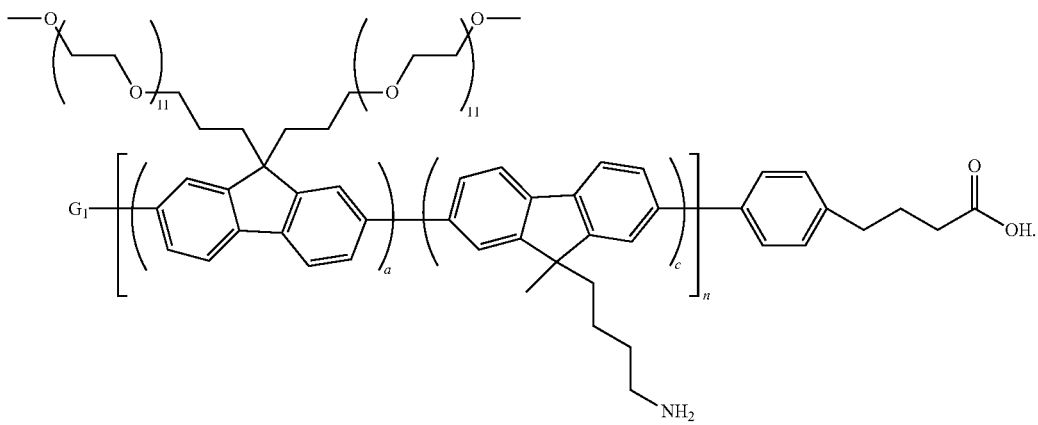

In some instances, a signaling chromophore is attached to the polymer via the NH$_2$ group. In certain instances, the signaling chromophore is Cy3 or Dylight 594 dye. In certain instances, the linker,

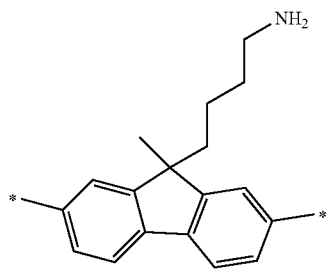

is about 10% of the entire polymer. In other instances, the polymer is conjugated to a secondary dye reporter and an antibody.

In some embodiments of conjugated polymers described herein, the polymer is further conjugated to additional molecules. In some embodiments, the polymer is conjugated to a streptavidin, antibody or nucleic acid and used as a direct fluorescent reporter. In certain embodiments, the polymer is conjugated to a streptavidin. In other embodiments, the polymer is conjugated to thiol groups at the hinge region of an antibody. In yet other embodiments, the polymer is conjugated to an amine group on a protein which is modified with a heterobifunctional linker. In further embodiments, the polymer is conjugated to a nucleic acid. In yet further embodiments, the polymer is conjugated to an antibody. In certain instances, the polymer is conjugated to a monoclonal antibody, a secondary antibody or a primary antibody. In other instances, a polymer antibody conjugate is excited at about 405 nm in a flow cytometry assay where the specific signal is at least 3 fold greater than the same antibody conjugated to Pacific Blue.

In some embodiments of conjugated polymers described herein, the polymer is purified by ion exchange chromatography. In other embodiments, the polymer is >95% pure.

In some embodiments of conjugated polymers described herein, the polymer is used in flow cytometry assays to identify different cell markers or cell types. In other embodiments, the polymer is used to sort cells. In yet other embodiments, the polymer is used to sort cells for use in therapeutics.

In some embodiments of conjugated polymers described herein, the polymer is used for intracellular staining. In certain instances, the polymer is used in flow cytometry assays to identify different cell markers or cell types.

In some embodiments of conjugated polymers described herein, the polymer comprises a minimum number average molecular weight of greater than 40,000 g/mol and a water solubility of greater than 50 mg/mL in pure water or a phosphate buffered saline solution.

In some embodiments of conjugated polymers described herein, the polymer comprises at least two unique conjugation linkers which can conjugated to two unique materials.

Also provided herein are assay methods comprising providing a sample that is suspected of containing a target biomolecule; providing a sensor protein conjugated to at least one signaling chromophore and is capable of interacting with the target biomolecule or a target-associated biomolecule; providing a water soluble conjugated polymer described herein; contacting the sample with the sensor protein and the conjugated polymer in a solution under conditions in which the sensor protein can bind to the target biomolecule or a target-associated biomolecule if present; applying a light source to the sample that can excite the conjugated polymer; and detecting whether light is emitted from the signaling chromophore.

In some embodiments, the sensor protein is an antibody. In other embodiments, the sensor protein comprises a plurality of sensor proteins conjugated to a plurality of signaling chromophores, wherein at least two of the plurality of chromophores emit different wavelengths of light upon energy transfer from the multichromophore.

Also provided herein are conjugated polymer complexes comprising a polymer coupled to at least one biomolecule selected from the group consisting of a sensor biomolecule, a bioconjugate and a target biomolecule wherein the polymer is covalently bound by at least one bioconjugation site pendant thereto, and the polymer comprises a signaling chromophore or a signaling chromophore optionally is covalently bound to the polymer or the sensor biomolecule; wherein the polymer comprises the structure of formula:

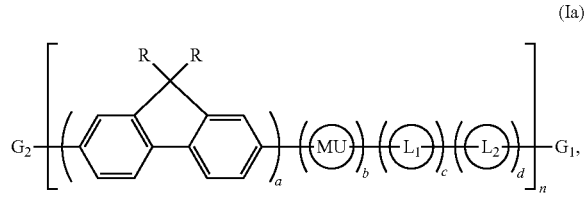

(Ia)

wherein:
  each R is a non-ionic side group capable of imparting solubility in water in excess of 10 mg/mL;
  MU is a polymer modifying unit or band gap modifying unit that is evenly or randomly distributed along the polymer main chain and is optionally substituted with one or more optionally substituted substituents selected from halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$(hetero)aryloxy, $C_2$-$C_{18}$(hetero)arylamino, $(CH_2)_{x'}(OCH_2CH_2)_{y'}OCH_3$ where each x' is independently an integer from 0-20, y' is independently an integer from 0 to 50, or a $C_2$-$C_{18}$(hetero)aryl group;
  each optional linker $L_1$ and $L_2$ are aryl or heteroaryl groups evenly or randomly distributed along the polymer main chain and are substituted with one or more pendant chains terminated with a functional group for conjugation to another molecule, substrate or biomolecule selected from amine, carbamate, carboxylic acid, carboxylate, maleimide, activated esters, N-hydroxysuccinimidyl, hydrazines, hydrazides, hydrazones, azide, alkyne, aldehydes, thiols, and protected groups thereof;
  $G_1$ and $G_2$ are each independently selected from hydrogen, halogen, amine, carbamate, carboxylic acid, maleimide, activated esters, N-hydroxysuccinimidyl, hydrazines, hydrazides, hydrazones, azide, alkyne, aldehydes, thiol, optionally substituted aryl, optionally substituted heteroaryl, halogen substituted aryl, boronic acid substituted aryl, boronic ester substituted aryl, boronic esters, boronic acids, optionally substituted fluorene and aryl or heteroaryl substituted with one or more pendant chains terminated with a functional group selected from amine, carbamate, carboxylic acid, carboxylate, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule;
  wherein the polymer comprises at least 1 functional group selected from amine, carbamate, carboxylic acid, carboxylate, maleimide, activated esters, N-hydroxysuccinimidyl, hydrazines, hydrazides, hydrazones, azide, alkyne, aldehydes, and thiols within $G_1$, $G_2$, $L_1$ or $L_2$ that allows, for functional conjugation to another molecule, substrate or biomolecule;
  n is an integer from 1 to about 10,000; and
  a, b, c and d define the mol % of each unit within the structure which each can be evenly or randomly repeated and where a is a mol % from 10 to 100%, b is a mol % from 0 to 90%,
  and each c and d are mol % from 0 to 25%.

In some embodiments, the sensor biomolecule is selected from the group consisting of an avidin, streptavidin, neutravidin, avidinDN, and avidinD. In other embodiments, the conjugated polymer complex is further configured to bind to a complex selected from the group consisting of a biotin-labeled antibody, biotin-labeled protein, and biotin-labeled target biomolecule.

In further embodiments, the sensor biomolecule is an antibody. In yet further embodiments, both the signaling chromophore and the sensor biomolecule are covalently linked to the multichromophore through a plurality of linkers. In some other embodiments, both the signaling chromophore and the sensor biomolecule are covalently linked to the polymer through a central linking site that covalently binds the polymer, the signaling chromophore and the sensor biomolecule. In yet other embodiments, the signaling chromophore, when covalently bound to the polymer or the sensor biomolecule, is an organic dye.

Also provided herein are water soluble conjugated polymer having the structure of Formula (Ia):

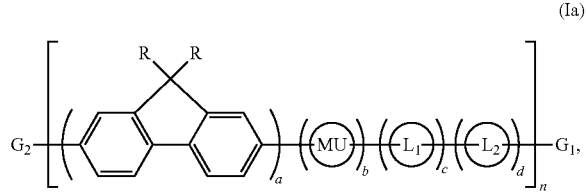

(Ia)

wherein:
  each R is independently $(CH_2)_x(OCH_2CH_2)_yOCH_3$ where each x is independently an integer from 0-20, y is independently an integer from 0 to 50, or a benzyl optionally substituted with one or more halogen, hydroxyl, $C_1$-$C_{12}$ alkoxy, or $(OCH_2CH_2)_zOCH_3$ where each z is independently an integer from 0 to 50;
  each optional linker $L_1$ or $L_2$ is selected from the group consisting of a-i having the structure a

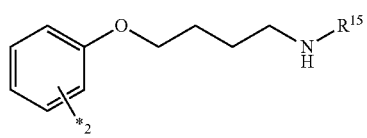

b

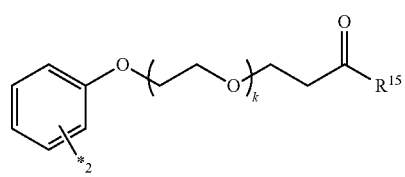

-continued

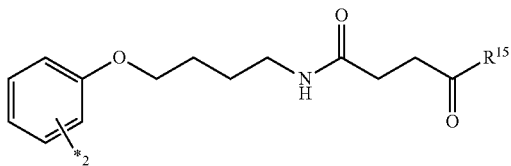
c

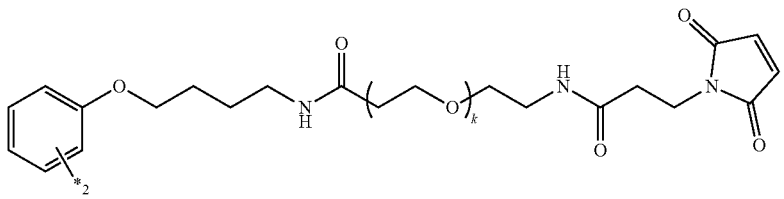
d

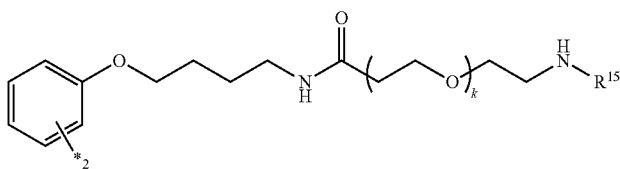
e

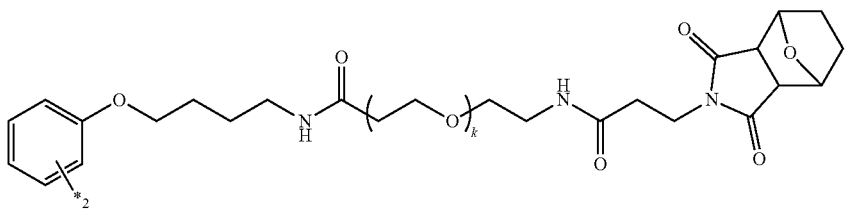
f

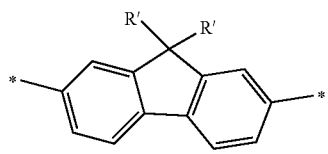
g

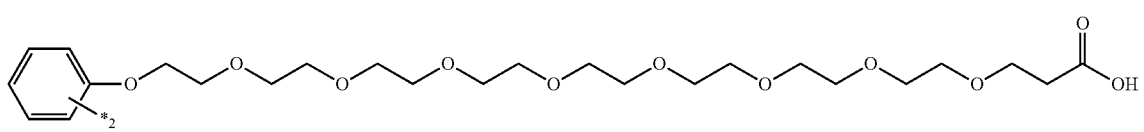
h

*=site for covalent attachment to unsaturated backbone wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$ cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$($OCH_2CH_2$)$_{x''}$$OCH_3$ where x'' is independently an integer from 0 to 50, or a benzyl optionally substituted with one or more halogen, hydroxyl, $C_1$-$C_{12}$ alkoxy, or ($OCH_2CH_2$)$_{y''}$$OCH_3$ where each y'' is independently an integer from 0 to 50 and R' is different from R;

wherein $R^{15}$ is selected from the group consisting of l-t having the structure:

*—OH
l

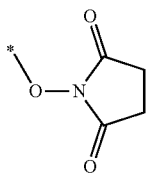
m

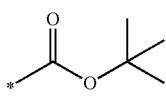
n

-continued
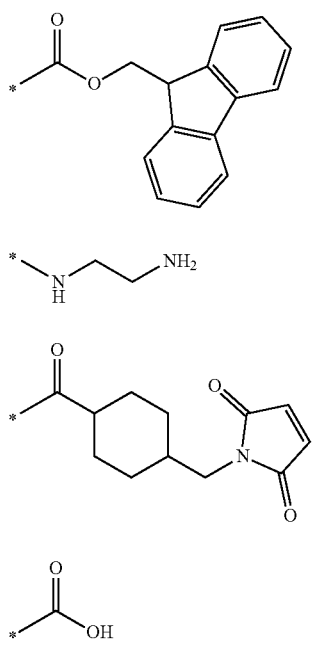
and k is 2, 4, 8, 12 or 24;
*=site for covalent attachment to backbone
MU is a polymer modifying unit or band gap modifying unit that is selected from the group consisting of a'-k' having the structure:
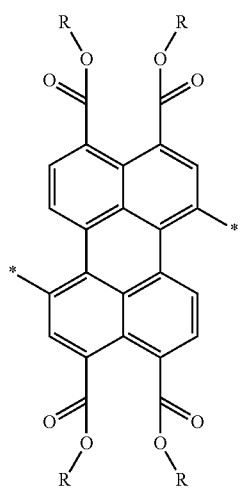
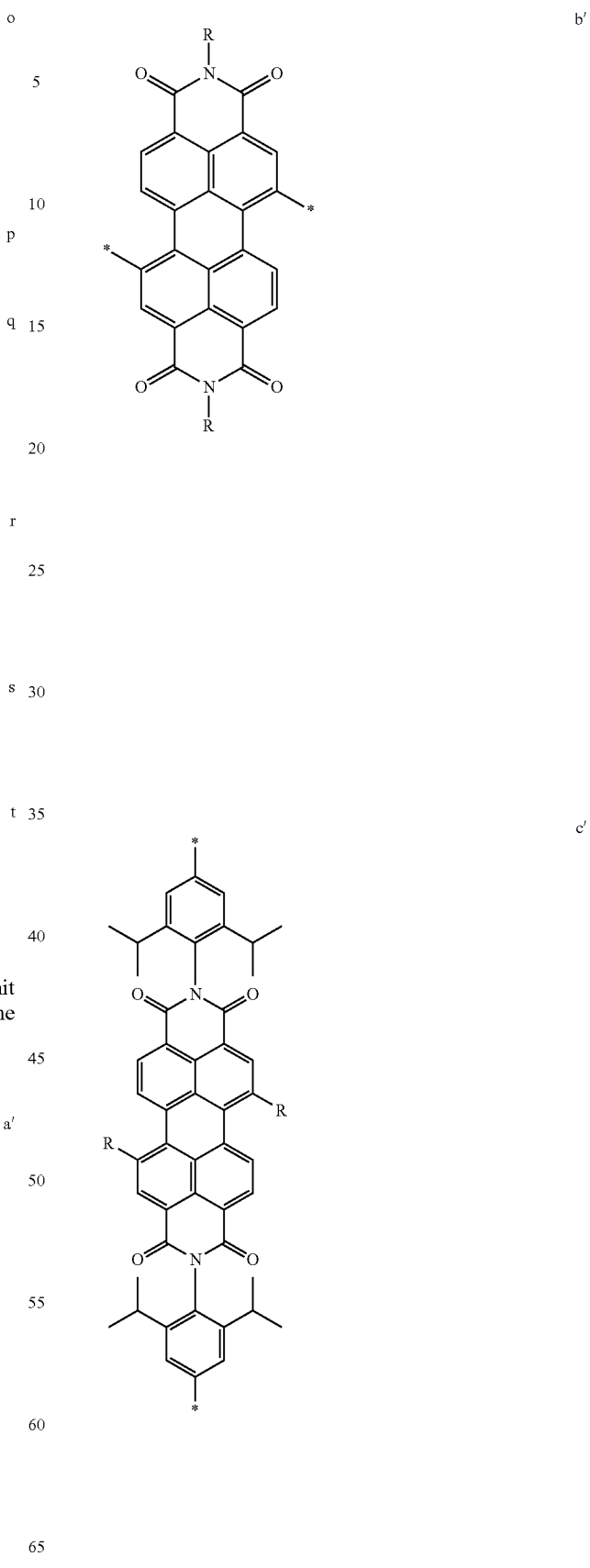

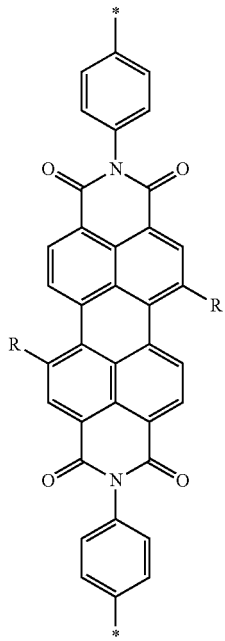
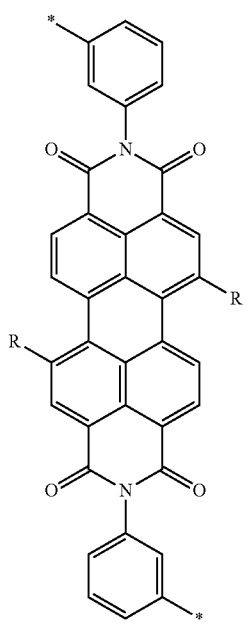
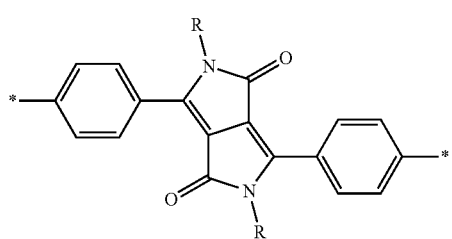
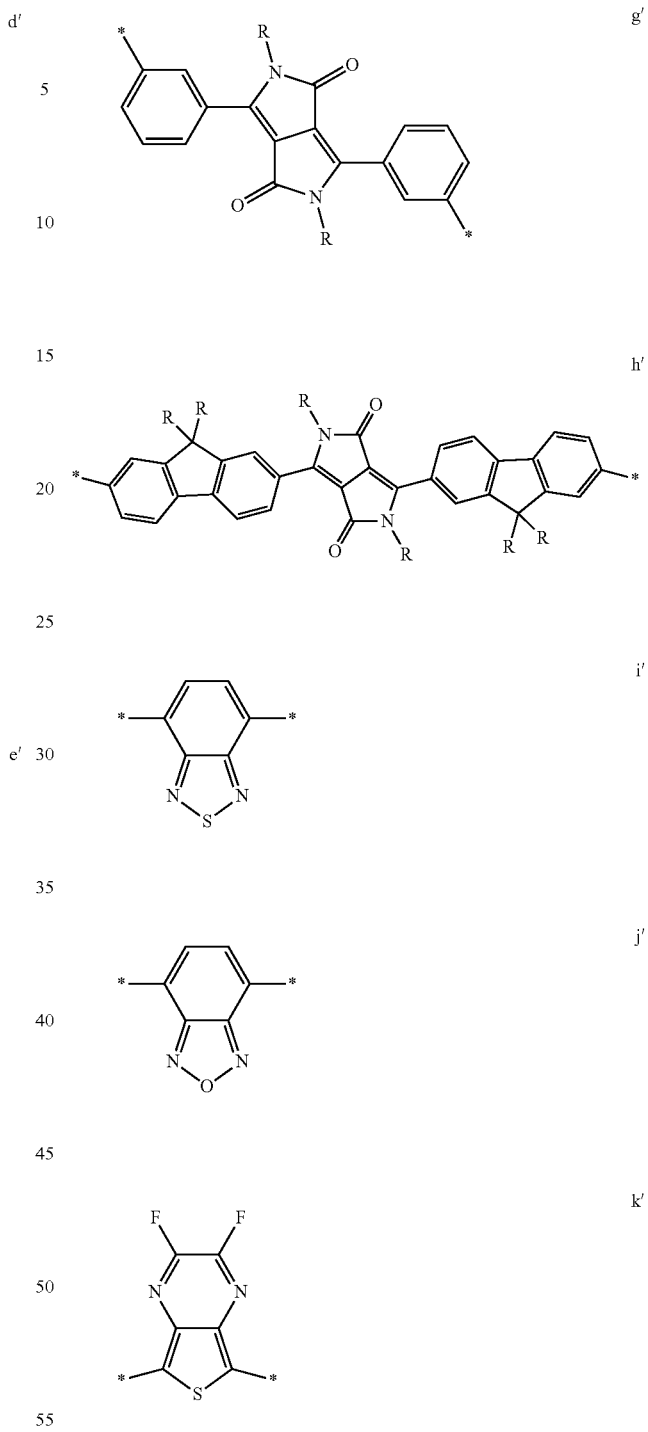
*=site for covalent attachment to unsaturated backbone;
wherein R is a non-ionic side group capable of imparting solubility in water in excess of 10 mg/mL;
$G_1$ and $G_2$ are each independently selected from the group consisting of 1-31 having the structures:

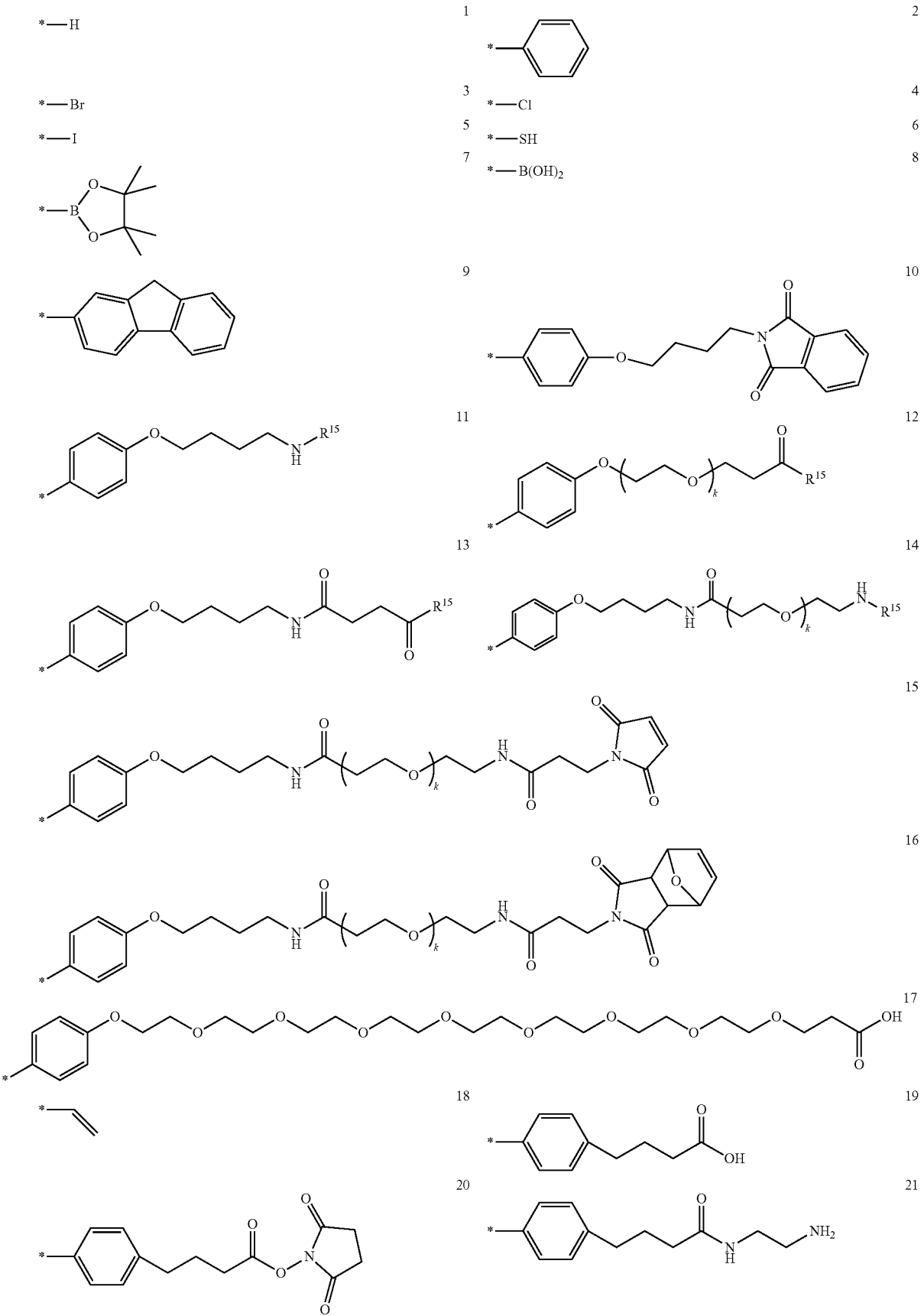

-continued

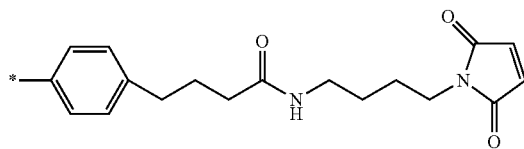
22

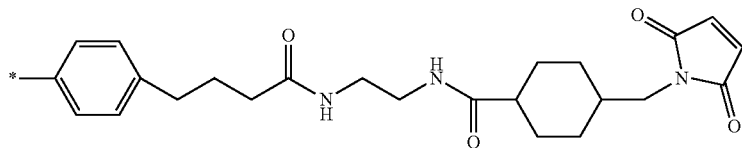
23

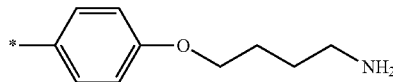
24

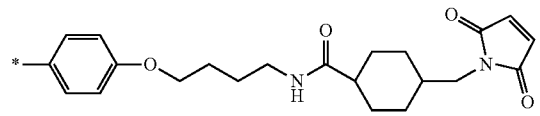
25

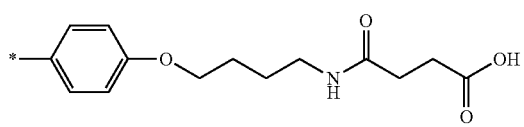
26

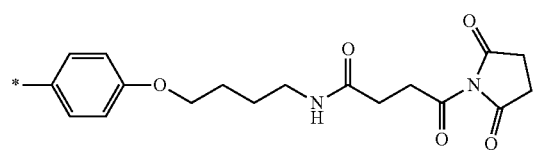
27

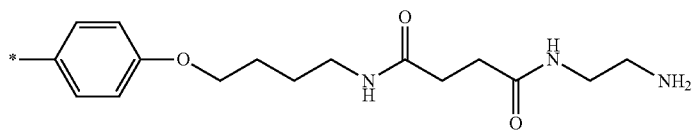
28

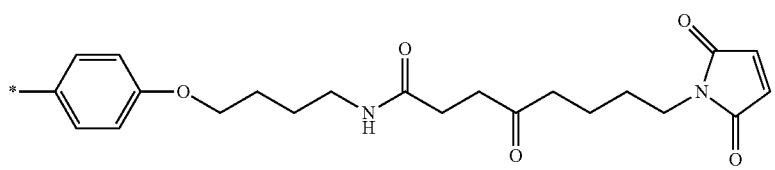
29

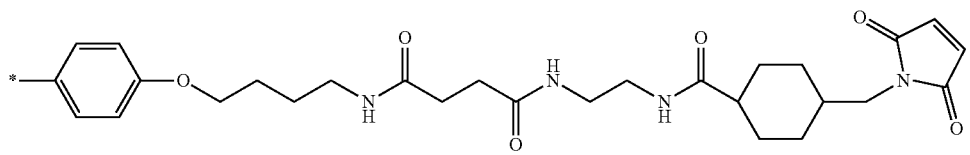
30

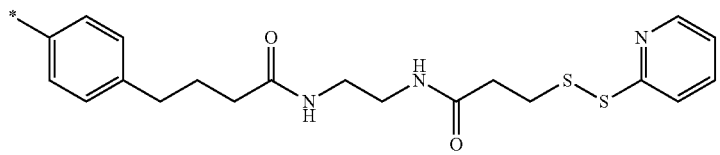
31 wherein the polymer comprises at least 1 functional group selected from amine, carbamate, carboxylic acid, carboxylate, maleimide, activated esters, N-hydroxysuccinimidyl, hydrazines, hydrazides, hydrazones, azide, alkyne, aldehydes, and thiols within $G_1$, $G_2$, $L_1$ or $L_2$ that allows, for functional conjugation to another molecule, substrate or biomolecule;

n is an integer from 1 to about 10,000; and a, b, c and d define the mol % of each unit within the structure which each can be evenly or randomly repeated and where a is a mol % from 10 to 100%, b is a mol % from 0 to 90%, and each c and d are mol % from 0 to 25%.

Also provided herein are water soluble conjugated polymer having the structure of Formula:

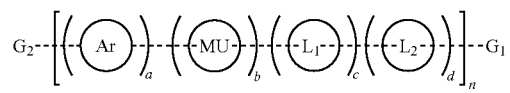

wherein Ar is an aryl or heteroaryl and is optionally substituted with one or more optionally substituted substituents selected from halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$(hetero)arylamino, $(CH_2)_{x'}$ $(OCH_2CH_2)_{y'}OCH_3$ where each x' is independently an integer from 0-20, y' is independently an integer from 0 to 50; and dashed bonds, $L_1$, $L_2$, $G_1$, $G_2$, MU, a, b, c, d and n are described previously for formula (I).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 39. Enrichment of linker-functionalized polymers.

FIG. 40. Conjugation of amine polymer to streptavidin protein.

DETAILED DESCRIPTION OF THE INVENTION

Figure 1:
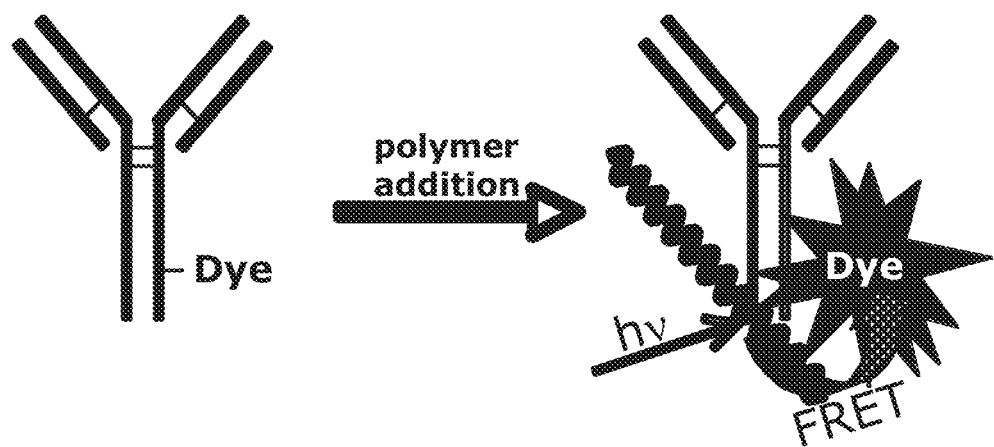
FIG. 1. Schematic of binding of a conjugated polymer in one embodiment of the invention.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "an aggregation sensor" includes a plurality of aggregation sensors, reference to "a probe" includes a plurality of probes, and the like. Additionally, use of specific plural references, such as "two," "three," etc., read on larger numbers of the same subject less the context clearly dictates otherwise.

Terms such as "connected," "attached," "conjugated" and "linked" are used interchangeably herein and encompass direct as well as indirect connection, attachment, linkage or conjugation unless the context clearly dictates otherwise; in one example, the phrase "conjugated polymer" is used in accordance with its ordinary meaning in the art and refers to a polymer containing an extended series of unsaturated bonds, and that context dictates that the term "conjugated" should be interpreted as something more than simply a direct or indirect connection, attachment or linkage.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

"Alkyl" refers to a branched, unbranched or cyclic saturated hydrocarbon group of 1 to 24 carbon atoms optionally substituted at one or more positions, and includes polycyclic compounds. Examples of alkyl groups include optionally substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, eicosyl, tetracosyl and the like, as well as cycloalkyl groups such as cyclopropyl, cyclobutyl, cyclopentyl, cyclohexyl, cycloheptyl, cyclooctyl, adamantyl, and norbornyl. The term "lower alkyl" refers to an alkyl group of 1 to 6 carbon atoms, preferably 1 to 4 carbon atoms. Exemplary substituents on substituted alkyl groups include hydroxyl, cyano, alkoxy, =O, =S, —NO$_2$, halogen, haloalkyl, heteroalkyl, carboxyalkyl, amine, amide, thioether and —SH.

"Alkoxy" refers to an "—Oalkyl" group, where alkyl is as defined above. A "lower alkoxy" group intends an alkoxy group containing one to six, more preferably one to four, carbon atoms.

"Alkenyl" refers to a branched, unbranched or cyclic hydrocarbon group of 2 to 24 carbon atoms containing at least one carbon-carbon double bond optionally substituted at one or more positions. Examples of alkenyl groups include ethenyl, 1-propenyl, 2-propenyl (allyl), 1-methylvinyl, cyclopropenyl, 1-butenyl, 2-butenyl, isobutenyl, 1,4-butadienyl, cyclobutenyl, 1-methylbut-2-enyl, 2-methylbut-2-en-4-yl, prenyl, pent-1-enyl, pent-3-enyl, 1,1-dimethylallyl, cyclopentenyl, hex-2-enyl, 1-methyl-1-ethylallyl, cyclohexenyl, heptenyl, cycloheptenyl, octenyl, cyclooctenyl, decenyl, tetradecenyl, hexadecenyl, eicosenyl, tetracosenyl and the like. Preferred alkenyl groups herein contain 2 to 12 carbon atoms. The term "lower alkenyl" intends an alkenyl group of 2 to 6 carbon atoms, preferably 2 to 4 carbon atoms. The term "cycloalkenyl" intends a cyclic alkenyl group of 3 to 8, preferably 5 or 6, carbon atoms. Exemplary substituents on substituted alkenyl groups include hydroxyl, cyano, alkoxy, =O, =S, —NO$_2$, halogen, haloalkyl, heteroalkyl, amine, thioether and —SH.

"Alkenyloxy" refers to an "—Oalkenyl" group, wherein alkenyl is as defined above.

"Alkylaryl" refers to an alkyl group that is covalently joined to an aryl group. Preferably, the alkyl is a lower alkyl. Exemplary alkylaryl groups include benzyl, phenethyl, phenopropyl, 1-benzylethyl, phenobutyl, 2-benzylpropyl and the like.

"Alkylaryloxy" refers to an "—Oalkylaryl" group, where alkylaryl is as defined above.

"Alkynyl" refers to a branched or unbranched hydrocarbon group of 2 to 24 carbon atoms containing at least one —C "Amide" refers to —C(O)NR'R", where R' and R" are independently selected from hydrogen, alkyl, aryl, and alkylaryl.

"Amine" refers to an —N(R')R" group, where R' and R" are independently selected from hydrogen, alkyl, aryl, and alkylaryl.

"Aryl" refers to an aromatic group that has at least one ring having a conjugated pi electron system and includes carbocyclic, heterocyclic, bridged and/or polycyclic aryl groups, and can be optionally substituted at one or more positions. Typical aryl groups contain 1 to 5 aromatic rings, which may be fused and/or linked. Exemplary aryl groups include phenyl, furanyl, azolyl, thiofuranyl, pyridyl, pyrimidyl, pyrazinyl, triazinyl, biphenyl, indenyl, benzofuranyl, indolyl, naphthyl, quinolinyl, isoquinolinyl, quinazolinyl, pyridopyridinyl, pyrrolopyridinyl, purinyl, tetralinyl and the like. Exemplary substituents on optionally substituted aryl groups include alkyl, alkoxy, alkyl carboxy, alkenyl, alkenyloxy, alkenylcarboxy, aryl, aryloxy, alkylaryl, alkylaryloxy, fused saturated or unsaturated optionally substituted rings, halogen, haloalkyl, heteroalkyl, —S(O)R, sulfonyl, —SO$_3$R, —SR, —NO$_2$, —NRR', —OH, —CN, —C(O)R, —OC(O)R, —NHC(O)R, —(CH$_2$)$_n$—CO$_2$R or —(CH$_2$)$_n$—CONRR' where n is 0-4, and wherein R and R' are independently H, alkyl, aryl or alkylaryl.

"Aryloxy" refers to an "—Oaryl" group, where aryl is as defined above.

"Carbocyclic" refers to an optionally substituted compound containing at least one ring and wherein all ring atoms are carbon, and can be saturated or unsaturated.

"Carbocyclic aryl" refers to an optionally substituted aryl group wherein the ring atoms are carbon.

"Halo" or "halogen" refers to fluoro, chloro, bromo or iodo. "Halide" refers to the anionic form of the halogens.

"Haloalkyl" refers to an alkyl group substituted at one or more positions with a halogen, and includes alkyl groups substituted with only one type of halogen atom as well as alkyl groups substituted with a mixture of different types of halogen atoms. Exemplary haloalkyl groups include trihalomethyl groups, for example trifluoromemyl.

"Heteroalkyl" refers to an alkyl group wherein one or more carbon atoms and associated hydrogen atom(s) are replaced by an optionally substituted heteroatom, and includes alkyl groups substituted with only one type of heteroatom as well as alkyl groups substituted with a mixture of different types of heteroatoms. Heteroatoms include oxygen, sulfur, and nitrogen. As used herein, nitrogen heteroatoms and sulfur heteroatoms include any oxidized form of nitrogen and sulfur, and any form of nitrogen having four covalent bonds including protonated forms. An optionally substituted heteroatom refers to replacement of one or more hydrogens attached to a nitrogen atom with alkyl, aryl, alkylaryl or hydroxyl.

"Heterocyclic" refers to a compound containing at least one saturated or unsaturated ring having at least one heteroatom and optionally substituted at one or more positions. Typical heterocyclic groups contain 1 to 5 rings, which may be fused and/or linked, where the rings each contain five or six atoms. Examples of heterocyclic groups include piperidinyl, morpholinyl and pyrrolidinyl. Exemplary substituents for optionally substituted heterocyclic groups are as for alkyl and aryl at ring carbons and as for heteroalkyl at heteroatoms.

"Heterocyclic aryl" refers to an aryl group having at least 1 heteroatom in at least one aromatic ring. Exemplary heterocyclic aryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl, perylene, perylene diimide, diketopyrrolopyrrole, benzothiadiazol, benzoxadiazol, thienopyrazine and the like.

"Hydrocarbyl" refers to hydrocarbyl substituents containing 1 to about 20 carbon atoms, including branched, unbranched and cyclic species as well as saturated and unsaturated species, for example alkyl groups, alkylidenyl groups, alkenyl groups, alkylaryl groups, aryl groups, and the like. The term "lower hydrocarbyl" intends a hydrocarbyl group of one to six carbon atoms, preferably one to four carbon atoms.

A "substituent" refers to a group that replaces one or more hydrogens attached to a carbon or nitrogen. Exemplary substituents include alkyl, alkylidenyl, alkylcarboxy, alkoxy, alkenyl, alkenylcarboxy, alkenyloxy, aryl, aryloxy, alkylaryl, alkylaryloxy, —OH, amide, carboxamide, carboxy, sulfonyl, =O, =S, —NO$_2$, halogen, haloalkyl, fused saturated or unsaturated optionally substituted rings, —S(O)R, —SO$_3$R, —SR, —NRR', —OH, —CN, —C(O)R, —OC(O)R, —NHC(O)R, —(CH2)$_n$CO$_2$R or —(CH2)$_n$CONRR' where n is 0-4, and wherein R and R' are independently H, alkyl, aryl or alkylaryl. Substituents also include replacement of a carbon atom and one or more associated hydrogen atoms with an optionally substituted heteroatom.

"Sulfonyl" refers to —S(O)$_2$R, where R is alkyl, aryl, —C(CN)=C-aryl, —CH$_2$CN, alkylaryl, or amine.

"Thioamide" refers to —C(S)NR'R", where R' and R" are independently selected from hydrogen, alkyl, aryl, and alkylaryl.

"Thioether" refers to —SR, where R is alkyl, aryl, or alkylaryl.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. Additional details for these terms as well as for details of base pair formation can be found in U.S. application Ser. No. 11/344,942, filed Jan. 31, 2006, which is incorporate herein by reference in its entirety.

"Complementary" or "substantially complementary" refers to the ability to hybridize or base pair between nucleotides or nucleic acids, such as, for instance, between a sensor peptide nucleic acid and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203(1984).

"Preferential binding" or "preferential hybridization" refers to the increased propensity of one polynucleotide or PNA to bind to its complement in a sample as compared to a noncomplementary polymer in the sample.

Hybridization conditions for polynucleotides will typically include salt concentrations of less than about 1M, more usually less than about 500 mM and preferably less than about 200 mM. In the case of hybridization between a peptide nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

"Having" is an open ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

The embodiments disclosed herein relate generally to compositions of conjugated polymer materials that contain active functional groups for conjugation (or attachment) to other molecules, substrates or the like. Certain embodiments describe methods and compositions that provide for specific control of the incorporation and subsequent conjugation of such functional sites. Linkers can be incorporated at one or both ends of a conjugated polymer chain or internally controlled by ratio of monomers used in the polymerizations. Such linkers can be the same or different to allow for more than one distinct entity to be attached to the conjugated polymer structure.

Further embodiments describe conjugated polymer compositions that not only provide for active conjugation sites but also are solubilized through the use of non-ionic side chains (no formal charges). Such embodiments exhibit exceptional water solubility and provide minimal interactions with biological molecules and other common biological assay components.

The embodiments disclosed herein further relate generally to assays and complexes including conjugated polymers useful for the identification of target biomolecules or biomolecules associated with target molecules through enhanced signal afforded by their unique properties.

In certain general embodiments the conjugated polymer serves directly as the optical reporter bound to a biomolecule, substrate or other assay component. The conjugated polymers act as extended light harvesting structures that when excited can absorb more energy than conventional organic dyes. The polymer then re-emits the light which can be detected or measured. The signals generated from such conjugated polymer complexes can be significantly greater than those obtained from other fluorescent reporters.

In other embodiments one aspect includes energy transfer from conjugated polymers to dyes bound to the polymer or to a sensor which can be a biomolecule including a bioconjugate (e.g., an antibody, a streptavidin or nucleic acid sequence). In such embodiments it is common to observe amplified dye signal (relative to direct dye excitation) as a result of the conjugated polymer excitation and subsequent energy transfer. Further it is possible to use a range of dyes with varying energy to create a basis for a multicolor or multiplex detection format.

In certain embodiments the neutral conjugated polymers are bound to antibodies for the identification of specific cell markers and cell types in flow cytometry and cell sorting assays. In other embodiments the conjugated polymers are further bound to a secondary dye reporter. In further embodiments the polymer and polymer-dye structures are bound to monoclonal antibodies.

In other embodiments the neutral conjugated polymers are bound to antibodies for use in various sandwich immunoassays.

In one embodiment, an approach modifying a format as followed in relation to nucleic acid sensor assays as described in Gaylord, Heeger, and Bazan, J. Am. Chem. Soc., 2003 can be followed. Specifically, signal amplification of conjugated polymers can be based on binding events to indicate a hybridization event. Any established conjugated polymers can be chosen as the donor, and one or more dye, preferably a dye with a history of efficient energy transfer, for example, fluorescein and Cy3, can be chosen as the acceptors. It is envisioned that the dye can be directly conjugated to a sensor molecule. As shown schematically in FIG. 1, the sensor can be a biomolecule (e.g., an antibody) in a solution or on a substrate, to which conjugated polymers can be added. In the embodiment shown in FIG. 1, a dye can be covalently linked (bioconjugated) to an antibody (Y-shaped structure), which possesses a net negative charge. Addition of conjugated polymers (shown as wavy lines) can result in interaction or binding between the conjugated polymer and the antibody, bringing the conjugated polymers and dye into close proximity. Interaction or binding can be achieved by any known method including, but not limited to, avidin/biotin labeling. Distance requirements for fluorescence resonance energy transfer (FRET) can thus be met, and excitation of the polymer with light (shown as hv) results in amplified dye emission. It is envisioned that the conjugated polymers can be excited at a wavelength where the dye does not have significant absorbance. In one embodiment the dye emission can be at a longer wavelength than the conjugated polymer emission. In use it is envisioned that an assay method can include the steps of providing a sample that is suspected of containing a target biomolecule, providing a sensor conjugated to a signaling chromophore and capable of interacting with the target biomolecule, providing a conjugated polymer that interacts with the sensor and upon excitation is capable of transferring energy to the sensor signaling chromophore and contacting the sample with the sensor and the conjugated polymer in a solution under conditions in which the sensor can bind to the target biomolecule if present. Next, the method can include applying a light source to the sample that can excite the conjugated polymer, and detecting whether light is emitted from the signaling chromophore.

As disclosed herein, interaction or binding between conjugated polymers and dye-labeled antibodies can be a viable approach for increasing detection sensitivities, for example of a biomolecule target. In a further embodiment, covalently attaching the conjugated polymers to a dye, biomolecule (e.g., an antibody complex) or both offers several advantages including reduced background and/or improved energy transfer. In the case of direct linkage to a biomolecule, biorecognition events, rather than non-specific polymer interaction or binding events (such as those described above in FIG. 1), should govern conjugated polymer presence. In this manner, nonspecific binding of conjugated polymers to biomolecules can be eliminated, reducing any background emission resulting from the conjugated polymer itself. The abovementioned biomolecules include but are not limited to proteins, peptides, affinity ligands, antibodies, antibody fragments, sugars, lipids, enzymes and nucleic acids (as hybridization probes and/or aptamers).

Figure 2:
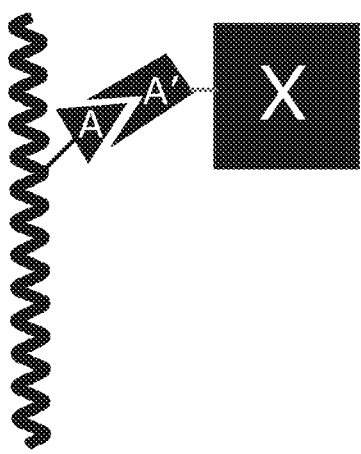
FIG. 2. Schematic of a bioconjugated polymer of one embodiment of the invention.

In general, in another aspect the invention includes the bioconjugation of polymers to affinity ligands (affinity ligands describing a biomolecule that has an affinity for another biomolecule). FIG. 2 illustrates a class of materials in which a conjugated polymer (shown as a wavy line) is linked to a dye, biomolecule, or biomolecule/dye complex (labeled X). Linking to the conjugated polymer can be via a first functionality linker A on the conjugated polymer that serves as a bioconjugation site capable of covalently linking with a second functionality linker A' linked to a biomolecule and/or dye (see X). This arrangement can fix the distance between the conjugated polymer and X, thereby ensuring only specific interactions between polymer and X. It is envisioned that a biomolecule component X in this embodiment can be any of the various biomolecules disclosed herein, including but not limited to an antibody, protein, affinity ligand, enzyme or nucleic acid.

Linker A can be anywhere on the conjugated polymer including terminal positions of the polymer, internally on a repeating subunit, in between repeating subunits or any combination thereof. Likewise, Linker A' can be linked anywhere on a biomolecule and/or dye. The linking chemistry for A-A' can include, but is not limited to, maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol; and amine/BMPH (N-[ß-Maleimidopropionic acid]hydrazide•TFA)/thiol.

It is envisioned that the X in this context can be, but is not limited to, a dye, fluorescence protein, nanomaterial (e.g., Quantum Dot), chemiluminescence-generating molecule, a conjugate between dye and chemiluminescence-generating molecule, a conjugate between fluorescence protein and chemiluminescence-generating molecule, a conjugate between nanomaterial (e.g., Quantum Dot) and chemiluminescence-generating molecule, streptavidin, avidin, enzyme, substrate for an enzyme, substrate analog for an enzyme, receptor, ligand for a receptor, ligand analog for a receptor, DNA, RNA, modified nucleic acid, DNA aptamer, RNA aptamer, modified nucleic aptamer, peptide aptamer, antibody, antigen, phage, bacterium or conjugate of any two of the items described above.

Figure 3:
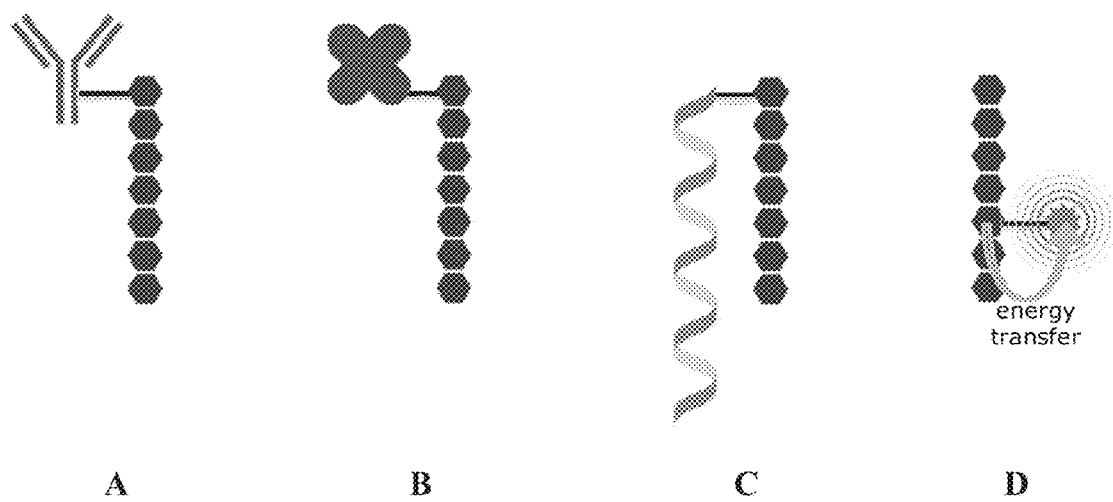
FIG. 3. Schematic of exemplary conjugated polymers conjugated (A) antibody; (B) an avidin; (C) nucleic acid; (D) dye, e.g., chromophore.

In another aspect, the invention includes the use of conjugated polymers as direct labels. FIG. 3 shows examples of labeled conjugated polymers. In one embodiment, FIG. 3A, a polymer (shown as encircled hexagons) is shown conjugated to an antibody which can be, for example, a 1° or 2° antibody. The conjugate of the polymer and the antibody can be used as a direct reporter, for example, in an assay. In additional embodiments, the signal from the polymer is not modulated by other assay components rather it is dependent on its presence in the assay at the time of detection as a function of specific biomolecule recognition. Excitation of the polymer with light (not shown) can result in polymer emission, indicating the presence of the antibody (1° or 2°) in the assay or assay solution. FIGS. 3B and 3C further exemplify the use of conjugated polymers as biomolecule labels capable of detecting specific targets and target associated biomolecules. FIG. 3B depicts a polymer avidin (streptavidin, neutraAvidin, etc.) conjugate capable of binding to biotin modified molecules, biomolecules or substrates. FIG. 3C depicts a nucleic acid (DNA, RNA, PNA, etc.) conjugate capable of hybridizing to complementary nucleic acid sequences. Linkage or conjugation of fluorescent conjugated polymer to a molecule capable of recognizing a target biomolecule or target associated molecule (such as those exemplified in FIG. 3) provides a direct means of detection. In additional embodiments, the signals generated from excitation of the conjugated polymer are not modulated by other assay components except those which are directly conjugated to the polymer. In such embodiments the polymer complex is acting directly as a fluorescent label.

In another embodiment shown in FIG. 3D, the conjugated polymer is labeled with a dye, for example, a chromophore. In this case, the conjugated polymer can act as a donor and the dye can act as an acceptor in an energy transfer process. Here, the conjugated polymer can act as a light harvester, and excitation of the conjugated polymer is followed by the channeling of the excitations to the dye via an energy transfer process including, but not limited to, FRET. This results in amplified dye emission (as compared to direct excitation of the dye). The fluorescence of the donor conjugated polymer, in one embodiment, can be quenched (e.g., >90% quenching). This is exemplified in Example 38 and shown in FIG. 21, by way of example only. In some instances, the conjugated polymer in FIG. 3D (and similar drawings disclosed herein) can have multiple dye attachments which can be positioned internally or at the terminus of the polymer structure (single dye shown for illustrative purposes only).

Figure 4:
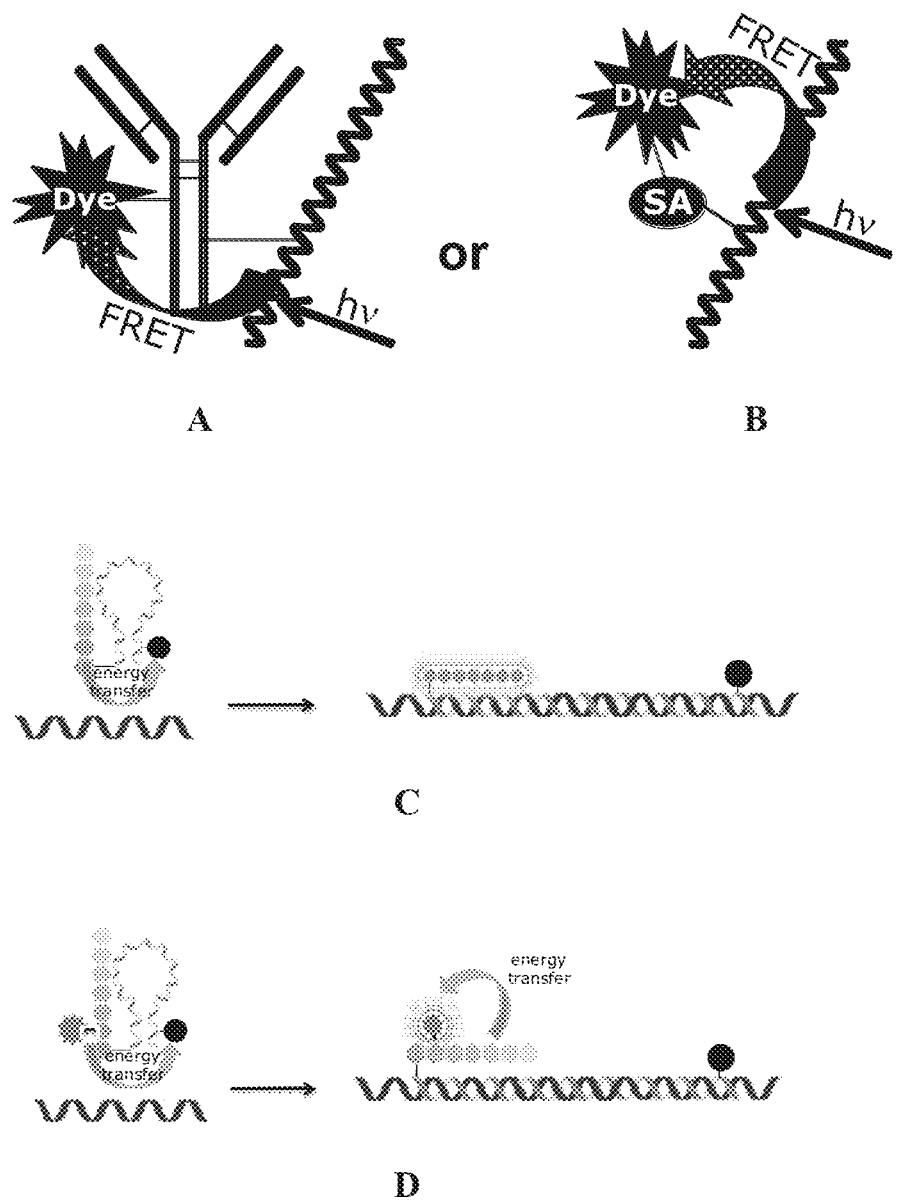
FIG. 4. Schematic of (A) a polymer conjugated to dye-labeled antibody resulting in FRET; (B) a polymer conjugated dye-labeled strepavidin resulting in FRET; (C) nucleic acid probe sequences labeled with a quencher molecule conjugated to a conjugated polymer; (D) nucleic acid probe sequences labeled with a quencher molecule conjugated polymer-dye tandem complex.
Figure 21:
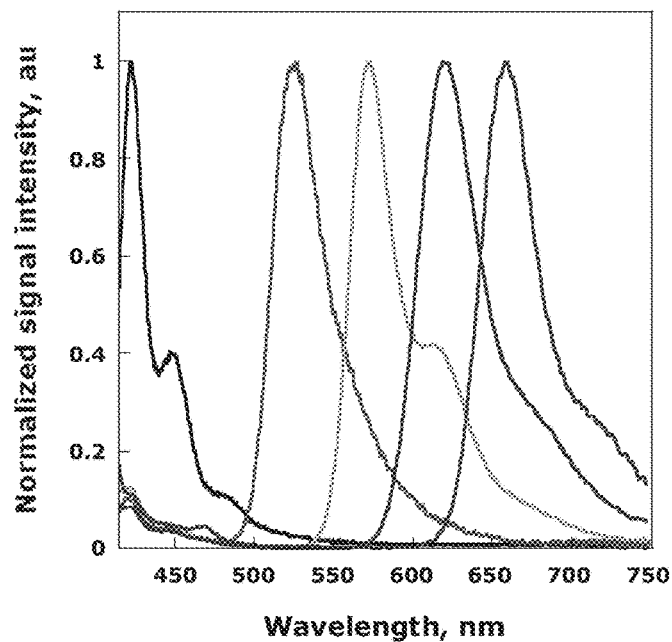
FIG. 21. (A) Polymer structure of Example 38b conjugated to (from left to right) FITC, Cy3, DyLight 594 and DyLight633; (B) Comparison of the fluorescence of the dye (DyLight594) excited near its absorbance maximum (lower curve) and polymer-dye conjugate excited at 405 nm (upper curve); (C) Comparison of the fluorescent signal of the base polymer (no dye, peak emission near 420 nm) to that of the polymer-dye conjugate (peak emission near 620 nm).
Figure 21:
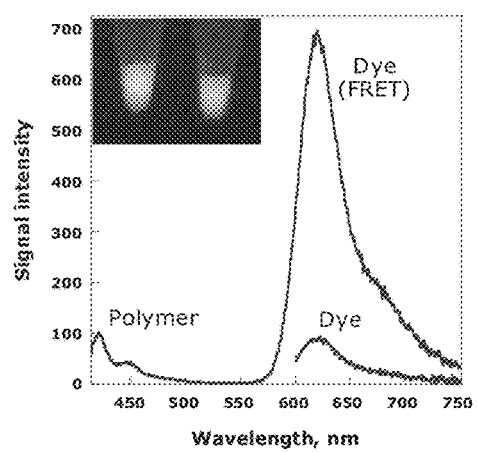
Figure 21:
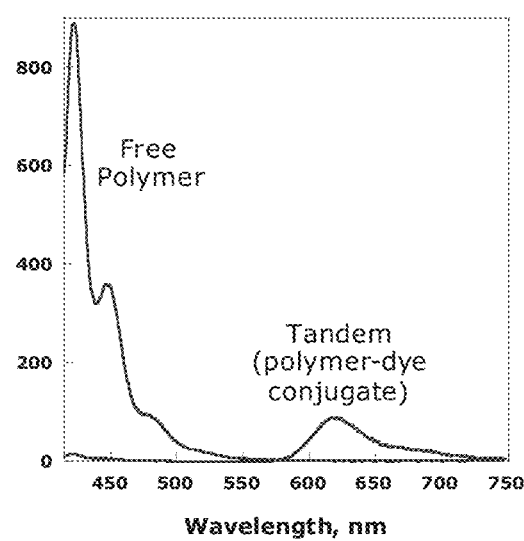

In the case of direct linkage to a dye (FIG. 3D) or biomolecule/dye complex (as exemplified in FIG. 4), donor-acceptor distances can be fixed, rather than dependent on the strength of interaction or binding, and energy transfer efficiency can be significantly increased. This has significant consequences in the context of improving dye signaling (or quenching) and reducing background fluorescence associated with donor-acceptor cross-talk. Cross-talk in this case refers to the overlap between conjugated polymer (donor) and dye (acceptor) emission peaks. Conjugated polymers which bind non-specifically at distances too great for energy transfer can contribute to the background fluorescence (or crosstalk). Shorter (fixed) distances between the donor and acceptor can not only facilitate direct dye amplification, but also can greatly quench the donor emission, as depicted in FIG. 21 by way of example only. This results in less donor emission at the acceptor emission wavelengths, which subsequently reduces or even eliminates the need for cross-talk correction.

Figure 5:
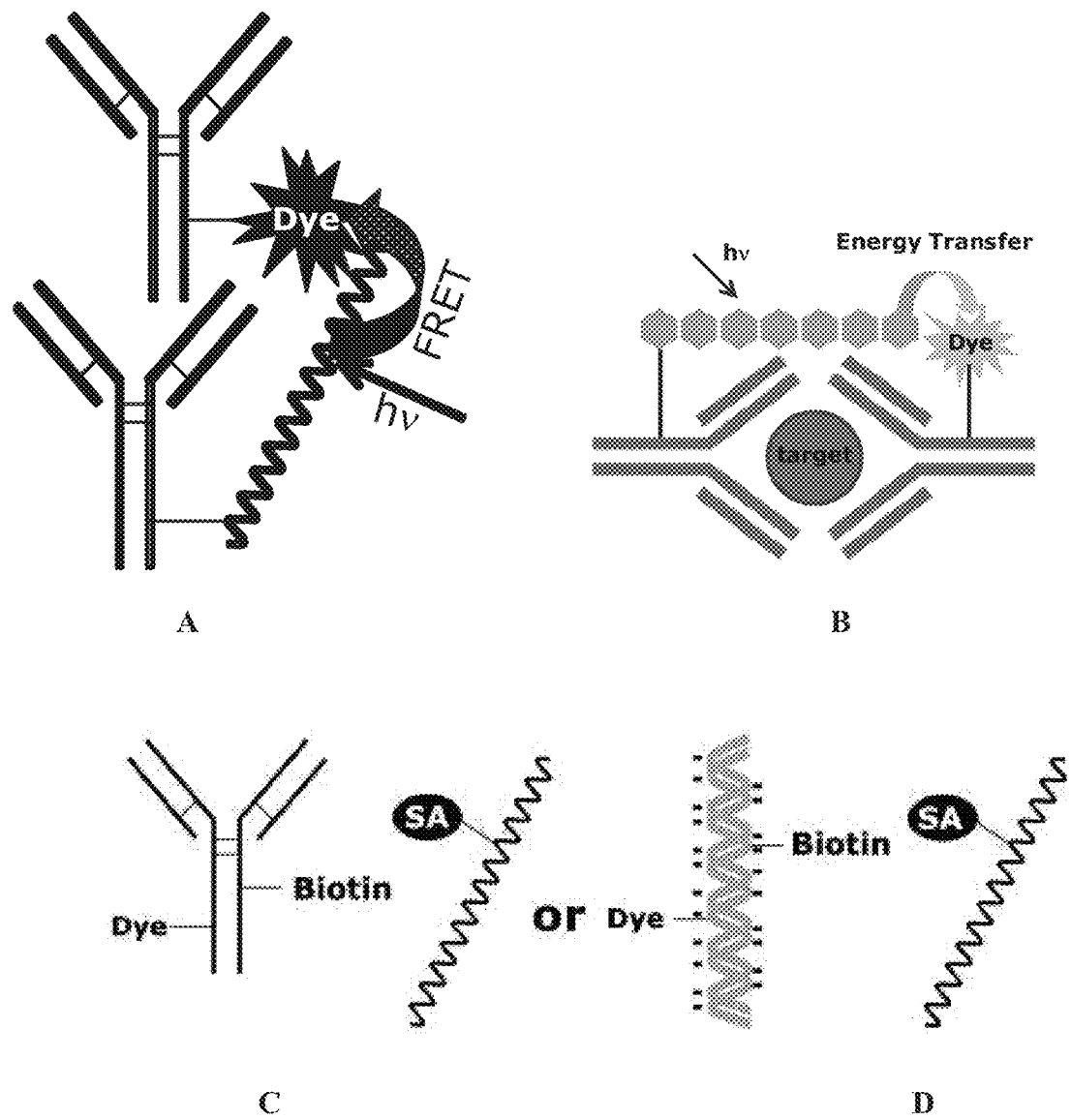
FIG. 5. Schematic of various methods of assaying for a target biomolecule or target associated biomolecule. (A) Conjugated polymer linked to a bioconjugate; (B) polymer and dye labeled antibodies recognize a common target; (C) sensor biomolecule conjugated to both a dye and a second bioconjugate; (D) second bioconjugate and the signaling chromophore both conjugated to a nucleic acid.

In further embodiments the localization of the conjugated polymer and a signaling chromophore are brought together by recognition event, for example by the binding of two affinity pairs or by co-recognition of the same target molecule or target associated molecule (FIG. 5). Such embodiments could be performed in solution based formats or in such configurations where one or more of elements is bound to another biomolecule (cell, tissue, protein, nucleic acid, etc.) or a substrate (bead, well plate, surface, tube, etc.).

In general, another aspect the invention includes a method of assaying for a target biomolecule or target associated biomolecule. As shown in FIG. 5A, in one embodiment a conjugated polymer (shown as a wavy line) can be linked to a first bioconjugate (shown as a Y-shaped object), for example, a 2° antibody that is specific for second a dye-labeled bioconjugate, for example, a 1° antibody. Here, the recognition event between the 1° and 2° antibody will result in the reduction of distance between the donor conjugated polymer and acceptor dye. In a similar embodiment depicted in FIG. 5B, polymer and dye labeled antibodies recognize a common target. After either of these recognition events, excitation of the donor conjugated polymer with light (shown as hv) will result in energy transfer, e.g., FRET, to the acceptor dye (shown as curved arrow), and amplified dye emission (in comparison with direct excitation of the dye) will be observed. In use it is envisioned that an assay method could include providing a sample that is suspected of containing a target biomolecule by the steps of providing a first bioconjugate, for example, a 1° antibody conjugated to a signaling chromophore and capable of interacting with the target biomolecule. This is followed by providing a second bioconjugate, for example, a 2° antibody or 1° antibody, conjugated to a polymer, wherein the second bioconjugate can bind to the first bioconjugate or target and wherein upon such binding excitation of the conjugated polymer is capable of transferring energy to the signaling chromophore. Next, the method includes contacting the sample with the first bioconjugate in a solution under conditions in which the first bioconjugate can bind to the target biomolecule if present and contacting the solution with the second bioconjugate. The method then includes applying a light source to the target biomolecule or tagged target biomolecule, wherein the light source can excite the conjugated polymer and subsequently detecting whether light is emitted from the signaling chromophore.

In another aspect, the invention includes a method of assaying a sample using a conjugated polymer and a sensor biomolecule complex. As shown in FIGS. 5C and D, a polymer (shown as a wavy line) can be conjugated to a first bioconjugate, for example, streptavidin (SA) which has a strong affinity for biotin. In FIG. 5C, a sensor biomolecule (e.g., an antibody which can be a 1° or 2° antibody), is conjugated to both a dye and a second bioconjugate (e.g., a biotin moiety). Similar embodiments are depicted in FIG. 5D where the second bioconjugate (e.g., a biotin moiety) and the signaling chromophore are both conjugated to a nucleic acid. After a biorecognition event between the first and second bioconjugates (e.g. between SA and biotin), the conjugated polymer and dye will be brought into close proximity, and excitation of the donor conjugated polymer will result in energy transfer to the acceptor dye. Dye emission will indicate the presence of the first bioconjugate (e.g., the antibody or nucleic acid). In comparison with direct excitation of the dye, amplification of the dye signal intensity will be observed when excited indirectly through an energy transfer process, e.g., FRET.

A method of using the embodiment shown in FIGS. 5C and D can include the steps of providing a sample that is suspected of containing a target biomolecule, providing a conjugated polymer comprising a covalently linked first bioconjugate (e.g., SA), providing a sensor biomolecule complex comprising a sensor biomolecule capable of interacting with the target molecule, a signaling chromophore, and covalently linked second bioconjugate capable of binding with the first bioconjugate, wherein upon such binding excitation of the conjugated polymer is capable of transferring energy to the signaling chromophore. The method can further include the steps of contacting the sample with the sensor biomolecule complex in a solution under conditions in which the sensor biomolecule can bind to the target biomolecule if present, contacting the solution with the conjugated polymer, applying a light source to the sample that can excite the conjugated polymer, and detecting whether light is emitted from the signaling chromophore.

Figure 6:
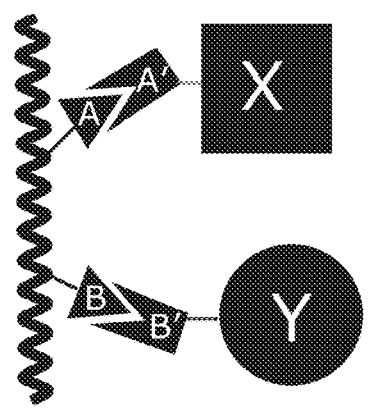
FIG. 6. Schematic of an addition of a second linking site within the polymer.

Further the conjugated polymer can contain additional linking site suitable for conjugation or attachment to more than one species. FIG. 6 exemplifies the addition of a second linking site within the polymer. Such linkers A and B can be the same or different to allow for orthogonal conjugation of different species. The linkers can be anywhere on the polymer including terminal and internal positions. The linking chemistry for A-A' and B-B' (and optionally C-C', D-D', etc.) can include, but is not limited to, maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4[N-maleimidomethyl]cyclohexane-1-carboxylate)/thiol; and amine/BMPH (N-[ß-Maleimidopropionic acid] hydrazide•TFA)/thiol. A tri-functional linker such as the commercially available Sulfo-SBED Sulfosuccinimidyl[2-6-(biotinamido)-2-(p-azidobenzamido)-hexanoamido]-ethyl-1,3'-dithiopropionate can serve well in the three way linkage among X, Y, and conjugated polymer.

In the embodiment illustrated in FIG. 6, X or Y can be, but are not limited to, a dye, fluorescence protein, nanomaterial (e.g., Quantum Dot), chemiluminescence-generating molecule, a conjugate between dye and chemluminescence-generating molecule, a conjugate between fluorescence protein and chemiluminescence-generating molecule, a conjugate between nanomaterial (e.g., Quantum Dot) and chemiluminescence-generating molecule, streptavidin, avidin, enzyme, substrate for an enzyme, substrate analog for an enzyme, receptor, ligand for a receptor, ligand analog for a receptor, DNA, RNA, modified nucleic acid, DNA aptamer, RNA aptamer, modified nucleic aptamer, peptide aptamer, antibody, antigen, phage, bacterium or conjugate of any two of the items described above.

Figure 7:
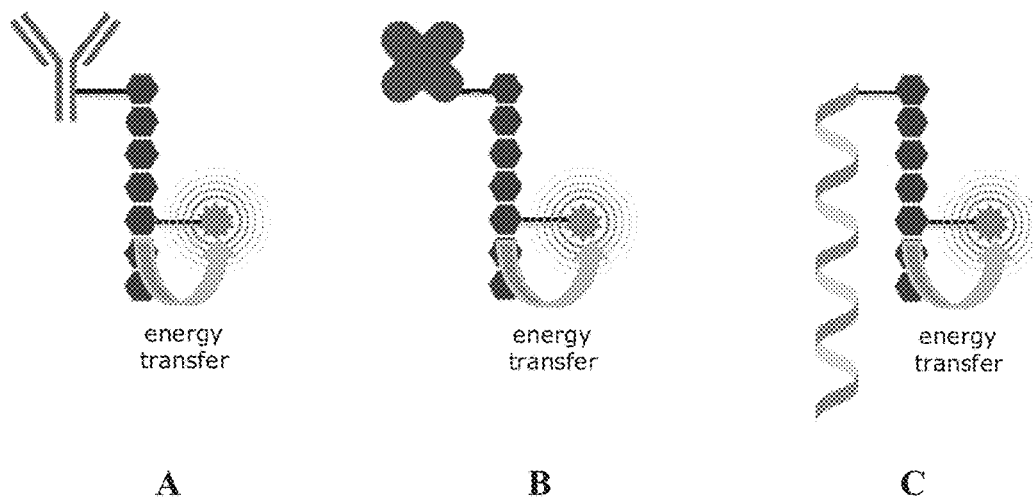
FIG. 7. Schematic of a polymer conjugated to a dye and a biomolecule and resulting energy transfer (A) polymer is conjugated to both a bioconjugate; (B) polymer is conjugated to a strepavidin and a dye; (C) polymer is conjugated to a nucleic acid and a dye.

In general, in another aspect the invention provides a conjugated polymer complex including a polymer, a sensor biomolecule and a signaling chromophore for identifying a target biomolecule. As shown in FIG. 6, in one embodiment a polymer (wavy line) can be bioconjugated to a dye X via linker functionalities A-A' and a biomolecule Y via linker functionalities B-B'. As depicted in FIG. 7, in one embodiment a polymer can be bioconjugated to both a dye and a biomolecule, for example a biorecognition molecule. Useful biomolecules can include but are not limited to antibodies (FIG. 7A), avidin derivatives (FIG. 7B) affinity ligands, nucleic acids (FIG. 7C), proteins, nanoparticles or substrates for enzymes. The benefits of covalently linking a dye in proximity to a polymer have been described above. By affixing both an acceptor dye and a biorecognition molecule to a polymer, the benefits are two fold, by both fixing donor-acceptor distances, such that an acceptor is guaranteed to be within the vicinity of a donor conjugated polymer (and vice versa), and also increasing the specificity of polymer binding to indicate a biorecognition event. These covalent complexes can be made via the monomer, polymer and linking chemistries described herein.

In use, the embodiments shown in FIG. 6 can be a conjugated polymer complex for identifying a target biomolecule wherein the complex includes a conjugated polymer, a signaling chromophore covalently linked to the conjugated polymer and a sensor biomolecule covalently linked to the conjugated polymer. The signaling chromophore of the complex is capable of receiving energy from the conjugated polymer upon excitation of the conjugated polymer and the sensor biomolecule is capable of interacting with the target biomolecule. It is envisioned that the biomolecules can include but are not limited to an antibody, protein, affinity ligand, peptide, or nucleic acid.

In one embodiment shown in FIG. 7A, a polymer is conjugated to both a bioconjugate, for example, an antibody (1° or 2°) and a dye. Covalent linkage between the donor conjugated polymer and acceptor dye ensures close proximity. Excitation of the donor conjugated polymer results in energy transfer, e.g., FRET, to the acceptor dye. Where the bioconjugate is an antibody, if the antibody binds to its target (e.g., antigen), this will be indicated by dye emission upon donor polymer excitation. In an alternative embodiment, as shown in FIG. 7B, a polymer can be conjugated to both a SA and a dye. Again, covalent linkage between the donor conjugated polymer and acceptor dye ensure close proximity, and excitation of the donor conjugated polymer results in energy transfer to the acceptor dye. The SA complex can be used to label or detect a biotin-labeled biomolecule such as a biotinylated antibody or nucleic acid. Polymer excitation followed by energy transfer to the dye label will result in greatly enhanced detection signals (i.e., greater sensitivity).

The example exemplified in FIG. 7A is a conjugated polymer labeled with a dye acceptor and further conjugated to an antibody. This Tandem configuration can be used in similar fashion as those described for the structure in FIG. 3A but are useful in generating a secondary signal for detection, often in multiplex formats. The conjugated polymer complexes in FIG. 7 can have multiple dye attachments which can be positioned internally or at the terminus of the polymer structure (single dye shown for illustrative purposes only).

In other embodiments as shown in FIGS. 3A and 7A, a sensor biomolecule for example a 1° antibody (Y shape) is conjugated covalently linked to the conjugated polymer (encircled hexagons) or conjugated polymer-dye tandem complex (hexagons with pendant encircled star). Upon conjugated polymer excitation, emission from the conjugated polymer (FIG. 3A) or dye (FIG. 7A) will indicate presence of the biocomplex and by extension with appropriate assay design that of the target recognized by the sensor molecule allowing use as a reporter, for example in an assay. FIGS. 29A and 29B represent comparable examples with covalent linkage of the conjugated polymer to a 2° antibody.

Figure 8:
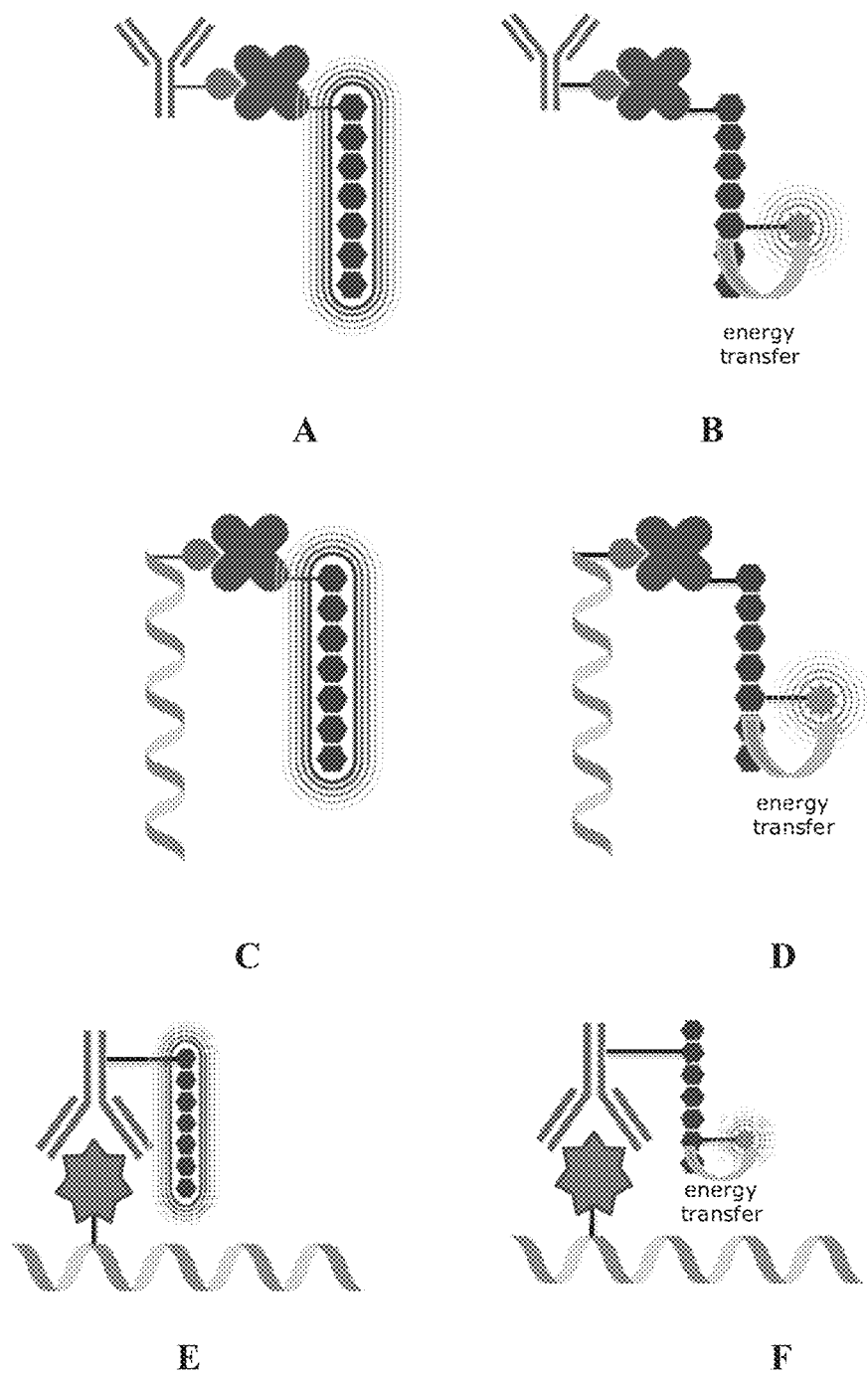
FIG. 8. Schematic of indirect associations with a sensor biomolecule or target associated biomolecule. (A) biotinylated antibody interacting with a covalent conjugate of the conjugated polymer; (B) biotinylated antibody conjugated polymer-dye tandem complex; (C) biotinylated nucleic acid interacting with a covalent conjugate of the conjugated polymer; (D) biotinylated nucleic conjugated polymer-dye tandem complex; (E) nucleic acid with digoxygenin moiety interacting with a covalent conjugate of the conjugated polymer; (F) nucleic acid with digoxygenin moiety conjugated polymer-dye tandem complex.

As an alternative embodiment, the conjugated polymer may be associated indirectly with the sensor biomolecule or target associated biomolecule. FIGS. 8C and 8D illustrate a sequence specific oligonucleotide probe (wavy line) covalently conjugated to a biotin moiety (drop shape). Here the conjugated polymer (encircled hexagons) or conjugated polymer-dye tandem complex (hexagons with pendant encircled star) is covalently bound or conjugated to a biotin recognizing protein (for example, avidin, streptavidin or similar with high specific affinity for the ligand biotin). FIGS. 8A and 8B illustrate comparable examples with a biotinylated antibody interacting with a covalent conjugate of the conjugated polymer (FIG. 8A) and conjugated polymer-dye tandem complex (FIG. 8B) to the biotin recognizing protein. Indirect association of the target associated biomolecule with the conjugated polymer is not limited to biotin mediated interactions. FIGS. 8E and F represent sequence specific oligonucleotides (wavy line) which have been covalently labeled with a digoxygenin moiety (7 pointed star). In turn the digoxygenin moiety has been recognized by a primary antibody covalently linked to the conjugated polymer (FIG. 8E) and the conjugated polymer-dye tandem complex (FIG. 8F). Although not shown pictorially, further embodiments employing indirect detection of digoxygenin using biotinylated antibodies and biotin recognizing proteins covalently linked to conjugated polymers (or conjugated polymer-dye tandem complexes) or unlabelled primary antibodies recognizing digoxygenin and appropriate secondary antibodies covalently linked to the conjugated polymer (or conjugated polymer-dye tandem complexes) are intended.

A number of further embodiments are also predicated on energy transfer (for example but not limited to FRET) between the conjugated polymer and an acceptor dye. Given the potential for multiplexing analysis, it is envisioned that the conjugated polymer can be linked to a number of dyes or signaling chromophores, including, but not limited to, fluorescein, 6-FAM, rhodamine, Texas Red, California Red, iFluor594, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dime1hoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODPY® R6G, BODIPY® TMR, BODIPY® TR, conjugates thereof, and combinations thereof. These embodiments include modifications of the above examples where the acceptor dye serves as the assay reporter (as exemplified in FIGS. 3D, 4D, 7, 8B, 8D, 8E, 29B, wherein the encircled ten pointed star represents the dye).

In certain embodiments the conjugated polymer conjugates provided in FIGS. 2-10, 29 and 30 are intended for but not limited to use in flow cytometry, cell sorting, molecular diagnostics, fluorescence in situ hybridization (FISH), immunohistochemistry (IHC), polymerase chain reaction, microscopy (fluorescent, confocal, 2 photon, etc.), blotting (e.g. northern, southern, western), cytomic bead arrays (Luminex formats, etc.), fluorescent immune assay (FIA or ELISA), nucleic acid sequencing and microarrays.

Embodiments are also envisaged where conjugated polymers are used to enhance the detection and quantification of nucleic acids using sequence specific fluorescent probes combined with nucleic acid amplification techniques such as but not limited to polymerase chain reaction, transcription mediated amplification, rolling circle amplification, recombinase polymerase amplification, helicase dependent amplification and Linear-After-The-Exponential polymerase chain reaction.

Figure 32:
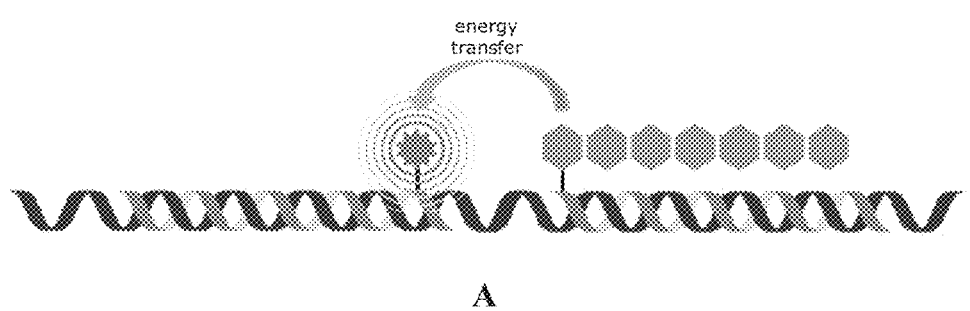
FIG. 32. Schematic of modifications of the HybProbe detection technique. (A) conjugated polymer covalently linked to the donor probe and resulting energy transfer to acceptor probe; (B) "Signal off" modification of the HybProbe approach where the conjugated polymer is quenched by an acceptor probe.
Figure 32:
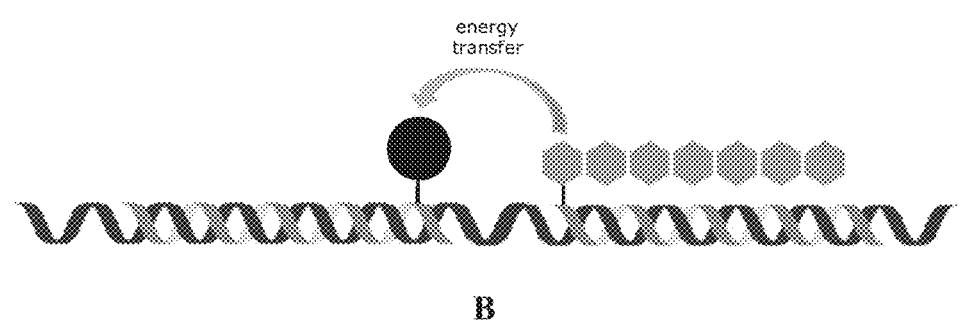

FIG. 32 represents modifications of the HybProbe detection technique. In FIG. 32A, the dye conventionally used as an energy transfer donor is replaced by the conjugated polymer (hexagon chain) which is covalently linked to the donor probe (wavey helical structure represented as right hand helical duplex due to association with nucleic acid target depicted a longer helical wavy line). Upon sequence specific hybridization the donor and acceptor (represented similarly to donor probe but on left hand side of nucleic acid target) probes are spatially juxtaposed on the target nucleic acid strand of interest in sufficiently close proximity to allow energy transfer to take place between the fluors. Excitation energy is transduced through the conjugated polymer and emitted as a readable signal by the dye (encircled ten pointed star) to allow nucleic acid quantification, detection and/or characterization. Presence of increased template allows increased numbers of probe co-hybridisation events and thus correlates to increased specific signal from the acceptor dye. In combination with the melt curve technique commonly employed in HybProbe experiments it is envisaged that sequence specific information corresponding to sequence variations will be collectable in appropriately designed experiments. FIG. 32B represents a "signal off" modification of the HybProbe approach where the conjugated polymer is quenched by an acceptor probe consisting of a small molecule fluorescence quencher (for example but not limited to Black Hole Quenchers™ Iowa Black® or Dabsyl).

Figure 31:
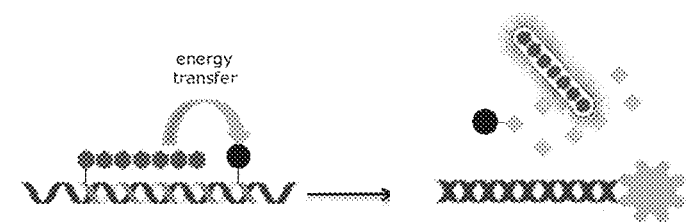
FIG. 31. (A) Schematic of nucleic acid probe sequences labeled with a quencher molecule conjugated to a conjugated polymer; (B) nucleic acid probe sequences labeled with a quencher molecule conjugated to a conjugated polymer-dye tandem complex.
Figure 31:
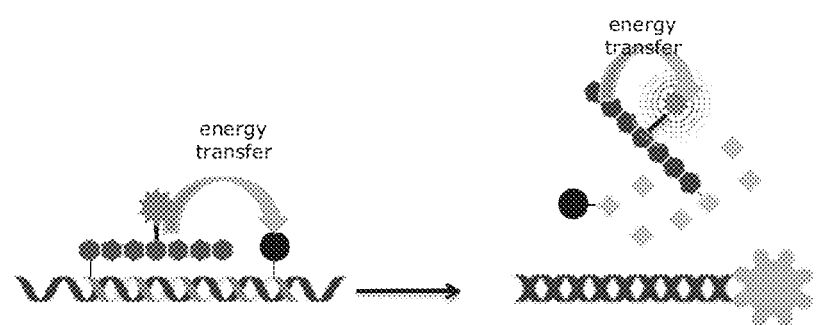

In another embodiment, conjugated polymer and conjugated polymer-dye tandem complexes similar to those described in FIGS. 4C and 4D are used in the detection, quantification and/or characterization of nucleic acid targets. Nucleic acid probe sequences labeled with a quencher molecule (black circle, for example but not limited to Black Hole Quenchers™, Iowa Black® or Dabsyl) are also conjugated to a conjugated polymer (FIGS. 4C and 31A) and a conjugated polymer-dye tandem complex (FIGS. 4D and 31B). In FIGS. 4C and D the recognition of the target sequence leads to a hybridization and separation of the quencher from the conjugated polymer or conjugated polymer-dye tandem complex and upon polymer excitation produces an increase in fluorescent signal. In FIGS. 31A and 31B the nucleic acid probe conjugate will hybridize to a complementary target sequence and by treatment with specific enzymes the probe sequence is cleaved or hydrolyzed freeing the conjugated polymer or conjugated polymer-dye tandem complex from the quencher and upon polymer excitation produces an increase in fluorescent signal. The most common example of the methods described in FIG. 31 is the use of DNA polymerase enzymes which contain nuclease activity (e.g. TaqMan PCR assays).

Figure 9:
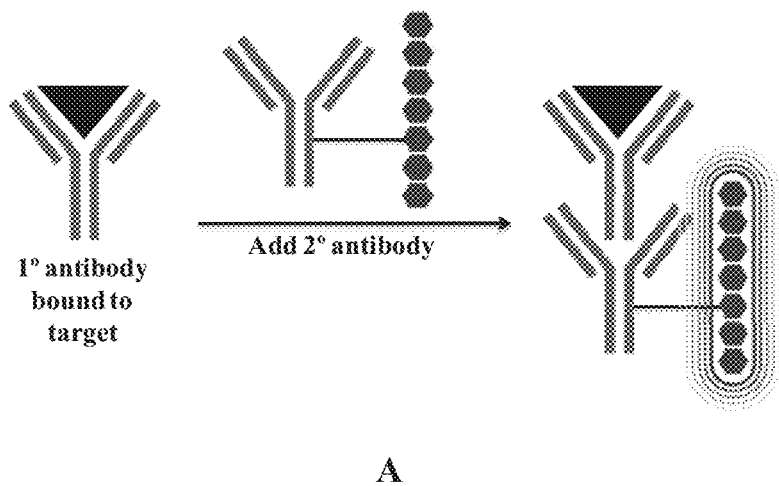
FIG. 9. Schematic of exemplary conjugated polymers conjugated to secondary antibodies ( ) and primary antibodies (B).
Figure 9:
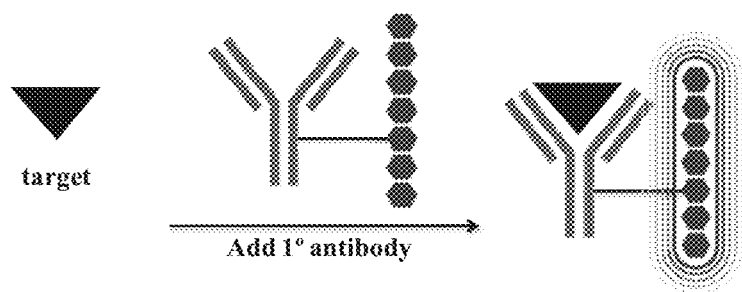

FIG. 9 shows examples of conjugated polymer (hexagons) conjugated to secondary antibodies (FIG. 9A) and primary antibodies (FIG. 9B) (antibodies shown as Y-shaped structures). In an assay, an unlabeled 1° antibody can bind to an antigen, for example, a target protein (shown as a black triangle). Addition of the 2° antibody, which is conjugated to a polymer, can bind specifically to the 1° antibody. After washing to remove unbound 2° antibody and upon application of light of suitable excitation wavelength, observance of polymer emission is indicative of specific binding (FIG. 9A). In other assay embodiments, a polymer-labeled 1° antibody can directly bind a target protein, shown as a black triangle, and after washing to remove unbound 1° antibody and upon application of light of suitable excitation wavelength, observance of polymer emission is indicative of specific binding (FIG. 9B). Optionally, whether conjugated to the 1° or 2° antibody, the polymer may be further conjugated to a dye. In such a case, optical excitation of the conjugated polymer can result in energy transfer to the dye, and amplified dye emission, in comparison to direct dye excitation results. Observance of dye emission is indicative of specific binding.

Figure 10:
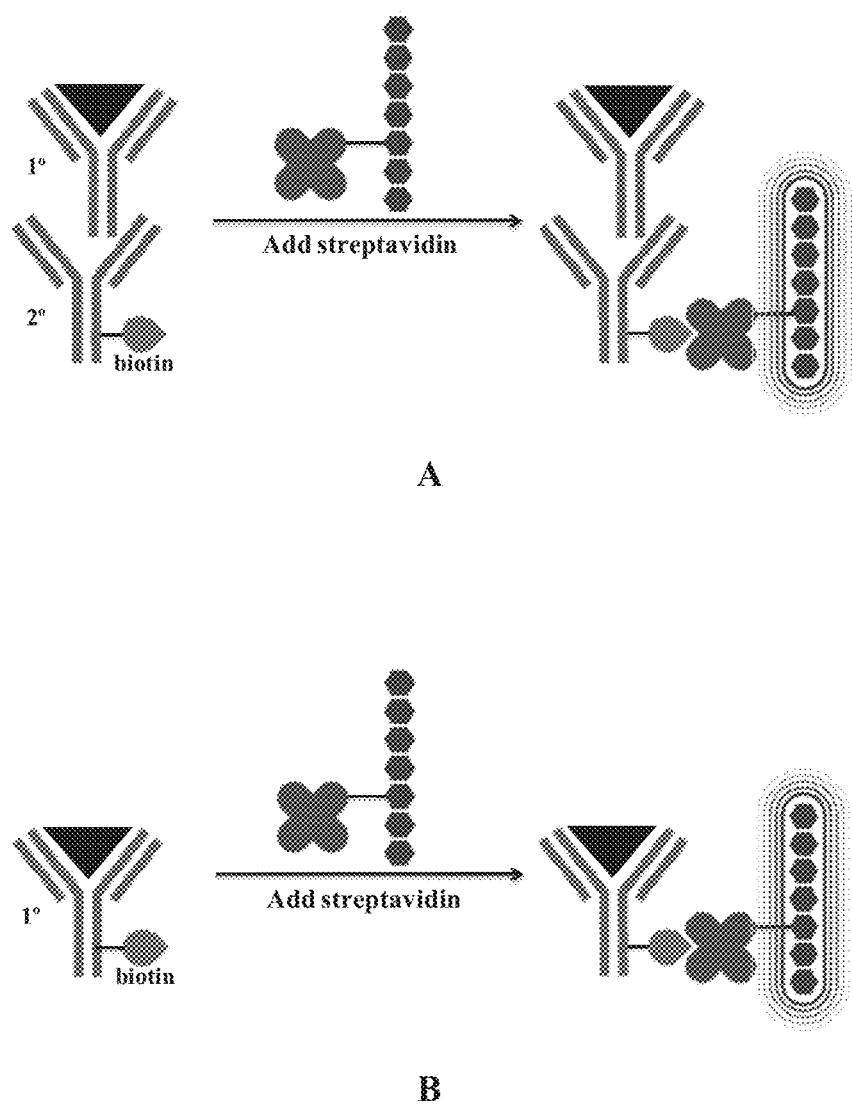
FIG. 10. Schematic of a sandwich-type complex. (A) conjugated polymer complex bioconjugated to a strepavidin; (B) biotin-labeled 1° antibody e used to probe the target protein directly.

FIG. 10 shows an example of a sandwich-type complex of one embodiment of the invention. In the assay shown in FIG. 10A the conjugated polymer complex is composed of a polymer (shown as hexagons) that is bioconjugated a biomolecule, for example, streptavidin (X shape). After an unlabeled 1° antibody binds the target (e.g. protein), shown as a black triangle, a biotin-labeled 2° antibody binds specifically to the 1° antibody. In a separate step, addition of the conjugated polymer complex will result in specific binding between the biotin and streptavidin. Excitation of the conjugated polymer will result in polymer emission, indicating the presence of the target protein. Additionally in another embodiment, a biotin-labeled 1° antibody may be used to probe the target protein directly (FIG. 10B). After this binding event takes place, addition of a streptavidin-polymer complex will result in specific binding between the biotin and streptavidin, and excitation of the conjugated polymer will result in polymer emission, indicating the presence of the target protein. Optionally, the polymer may be further conjugated to a dye. In such a case, optical excitation of the polymer will result in amplified dye emission, as compared to direct excitation of the dye. Signals arising from dye emission will indicate the presence of the target protein.

Figure 30:
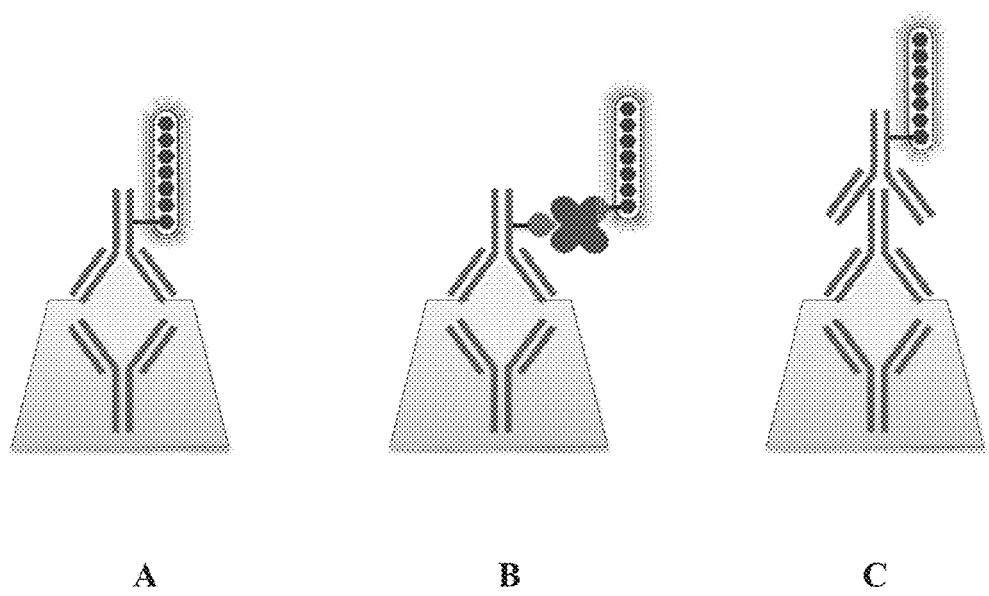
FIG. 30. Schematic of conjugated polymers in Fluorescent Immuno Assay (FIA). (A) conjugated polymer covalently linked to a detection antibody; (B) biotin binding protein covalently bound to the conjugated polymer and interacting with a biotinylated detection antibody; (C) secondary antibody covalently linked to the conjugated polymer and interacting with a detection antibody.

FIG. 30 depicts example embodiments around the use of conjugated polymers in Fluorescent Immuno Assay (FIA). In FIG. 30 panels A-C analyte antigen is immobilised on a surface which can include but is not limited to a microtitre plate well, bead particle, glass slide, plastic slide, lateral flow strip, laminar flow device, microfluidic device, virus, phage, tissue or cell surface. Analyte molecules are then detected by use of labelled detection conjugates or sensor biomolecules. In FIG. 30A, a conjugated polymer covalently linked to a detection antibody is utilized for detection. In FIG. 30B, a biotin binding protein (for example but not limited to avidin, streptavidin or other high affinity biotin specific derivatives) covalently bound to the conjugated polymer and interacting with a biotinylated detection antibody is utilized for detection. In FIG. 30C, a secondary antibody covalently linked to the conjugated polymer and interacting with a detection antibody is utilized for detection. In FIG. 5B, a homogenous, solution based example is also embodied where two separate antibodies each bind to the antigen of interest. One antibody is covalently linked to the conjugated polymer, the other to a dye. When bound to the antigen, the respective fluorophores are brought into sufficient spatial proximity for energy transfer to occur. In assays predicated on the designs in FIG. 30 and FIG. 5B, the sample is interrogated with light matched to the excitation of the conjugated polymer and signal reported at the emission wavelength of the dye. In the examples embodied in FIG. 30 A-C the use of a polymer-dye tandem complex is further disclosed. In such cases, optical excitation of the polymer will result in amplified dye emission, as compared to direct excitation of the dye. Signals arising from dye emission will indicate the presence of the target.

In a further aspect, the invention provides for the multiplexing of donor energy transfer to multiple acceptors. By using a conjugated polymer as a donor in an energy transfer system, benefits also include the ability to multiplex. A single donor can transfer energy to several dyes; thus with a single excitation source, the intensity of multiple dyes can be monitored. This is useful for applications including but not limited to cell imaging (i.e. immunohistochemistry), flow cytometry and cell sorting, where the different types of cells can be monitored by protein-antibody recognition events.

In one embodiment, two dye-labeled antibodies can be incubated with a biological material, for example, a cultured cell line, tissue section or blood sample. Antibodies are able to recognize cells with a target protein expressed on its surface and specifically bind only to those proteins. By labeling the two antibodies with different dyes, it is possible to monitor for the expression of two different proteins or different cell types simultaneously. Typically, this would require two scans, excitations or images, once each with the correct excitation wavelength. As a final step prior to analysis, these two images or data sets would have to be overlaid or combined. By using antibodies conjugated with both a dye and a conjugated polymer, one excitation wavelength can be used for the conjugated polymer to excite both dyes, and a single image or scan will include data sets from each of the two antibodies. This can be done with any number of antibody combinations provided there is sufficient ability to resolve the resulting signals.

It is envisioned that the invention described herein can be used to increase the sensitivity of any of a number of commercially available tests including but not limited to the OraQuick Rapid HIV-1/2 Antibody Test, manufactured by OraSure Technologies, Inc. (Bethlehem, Pa.), which is a FDA-approved HIV diagnostic test for oral fluid samples. This test can provide screening results with over 99 percent accuracy in as little as 20 minutes.

Conjugated Polymers

Light harvesting conjugated polymer systems can efficiently transfer energy to nearby luminescent species. Mechanisms for energy transfer include, for example, resonant energy transfer (Forster (or fluorescence) resonance energy transfer, FRET), quantum charge exchange (Dexter energy transfer) and the like. Typically, however, these energy transfer mechanisms are relatively short range, and close proximity of the light harvesting conjugated polymer system to the signaling chromophore is required for efficient energy transfer. Amplification of the emission can occur when the number of individual chromophores in the light harvesting conjugated polymer system is large; emission from a fluorophore can be more intense when the incident light (the "pump light") is at a wavelength which is absorbed by the light harvesting conjugated polymer system and transferred to the fluorophore than when the fluorophore is directly excited by the pump light.

The conjugated polymers used in the present invention can be charge neutral, cationic or anionic. In some embodiments, the conjugated polymers are polycationic conjugated polymers. In other embodiments, the conjugated polymers are polyanionic conjugated polymers. In further embodiments, the conjugated polymers can include cationic, anionic, and/or neutral groups in various repeating subunits. In yet other embodiments, the conjugated polymers are neutral conjugated polymers. In some instances, conjugated polymers contain groups such as ethylene glycol oligomers, ethylene glycol polymers, ω-ammonium alkoxy salts, and/or w-sulfonate alkoxy salts that impart solubility in aqueous solutions. In some instances the neutral conjugated polymers with non-ionic side chains are soluble in greater than 10 mg/mL in water or phosphate buffered saline solutions and in certain cases the solubility is greater than 50 mg/mL. In some embodiments the conjugated polymers contain either a terminal linking site (e.g., capping unit), internal linking site or both.

In some embodiments, a conjugated polymer is one that comprises "low bandgap repeat units" of a type and in an amount that contribute an absorption to the polymer in the range of about 450 nm to about 1000 nm. The low bandgap repeat units may or may not exhibit such an absorption prior to polymerization, but does introduce that absorption when incorporated into the conjugated polymer. Such absorption characteristics allow the polymer to be excited at wavelengths that produce less background fluorescence in a variety of settings, including in analyzing biological samples and imaging and/or detecting molecules. Shifting the absorbance of the conjugated polymer to a lower energy and longer wavelength thus allows for more sensitive and robust methods. Additionally, many commercially available instruments incorporate imaging components that operate at such wavelengths at least in part to avoid such issues. For example, thermal cyclers that perform real-time detection during amplification reactions and microarray readers are available which operate in this region. Providing polymers that absorb in this region allows for the adaptation of detection methods to such formats, and also allows entirely new methods to be performed.

Incorporation of repeat units that decrease the band gap can produce conjugated polymers with such characteristics. Exemplary optionally substituted species which result in polymers that absorb light at such wavelengths include 2,1,3-benzothiadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefins, and cyano-substituted olefins and isomers thereof. Further details relating to the composition, structure, properties and synthesis of suitable conjugated polymers can be found in U.S. patent application Ser. No. 11/329,495, filed Jan. 10, 2006, now published as US 2006-0183140 A1, which is incorporated herein by reference in the entirety.

In one aspect, provided herein are conjugated polymers of Formula (I):

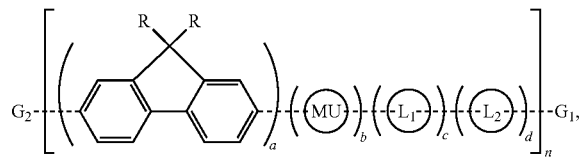

wherein:
each R is independently a non-ionic side group capable of imparting solubility in water in excess of 10 mg/mL;
MU is a polymer modifying unit or band gap modifying unit that is evenly or randomly distributed along the polymer main chain and is optionally substituted with one or more optionally substituted substituents selected from halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$(hetero)aryloxy, $C_2$-$C_{18}$(hetero)arylamino, $(CH_2)_{x'}(OCH_2CH_2)_{y'}OCH_3$ where each x' is independently an integer from 0-20, y' is independently an integer from 0 to 50, or a $C_2$-$C_{18}$(hetero)aryl group;
each optional linker $L_1$ and $L_2$ are aryl or heteroaryl groups evenly or randomly distributed along the polymer main chain and are substituted with one or more pendant chains terminated with a functional group for conjugation to another substrate, molecule or biomolecule selected from amine, carbamate, carboxylic acid, maleimide, activated esters, N-hydroxysuccinimidyl, hydrazines, hydrazides, hydrazones, azide, alkyne, aldehydes, thiols, and protected groups thereof;
$G_1$ and $G_2$ are each independently selected from hydrogen, halogen, amine, carbamate, carboxylic acid, maleimide, activated esters, N-hydroxysuccinimidyl, hydrazines, hydrazides, hydrazones, azide, alkyne, aldehydes, thiol, optionally substituted aryl, optionally substituted heteroaryl, halogen substituted aryl, boronic acid substituted aryl, boronic ester substituted aryl, boronic esters, optionally substituted fluorine and aryl or heteroaryl substituted with one or more pendant chains terminated with a functional group, molecule or biomolecule selected from amine, carbamate, carboxylic acid, carboxylate, maleimide, activated esters, N-hydroxysuccinimidyl, hydrazines, hydrazones, azide, alkyne, aldehydes, thiols, and protected groups thereof for conjugation to another substrate, molecule or biomolecule;
wherein the polymer comprises at least 1 functional group selected from amine, carbamate, carboxylic acid, carboxylate, maleimide, activated esters, N-hydroxysuccinimidyl, hydrazines, hydrazides, hydrazones, azide, alkyne, aldehydes, and thiols within $G_1$, $G_2$, $L_1$ or $L_2$ that allows, for functional conjugation to another molecule, substrate or biomolecule;
each dashed bond, ------, is independently a single bond, triple bond or optionally substituted vinylene ($—CR^5=CR^5—$) wherein each $R^5$ is independently hydrogen, cyano, $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group, wherein each $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero) aryl group is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, or $C_1$-$C_{12}$ haloalkyl; and
n is an integer from 1 to about 10,000; and a, b, c and d define the mol % of each unit within the structure which each can be evenly or randomly repeated and where a is a mol % from 10 to 100%, b is a mol % from 0 to 90%, and each c and d are mol % from 0 to 25%.

Non-ionic side groups capable of imparting solubility in water as used herein refer to side groups which are not charged and allow the resulting polymer to be soluble in water or aqueous solutions with no visible particulates. In some embodiments, each R is independently a non-ionic side group capable of imparting solubility in water in excess of 10 mg/mL, in excess of 15 mg/mL, in excess of 20 mg/mL, in excess of 25 mg/mL, in excess of 30 mg/mL, in excess of 35 mg/mL, in excess of 40 mg/mL, in excess of 45 mg/mL, in excess of 50 mg/mL, in excess of 60 mg/mL, in excess of 70 mg/mL, in excess of 80 mg/mL, in excess of 90 mg/mL or in excess of 100 mg/mL.

In some embodiments, conjugated polymers described herein comprises a minimum number average molecular weight of greater than 5,000 g/mol, greater than 10,000 g/mol, greater than 15,000 g/mol, greater than 20,000 g/mol, greater than 25,000 g/mol, greater than 30,000 g/mol, greater than 40,000 g/mol, greater than 50,000 g/mol, greater than 60,000 g/mol, greater than 70,000 g/mol, greater than 80,000 g/mol, greater than 90,000 g/mol, or greater than 100,000 g/mol.

In some embodiments, each R is independently $(CH_2)_x(OCH_2CH_2)_yOCH_3$ where each x is independently an integer from 0-20, each y is independently an integer from 0 to 50, or a benzyl optionally substituted with one or more halogen, hydroxyl, $C_1$-$C_{12}$ alkoxy, or $(OCH_2CH_2)_zOCH_3$ where each z is independently an integer from 0 to 50. In some instances, each R is $(CH_2)_3(OCH_2CH_2)_{11}OCH_3$.

In other embodiments, each R is independently a benzyl substituted with at least one $(OCH_2CH_2)_zOCH_3$ group where each z is independently an integer from 0 to 50. In some instances, each R is a benzyl substituted with at least one $(OCH_2CH_2)_{10}OCH_3$ group. In other instances, each R is a benzyl substituted with at least two $(OCH_2CH_2)_{10}OCH_3$ groups. In further instances, each R is a benzyl substituted with at least three $(OCH_2CH_2)_{10}OCH_3$ groups.

In further embodiments, each R is independently

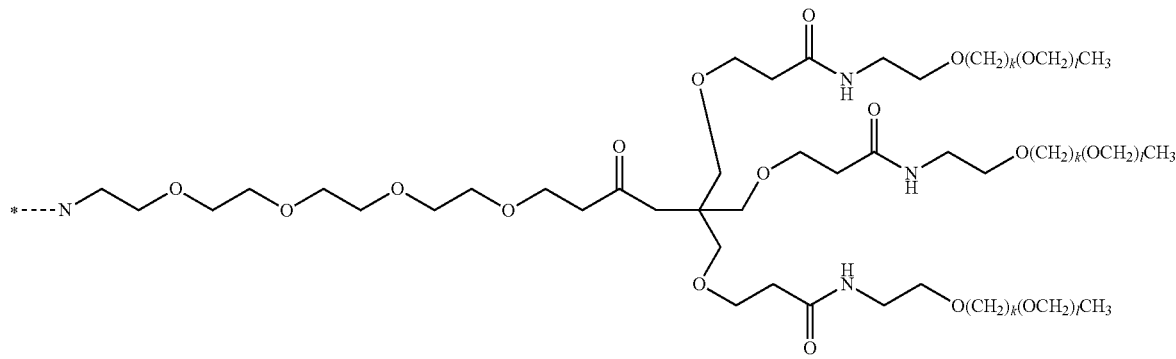

where k and l are independent integers from 0 to 25; *=site for covalent attachment.

In yet further embodiments, each R is independently is a dendrimer of PAMAM, PEA, PEHAM, PPI, tri-branched benzoate, or glycerol with a generation of 1 to 4 and optionally terminal substitutions, said optionally terminal substitutions are (- - - - -)$CH_2CH_2O)_jCH_3$ or (- - - - -)$(OCH_2CH_2)_jCH_3$ and j is an integer from 0 to 25 and the dotted lines (- - - - -) are each independently selected from any one or a combination of, $C_1$-$C_{12}$ alkyl, $C_1$-$C_{12}$ alkoxy, $C_2$-$C_{12}$ alkene, amido, amino, aryl, $(CH_2)_r$-$(OCH_2CH_2)_s(CH_2)_r$ where each r is independently an integer from 0-20, s is independently an integer from 0 to 50, carbamate, carboxylate, $C_3$-$C_{12}$ cycloalkyl, imido, phenoxy, or $C_4$-$C_{18}$(hetero)aryl groups.

In alternative embodiments, each R is independently,

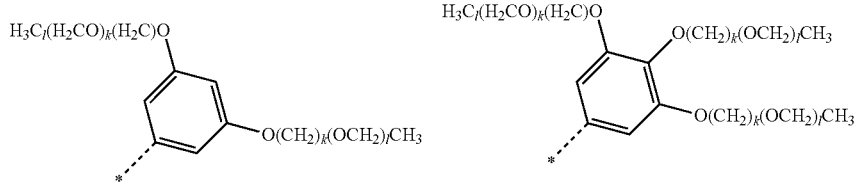

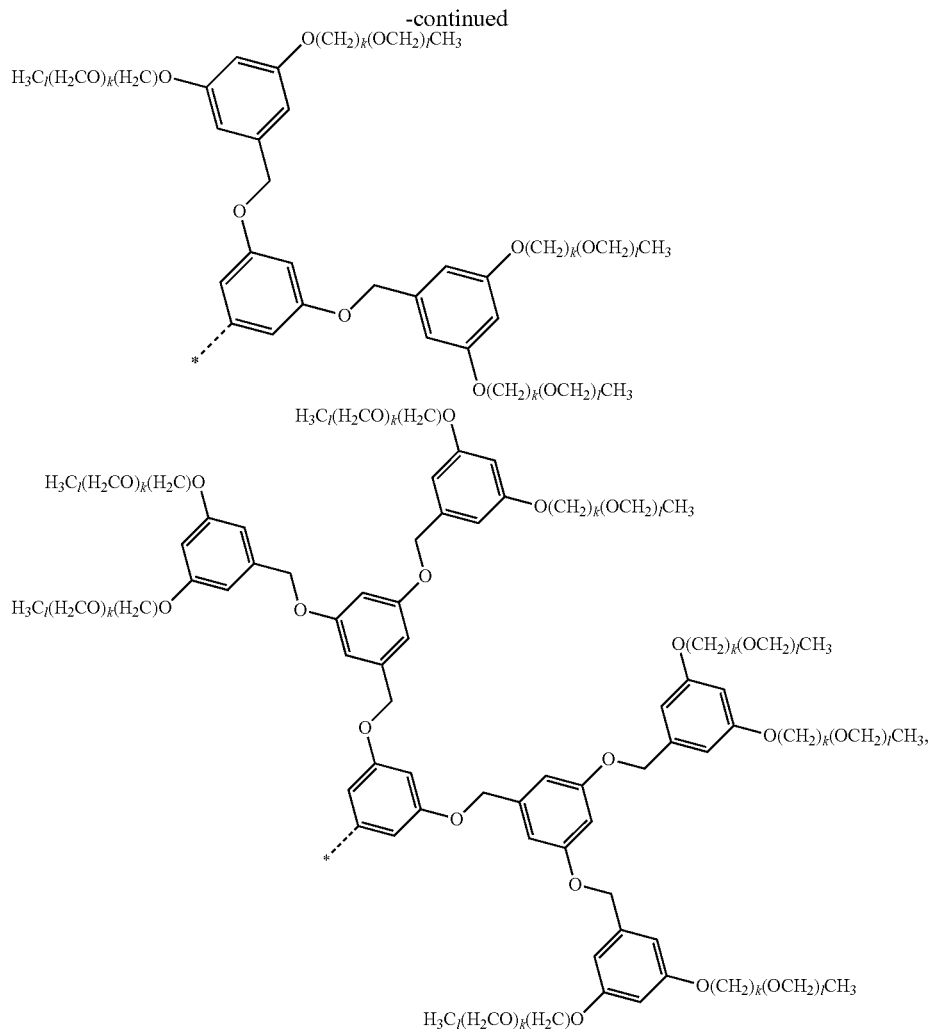

Where k and l are independent integers from 0 to 25 and the dotted lines (- - - - -) are each independently selected from any one or a combination of, $C_1$-$C_{12}$ alkyl, $C_1$-$C_{12}$ alkoxy, $C_2$-$C_{12}$ alkene, amido, amino, aryl, $(CH_2)_r$ $(OCH_2CH_2)_s(CH_2)_r$ where each r is independently an integer from 0-20, s is independently an integer from 0 to 50, carbamate, carboxylate, $C_3$-$C_{12}$ cycloalkyl, imido, phenoxy, or $C_4$-$C_{18}$(hetero)aryl groups; *=site for covalent attachment.

In alternative embodiments, each R is independently,

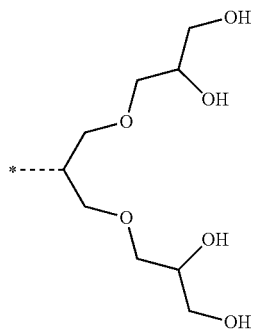

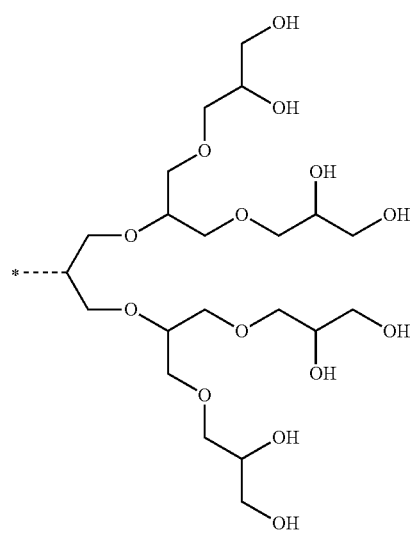

-continued

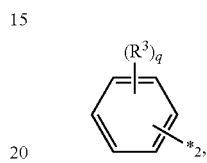

Where k and l are independent integers from 0 to 25 and the dotted lines (- - - - -) are each independently selected from any one or a combination of, $C_1$-$C_{12}$ alkyl, $C_1$-$C_{12}$ alkoxy, $C_2$-$C_{12}$ alkene, amido, amino, aryl, $(CH_2)_r$ $(OCH_2CH_2)_s(CH_2)_r$ where each r is independently an integer from 0-20, s is independently an integer from 0 to 50, carbamate, carboxylate, $C_3$-$C_{12}$ cycloalkyl, imido, phenoxy, or $C_4$-$C_{18}$(hetero)aryl groups; *=site for covalent attachment.

In some embodiments, conjugated polymers described herein contain no optional linkers, $L_1$ and/or $L_2$. In other embodiments, conjugated polymers contain at least about 0.01 mol %, at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or about 25 mol % of optional linkers, $L_1$ and/or $L_2$. In some embodiments, conjugated polymers contain up to 50 mol % total of optional linkers, $L_1$ and $L_2$, and may contain about 40 mol % or less, about 30 mol % or less, about 25 mol % or less, about 20 mol % or less, about 15 mol % or less, about 10 mol % or less, or about 5 mol % or less. Linkers can be evenly or randomly distributed along the polymer main chain.

In some embodiments, optional linkers $L_1$ or $L_2$ have the structure:

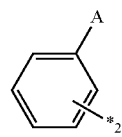

*=site for covalent attachment to unsaturated backbone
wherein $R^3$ is independently hydrogen, halogen, hydroxyl, $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group, wherein each $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, or $C_1$-$C_{12}$ haloalkyl; and q is an integer from 0 to 4.

In some embodiments, optional linkers $L_1$ or $L_2$ have the structure represented by:

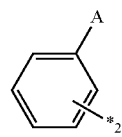

*=site for covalent attachment to unsaturated backbone
wherein A is a site for conjugation, chain extension or crosslinking and is —[O—$CH_2$—$CH_2$]$_t$—W, or ($C_1$-$C_{12}$) alkoxy-X;

W is —OH or —COOH;

X is —$NH_2$, —NHCOOH, —NHCOOC($CH_3$)$_3$, —NHCO($C_3$-$C_{12}$)cycloalkyl(C1-C4)alkyl-N-maleimide; or —NHCO[$CH_2$—$CH_2$—O]$_u$$NH_2$;

t is an integer from 1 to 20; and
u is an integer from 1 to 8.

In other embodiments, optional linkers $L_1$ or $L_2$ are selected from the group consisting of a-h having the structure:

a
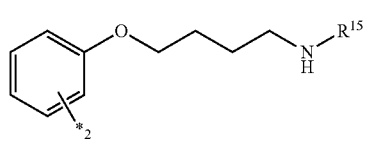

b
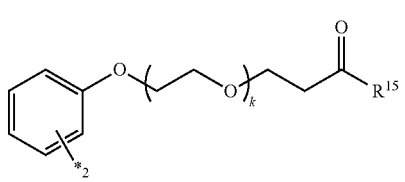

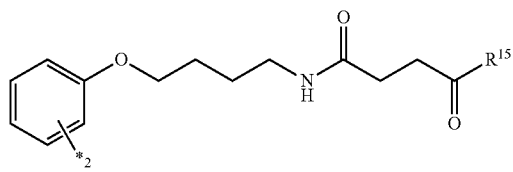

c

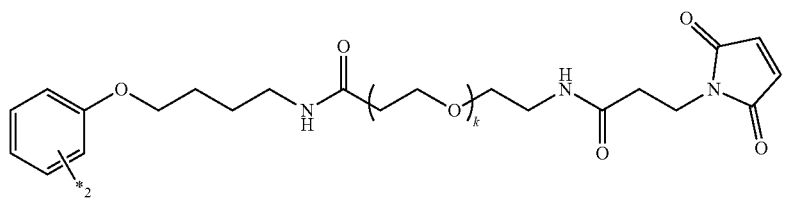

d

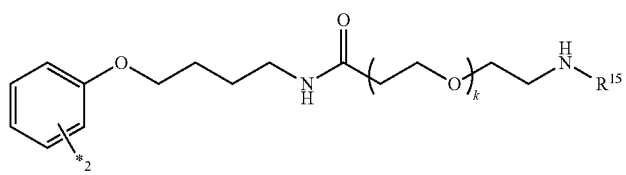

e

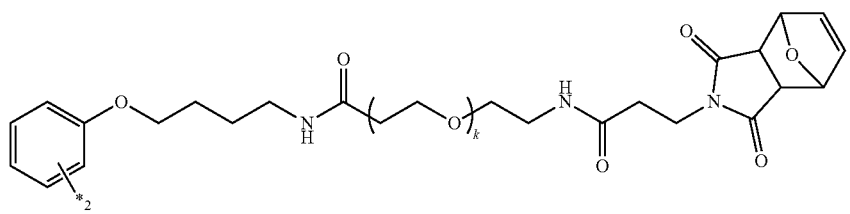

f

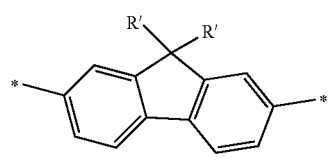

g

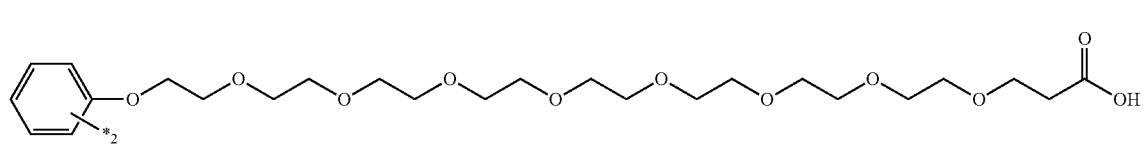

h

*=site for covalent attachment to unsaturated backbone wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$ cycloalkyl, $C_1$-$C_{12}$ haloalkyl, $C_2$-$C_{18}$(hetero) aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$(O$CH_2$$CH_2$)$_{x''}$O$CH_3$ where x'' is independently an integer from 0 to 50, or a benzyl optionally substituted with one or more halogen, hydroxyl, $C_1$-$C_{12}$ alkoxy, or (O$CH_2$$CH_2$)$_{y''}$O$CH_3$ where each y'' is independently an integer from 0 to 50 and R' is different from R;

wherein $R^{15}$ is selected from the group consisting of l-t having the structure:

*—OH l

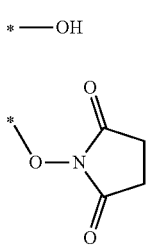

m

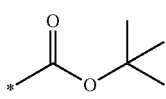

n

-continued o
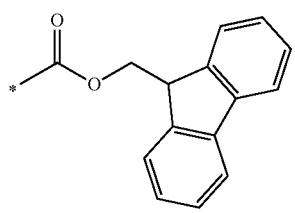

p
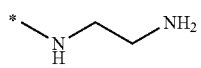

q
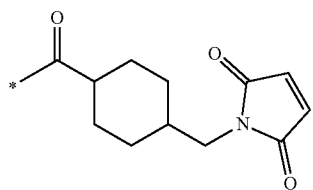

r
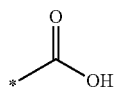

s

t

and k is 2, 4, 8, 12 or 24; *=site for covalent attachment to backbone.

In certain embodiments, optional linkers $L_1$ or $L_2$ are

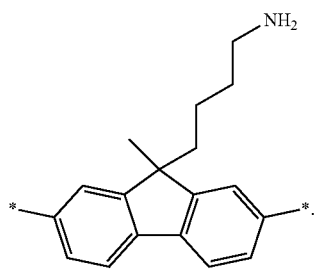

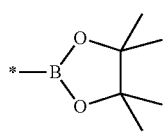

In some embodiments, $G_1$ and $G_2$ are optionally substituted aryl wherein the optional substituent is selected from halogen, amine, carbamate, carboxylic acid, maleimide, activated esters, N-hydroxysuccinimidyl, hydrazines, hydrazides, hydrazones, azide, alkyne, aldehydes, boronic acid, boronate radical, boronic esters and optionally substituted fluorene.

In other embodiments, $G_1$ and $G_2$ are the same. In further embodiments, $G^1$ and $G^2$ are different. $G^1$ and $G^2$ can be activated units that allow further conjugation, crosslinking, or polymer chain extension, or they may be nonactivated termination units.

In some embodiments, $G_1$ and $G_2$ are independently selected from structures represented by:

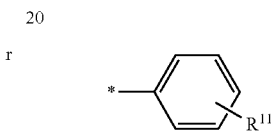

*=site for covalent attachment to backbone wherein $R^{11}$ is any one of or a combination of a bond, $C_1$-$C_{20}$ alkyl, $C_1$-$C_{20}$ alkoxy, $C_2$-$C_{20}$ alkene, $C_2$-$C_{20}$ alkyne, $C_3$-$C_{20}$ cycloalkyl, $C_1$-$C_{20}$ haloalkyl, $(CH_2)_x$ $(OCH_2CH_2)_p(CH_2)_x$ where each x is independently an integer from 0-20, p is independently an integer from 0 to 50, aryl, $C_2$-$C_{18}$(hetero)aryl, phenoxy, amido, amino, carbamate, carboxylate, carbonates, sulfide, disulfide, or imido groups terminated with a functional group selected from amine, carbamate, carboxylate, carboxylic acid, maleimide, activated esters, N-hydroxysuccinimidyl, hydrazines, hydrazides, hydrazones, azide, alkyne, aldehydes, thiols, and protected groups thereof for conjugation to another substrate, molecule or biomolecule.

In other embodiments, $G_1$ and $G_2$ are independently selected from the group consisting of 1-18 having the structure:

| 1 | 2 |
|---|---|
|   | 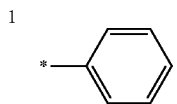 |
| 3 | 4 |
| *—Cl |  |
| 5 | 6 |
| *—SH |  |
| 7 | 8 |
| *—B(OH)$_2$ |  |

-continued
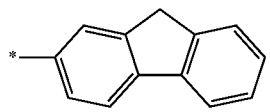
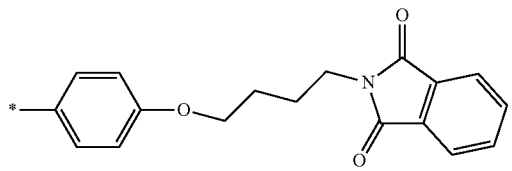
10
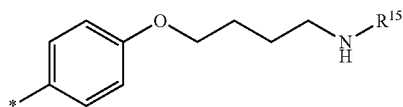
11
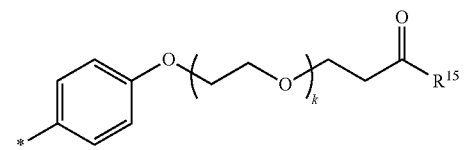
12
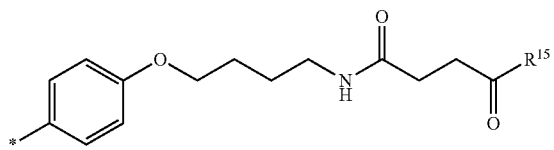
13
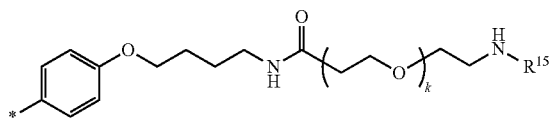
14
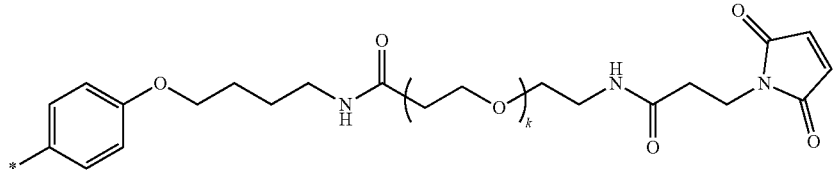
15
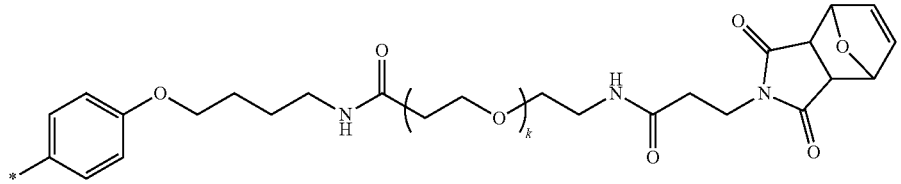
16
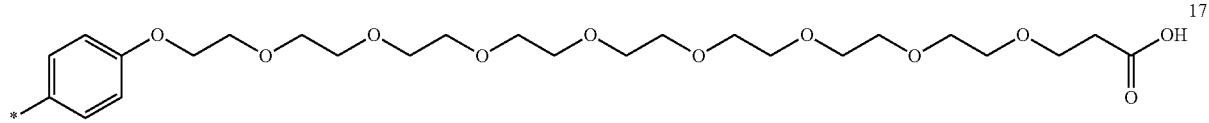
17
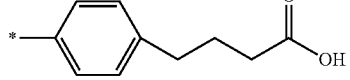
18
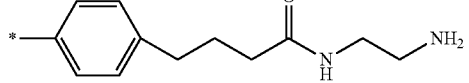
19
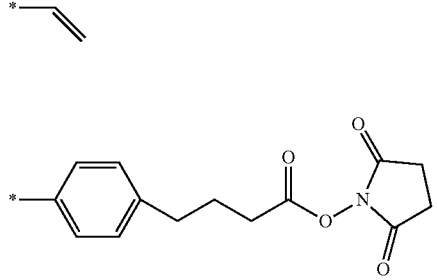
20
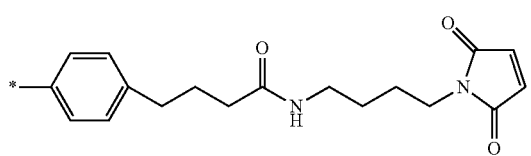
21
22
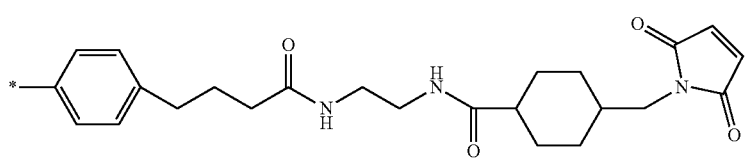
23

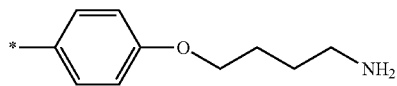
24
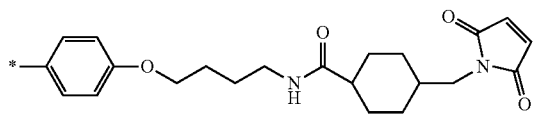
25
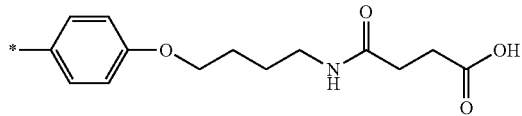
26
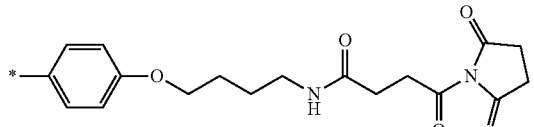
27
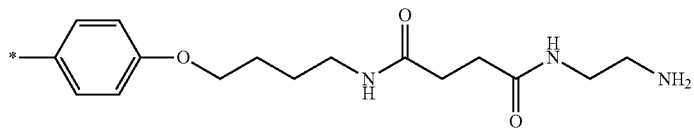
28
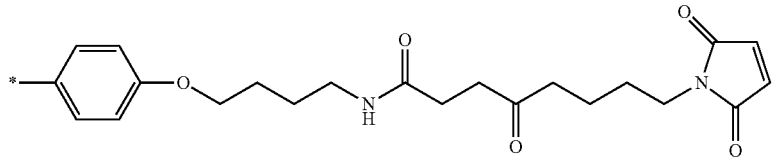
29
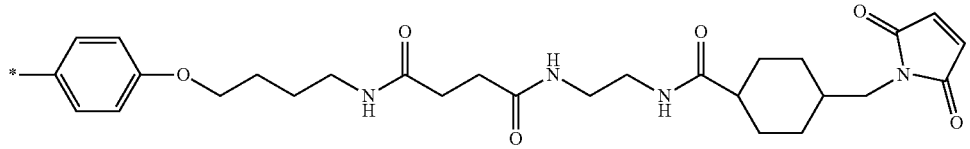
30
*=site for covalent attachment to backbone
wherein $R^{15}$ is selected from the group consisting of l-t having the structure:
l
m
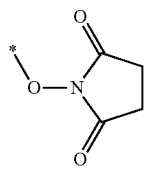
n
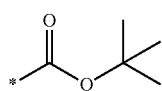
o
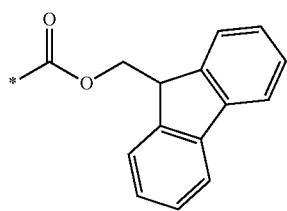
p
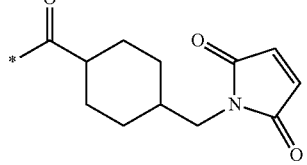
q
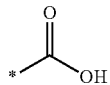
r
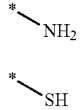
s
*—SH
t
and k is 2, 4, 8, 12 or 24.
In further embodiments, $G_1$ and $G_2$ is
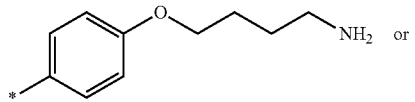 or
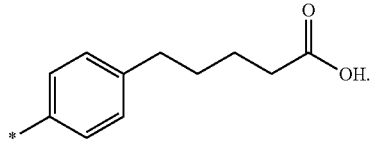

In some embodiments, optional linkers, $L_1$ and/or $L_2$, $G_1$, and/or $G_2$ can be further conjugated to an organic dye, a biomolecule or a substrate. Covalent linkage can be introduced by any known method and can include, but is not limited to, chemistry involving maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol; and amine/BMPH (N-[ß-Maleimidopropionic acid] hydrazide•TFA)/thiol.

In some embodiments, MU is selected from the group consisting of a'-k' having the structure:

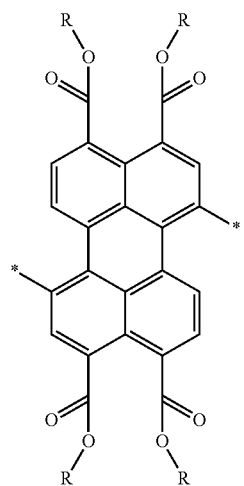

a'

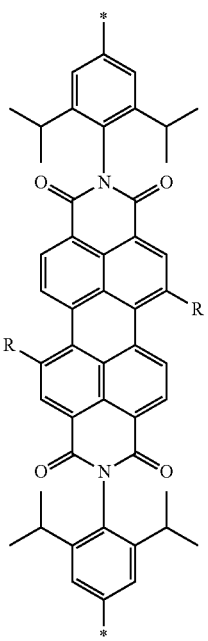

c'

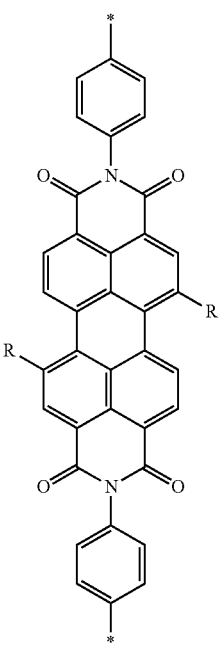

d' b'

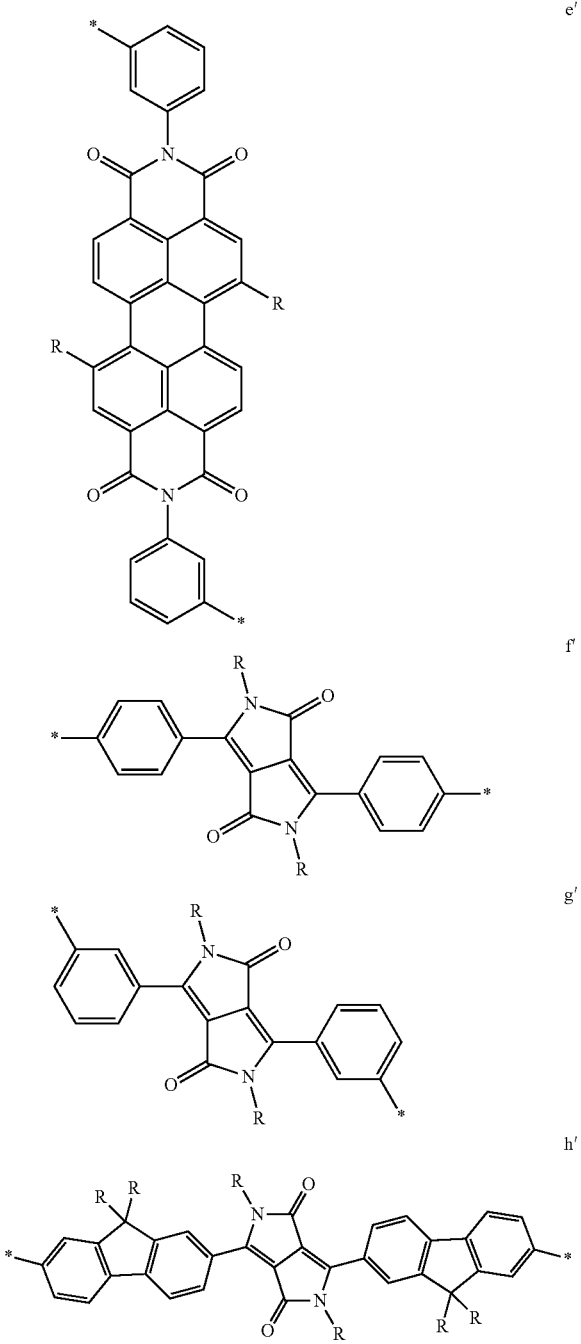

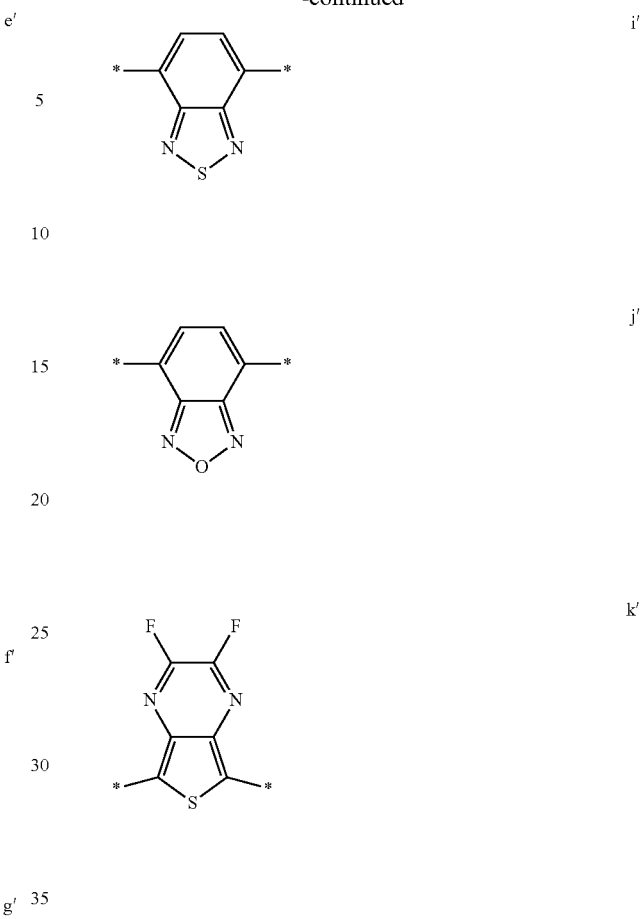

=site for covalent attachment to unsaturated backbone
wherein R is a non-ionic side group capable of imparting solubility in water in excess of 10 mg/mL. Non-ionic side groups include those previously described for polymers of Formula (I).

As used herein, in some embodiments, a pendant chain is any one of or a combination of a bond, $C_1$-$C_{20}$ alkyl, $C_1$-$C_{20}$ alkoxy, $C_2$-$C_{20}$ alkene, $C_2$-$C_{20}$ alkyne, $C_3$-$C_{20}$ cycloalkyl, $C_1$-$C_{20}$ haloalkyl, $(CH_2)_x(OCH_2CH_2)_p(CH_2)_x$ where each x is independently an integer from 0-20, p is independently an integer from 0 to 50, aryl, $C_2$-$C_{18}$(hetero)aryl, phenoxy, amido, amino, carbamate, carboxylate, carbonates, sulfide, disulfide, or imido groups which connects a polymer with a functional group for conjugation to another substrate, molecule, or biomolecule.

In some embodiments, conjugated polymers of Formula (I) have the structure of Formula (Ia):

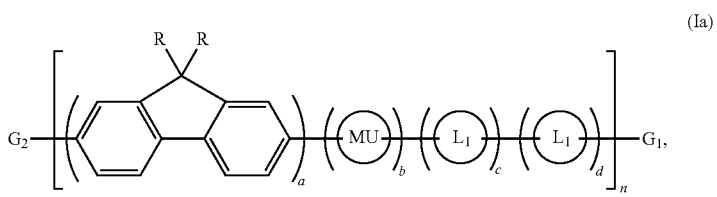

(Ia)

wherein R, $L_1$, $L_2$, $G_1$, $G_2$, MU, a, b, c, d and n are described previously for formula (I).

In a further aspect, conjugated polymers of Formula I have the structure of Formula (Ib):

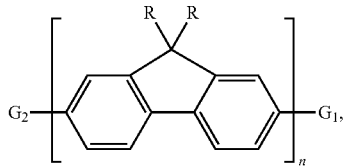
(Ib)

wherein at least one of $G_1$ or $G_2$ comprises a functional conjugation cite.

In a further aspect, conjugated polymers of Formula I have the structure of Formula (Ic):

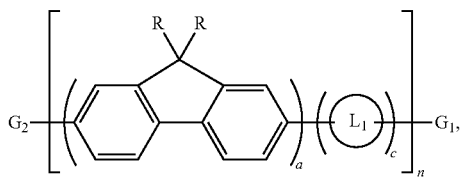
(Ic)

wherein $L_1$ comprises a functional conjugation cite.

In a further aspect, conjugated polymers of Formula I have the structure of Formula (Id):

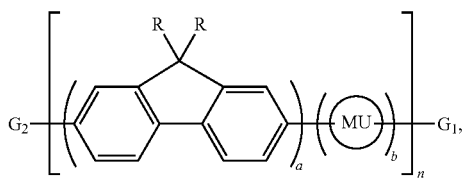
(Id)

wherein at least one of $G_1$ or $G_2$ comprises a functional conjugation cite.

In a further aspect, conjugated polymers of Formula I have the structure of Formula (II):

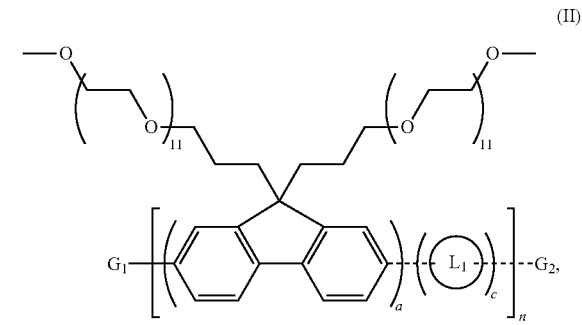
(II)

wherein $L_1$, $G_1$, $G_2$, a, c, n and dashed bonds are described previously for formula (I).

In some embodiments, conjugated polymers of Formula (II) have the structure of Formula (IIa):

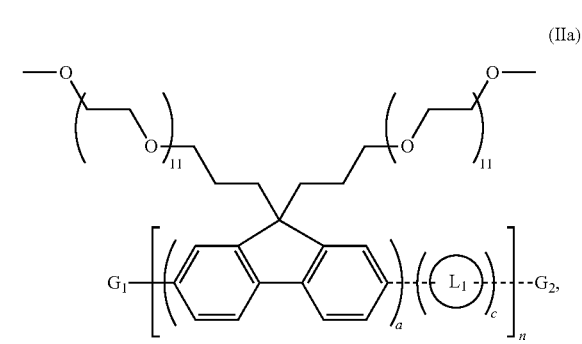
(IIa)

wherein $L_1$, $G_1$, $G_2$, a, c, and n are described previously for formula (I).

In a further aspect, conjugated polymers of Formula I have the structure of Formula (III):

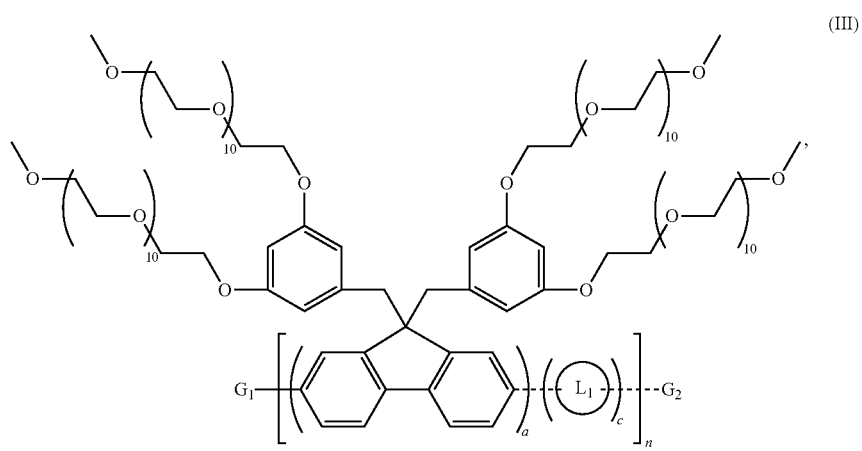
(III)

wherein L$_1$, G$_1$, G$_2$, a, c, n and dashed bonds are described previously for formula (I).

In some embodiments, conjugated polymers of Formula (III) have the structure of Formula (IIIa):

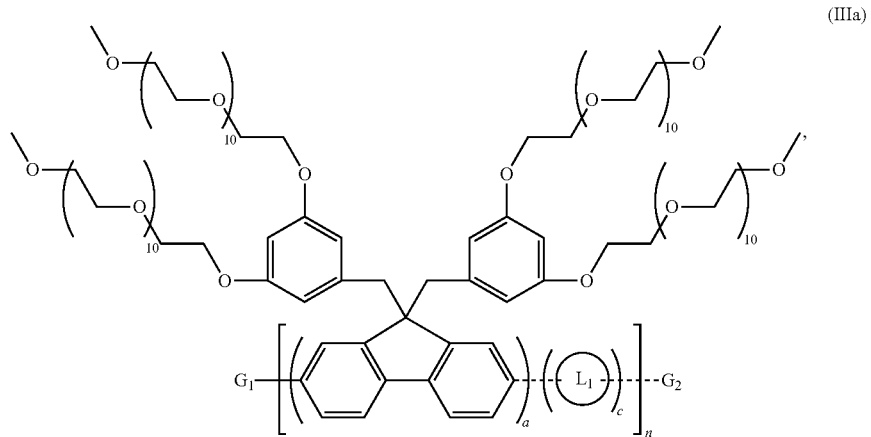

(IIIa)

wherein L$_1$, G$_1$, G$_2$, a, c, and n are described previously for formula (I).

In a further aspect, conjugated polymers of Formula I have the structure of Formula (IV):

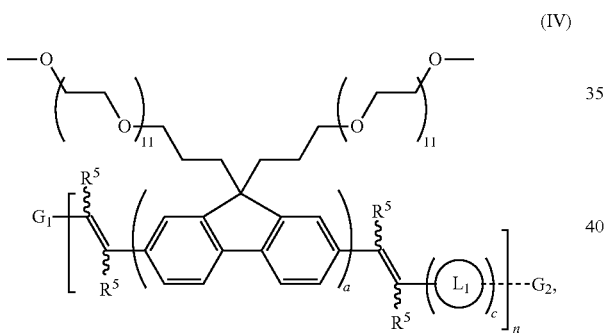

(IV)

wherein each R$^5$ is independently hydrogen, cyano, C$_1$-C$_{12}$ alkyl, C$_2$-C$_{12}$ alkene, C$_2$-C$_{12}$ alkyne, C$_3$-C$_{12}$ cycloalkyl or a C$_2$-C$_{18}$(hetero)aryl group, wherein each C$_1$-C$_{12}$ alkyl, C$_2$-C$_{12}$ alkene, C$_2$-C$_{12}$ alkyne, C$_3$-C$_{12}$ cycloalkyl or a C$_2$-C$_{18}$(hetero)aryl group is optionally substituted with one or more halogen, hydroxyl, C$_1$-C$_{12}$ alkyl, C$_2$-C$_{12}$ alkenyl, C$_2$-C$_{12}$ alkynyl group, C$_1$-C$_{12}$ alkoxy, or C$_1$-C$_{12}$ haloalkyl; and L$_1$, G$_1$, G$_2$, a, c, n and dashed bonds are described previously for formula (I).

In a further aspect, conjugated polymers of Formula I have the structure of Formula (V):

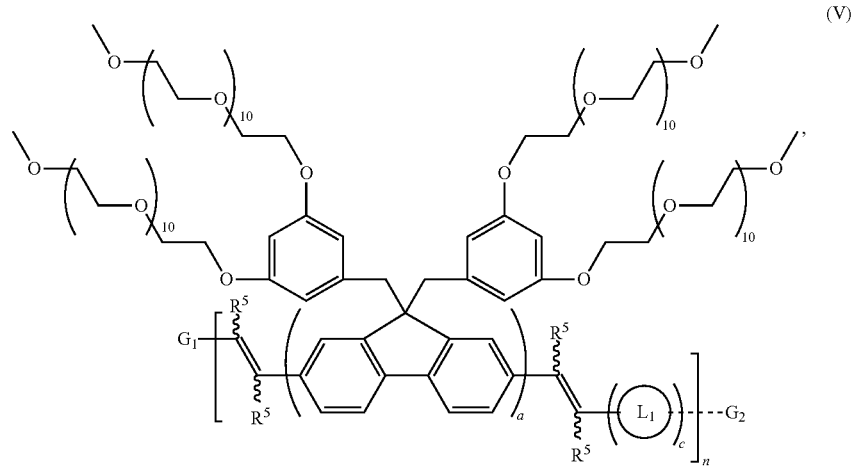

(V)

wherein each $R^5$ is independently hydrogen, cyano, $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group, wherein each $C_1$-$C_{12}$ alkyl, $C_2$-$C_{12}$ alkene, $C_2$-$C_{12}$ alkyne, $C_3$-$C_{12}$ cycloalkyl or a $C_2$-$C_{18}$(hetero)aryl group is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, or $C_1$-$C_{12}$ haloalkyl; and $L_1$, $G_1$, $G_2$, a, c, n and dashed bonds are described previously for formula (I).

Also provided herein are polymers having the structure of the following formula:

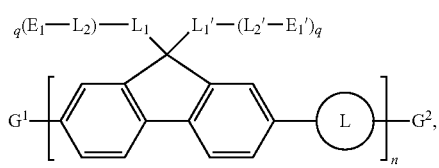

wherein: $G^1$ and $G^2$ are each independently selected from hydrogen, halogen, amine, carbamate, carboxylic acid, maleimide, activated esters, N-hydroxysuccinimidyl, hydrazines, hydrazides, hydrazones, azide, alkyne, aldehydes, optionally substituted aryl, halogen substituted aryl, boronic acid substituted aryl, boronic ester substituted aryl, boronic esters and optionally substituted fluorene; L is a bond or an aryl or heteroaryl group that is evenly or randomly distributed along the polymer main chain and is optionally substituted with one or more optionally substituted substituents selected from halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$(hetero)aryloxy, $C_2$-$C_{18}$(hetero)arylamino, $(CH_2)_x(OCH_2CH_2)_pOCH_3$ where each x is independently an integer from 0-20, p is independently an integer from 0 to 50, or a $C_2$-$C_{18}$(hetero)aryl group; $L^1$, $L^{1'}$, $L^2$ and $L^{2'}$ are each independently a covalent bond, a C1-C12 alkylene, a C3-C12 cycloalkylene, a $C_2$-$C_{12}$ alkenylene, a $C_2$-$C_{12}$ alkynylene, a $(C_6$-$C_{18})$aryl$(C_1$-$C_{12})$alkylene, a $(C_6$-$C_{18})$aryl$(C_2$-$C_{12})$alkenylene, a $(C_6$-$C_{18})$aryl$(C_1$-$C_{12})$alkynylene, a $C_6$-$C_{18}$ arylene group, —$Y_1$—[O—$Y_2$]$_p$—, —O—$Y_1$—[O—$Y_2$]$_p$— wherein each $C_1$-$C_{12}$ alkylene, $C_3$-$C_{12}$ cycloalkylene, $(C_6$-$C_{18})$aryl$(C_1$-$C_{12})$alkylene, or $C_6$-$C_{18}$ arylene group is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, $C_1$-$C_{12}$ haloalkyl, —$Y_1$—[O—$Y_2$]$_p$— or —O—$Y_1$—[O—$Y_2$]$_p$—; q is 0 or an integer from 1 to 8; p is 0 or an integer from 1 to 24; $Y_1$ and $Y_2$ are each independently a covalent bond, or a $C_{1-12}$ alkylene group, a $C_3$-$C_{12}$ cycloalkylene, a $C_2$-$C_{18}$(hetero)arylene, a $(C_6$-$C_{18})$aryl$(C_1$-$C_{12})$alkylene, wherein each $C_{1-12}$ alkylene group, a $C_3$-$C_{12}$ cycloalkylene, a $C_2$-$C_{18}$(hetero)arylene, a $(C_6$-$C_{18})$aryl$(C_1$-$C_{12})$alkylene is optionally substituted with one or more halogen, hydroxyl, $C_1$-$C_{12}$ alkyl, $C_2$-$C_{12}$ alkenyl, $C_2$-$C_{12}$ alkynyl group, $C_1$-$C_{12}$ alkoxy, or $C_1$-$C_{12}$ haloalkyl; $E^1$ and $E^{1'}$ are each independently, hydrogen, C1-C6 alkyl, —OH, —COOH, —SH, —SR, —SHR$^+$, SR$_2^+$, —SO$_3^-$, —PO$_4^-$, Br, —NH$_2$, —NHR, —NR$_2$, —NH$_3^+$, —NH$_2$R$^+$, —NHR$_2^+$ or —NR$_3$, wherein and each R is independently a $C_1$-$C_6$ alkyl and —SHR$^+$, SR$_2^+$, —SO$_3^-$, —PO$_4^-$, —NH$_3^+$, —NH$_2$R$^+$, —NHR$_2^+$ or —NR$_3^+$ each optionally has an associated counterion; and n is an integer from 1 to about 1,000.

Also provided herein are polymers having the structure of the following formula:

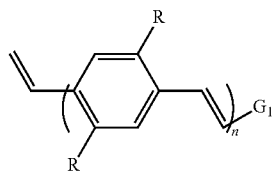

wherein each R is independently O(CH$_x$), or (CH$_2$)$_3$(OCH$_2$CH$_2$)pOCH$_3$ where each x is independently an integer from 0-20, each p is independently an integer from 0 to 50, or a benzyl optionally substituted with one or more halogen, hydroxyl, $C_1$-$C_{12}$ alkoxy, or (OCH$_2$CH$_2$)mOCH$_3$ where each m is independently an integer from 0 to 50; G1 is selected from hydrogen, halogen, amine, carbamate, carboxylic acid, maleimide, activated esters, N-hydroxysuccinimidyl, hydrazines, hydrazides, hydrazones, azide, alkyne, aldehydes, optionally substituted aryl, halogen substituted aryl, boronic acid substituted aryl, boronic ester substituted aryl, boronic esters and optionally substituted fluorene; and n is an integer from 1 to about 10,000.

Additional embodiments of conjugated polymers are described in the following Examples.

Preparation of Conjugated Polymers

The synthesis of conjugated polymers described herein may be accomplished using means described in the chemical literature, using the methods described herein, or a combination thereof.

Conjugated polymers described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of the conjugated polymers of Formula (1) and polymers having the structures described in the prior section as described herein can be obtained from commercial sources, such as Aldrich Chemical Co. (Milwaukee, Wis.), Sigma Chemical Co. (St. Louis, Mo.), or the starting materials can be synthesized. The polymers described herein, and other related polymers having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of polymers as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Generally, polymerization of fluorene polymeric structures may be accomplished using polymerization techniques known to those of skill in the art or using methods known in the art in combination with methods described herein. For example, polymerization can be achieved via Suzuki coupling with a commercially available fluorene-dihalide monomer, e.g., 2,7-dibromofluorene, and its diboronic acid or ester derivative:

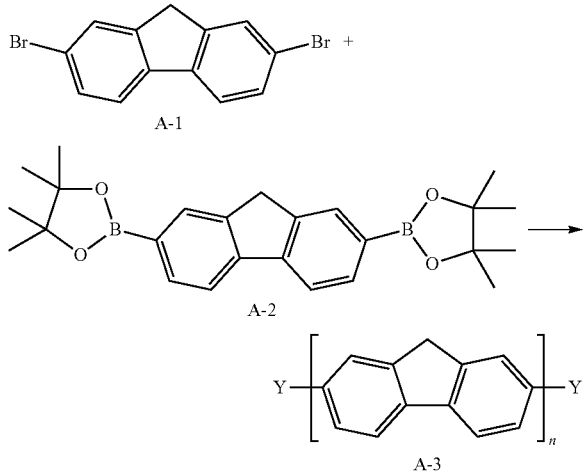

Structures A-1 and A-2 are catalyzed by a metal catalyst to form exemplary polymer A-3 with termination points, labeled Y. Each Y is independently —H, —Br, —B(OH)$_2$, or boronic ester, e.g., 4,4,5,5-tetramethyl-1,3,2-dioxaborolanyl.

Synthesis of diboronic ester derivatives from a fluorene-dihalide monomer can also be accomplished via Suzuki coupling with bis(pinacolato)diboron:

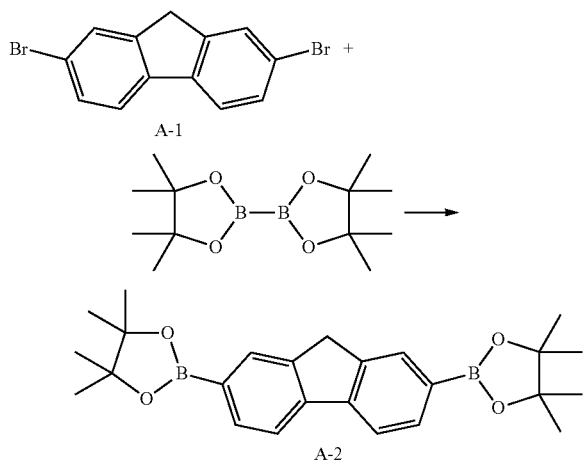

Substituents such as ethylene glycol oligomers or ethylene glycol polymers may be attached to monomers prior to polymerization or to the polymer itself after polymerization. An exemplary scheme of synthesizing substituted fluorene monomers with mPEGylated groups is as follows:

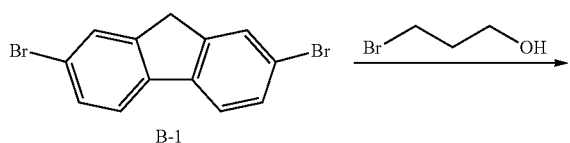

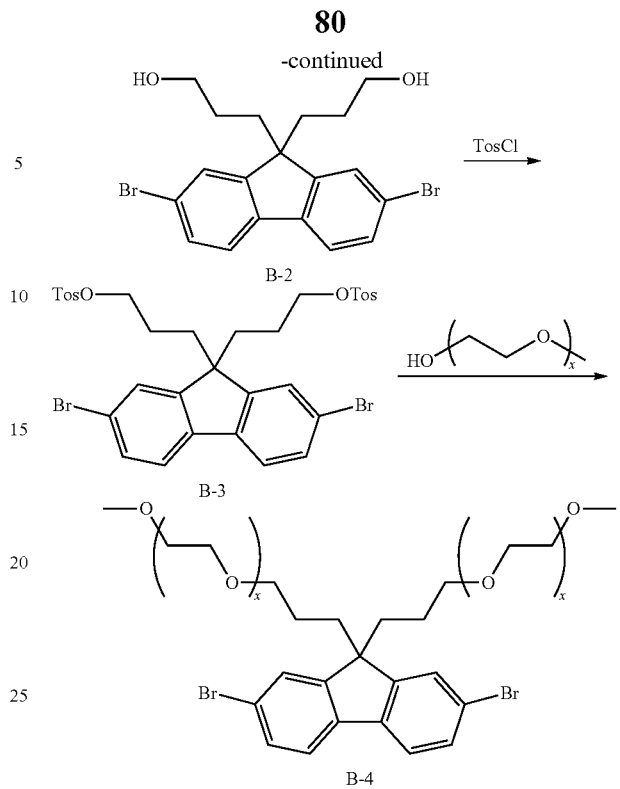

2,7-dibromofluorene (B-1) and 3-bromopropanol in the presence of a strong base such as sodium hydroxide, potassium hydroxide, or the like and a phase transfer catalyst, e.g. tetrabutylammonium bromide, is heated and reacted to completion to form 2,7-dibromo-9,9-di(3'-hydroxypropanyl)fluorene (B-2). —OH groups of B-2 are tosylated with tosyl chloride in the presence of pyridine and allowed to react to completion to form 2,7-dibromo-9,9-di(3'-methylbenzenesulfonatopropanyl)fluorene (B-3). B-3 is then reacted with a mPEG(x) alcohol in the presence of potassium tert-butoxide to form B-4 with attached mPEG chains. mPEG alcohols can have 1-50 mPEG chains. Typical sizes include but are not limited to mPEG5, mPEG8, mPEG11, mPEG24. In an alternative scheme, mPEG alcohols can be tosylated first via tosyl chloride and then reacted to B-2 to form B-4.

Substituted monomers, such as exemplary structure B-4, can be further derivatized to diboronic esters in the schemes disclosed herein and subsequently be used for polymerization such as via Suzuki coupling. Polymeric fluorenes may also be obtained through the use of other reaction schemes involving organometallic catalysis. For example, the Yamamoto reaction uses a nickel(0)-based catalyst for the homo-coupling of aryl halide monomers like exemplary structure B-4. Additionally, conjugated polymers can be synthesized using Stille, Heck, and Sonogashira coupling reactions. See, e.g., Yamamoto et al., Macromolecules 25: 1214-1223, 1992; Kreyenschmidt et al., Macromolecules 28: 4577-4582, 1995; and Pei et al., J. Am. Chem. Soc. 118: 7416-7417, 1996 regarding Yamamoto reaction schemes. See, also, Leclerc, Polym. Sci. Part A: Polym. Chem. 39: 2867-2873, 2001 for Stille reaction schemes; Mikroyannidis et al., J. Polym. Sci. Part A: Polym. Chem. 45: 4661-4670, 2007 for Heck reaction schemes; and Sonogashira et al., Tetrahedron Lett. 16: 4467-4470, 1975 and Lee et al., Org. Lett. 3: 2005-2007, 2001 for Sonogashira reaction schemes.

Figure 11:
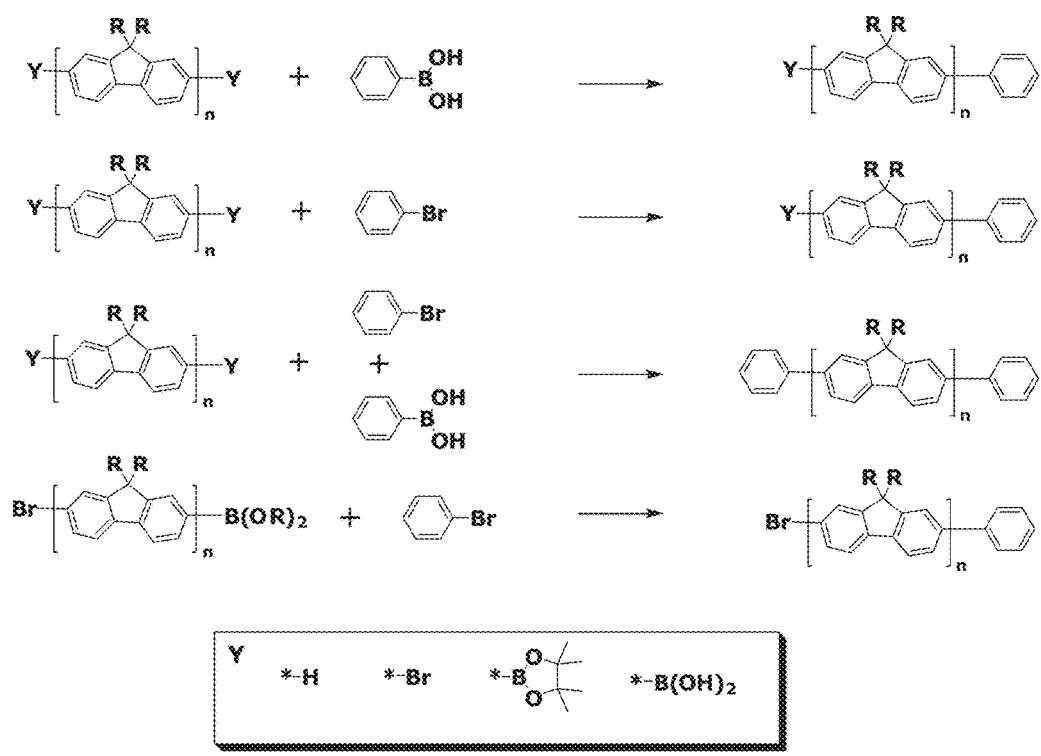
FIG. 11. Schematic of appending one or two phenyl capping units to a fluorene polymer.

Linkers and capping units can be conjugated to a fluorene polymer backbone via similar mechanisms as described previously. For example, bromo- and boronic esters of capping units can be used to append one or both ends of a polymer. Utilizing both bromo- and boronic esters of capping units will append both ends of polymer. Utilizing only one form, either a bromo- or boronic ester of a capping unit, will append only those ends terminated with its respective complement and for symmetric A-A+B-B polymerizations can be used to statistically modify only one end of a polymer. For asymmetric polymers this approach is used to chemically ensure the polymers are only modified at a single chain terminus. FIG. 11 depicts appending an exemplary fluorene polymer with Y ends with one or more phenyl groups with bromobenzene, phenyl boronic acid or both using Suzuki coupling.

Capping units can also be appended asymmetrically by first reacting a bromo-capping unit with a polymer with Y ends and subsequently reacting the polymer with a boronic ester capping unit. Exemplary bromo- and boronic ester capping units include but are not limited to the following structures:

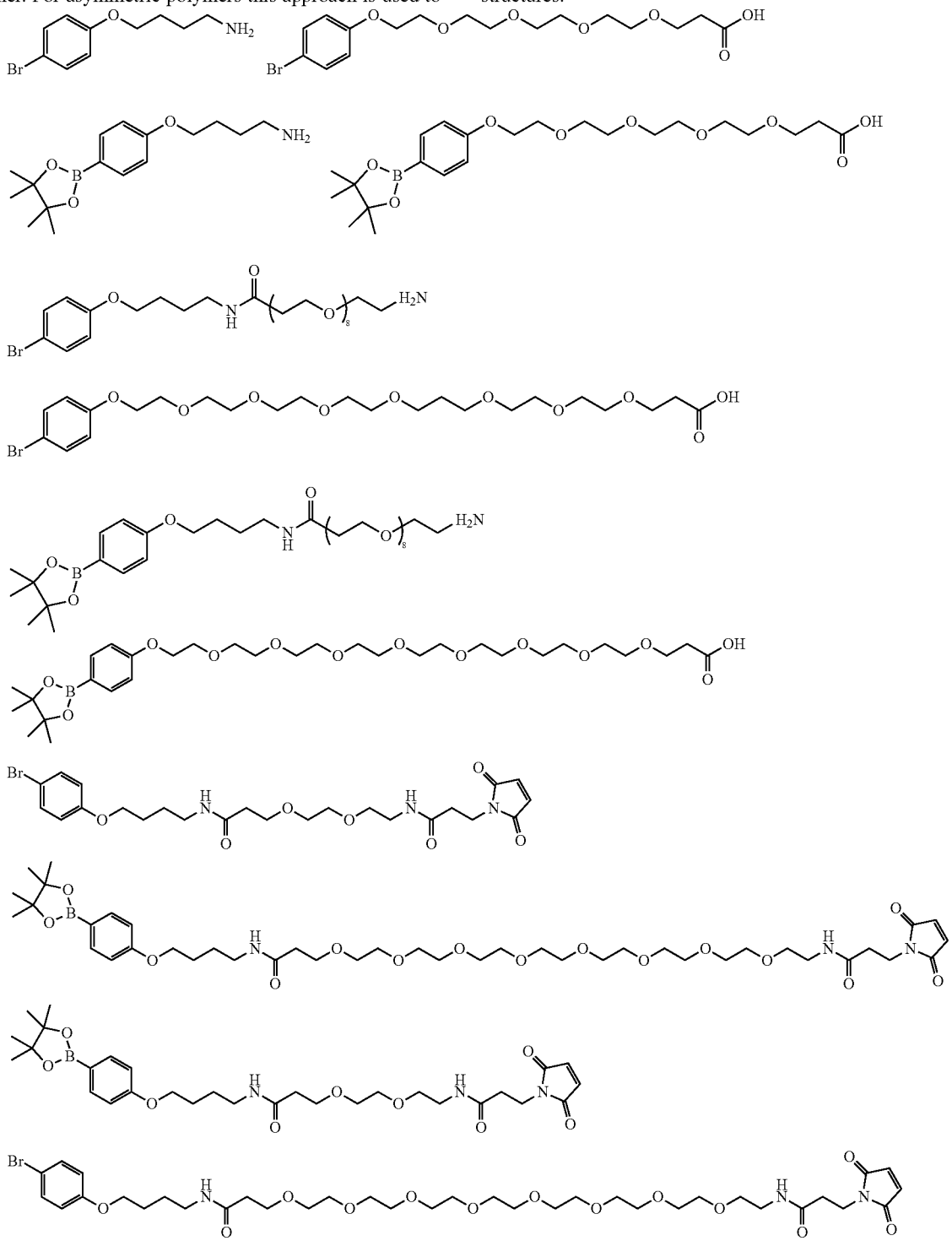

Further capping units can be found in structures 1-31 described herein or in the following Examples and methods for their attachment.

The incorporation of optional linkers into conjugated polymer backbones further described in U.S. application Ser. No. 11/868,870, filed Oct. 8, 2007 and published as U.S. Application No. 2008/0293164, which application is herein incorporated by reference in its entirety.

A desired optional linker incorporation can be achieved by varying the molar ratio of optional linker to bi-functional monomer. For example, an optional linker can be incorporated by substituting a percentage of one of the bi-functional monomers with a similar bi-functional optional linker which comprises the conjugation site of interest. The number and type of linking site included in the polymer is controlled by the feed ratio of the monomers to optional linker in the polymerization reaction. By varying the feed ratio, conjugated polymers can contain at least about 0.01 mol % of linker, L, and may contain at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or at least about 30 mol %. The conjugated polymers may contain up to 100 mol % of linker, L, and may contain about 99 mol % or less, about 90 mol % or less, about 80 mol % or less, about 70 mol % or less, about 60 mol % or less, about 50 mol % or less, or about 40 mol % or less. Linkers can be evenly or randomly distributed along the polymer main chain. In further embodiments, an optional linker can further allow covalent attachment of the resulting polymer to biomolecules, secondary reporters or other assay components.

In alternative embodiments, the methods described herein to incorporate optional linkers may be used in combination with methods of introducing capping units with linking sites to produce polymers with both internal and terminal linking sites for conjugation. A non-limiting application of a polymer with both optional linkers and terminal capping units with linking sites for conjugation are polymer-dye-biomolecule tandem conjugates where the polymer is used as an energy transfer donor, such as in FRET, to a secondary dye acceptor thus shifting the emission wavelength to that of the corresponding dye.

The person skilled in the art may further appreciate various syntheses and polymerization methods and embodiments of the present disclosure upon review of the following illustrative and non-limiting Examples.

Antigen-Antibody Interactions

The interactions between antigens and antibodies are the same as for other noncovalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Certain physical forces contribute to antigen-antibody binding, for example, the fit or complimentary of epitope shapes with different antibody binding sites. Moreover, other materials and antigens may cross-react with an antibody, thereby competing for available free antibody.

Measurement of the affinity constant and specificity of binding between antigen and antibody is a pivotal element in determining the efficacy of an immunoassay, not only for assessing the best antigen and antibody preparations to use but also for maintaining quality control once the basic immunoassay design is in place.

Antibodies

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain.

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The subunit structures and three-dimensional configurations of different classes of immunoglobulins are well known. Further details regarding antibody structure, function, use and preparation are discussed in U.S. Pat. No. 6,998,241, issued Feb. 14, 2006, the entire contents of which are incorporated herein by reference.

Sandwich Assays

Antibody or multiple antibody sandwich assays are well known to those skilled in the art including a disclosed in U.S. Pat. No. 4,486,530, issued Dec. 4, 1984, and references noted therein. The structures described in FIGS. 6, 7, 8, 9, 10 and 14 can be used directly as described or in various sandwich configurations including those described in Example 37. A sandwich configuration or a sandwich assay refers to the use of successive recognition events to build up layers of various biomolecules and reporting elements to signal the presence of a particular biomolecule, for example a target biomolecule or a target-associated biomolecule. A standard example of this would be the successive use of antibodies. In these assays, a primary antibody binds the target, the secondary antibody binds the primary, a third antibody can bind the secondary and so on. With each successive layer additional reporting groups can be added. Another strategy is using a repetitive addition of alternating layers of two (or more) mutually-recognizable components, or more than two components in a chain-recognition relationship, which comprise one or both of the components in a form of multimeric structure. In such a setup, one or more of the functional group(s) in each of the multimeric structure can be labeled with reporting group(s) and the unoccupied functional group(s) can serve as the recognition site for the other component(s), and this system will subsequently provide a platform for signal amplification. A typical example of this approach is the use of streptavidin-reporter conjugate and biotinylated anti-streptavidin antibody. In such assays, a biotinylated sensor molecule (nucleic acid or antibody) can be used to bind a target biomolecule, which is subsequently recognized by a detection system containing a streptavidin-reporter conjugate and biotinylated anti-streptavidin antibody. The sandwich structure in this case can be built up by successive rounds of biotinylated antibodies and labeled streptavidin complexes interaction to achieve the signal amplification. With an additional conjugation of a conjugated polymer to either the biotinylated antibody or the streptavidin-reporter complex, it is possible to further increase the signal output. In essence, the integration of a conjugated polymer in this type of signal amplification system can further amplify signals to a higher level.

Figure 14:
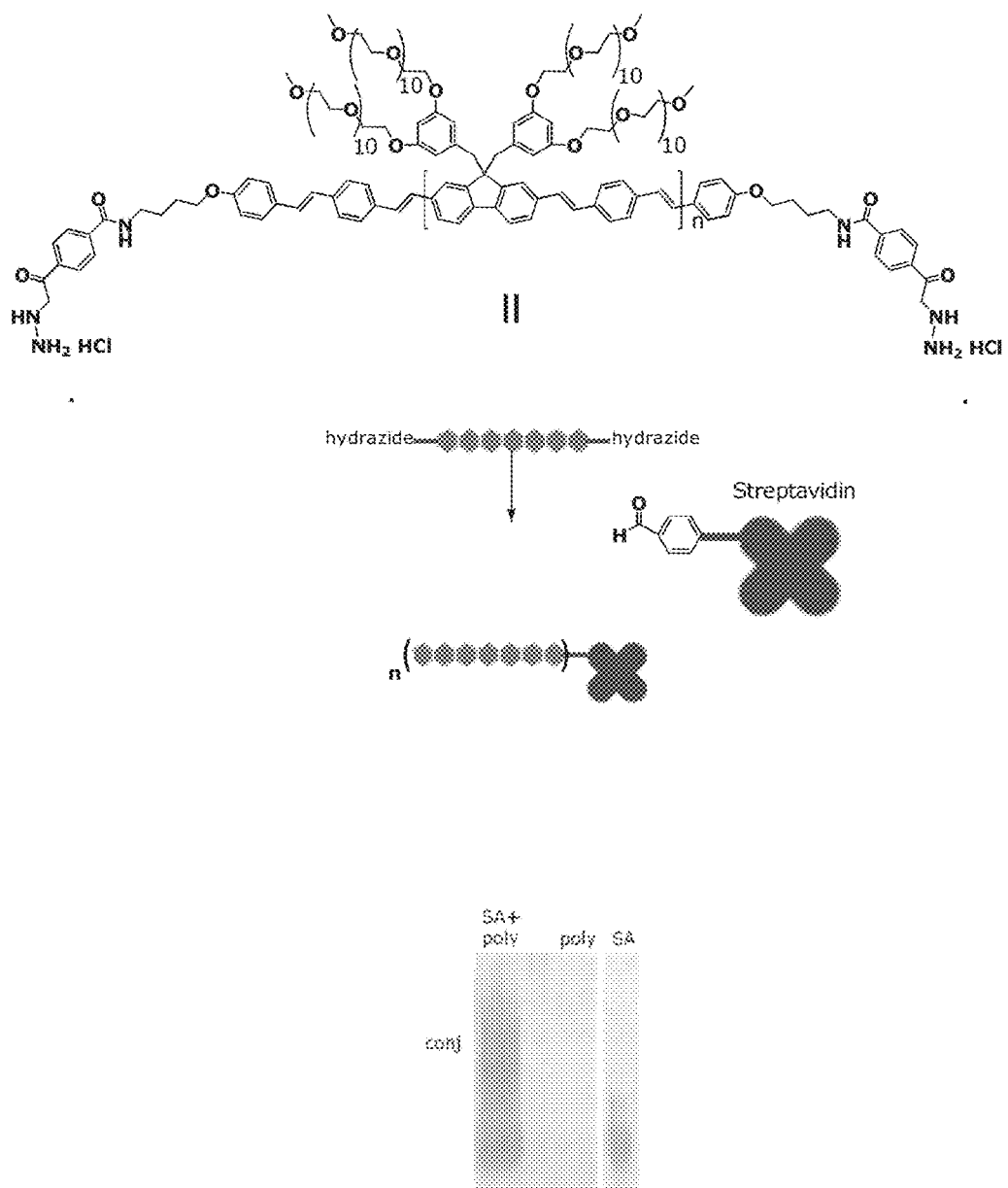
FIG. 14. Schematic of a streptavidin conjugation with a conjugated polymer and the resulting conjugate structure (top) and Coomassie stained agarose gel representative of the streptavidin-attached CP (below).

The bioconjugated polymer complexes described in FIGS. 6, 7, 8, 9, 10, 14, 15, 16 and 17 can be used to create optically enhanced sandwich assays by directly integrating a light harvesting conjugated polymer into commonly utilized recognition elements. The benefits of the conjugated polymer conjugated structures can also be applied directly to the primary target recognition elements without the need for successive recognition elements. For example, a primary antibody can be directly conjugated to polymer-dye complex such as shown in FIG. 14. Such a complex can be used to directly probe the presence of a target biomolecule.

Polynucleotides

Amplified target polynucleotides may be subjected to post amplification treatments. For example, in some cases, it may be desirable to fragment the target polynucleotide prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow the sensor polynucleotide to hybridize to the amplification product during at least part of an amplification cycle. When the assay is performed in this manner, real-time detection of this hybridization event can take place by monitoring for light emission during amplification.

Real time PCR product analysis (and related real time reverse-transcription PCR) provides a well-known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" Clin Chem 45(7):982-6; Laurendeau et al. (1999) "Quantitation of MYC gene expression in sporadic breast tumors with a real-time reverse transcription-PCR assay" Clin Chem 59(12):2759-65; and Kreuzer et al. (1999) "LightCycler technology for the quantitation of bcr/abl fusion transcripts" Cancer Research 59(13):3171-4, all of which are incorporated by reference).

Samples

In principle, a sample can be any material suspected of containing a target biomolecule (e.g., antibody, protein, affinity ligand, peptide, nucleic acid and the like) capable of causing excitation of a conjugated polymer complex. In some embodiments, the sample can be any source of biological material which comprises biomolecules that can be obtained from a living organism directly or indirectly, including cells, tissue or fluid, and the deposits left by that organism, including viruses, *mycoplasma*, and fossils. The sample may comprise a target biomolecule prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the target biomolecule or a surrogate therefore. A negative control sample can also be used which, although not expected to contain the target biomolecule, is suspected of containing it (via contamination of one or more of the reagents) or another component capable of producing a false positive, and is tested in order to confirm the lack of contamination by the target biomolecule of the reagents used in a given assay, as well as to determine whether a given set of assay conditions produces false positives (a positive signal even in the absence of target biomolecule in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

Organic Dyes

Organic dyes include signaling chromophores and fluorophores. In some embodiments, a signaling chromophore or fluorophore may be employed, for example to receive energy transferred from an excited state of an optically active unit, or to exchange energy with a labeled probe, or in multiple energy transfer schemes. Fluorophores useful in the inventions described herein include any substance which can absorb energy of an appropriate wavelength and emit or transfer energy. For multiplexed assays, a plurality of different fluorophores can be used with detectably different emission spectra. Typical fluorophores include fluorescent dyes, semiconductor nanocrystals, lanthanide chelates, and fluorescent proteins.

Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2 ®, Cy3 ®, Cy3.5®, Cy5®, Cy5.5®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimelhoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

Exemplary polynucleotide-specific dyes include acridine orange, acridine homodimer, actinomycin D, 7-aminoactmomycin D (7-AAD), 9-amino-6-chlor-2-methoxyacridine (ACMA), BOBO™-1 iodide (462/481), BOBO™-3 iodide (570/602), BO-PRO™-1 iodide (462/481), BO-PRO™-3 iodide (575/599), 4',6-diamidino-2-phenylindole, dihydrochloride (DAPI), 4',6-diamidino-2-phenylindole, dihydrochloride (DAPI), 4',6-diamidino-2-phenylindole, dilactate (DAPI, dilactate), dihydroethidium (hydroethidine), dihydroethidium (hydroethidine), dihydroethidium (hydroethidine), ethidium bromide, ethidium diazide chloride, ethidium homodimer-1 (EthD-1), ethidium homodimer-2 (EthD-2), ethidium monoazide bromide (EMA), hexidium iodide, Hoechst 33258, Hoechst 33342, Hoechst 34580, Hoechst S769121, hydroxystilbamidine, methanesulfonate, JOJO™-1 iodide (529/545), JO-PRO™-1 iodide (530/546), LOLO™-1 iodide (565/579), LO-PRO™-1 iodide (567/580), NeuroTrace™ 435/455, NeuroTrace™ 500/525, NeuroTrace™ 515/535, NeuroTrace™ 530/615, NeuroTrace™ 640/660, OliGreen, PicoGreen® ssDNA, PicoGreen® dsDNA, POPO™-1 iodide (434/456), POPO™-3 iodide (534/570), PO-PRO™-1 iodide (435/455), PO-PRO™-3 iodide (539/567), propidium iodide, RiboGreen®, SlowFade®, SlowFade® Light, SYBR® Green I, SYBR® Green II, SYBR® Gold, SYBR® 101, SYBR® 102, SYBR® 103, SYBR® DX, TO-PRO®-1, TO-PRO®-3, TO-PRO®-5, TOT™-1, TOTO®-3, YO-PRO®-1 (oxazole yellow), YO-PRO®-3, YOYO®-1, YOYO®-3, TO, SYTOX® Blue, SYTOX® Green, SYTOX® Orange, SYTO® 9, SYTO® BC, SYTO® 40, SYTO® 41, SYTO® 42, SYTO® 43, SYTO® 44, SYTO® 45, SYTO® Blue, SYTO® 11, SYTO® 12, SYTO® 13, SYTO® 14, SYTO® 15, SYTO® 16, SYTO® 20, SYTO® 21, SYTO® 22, SYTO® 23, SYTO® 24, SYTO® 25, SYTO® Green, SYTO® 80, SYTO® 81, SYTO® 82, SYTO® 83, SYTO® 84, SYTO® 85, SYTO® Orange, SYTO® 17, SYTO® 59, SYTO® 60, SYTO® 61, SYTO® 62, SYTO® 63, SYTO® 64, SYTO® Red, netropsin, distamycin, acridine orange, 3,4-benzopyrene, thiazole orange, TOMEHE, daunomycin, acridine, pentyl-TOTAB, and butyl-TOTIN. Asymmetric cyanine dyes may be used as the polynucleotide-specific dye. Other dyes of interest include those described by Geierstanger, B. H. and Wemmer, D. E., Annu. Rev. Vioshys. Biomol. Struct. 1995, 24, 463-493, by Larson, C. J. and Verdine, G. L., Bioorganic Chemistry: Nucleic Acids, Hecht, S. M., Ed., Oxford University Press: New York, 1996; pp 324-346, and by Glumoff, T. and Goldman, A. Nucleic Acids in Chemistry and Biology, $2^{nd}$ ed., Blackburn, G. M. and Gait, M. J., Eds., Oxford University Press: Oxford, 1996, pp 375-441. The polynucleotide-specific dye may be an intercalating dye, and may be specific for double-stranded polynucleotides.

The term "fluorescent protein" includes types of protein known to absorb and emit light. One of the more commonly used classes of such materials are phycobiliproteins. Examples include but are not limited to phycoerythrin (PE and R-PE), allophycocyanin (APC) and PerCP. Other classes include green fluorescent protein and related versions.

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R. et al. (1994) Proc. Natl. Acad. Sci. USA 91:12501-12504; Heim, R. et al. (1995) Nature 373: 663-664). Delgrave et al. isolated mutants of cloned *Aequorea victoria* GFP that had red-shifted excitation spectra. Bio/Technology 13:151-154 (1995). Heim, R. et al. reported a mutant (Tyr66 to His) having a blue fluorescence (Proc. Natl. Acad. Sci. (1994) USA 91:12501-12504).

Substrates

In some embodiments, an assay component can be located upon a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethyleneco-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

Polynucleotide or polypeptide probes can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl. No. PCT/US93/04145 and pin based methods such as those described in U.S. Pat. No. 5,288,514.

Additional flow channel or spotting methods applicable to attachment of sensor polynucleotides or polypeptides to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Excitation and Detection

Any instrument that provides a wavelength that can excite the conjugated polymer complex and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of the signaling chromophore upon excitation of the conjugated polymer.

Compositions of Matter

Also provided are compositions of matter of any of the molecules described herein in any of various forms. The conjugated polymers and complexes including conjugated polymers as described herein may be provided in purified and/or isolated form. The conjugated polymers and complexes including conjugated polymers may be provided in either crystalline or amorphous form.

The conjugated polymers and complexes including conjugated polymers may be provided in solution, which may be a predominantly aqueous solution, which may comprise one or more of the additional solution components described herein, including without limitation additional solvents, buffers, biomolecules, polynucleotides, fluorophores, etc. In addition, a mixture of CPs in solution is also able to provide improved detection sensitivity as compared to that for a single CP/dye system. The conjugated polymers and complexes including conjugated polymers can be present in solution at a concentration at which a first emission from the first optically active units can be detected in the absence of biomolecule target or a biomolecule associated therewith. The solution may comprise additional components as described herein, including labeled probes such as fluorescently labeled antibodies or polynucleotides, specific for a species or a class of biomolecule target or a biomolecule associated therewith for the conjugated polymers and complexes including conjugated polymers.

The conjugated polymers and complexes including conjugated polymers may be provided in the form of a film. The compositions of matter may be claimed by any property described herein, including by proposed structure, by method of synthesis, by absorption and/or emission spectrum, by elemental analysis, by NMR spectra, or by any other property or characteristic.

In some embodiments expression of a gene is detected in a sample. In a further embodiment identification of a cell marker or cell type is detected in a sample either in a flow cytometer, cell sorter, microscope, plate reader or fluorescence imager. In a further embodiment the identification of cell type or marker is used in the diagnosis of lymphoma or other circulating cancers. In a further embodiment the identification of cell type or marker is used in the diagnosis and monitoring of HIV infection. In a further embodiment the identification of cell type or marker is used to sort cells for therapeutic application. In a further embodiment, a measured result of detecting a biomolecule target or a biomolecule associated therewith can be used to diagnose a disease state of a patient. In yet another embodiment the detection method of the invention can further include a method of diagnosing a disease state. In a related embodiment, the method of diagnosing a disease can include reviewing or analyzing data relating to the presence of a biomolecule target or a biomolecule associated therewith and providing a conclusion to a patient, a health care provider or a health care manager, the conclusion being based on the review or analysis of data regarding a disease diagnosis. Reviewing or analyzing such data can be facilitated using a computer or other digital device and a network as described herein. It is envisioned that information relating to such data can be transmitted over the network.

In practicing the methods of the present invention, many conventional techniques in molecular biology are optionally utilized. These techniques are well known and are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5$^{th}$ Ed., John Wiley & Sons, Inc. (2002), Sambrook et al., Molecular Cloning: A Laboratory Manual, 3rd Ed., Cold Spring Harbor Laboratory Press (2000), Innis et al. (Eds.) PCR Protocols: A Guide to Methods and Applications, Elsevier Science & Technology Books (1990), and Greg T. Hermanson, Bioconjugate Techniques, 2$^{nd}$ Ed., Academic Press, Inc. (2008) all of which are incorporated herein by reference.

Figure 12:
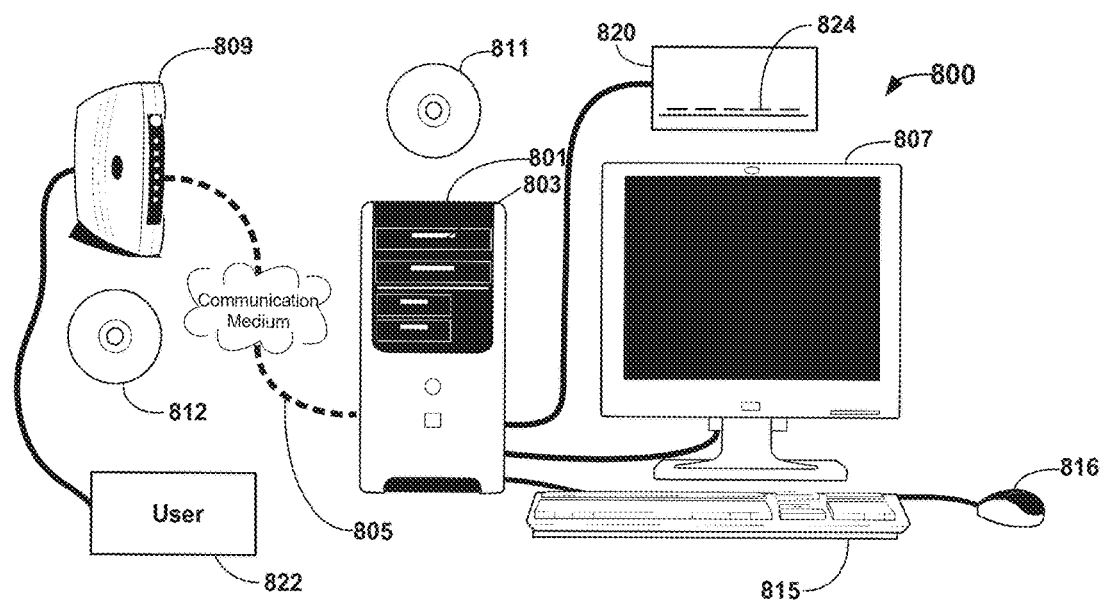
FIG. 12. Block diagram showing a representative example logic device.

FIG. 12 is a block diagram showing a representative example logic device through which reviewing or analyzing data relating to the present invention can be achieved. Such data can be in relation to a disease, disorder or condition in a subject. FIG. 12 shows a computer system (or digital device) 800 connected to an apparatus 820 for use with the conjugated polymers or conjugated polymers complexes 824 to, for example, produce a result. The computer system 800 may be understood as a logical apparatus that can read instructions from media 811 and/or network port 805, which can optionally be connected to server 809 having fixed media 812. The system shown in FIG. 12 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. It is envisioned that data relating to the present invention can be transmitted over such networks or connections.

In one embodiment, a computer-readable medium includes a medium suitable for transmission of a result of an analysis of a biological sample. The medium can include a result regarding a disease condition or state of a subject, wherein such a result is derived using the methods described herein.

Kits

Kits comprising reagents useful for performing described methods are also provided.

In some embodiments, a kit comprises reagents including conjugated polymers or conjugated polymers complexes, bioconjugates, for example, antibodies, nucleic acids, and other components as described herein.

The kit may optionally contain one or more of the following: one or more labels that can be incorporated into conjugated polymers or conjugated polymers complexes; and one or more substrates which may or may not contain an array, etc.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target biomolecules or biomolecules associated therewith.

Figure 13:
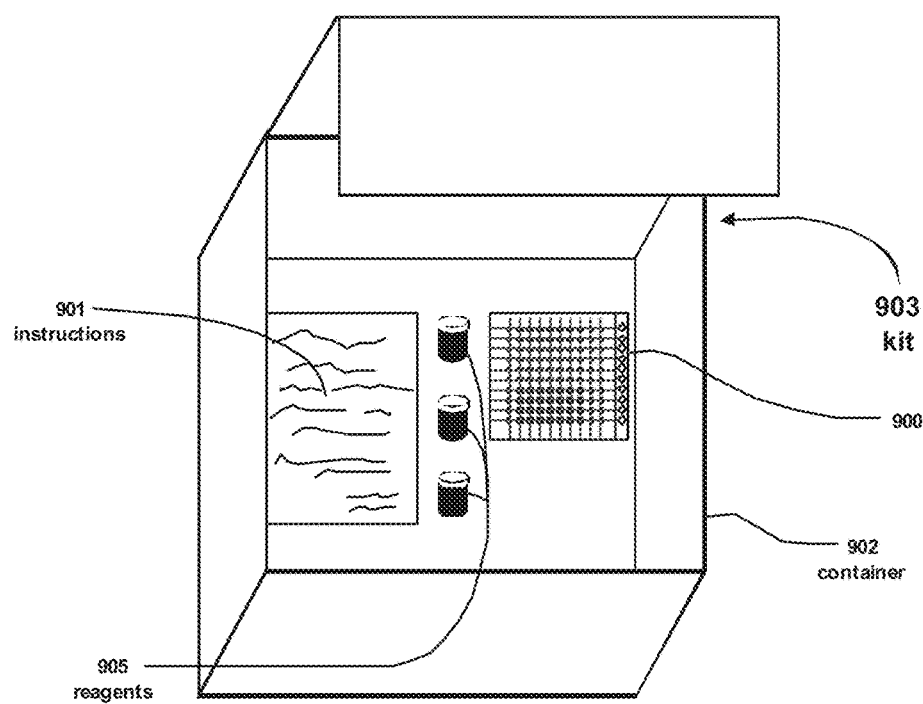
FIG. 13. Block diagram showing a representative example of a kit.

As described herein and shown in FIG. 13, in certain embodiments a kit 903 can include a container or housing 902 for housing various components. As shown in FIG. 13, and described herein, in one embodiment a kit 903 comprising one or more conjugated polymers or conjugated polymers complexes reagents 905, and optionally a substrate 900 is provided. As shown in FIG. 13, and described herein, the kit 903 can optionally include instructions 901. Other embodiments of the kit 903 are envisioned wherein the components include various additional features described herein.

EXAMPLES

The following examples provide illustrative methods for making and testing the effectiveness of the conjugated polymers described herein. These examples are provided for illustrative purposes only and not to limit the scope of the claims provided herein. All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit and scope of the claims. All such similar substitutes and modifications apparent to those skilled in the art are deemed to be within the spirit, scope and concept of the appended claims.

Example 1: Synthesis of a Polymer of Formula (I)

Example 1a: Synthesis of Monomers, 2,7-dibromo-9,9-di(2',5',8',11',14',17',23',26',29',32',35'-dodecaoxaoctatriacontan-38'-yl)fluorene (A) and 9,9-di(2',5',8',11',14',17',20',23',26',29',32',35'-dodecaoxaoctatriacontan-38'-yl)-2,7-di(4",4",5",5"-tetramethyl-1",3",2"-dioxaborolanyl)fluorene (B) for Subsequent Polymerization

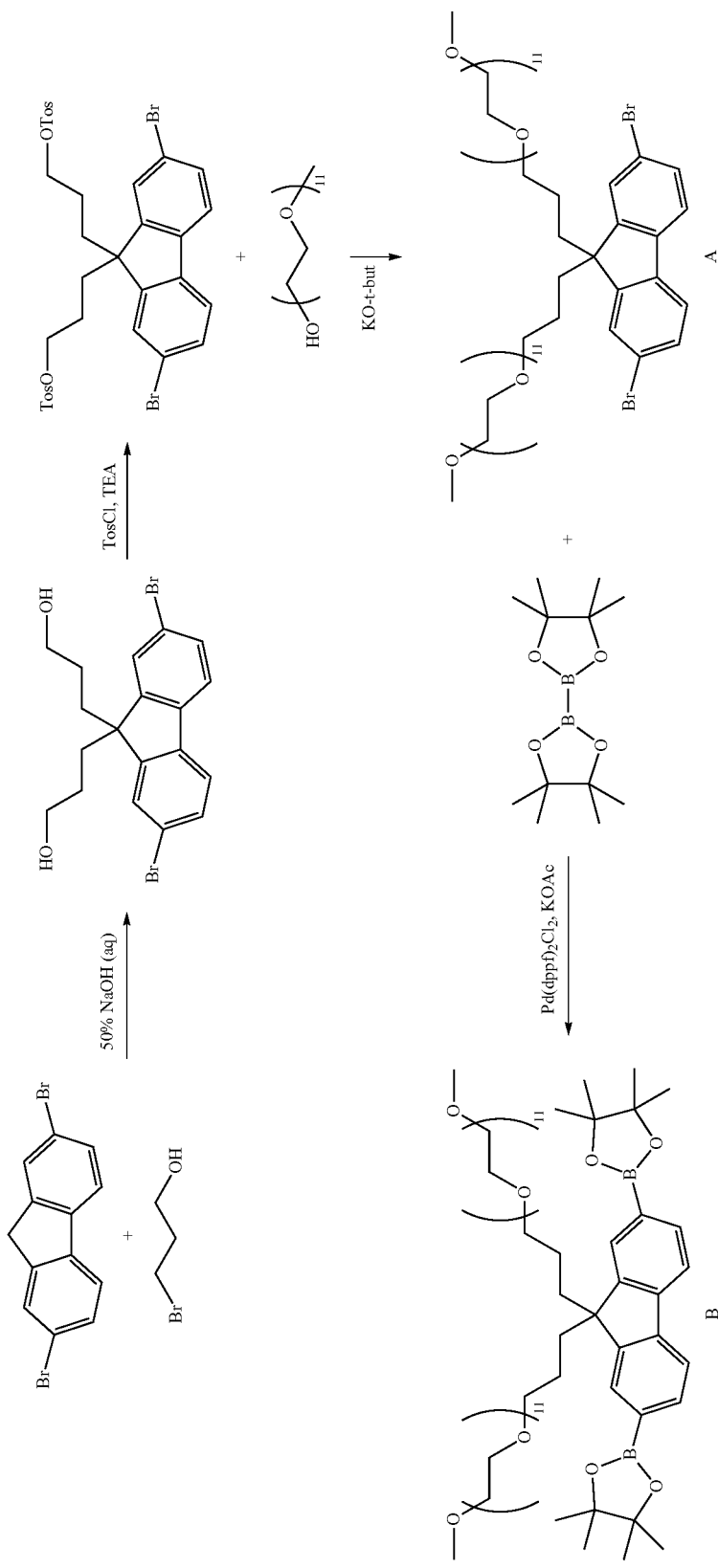

Step 1: 2,7-dibromo-9,9-di(3'-hydroxypropanyl)fluorene 2,7-dibromofluorene (9.72 g, 30 mmol), tetrabutylammonium bromide (300 mg, 0.93 mmol), and DMSO (100 mL) were added to a 3-neck flask under nitrogen(g), followed by the addition of 50% NaOH (15 mL, 188 mmol) via syringe. The mixture was heated to 80° C., and 3-bromopropanol (6.70 mL, 77 mmol) was added dropwise via addition funnel, and the reaction mixture was stirred at 80° C. for another 2 hours. Upon completion, the mixture was cooled to room temperature and quenched with water (250 mL). The aqueous layer was extracted with ethyl acetate (3 150 mL portions). The organic layers were combined, washed with water, then dried over MgSO₄, and filtered. The solvent was removed and the residual was recrystallized in chloroform to yield pale yellow needle crystals (9.20 g, 70%).

Step 2: 2,7-dibromo-9,9-di(3'-methylbenzenesulfonatopropanyl)fluorene 2,7-dibromo-9,9-di(3'-hydroxypropanyl)fluorene (500 mg, 1.14 mmol) was dissolved in dichloromethane (5 mL) at 0° C. under nitrogen(g). To the mixture, added p-toluenesulfonyl chloride (650 mg, 3.40 mmol), followed by pyridine (0.39 mL, 4.77 mmol). Allowed reaction to stir at 0° C. and naturally rise to room temperature over night. The reaction was quenched with water (15 mL). Removal of solvent by vacuo resulted solids formation. Filtered off solids to yield white solids (758 mg, 89%).

Step 3: 2,7-dibromo-9,9-di(2',5',8',11',14',17',23',26',29',32',35'-dodecaoxaoctatriacontan-38'-yl)fluorene (A)

mPEG11 alcohol (770 mg, 1.49 mmol) was dissolved in anhydrous THF (2 mL) at 0° C. under nitrogen. To the mixture, was added potassium tert-butoxide (1.63 mmol, 1.63 mL, 1M in THF). After 10 min stirring, 2,7-dibromo-9,9-di(3'-methylbenzenesulfonatopropanyl)fluorene (504 mg, 0.673 mmol) in 10 mL of THF was added via a syringe. The mixture was allowed to room temperature and stirred overnight. The reaction mixture was diluted with THF. The insoluble inorganic salt was removed by filtration. Concentration of the filtrate yielded crude product, which was purified by column chromatography (DCM-MeOH) to yield a colorless oil (605 mg, 62.5%).

Step 4: 9,9-di(2',5',8',11',14',17',20',23',26',29',32',35'-dodecaoxaoctatriacontan-38'-yl)-2,7-di(4'',4'',5'',5''-tetramethyl-1'',3'',2''-dioxaborolanyl)fluorene (B)

2,7-dibromo-9,9-di(2',5',8',11',14',17',23',26',29',32',35'-dodecaoxaoctatriacontan-38'-yl)fluorene (1.510 g, 1.501 mmol), bis(pinacolato)diboron (800 mg, 3.15 mmol), potassium acetate (619 mg, 6.31 mmol), Pd(dppf)Cl₂ [1,1'-Bis(diphenylphosphino)ferrocene]dichloropalladium(II)] (51.5 mg, 0.063 mmol) and DMSO (30 mL) were mixed under N₂. The mixture was heated at 80° C. for 5.5 hour. Upon completion, the DMF was distilled and water (50 mL) was added. The product was extracted with DCM (3×40 mL). The organic layers were combined and concentrated. The crude product was purified by column chromatography (DCM-MeOH) to give colorless oil (1.015 g, 63%).

Example 1b: Polymerization of Monomers (A) and (B)

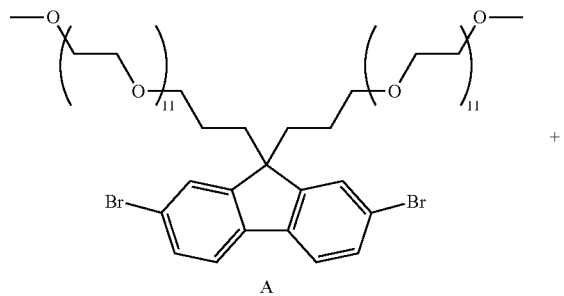

A

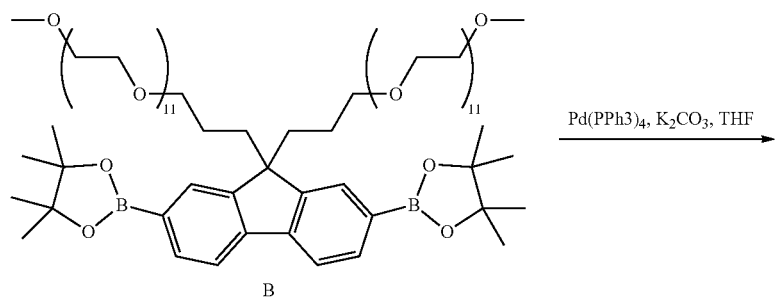

B

Pd(PPh3)₄, K₂CO₃, THF

-continued

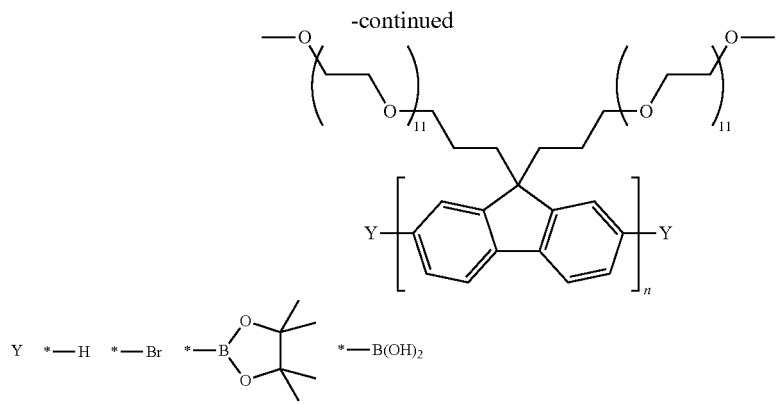

Y  *—H   *—Br   *—B(pinacol)   *—B(OH)₂

2,7-dibromo-9,9-di(2',5',8',11',14',17',23',26',29',32',35'-dodecaoxaoctatriacontan-38'-yl)fluorene (A) (0.084 mmol, 120 mg), 9,9-di(2',5',8',11',14',17',20',23',26',29',32',35'-dodecaoxaoctatriacontan-38'-yl)-2,7-di(4",4",5",5"-tetramethyl-1",3",2"-dioxaborolanyl)fluorene (B) (0.088 mmol, 135 mg), and palladium tetra(triphenylphosphine) (0.0035 mmol, 4 mg) were combined in a round bottom flask equipped with a stirbar. Next, 0.35 mL of 2M potassium carbonate (aq) and 1.9 mL of tetrahydrofuran were added and the flask is fitted with a vacuum adaptor and put on a Schlenk line. The mixture was degassed using 3 freeze-pump-thaw cycles. The degassed mixture was heated to 80° C. under nitrogen with vigorous stirring for 18 hours. The reaction mixture was then cooled and the solvent removed with rotary evaporation. The resulting semisolid was diluted with ca. 50 mL water and filtered through glass fiber filter paper. Ethanol was added to adjust the solvent to 20% ethanol in water. Preparative gel permeation chromatography was performed with G-25 desalting medium to remove excess salts from the polymer. Solvent in the fractions was removed with rotary evaporation and 100 mg of poly[2,7{9,9-bis (2,5,8,11,14,17,20,23,26,29,32,35-dodecaoxaoctatriacontane)fluorene] was collected as an amber oil.

Example 2: Synthesis of Asymmetric Polymers of Formula (I) Via Suzuki Coupling

Example 2a: Synthesis of Asymmetric Monomer, 2-bromo-9,9-di(2',5',8',11',14',17',20',23',26',29',32',35'-dodecaoxaoctatriacontan-38'-yl)-7-(4",4",5",5"-tetramethyl-1",3",2"-dioxaborolan-2-yl)fluorene (C) for Subsequent Polymerization

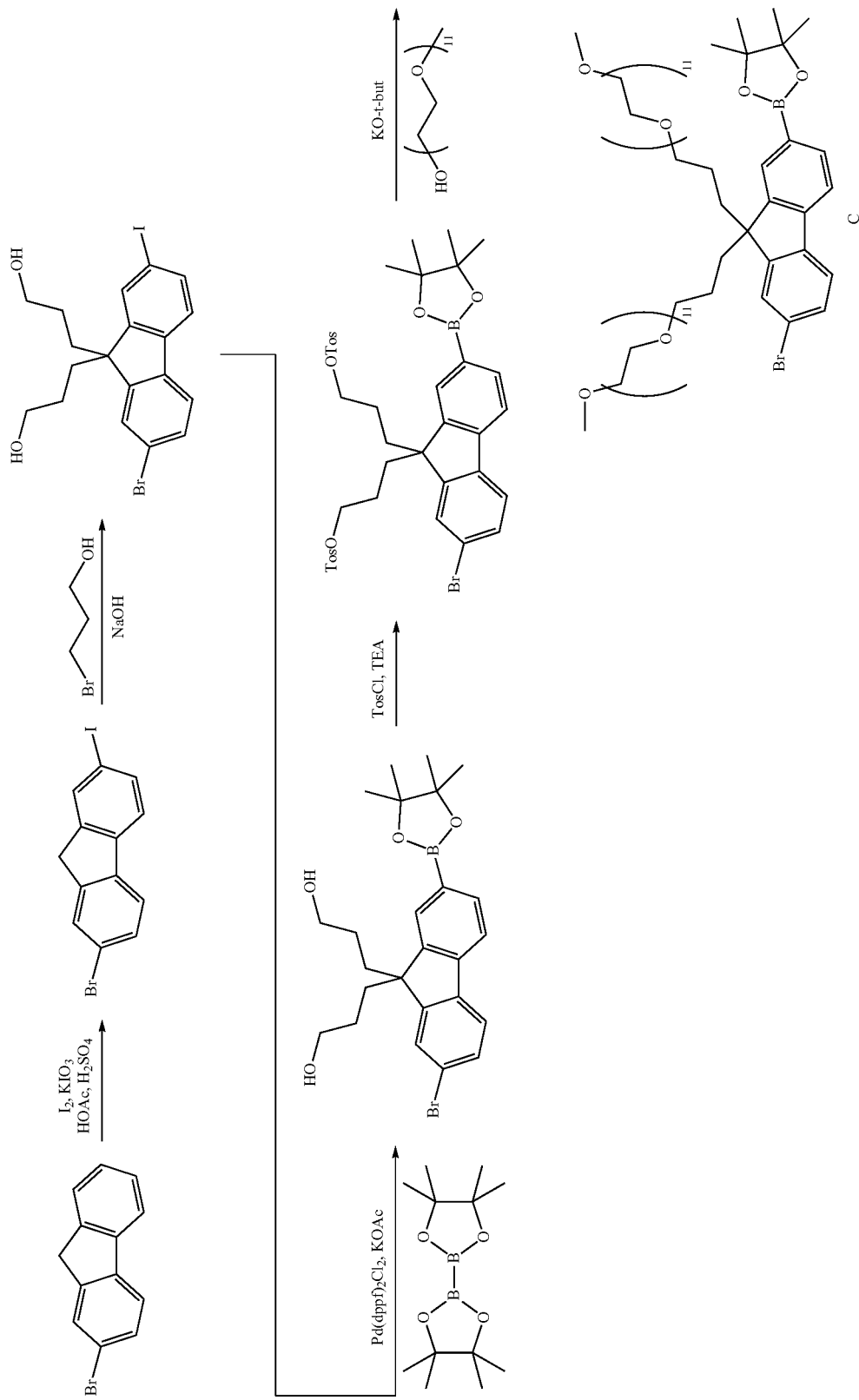

Step 1: 2-dibromo-7-iodofluorene 2-bromofluorene (10.01 g, 40.84 mmol), acetic acid (170 mL), water (8 mL), iodine (4.34 g, 17.20 mmol), potassium iodate (2.18 g, 10.19 mmol) and sulfuric acid (4 mL) were mixed under nitrogen. The resulting mixture was heated at 80° C. for 2 h and cooled to room temperature. The formed precipitate which is the desired product was collected after filtration and acetic acid wash (13.68 g, 90%).

Step 2: 2-dibromo-9,9-di(3'hydroxypropanyl)-7-iodofluorene 2-dibromo-7-iodofluorene (2.186 g, 5.892 mmol), tetrabutylammonium bromide (60 mg, 0.186 mmol), and DMSO (25 mL) were added to a 3-neck flask under nitrogen(g), followed by the addition of 50% NaOH (4 mL, 50 mmol) via syringe. The mixture was heated to 80° C., and 3-bromopropanol (1.33 mL, 14.7 mmol) was added slowly, and the reaction was stirred at 80° C. for another 1 hour. Upon completion, the mixture was cooled to room temperature and quenched with water. The precipitate as crude product was collected after filtration. The crude product was purified by column chromatography (eluant: hexane-ethylacetate) to give pale yellow solid (2.15 g, 75%).

Step 3: 2-bromo-9,9-di(3'-hydroxypropanyl)-7-(4",4",5",5"-tetramethyl-1",3",2"-dioxaborolan-2-yl)fluorene 2-dibromo-9,9-di(3'hydroxypropanyl)-7-iodofluorene (2.454 g, 5.037 mmol), bis(pinacolato)diboron (1.407 g, 5.541 mmol), potassium acetate (1.483 g, 15.11 mmol), Pd(dppf)Cl$_2$ (123 mg, 0.15 mmol) and DMSO (25 mL) were mixed under N$_2$. The mixture was heated at 80° C. for 1.5 hour. Upon completion, the mixture was cooled to room temperature and quenched with water (50 mL). The product was extracted with DCM (3×40 mL). The organic layers were combined and concentrated. The crude product was purified by column chromatography (eluant: hexane-ethylacetate) to give pale solid (2.09 g, 85%).

Step 4: 2-bromo-9,9-di(3'-methanesulfanotopropanyl)-7-(4",4",5",5"-tetramethyl-1",3",2"-dioxaborolan-2-yl)fluorene 2-bromo-9,9-di(3'-hydroxypropanyl)-7-(4",4",5",5"-tetramethyl-1",3",2"-dioxaborolan-2-yl)fluorene (2.280 g, 4.694 mmol) and p-toluenesulfonyl chloride (2.684 g, 14.08 mmol) were dissolved in dichloromethane at room temperature under N$_2$. Triethylamine (3.95 mL, 28.2 mmol) was added slowly via syringe. The mixture was stirred at room temperature over night. The mixture was then concentrated and purified by column chromatography (Hexane-EtOAc) to yield pale solid (2.66 g, 72%).

Step 5: 2-bromo-9,9-di(2',5',8',11',14',17',20',23',26',29',32',35'-dodecaoxaoctatriacontan-38'-yl)-7-(4",4",5",5"-tetramethyl-1",3",2"-dioxaborolan-2-yl)fluorine (C)

mPEG11 alcohol (3.331 g, 6.448 mmol) was dissolved in anhydrous THF (20 mL) at 0° C. under nitrogen. To the mixture, was added potassium tert-butoxide (7.74 mmol, 7.74 mL, 1M in THF). After 10 min stirring, 2-bromo-9,9-di(3'-methanesulfanotopropanyl)-7-(4",4",5",5"-tetramethyl-1",3",2"-dioxaborolan-2-yl)fluorine (2.052 g, 2.579 mmol) in 20 mL of anhydrous THF was added via a syringe. The mixture was allowed to room temperature and stirred overnight. After evaporation of THF, brine (50 mL) was added and crude product was extracted with dichloromethane (3×40 mL). The combined organic layers were concentrated and purified by column chromatography (DCM-isopropanol) to give colorless gel-like product (2.164 g, 57%).

Example 2b: Synthesis of an Asymmetric Polymer Via Suzuki Coupling Polymerization

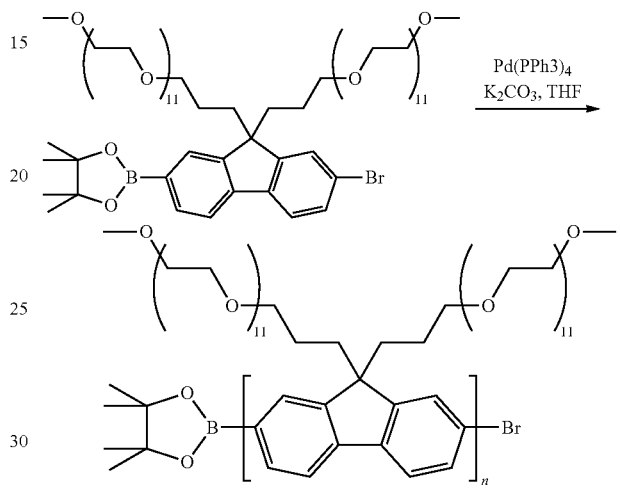

Asymmetric polymers are synthesized using conditions similar to polymerization conditions as described in Example 1b.

Example 3: Synthesis of a Linker or Capping Unit

Example 3a: Synthesis of Linker or Capping Unit, Tert-butyl 4-(3,5-dibromophenoxy)butylcarbamate

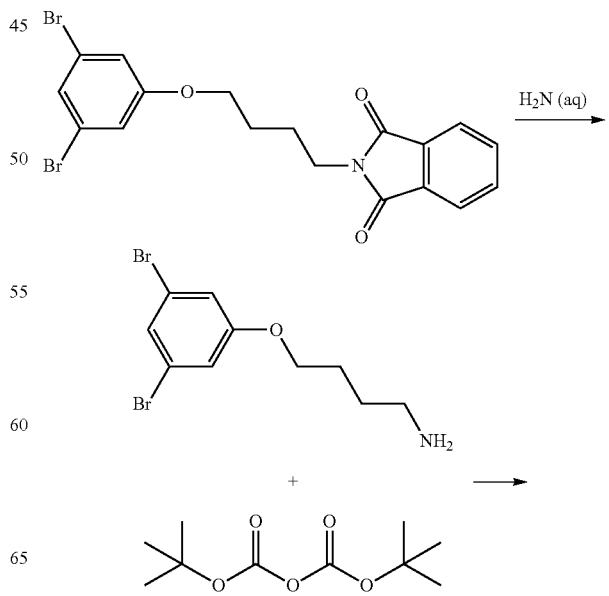

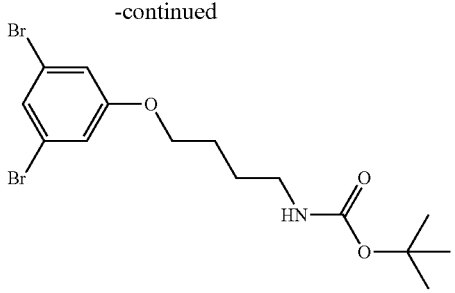

Step 1: 4-(3,5-dibromophenoxy)butan-1-amine 1-(4'-phthalimidobutoxy)3,5-dibromobenzene (1.0 g, 2.20 mmol) was dissolved in ethanol (45 mL) for 5 minutes under nitrogen. Hydrazine monohydrate (610 mg, 12.1 mmol) was added and the reaction was refluxed at 80° C. for 2 hours. To the reaction aqueous 1M HCl (17.7 mL, 17.7 mmol) was added and refluxed at 105° C. for another 2 hours. The aqueous layer was extracted with dichloromethane (2×150 mL). The organic layers were combined, washed with saturated NaHCO₃ (3×), water, and brine, then dried over MgSO₄, and filtered. Removal of solvent yielded a yellow oil (560 mg, 78%).

Step 2: Tert-butyl 4-(3,5-dibromophenoxy)butylcarbamate 4-(3,5-dibromophenoxy)butan-1-amine (397 mg, 1.23 mmol) was dissolved in anhydrous THF (24.6 mL) under nitrogen. Di-tert-butyl dicarbonate (423 mL, 1.84 mmol) was added to the mixture and refluxed reaction at 40° C. for 2 hours. After extraction of the reaction with dichloromethane (2×50 mL), the organic layers were combined, washed with saturated NaHCO₃, water, and brine, then dried over MgSO₄, and filtered. The solvent is removed and the residue is purified by column chromatography (9:1, hexanes: EtOAc) to give a white solid (306 mg, 59%).

Example 3b: Synthesis of Linker or Capping Unit, Tert-butyl-4-(2,7-dibromo-9-methyl-9H-fluoren-9-yl)butylcarbamate

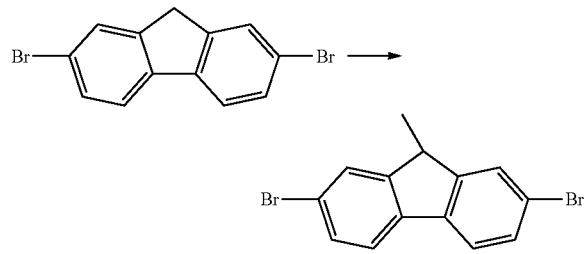

Step 1: 2,7-dibromo-9-methyl-9H-fluorene 2,7-dibromofluorene (30 g, 92.59 mmol) was dissolved in anhydrous THF (300 mL) under nitrogen and cooled to −78° C. To solution at −78° C., added n-butyllithium (40.36 mL, 100.9 mmol) over 5 minutes and allowed reaction stir for another 10 minutes. To reaction, then add methyl iodide (6.29 mL, 100.9 mmol) and allowed reaction to stir at −78° C. for 2.0 hours. The reaction was poured into a mixture of dichloromethane and water. The organic layer was collected, and the water layer was further extracted with dichloromethane. Combined all organic layers and removed solvent via vacuo. The crude material was triturated with hexanes and filtered using Buchner funnel to give white solids (22 g, 70%). ¹H NMR (500 MHz, CDCl₃): δ=7.62 (s, 2H), 7.56-7.58 (d, 2H), 7.48-7.50 (dd, 2H), 3.90-3.94 (q, 1H), 1.49-1.51 (d, 3H).

Step 2: 2-(4-(2,7-dibromo-9-methyl-9H-fluoren-9-yl)butyl)isoindoline-1,3-dione 2,7-dibromo-9-methyl-9H-fluorene (10.0 g, 29.58 mmol) was dissolved in 50 mL DMSO under nitrogen. To mixture was added KOH (2.01 g, 35.79 mmol), water (1.5 mL), N-(4-bromobutyl)phthalimide (9.93 g, 35.2 mmol), and stirred reaction at room temperature for 2.0 hours, then at 50° C. for 3.0 hours. The reaction was cooled to room temperature and diluted with dichloromethane. The organic layer was washed with brine (2×), and water. Removal of solvent yield a solid, which was purified by column chromatography (7:3, hexanes:EtOAc) to yield white solids (3.08 g, 20%). ¹H NMR (500 MHz, CDCl₃): δ=7.81-7.83 (m, 2H), 7.68-7.71 (m, 2H), 7.48-7.51 (m, 4H), 7.41-7.44 (dd, 2H), 3.46-3.49 (t, 2H), 2.00-2.04 (p, 2H), 1.47-1.49 (m, 2H), 1.45 (s, 3H), 0.65-0.68 (m, 2H).

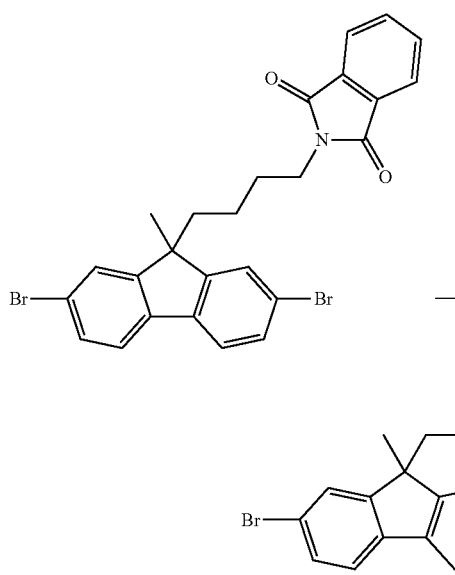

Step 3: 4-(2,7-dibromo-9-methyl-9H-fluoren-9-yl)butan-1-amine 2-(4-(2,7-dibromo-9-methyl-9H-fluoren-9-yl)butyl)isoindoline-1,3-dione (3.08, 5.71 mmol) was dissolved in ethanol (250 mL) under nitrogen. To the mixture was added hydrazine monohydrate (2.77 mL, 57.1 mmol), and the reaction was refluxed at 80° C. for 3.0 hours. The reaction was cooled to room temperature, and added 1M HCl (~100 mL). The mixture was stirred for 30 minutes or until all solids were dissolved. Dichloromethane was added to the solution and the organic layer was extracted with saturated NaHCO₃ three times, and washed with water. The organic layers were collected and removed solvent by vacuo to give an yellow oil (2.33 g, 100%). $^1$H NMR (500 MHz, CD$_2$Cl$_2$): δ=7.57 (d, 2H), 7.52 (d, 2H), 7.46-7.48 (dd, 2H), 2.39-2.42 (t, 2H), 1.95-1.98 (t, 2H), 1.44 (s, 3H), 1.17-1.23 (m, 2H), 0.59-0.65 (m, 2H).

Step 4: tert-butyl-4-(2,7-dibromo-9-methyl-9H-fluoren-9-yl)butylcarbamate 4-(2,7-dibromo-9-methyl-9H-fluoren-9-yl)butan-1-amine (2.39 g, 5.84 mmol) was dissolved in anhydrous THF (20 mL) under nitrogen. To solution, was added di-tert-butyl-dicarbonate (2.01 mL, 8.76 mmol), and the reaction was stirred at 40° C. for 3 hours. The reaction was cooled to room temperature and concentrated via vacuo. Crude solids were triturated with hexanes and filtered using buchner funnel to yield the desired white solids (2.34 g, 79%). $^1$H NMR (500 MHz, CDCl$_3$): δ=7.53 (d, 2H), 7.45-7.47 (d, 4H), 4.30 (s, 1H), 2.88-2.90 (q, 2H), 1.93-1.96 (t, 2H), 1.43 (s, 3H), 1.41 (s, 9H), 1.25-1.28 (m, 2H), 0.59-0.66 (m, 2H).

Example 4: Synthesis of a Linker or Capping Unit

Example 4a: Synthesis of Tert-butyl 4-(4-bromophenoxy)butylcarbamate

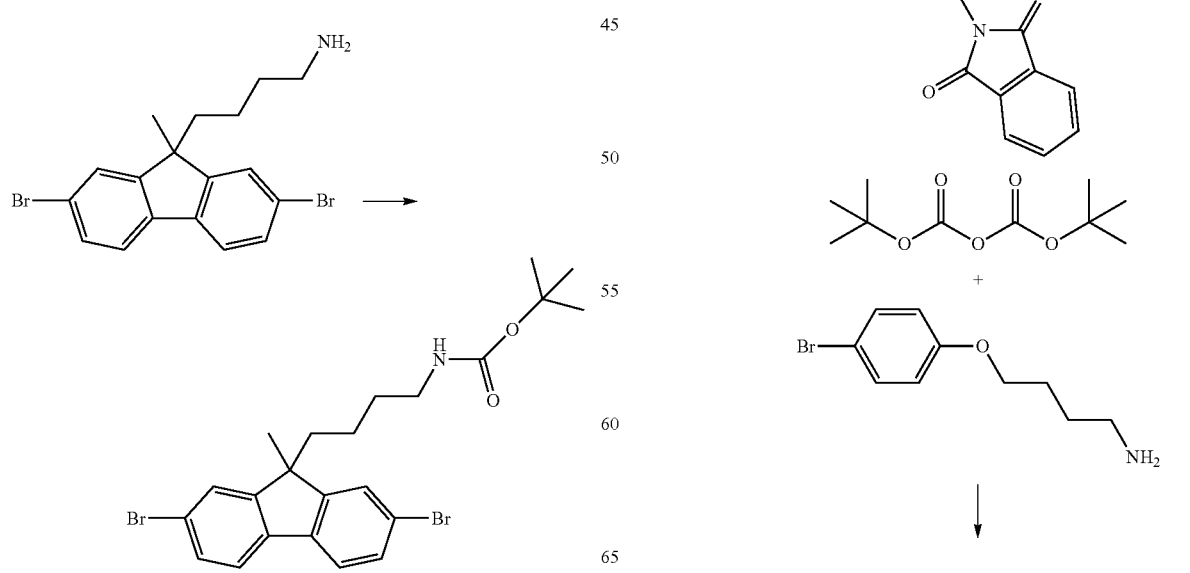

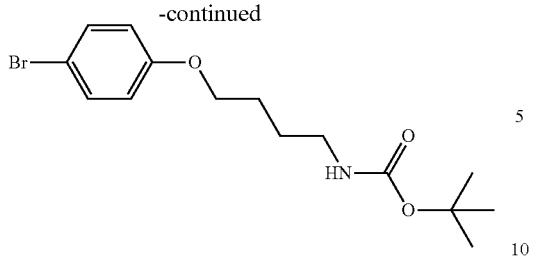

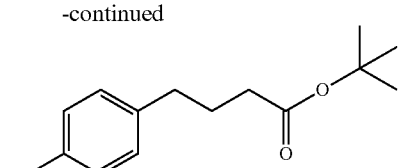

Step 1: N(4-(4-bromophenoxy)butyl)phthalimide

Combined 4-bromophenol (4.64 g, 26.8 mmol), N-(4-bromobutylphthalimide) (6.30 g, 22.33 mmol), K$_2$CO$_3$ (11.09 g, 80.38 mmol), 18-crown-6 (265 mg, 1.00 mmol), and acetone (100 mL), and refluxed reaction under nitrogen at 70° C. over night. The reaction was cooled to room temperature and removed solvent by vacuum. The crude mixture was diluted with dichloromethane (200 mL) and washed with water (3×), then dried over MgSO$_4$, and filtered. Removal of solvent, followed by trituration with hexanes, and filtered using Buchner funnel to yield a white solid (6.03 g, 71%).

Step 2: 4-(4-bromophenoxy)butan-1-amine

N(4-(4-bromophenoxy)butyl)phthalimide (6.01 g, 16.1 mmol) is dissolved in ethanol (200 mL) under nitrogen, followed by the addition of hydrazine monohydrate (7.8 mL, 161 mmol). The reaction was refluxed at 80° C. for 2 hours. Once reaction completed (solids formed at the top layer), cooled reaction to room temperature and neutralized with 1M HCl (50 mL). The mixture is allowed to stir until all solids are completely dissolved and diluted with dichloromethane (150 mL). The solution was extracted with two portions of saturated NaHCO$_3$ (2×). The organic layers were combined, washed with brine and water, then dried over MgSO$_4$, and filtered. Removal of solvent yields a yellow oil (2.93 g, 75%).

Step 3: Tert-butyl 4-(4-bromophenoxy)butylcarbamate 4-(4-bromophenoxy)butan-1-amine (1.0 g, 4.09 mmol) was dissolved in anhydrous THF (20 mL) under nitrogen and stirred until solution is homogenous. Di-tert-butyl-dicarbonate (1.34 g, 6.14 mmol) was added and the reaction was stirred at 40° C. for 2 hours. The reaction was quenched with water (30 mL) and stirred at room temperature for 1.0 hour. The aqueous layer was extracted with ethyl acetate (50 mL×2). The organic layers were combined, washed with saturated NaHCO$_3$, water, and brine, then dried over MgSO$_4$, and filtered. Removal of solvent yield a solid, which was purified by column chromatography (9:1, hexanes:EtOAc) to yield white solids (1.0 g, 71%).

Example 4b: Synthesis of tert-butyl 4-(4-bromophenyl)butanoate

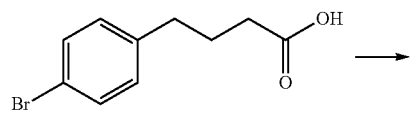

Allowed tert-butanol to melt and added 20 mL to round bottom flask. To the solution, added di-tert-butyl-dicarbonate (1.79 g, 8.22 mmol) and 4-(4-bromophenyl)butyric acid (1.0 g, 4.11 mmol). To reaction, then added DMAP (150.7 mg, 1.23 mmol) and stirred reaction at room temperature over night. The reaction was concentrated via vacuo, and re-diluted in ethyl acetate. The organic layer was washed with 1M HCl, brine, and water. After removal of solvent, the crude solids were purified via column chromatography (20:1, hexanes:EtOAc) to give the desired product (570 mg, 46%), which is a clear oil. $^1$H NMR (500 MHz, CD$_2$Cl$_2$): δ=7.39-7.41 (d, 2H), 7.03-7.09 (d, 2H), 2.57-2.60 (t, 2H), 2.18-2.21 (t, 2H), 1.83-1.186 (p, 2H), 1.42 (s, 9H).

Example 4c: Synthesis of 4-(4-(4,4,5,5-tetramethyl-1,3,2-dioxaborolan-2-yl)phenyl)butanoic acid

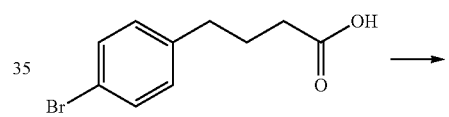

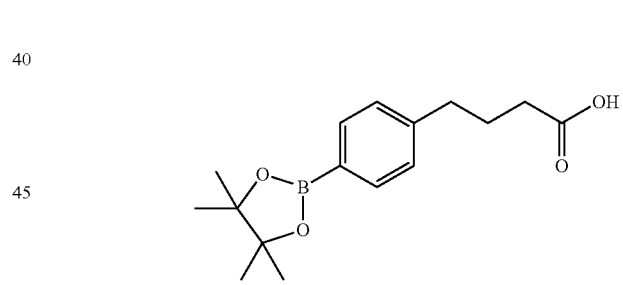

Combined 4-(4-bromophenyl)butyric acid (10 g, 41.13 mmol), bis(pinacolato)diboron (15.67 g, 61.70 mmol), potassium acetate (12.11 g, 123.4 mmol), and DMSO (100 mL), and purged mixture with nitrogen for 10 minutes at room temperature. To reaction under nitrogen, added Pd(dppf)Cl$_2$ and purged reaction again with nitrogen for another 20 minutes at room temperature. The reaction was then refluxed at 80° C. over night. After cooling to room temperature, the reaction was quenched with water and stirred for 1.0 hour. The solids formed were filtered using Buchner funnel. The crude solids were purified via column chromatography (8.5:1.5, hexanes:EtOAc). The desired fractions were collected and concentrated via vacuo, and triturated with hexanes and filtered to give the desired white solids (6.7 g, 56%).

Example 5: Synthesis of Linker or Capping Unit, Tert-butyl 4-(4-(4,4,5,5-tetramethyl-1,3,2-dioxaborolan-2-yl)phenoxy)butylcarbamate

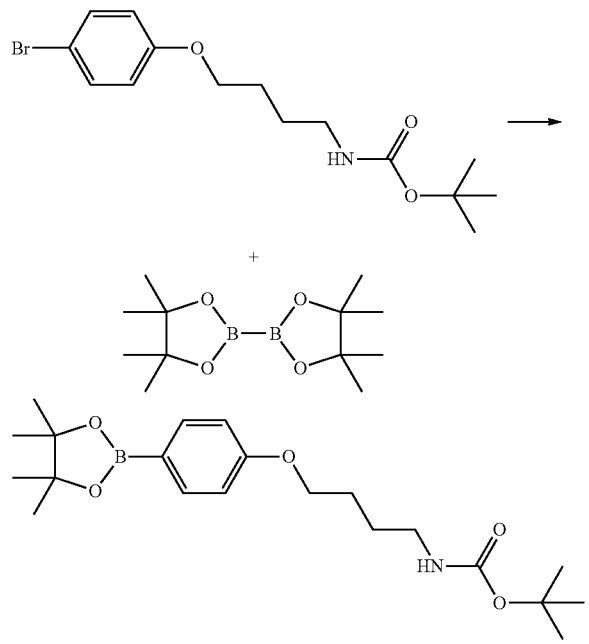

Combined tert-butyl 4-(4-bromophenoxy)butylcarbamate from Example 4a (500 mg, 1.45 mmmol), potassium acetate (428 mg, 4.36 mmol), bis(pinacolato)diboron (737 mg, 2.90 mmol) and DMSO (12 mL), and purged mixture with nitrogen for 10 minutes at room temperature. To mixture was added Pd(dppf)Cl$_2$ (59.3 mg, 0.07 mmol) and continued to stir solution at room temperature under nitrogen for another 20 minutes. After refluxing at 80° C. for 3 hours, the reaction was cooled to room temperature and quenched with water (30 mL). The aqueous layer was extracted with dichloromethane (50 mL×2). The organic layers were combined, washed with brine, then dried over MgSO$_4$, and filtered. Removal of solvent yield a dark brown oil, which was purified by column chromatography (9:1, hexanes: EtOAc) to yield a light yellow oil (539 mg, 95%).

Example 6: Synthesis of Linker or Capping Unit with Long Oligoether Spacer Between Arylhalide Phenyl and FMOC Protected Primary Amine 4-(4-bromophenoxy)butan-1-amine+oligoether-FMOC+N,N'-dicyclohexylcarbodiimide (DCC)

(9H-fluoren-9-yl)methyl 80-(4-bromophenoxy)-75-oxo-3,6,9,12,15,18,21,24,27,30,33,36,39,42,45,48,51,54,57,60,63,66,69,72-tetracosaoxa-76-azaoctacontylcarbamate. 4-(4-bromophenoxy)butan-1-amine (21.5 mg, 0.09 mmol), 1-(9H-fluoren-9-yl)-3-oxo-2,7,10,13,16,19,22,25,28,31,34,37,40,43,46,49,52,55,58,61,64,67,70,73,76-pentacosaoxa-4-azanonaheptacontan-79-oic acid (100 mg, 0.073 mmol), and N,N'-dimethylaminopyridine (5.4 mg, 0.044 mmol) were combined in a round bottom flask flushed with nitrogen and charged with a Teflon stirbar. Next 5 mL of anhydrous dichloromethane was added via syringe. N,N-Dicyclohexylcarbodiimide (23 mg, 0.11 mmol) is transferred to a second flask flushed with nitrogen and charged with a stirbar and 5 mL of anhydrous dichloromethane is added via syringe. While stirring the first solution, add the dicyclohexylcarbodiimide solution slowly, dropwise. The reaction is then allowed to proceed overnight. The following day solids from the reaction were filtered off and the filtrate was concentrated onto silica. Column chromatography in methanol and dichloromethane gave a clear thick oil (83.3 mg, 71% yield).

Example 7: Synthesis of Polymer, Poly[2,7{9,9-bis(2,5,8,11,14,17,20,23,26,29,32,35-dodecaoxaoctatriacontane)fluorene}-co-3,5-phenylbut-V-oxy-4"-amine], with an Internal Linking Site The incorporation of internal conjugation sites into conjugated polymer backbones is described in U.S. application Ser. No. 11/868,870, filed Oct. 8, 2007 and published as U.S. Application No. 2008/0293164, which application is herein incorporated by reference in its entirety. Provided is a modified synthesis based on the protocol.

2,7-dibromo-9,9-di(2',5',8',11',14',17',23',26',29',32',35'-dodecaoxaoctatriacontan-38'-yl)fluorene (0.084 mmol, 120 mg), 9,9-di(2',5',8',11',14',17',20',23',26',29',32',35'-dodecaoxaoctatriacontan-38'-yl)-2,7-di(4",4",5",5"-tetramethyl-1",3",2"-dioxaborolanyl)fluorene (0.088 mmol, 135 mg), tert-butyl-4-(3,5-dibromophenoxy)butylcarbamate (0.0044 mmol, 2.0 mg), and palladium tetra(triphenylphosphine) (0.0035 mmol, 4 mg) are combined in a round bottom flask equipped with a stirbar. Next, 0.35 mL of 2M potassium carbonate (aq) and 1.9 mL of tetrahydrofuran are added and the flask is fitted with a vacuum adaptor and put on a Schlenk

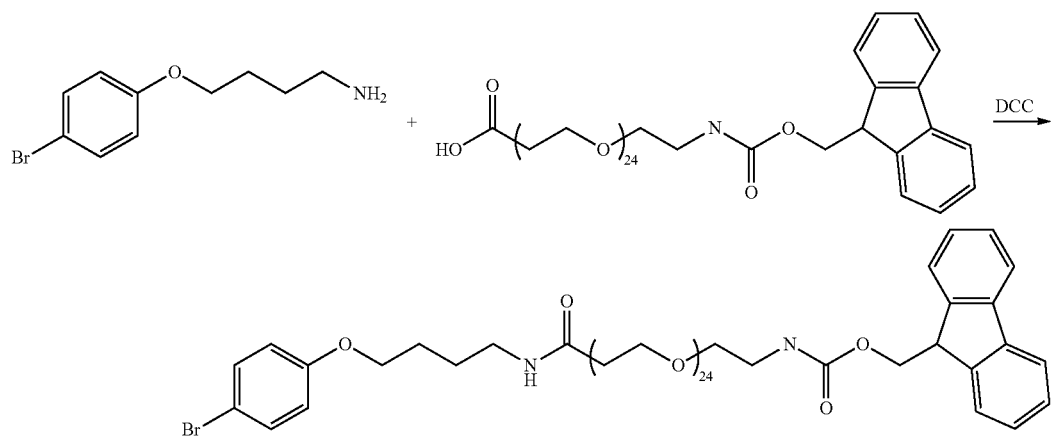

line. The mixture is degassed using 3 freeze-pump-thaw cycles. The degassed mixture is heated to 80 C under nitrogen with vigorous stirring for 18 hours. The reaction mixture is then cooled and the solvent is removed with rotary evaporation. Next, 4 mL of 4 M HCl in dioxane is added and the mixture is stirred for no less than 4 hours. The solution is neutralized with 2M potassium carbonate solution. The bulk of the solvent is again removed with rotary evaporation. The resulting semisolid is diluted with ca. 50 mL water and filtered through glass fiber filter paper. Ethanol is added to adjust the solvent to 20% ethanol in water.

Preparative gel permeation chromatography is performed with G-25 desalting medium to remove excess salts from the polymer. Solvent in the fractions is removed with rotary evaporation and 100 mg of poly [2,7{9,9-bis(2,5,8,11,14,17,20,23,26,29,32,35-dodecaoxaoctatriacontane)fluorene}-co-3,5-tert-butyl-4-(4-bromophenoxy)amine] is collected as an amber oil.

Example 8: Synthesis of Phenylene Vinylene Co-Polymer with an Internal Linking Site

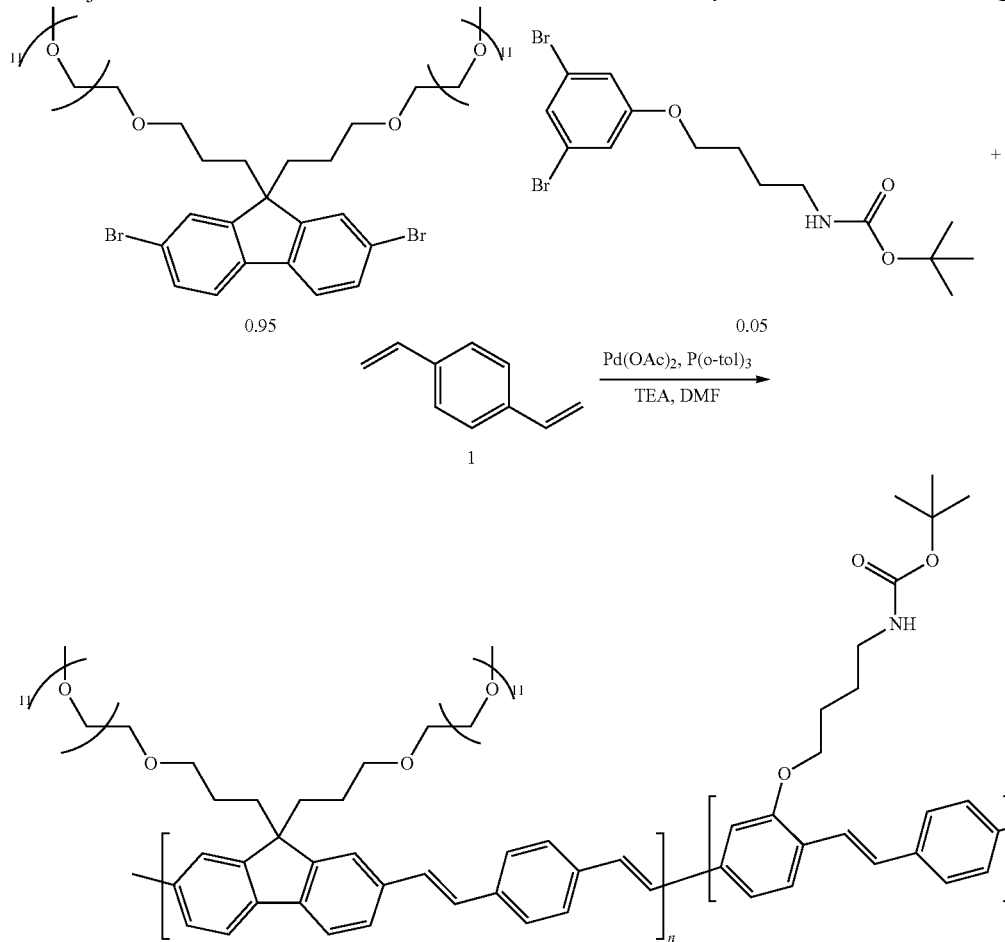

A modified synthesis similar to that described in Examples 7 and 15.

Example 9: Synthesis of Polymer with Exclusively Terminal Amine Capping Units

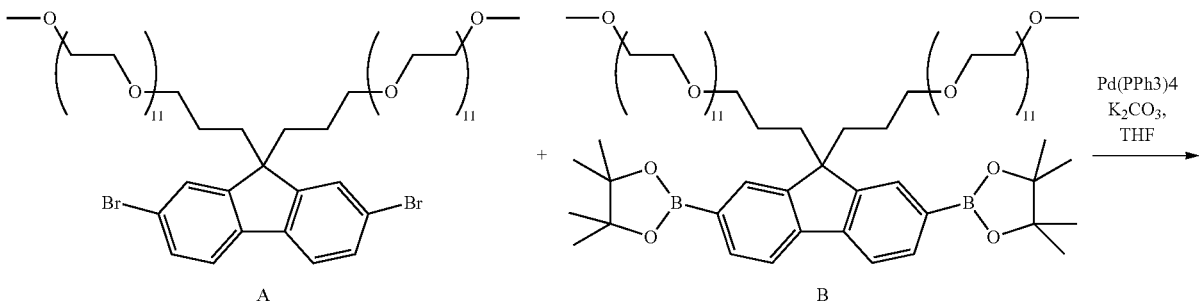

-continued
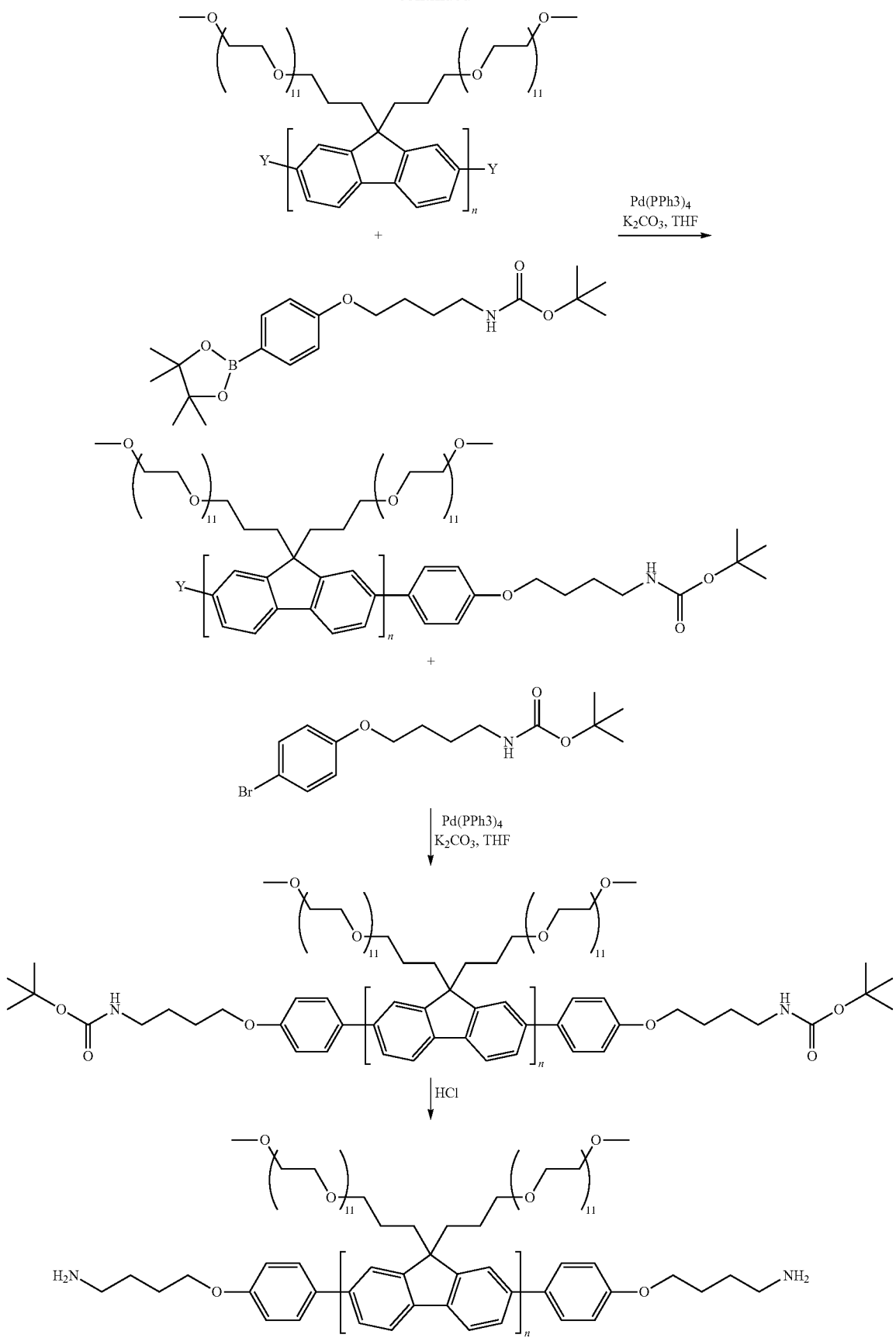

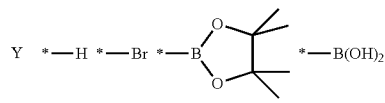

2,7-(Poly [2,7{9,9-bis(2,5,8,11,14,17,20,23,26,29, 32,35-dodecaoxaoctatriacontane)fluorene])-diphen-4-oxybutyl-4'-amine 2,7-dibromo-9,9-di(2',5',8',11',14',17',23',26',29',32',35'-dodecaoxaoctatriacontan-38'-yl)fluorene (0.163 mmol, 235 mg), 9,9-di(2',5',8',11',14',17',20',23',26',29',32',35'-dodecaoxaoctatriacontan-38'-yl)-2,7-di(4",4",5",5"-tetramethyl-1",3",2"-dioxaborolanyl)fluorene (0.163 mmol, 250 mg), and palladium tetra(triphenylphoshine) (0.0065, 7.5 mg) are combined in a round bottom flask equipped with a stirbar. Next, 0.75 mL of 2M potassium carbonate (aq) and 3 mL of tetrahydrofuran are added and the flask is fitted with a vacuum adaptor. The reaction mixture is put on a Schenk line and is degassed with three freeze-pump-thaw cycles and then heated to 80 C under nitrogen with vigorous stirring for 18 hours. A solution of tert-butyl 4-(4-(4,4,5,5-tetramethyl-1,3,2-dioxaborolan-2-yl)phenoxy)butylcarbamate (0.064 mmol, 25 mg) in 0.5 mL tetrahydrofuran is degassed with three freeze-pump-thaw cycles and then added to the polymerization reaction via cannula under excess nitrogen pressure. The reaction is allowed to continue for an additional 4 hours at 80 C with stirring. Next, a solution of tert-butyl 4-(4-bromophenoxy)butylcarbamate (0.192 mmol, 66 mg) in 0.5 mL of THF is degassed with three freeze-pump-thaw cycles and then added to the polymerization reaction via cannula under excess nitrogen pressure. The reaction was allowed to proceed overnight. The reaction mixture was allowed to cool and solvent was removed with rotary evaporation. A 4 mL portion of 4M HCl in dioxane was added to the residue and stirred for a minimum of 4 hours. The solution was neutralized with 2 M potassium carbonate (aq) and then the solvent was removed under vacuum. The resulting residue was diluted to ~30 mL with 20% ethanol in water and filtered. Preparative gel permeation chromatography is performed with G-25 desalting medium to remove excess salts from the polymer. Solvent in the fractions is removed with rotary evaporation and 337 mg of polymer is collected as an amber oil.

The order of end linker addition (aryl hylide or boronic ester/acid) can be reversed. Similar processes can be used to add alternative linkers or end capping units.

Example 10: Synthesis of Polymer, 2-(Poly [2,7{9,9-bis(2,5,8,11,14,17,20,23,26,29,32,35-dodecaoxaoctatriacontane)fluorene])-phen-4-oxybutyl-4'-amine, Statistically Enriched in Chains with a Single Terminal Amine Capping Unit

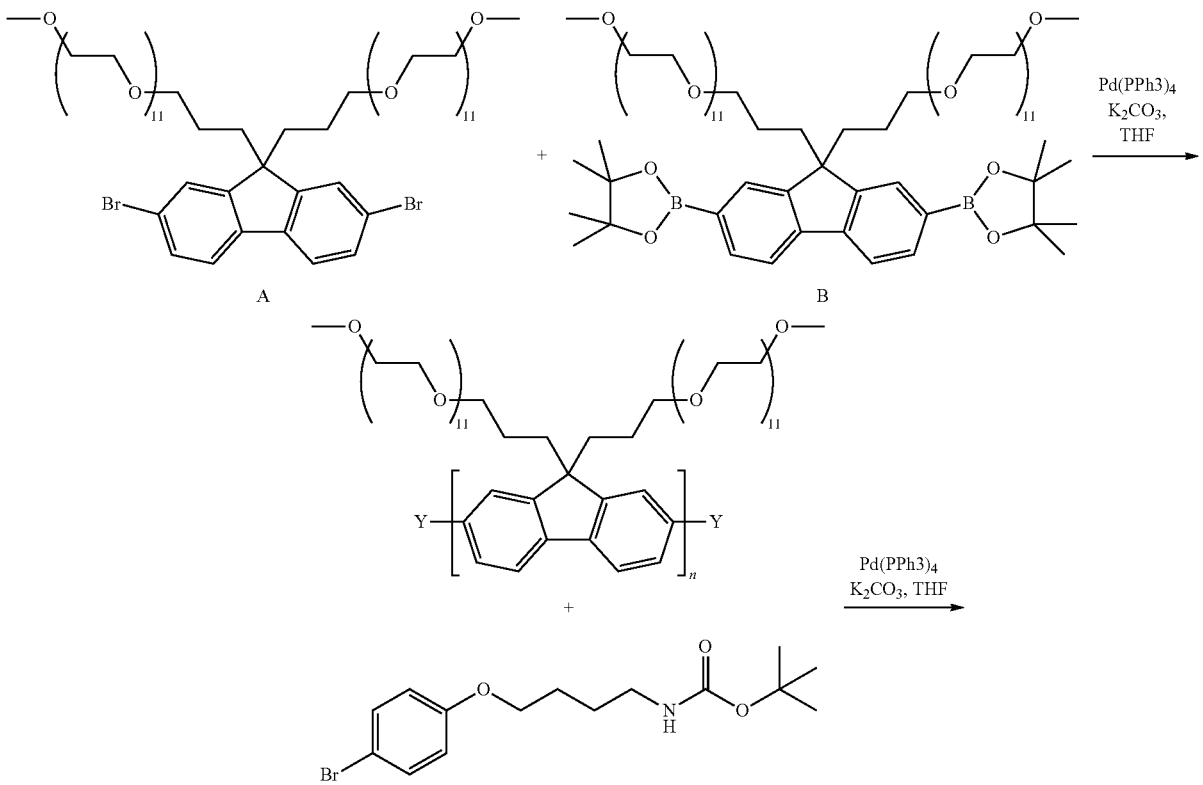

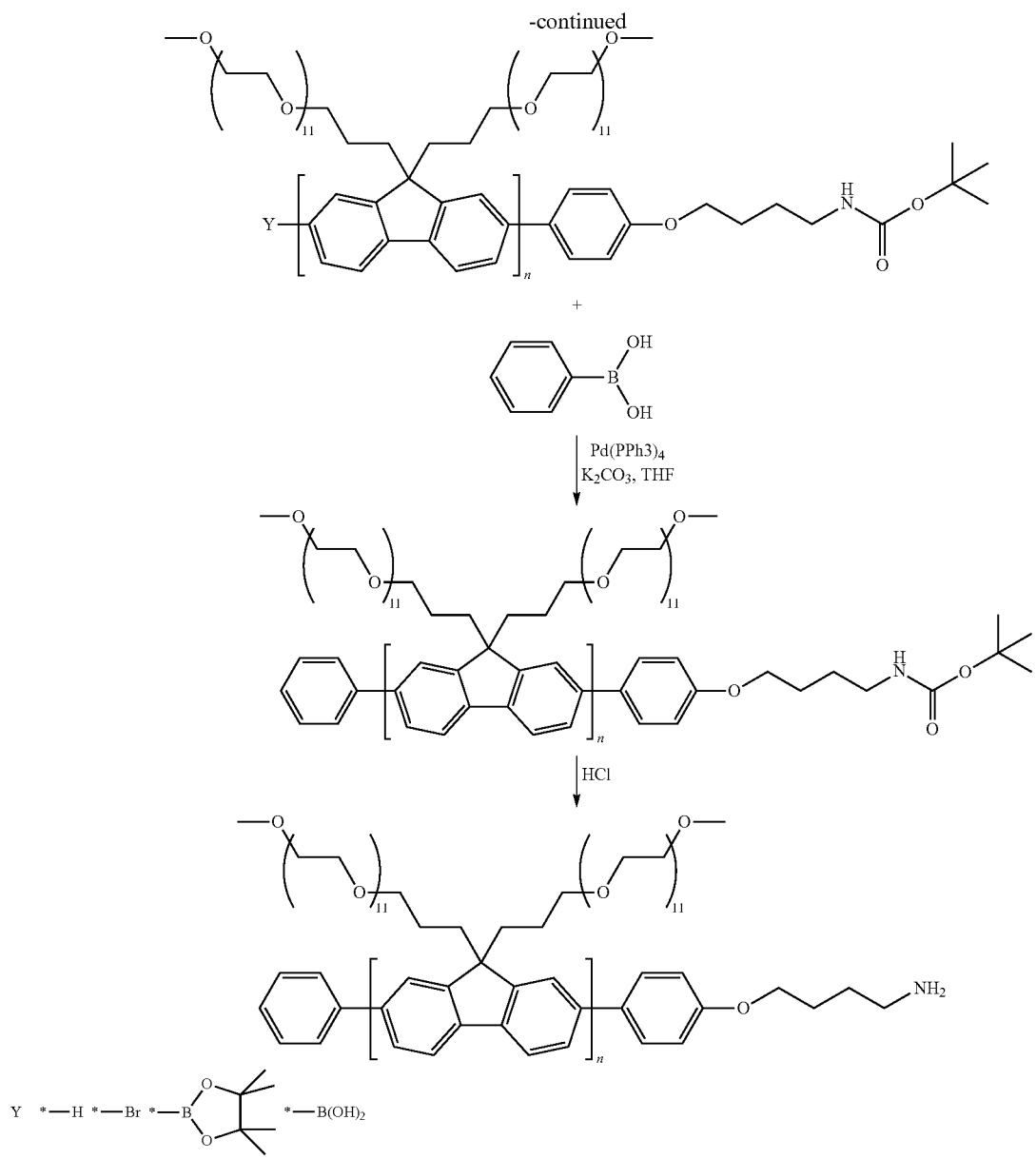

2,7-dibromo-9,9-di(2',5',8',11',14',17',23',26',29',32',35'-dodecaoxaoctatriacontan-38'-yl)fluorene (0.163 mmol, 235 mg), 9,9-di(2',5',8',11',14',17',20',23',26',29',32',35'-dodecaoxaoctatriacontan-38'-yl)-2,7-di(4",4",5",5"-tetramethyl-1",3",2"-dioxaborolanyl)fluorene (0.163 mmol, 250 mg), and palladium tetra(triphenylphoshine) (0.0065, 7.5 mg) are combined in a round bottom flask equipped with a stirbar. Next, 0.75 mL of 2M potassium carbonate (aq) and 3 mL of tetrahydrofuran are added and the flask is fitted with a vacuum adaptor. The reaction mixture is put on a Schenk line and is degassed with three freeze-pump-thaw cycles and then heated to 80 C under nitrogen with vigorous stirring for 18 hours. A solution of tert-butyl 4-(4-bromophenoxy)butylcarbamate (0.049 mmol, 17 mg) in 0.5 mL tetrahydrofuran is degassed with three freeze-pump-thaw cycles and then added to the polymerization reaction via cannula under excess nitrogen pressure. The reaction is allowed to continue for an additional 4 hours at 80 C with stirring. Next, a solution of phenylboronic acid (0.150 mmol, 18 mg) in 0.5 mL of THF is degassed with three freeze-pump-thaw cycles and then added to the polymerization reaction via cannula under excess nitrogen pressure. The reaction was allowed to proceed overnight. The reaction mixture was allowed to cool and solvent was removed with rotary evaporation. A 4 mL portion of 4M HCl in dioxane was added to the residue and stirred for a at least 4 hours. The solution was neutralized with 2 M potassium carbonate (aq) and then the solvent was removed under vacuum. The resulting residue was diluted to ~30 mL with 20% ethanol in water and filtered. Preparative gel permeation chromatography is performed with G-25 desalting medium to remove excess salts from the polymer. Solvent in the fractions is removed with rotary evaporation and 315 mg of polymer is collected as an amber oil. Resulting polymers contain chains with an enriched fraction of chains with one amine linker plus chains with 2 linkers and no linkers.

Example 11: Synthesis of Polymer Statistically Enriched in Chains with a Single Terminal Capping Unit with a Long Oligoether Spacer (24 Repeats) Between the Polymer Chain and the Primary Amine Linking Group
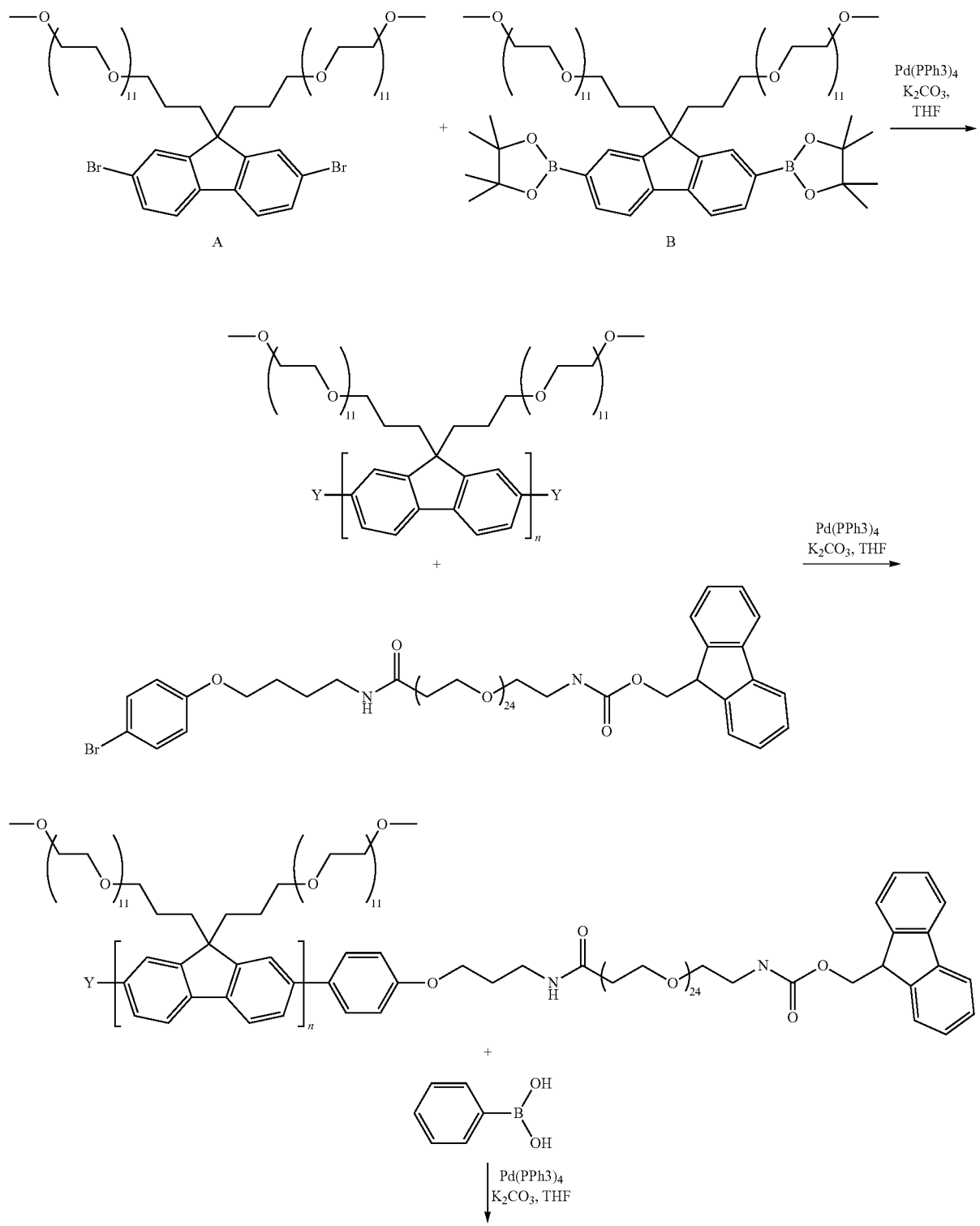

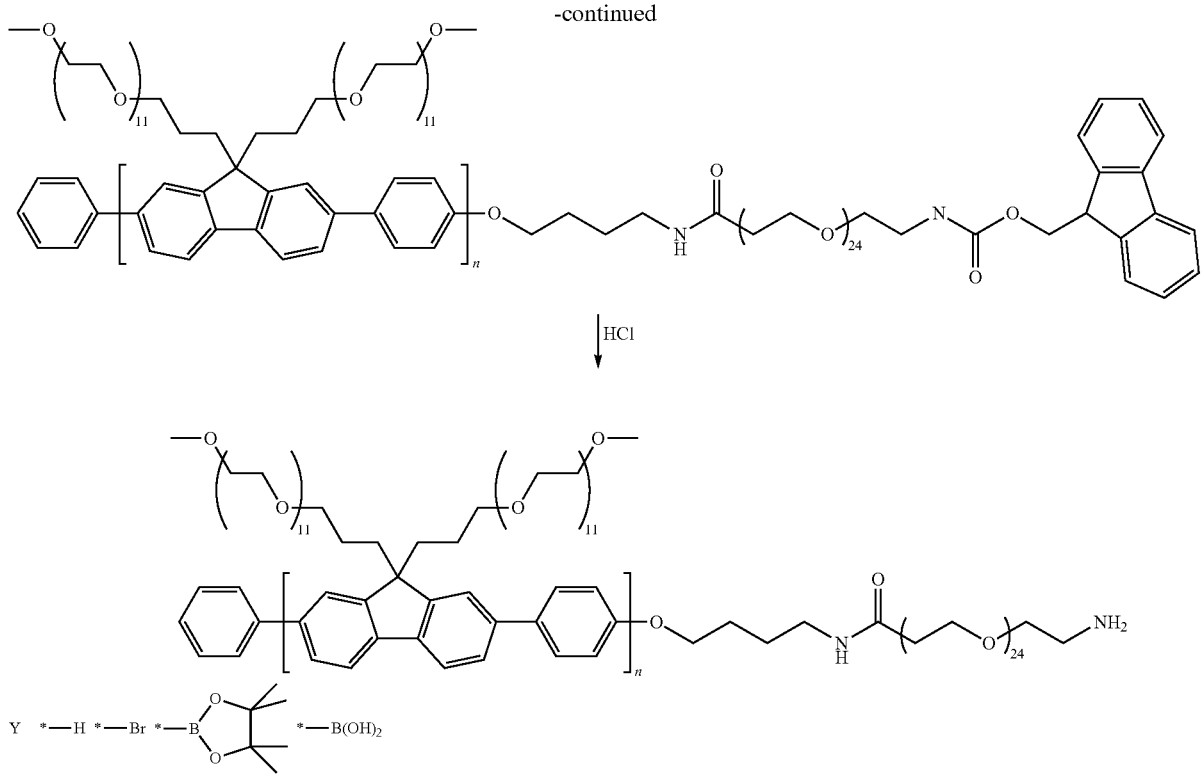

Y  *—H  *—Br  *—B(pinacol)  *—B(OH)₂

2-(Poly [2,7{9,9-bis(2,5,8,11,14,17,20,23,26,29,32,35-dodecaoxaoctatriacontane)fluorene])-phen-4-oxybutyl-4'-amine. 2,7-dibromo-9,9-di(2',5',8',11',14',17',23',26',29',32',35'-dodecaoxaoctatriacontan-38'-yl)fluorene (0.163 mmol, 235 mg), 9,9-di(2',5',8',11',14',17',20',23',26',29',32',35'-dodecaoxaoctatriacontan-38'-yl)-2,7-di(4'',4'',5'',5''-tetramethyl-1'',3'',2''-dioxaborolanyl)fluorene (0.163 mmol, 250 mg), and palladium tetra(triphenylphoshine) (0.0065, 7.5 mg) are combined in a round bottom flask equipped with a stirbar. Next, 0.75 mL of 2M potassium carbonate (aq) and 3 mL of tetrahydrofuran are added and the flask is fitted with a vacuum adaptor. The reaction mixture is put on a Schenk line and is degassed with three freeze-pump-thaw cycles and then heated to 80 C under nitrogen with vigorous stirring for 18 hours. A solution of tert-butyl 4-(4-bromophenoxy)butylcarbamate (0.049 mmol, 17 mg) in 0.5 mL tetrahydrofuran is degassed with three freeze-pump-thaw cycles and then added to the polymerization reaction via cannula under excess nitrogen pressure. The reaction is allowed to continue for an additional 4 hours at 80 C with stirring. Next, a solution of phenylboronic acid (0.150 mmol, 18 mg) in 0.5 mL of THF is degassed with three freeze-pump-thaw cycles and then added to the polymerization reaction via cannula under excess nitrogen pressure. The reaction was allowed to proceed overnight. The reaction mixture was allowed to cool and solvent was removed with rotary evaporation. A 4 mL portion of 4M HCl in dioxane was added to the residue and stirred for a minimum of 4 hours. The solution was neutralized with 2 M potassium carbonate (aq) and then the solvent was removed under vacuum. The resulting residue was diluted to ~30 mL with 20% ethanol in water and filtered. Preparative gel permeation chromatography is performed with G-25 desalting medium to remove excess salts from the polymer. Solvent in the fractions is removed with rotary evaporation and 315 mg of polymer is collected as an amber oil.

Example 12: Synthesis of an Asymmetric Polymer with a Terminal Carboxylic Capping Unit Added During Polymerization Reaction

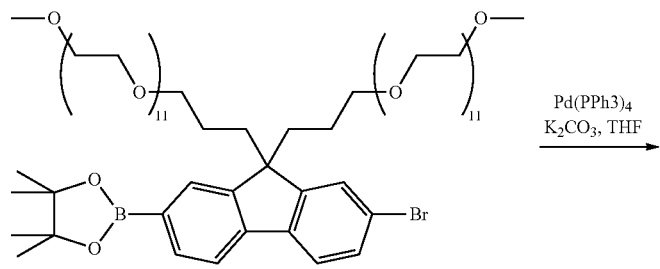

-continued
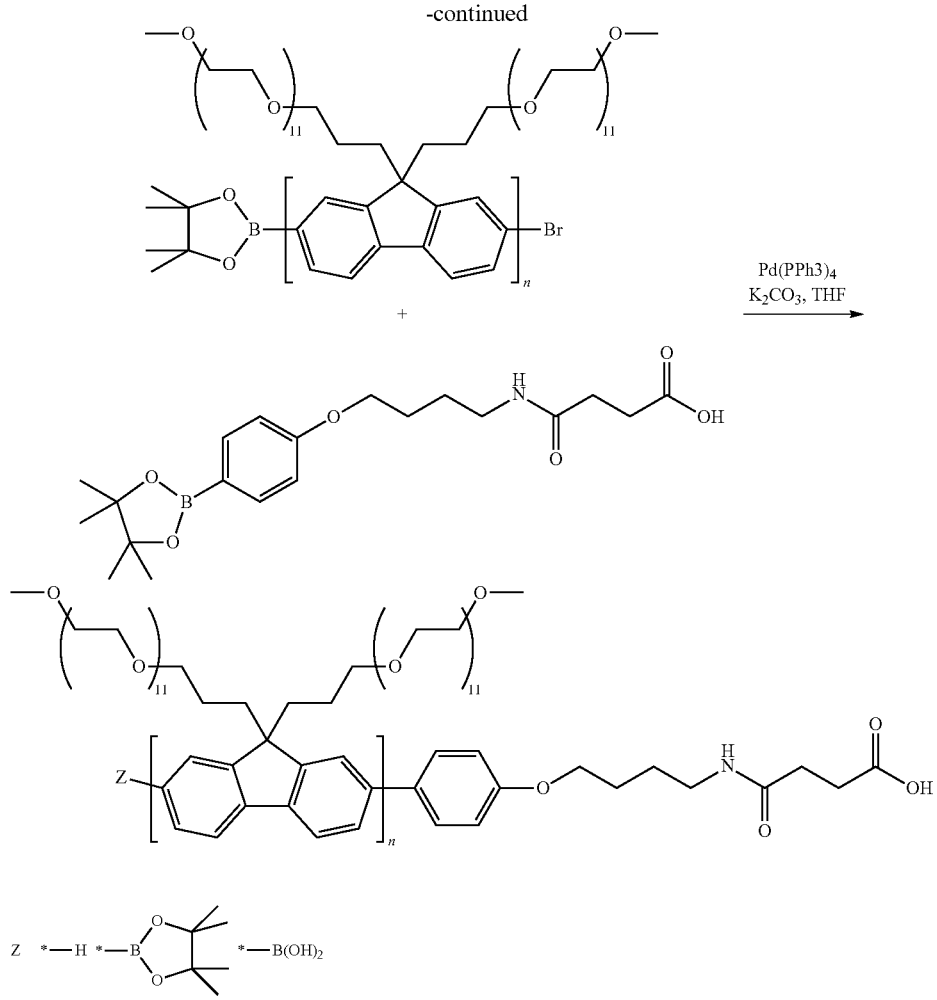
The linking monomer is added during the polymerization reaction as described in Examples 9, 10 and 11. The carboxylic acid group can later be converted to an activated ester such as N-hydroxysuccinimidyl as is described in Example 29.
Example 13: Synthesis of an Asymmetric Polymer with a Terminal Carboxylic Acid Capping Unit Added Post Polymerization
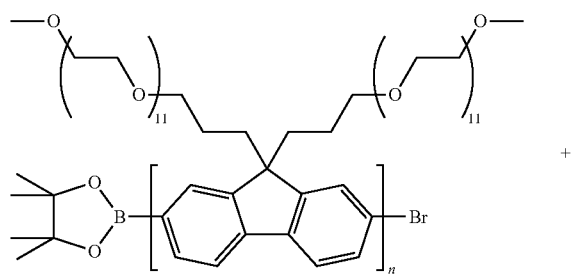

-continued

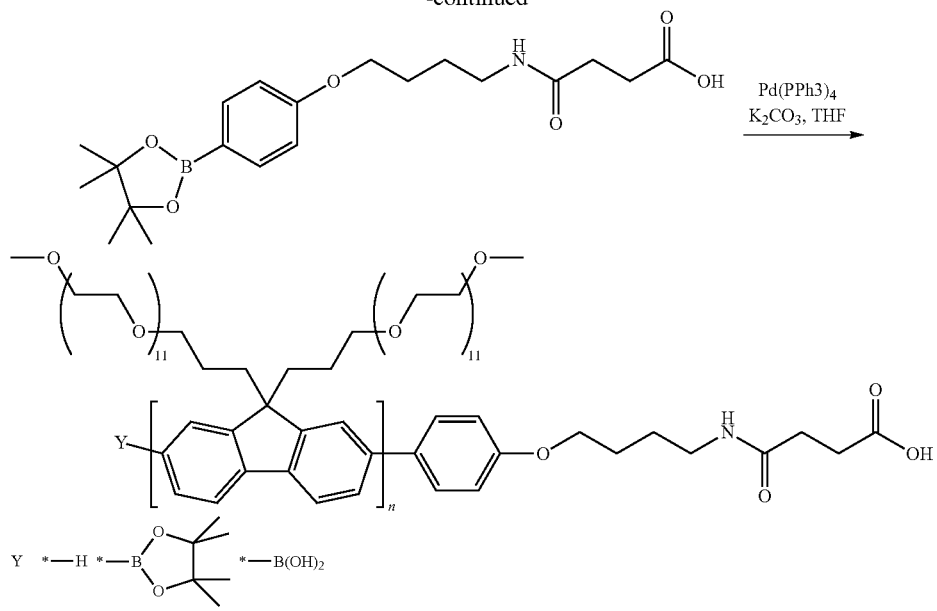

The linking monomer is added after the polymerization reaction is completed and polymer purified. Linker addition is done under similar reaction conditions as those described in Examples 9, 10 and 11. The carboxylic acid group can later be converted to an activated ester such as N-hydroxysuccinimidyl as is described in Example 29.

Example 14: Synthesis of an Polymer with Branched PEG Groups

Example 14a: Synthesis of Monomers, (D) and (E) for Subsequent Polymerization

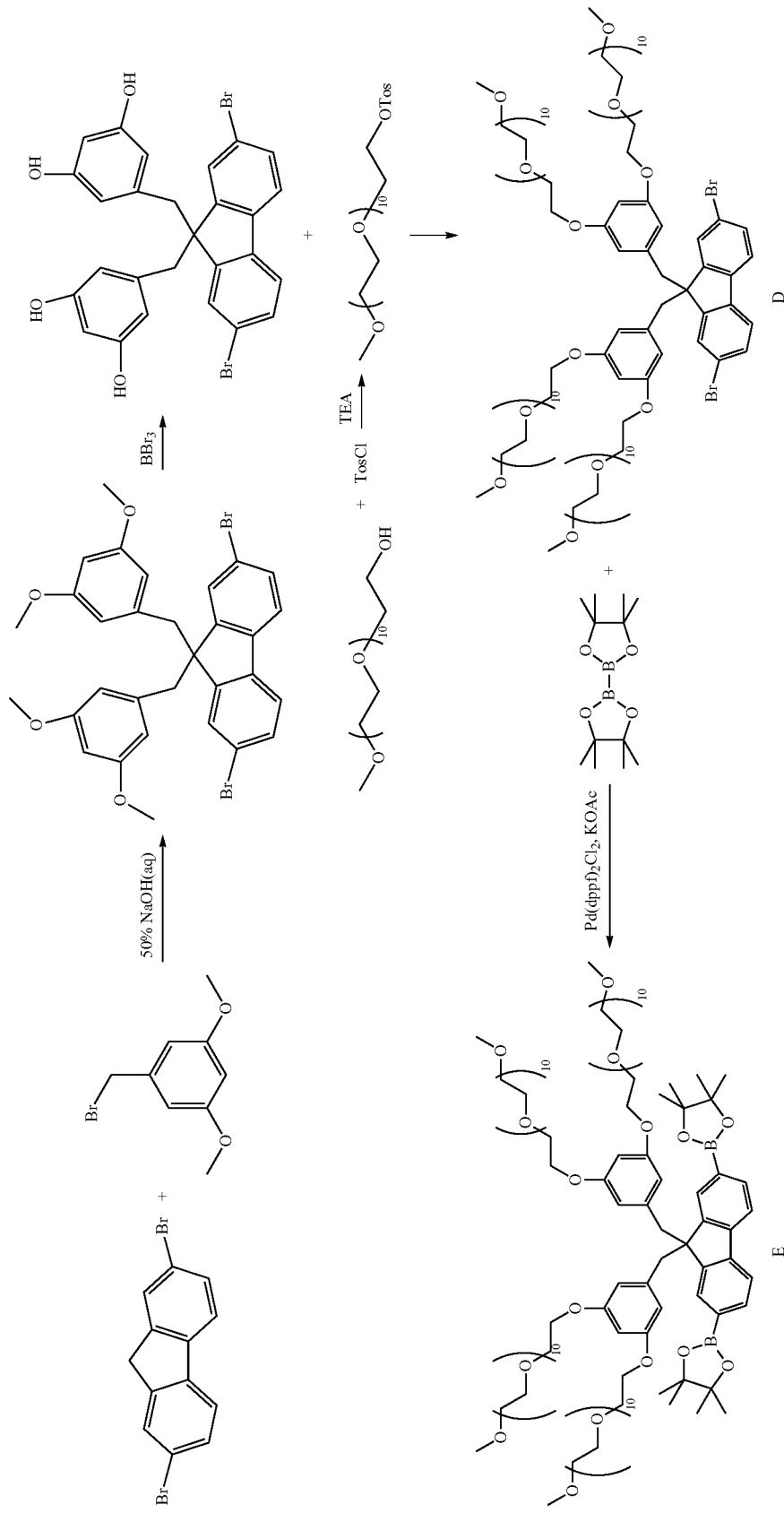

Step 1:
2,7-dibromo-9,9-bis(3,5-dimethoxybenzyl)fluorene 2,7-dibromofluorene (4.16 g, 12.8 mmol) and tetrabutylammonium bromide (362 mg, 1.12 mmol) were added to a round bottom flask charged with a Teflon stirbar. Next, 60 mL of dimethylsulfoxide was added to the flask and the mixture was stirred for 5 minutes. A portion of 50% NaOH aqueous solution (5.2 mL) was added followed immediately by 3,5-dimethoxybenzyl bromide (7.14 g, 31 mmol). Over the course of 2 hours the solution changes color from orange to blue. The reaction is stirred overnight. The resulting mixture is slowly poured into 200 mL of water and then extracted with three 100 mL portions of dichloromethane. The organic layers are combined and dried over magnesium sulfate and then filtered. The crude product is purified by column chromatography using hexanes and dichloromethane as eluent to give a pale yellow solid (6.63 g, 79% yield).

Step 2: 2,7-dibromo-9,9-bis(3,5-dihydroxybenzyl)-9H-fluorene 2,7-dibromo-9,9-bis(3,5-dimethoxybenzyl)-9H-fluorene (1.3 g, 2.08 mmol) was added to a round bottom flask charged with a stirbar and equipped with a rubber septum. The flask is purged with nitrogen for 10 min. Anhydrous dichloromethane (20 mL) is transferred to the flask via cannula and the mixture is stirred until the solids are completely dissolved. The solution is then cooled with a dry ice/acetone bath for 10 minutes. BBr$_3$ (6.1 mL, 63.3 mmol) is added dropwise via cannula with constant stirring. The bath is allowed to warm to room temperature and the mixture is stirred overnight. The reaction is quenched with the slow addition of 125 mL of water. The solution is then extracted with 3 portions of ethyl acetate (50 mL). The organic layer is dried over MgSO$_3$, filtered, and dried onto silica. Flash chromatography of the crude using ethyl acetate in dichloromethane gives an off-white crystalline solid (800 mg, 68% yield).

Step 3: 2,7-dibromo-9,9-bis(3,5-(2,5,8,11,14,17,20,23,26,29,32-undecaoxatetratriacontan-34-yl) benzyl)-9H-fluorene (D)

2,7-dibromo-9,9-bis(3,5-dihydroxybenzyl)-9H-fluorene (537 mg, 0.945 mmol), 2,5,8,11,14,17,20,23,26,29,32-undecaoxatetratriacontan-34-yl 4-methylbenzenesulfonate (2.788 g, 4.156 mmol), potassium carbonate (1.57 g, 11.34 mmol) and acetone (80 mL) are transferred to a round bottom flask charged with a Teflon stirbar and equipped with a reflux condenser. The mixture is refluxed with constant stirring overnight. The mixture is then allowed to cool to room temperature and the acetone is removed under vacuum. After extracting with 3 portions of dichloromethane, the organic layer is dried over MgSO$_4$, filtered, and the filtrate is concentrated onto silica. Column chromatography using methanol and dichloromethane affords the product as a slightly colored thick oil (1.69 g, 70% yield).

Step 4: 2,7-di(4",4",5",5"-tetramethyl-1",3",2"-dioxaborolanyl)-9,9-bis(3,5-(2,5,8,11,14,17,20,23,26,29,32-undecaoxatetratriacontan-34-yl) benzyl)-9H-fluorene (E)

Monomer (E) is synthesized using conditions similar to conditions as described in Example 1.

Example 14b: Polymerization of (D) and (E)

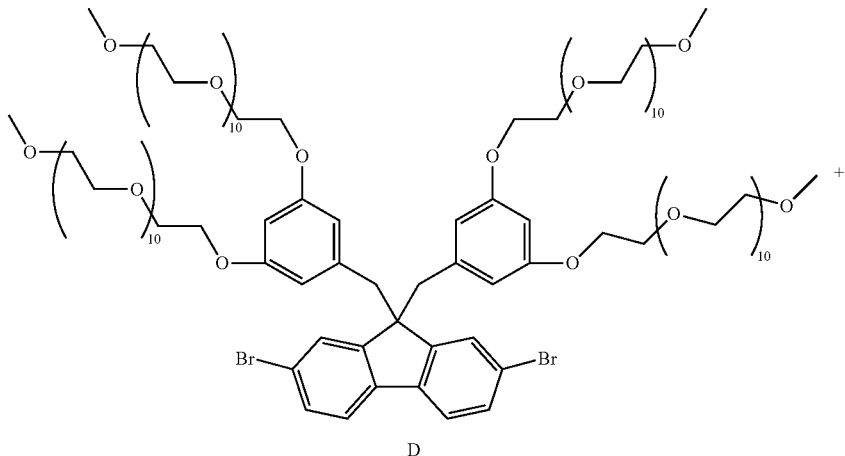

D

-continued
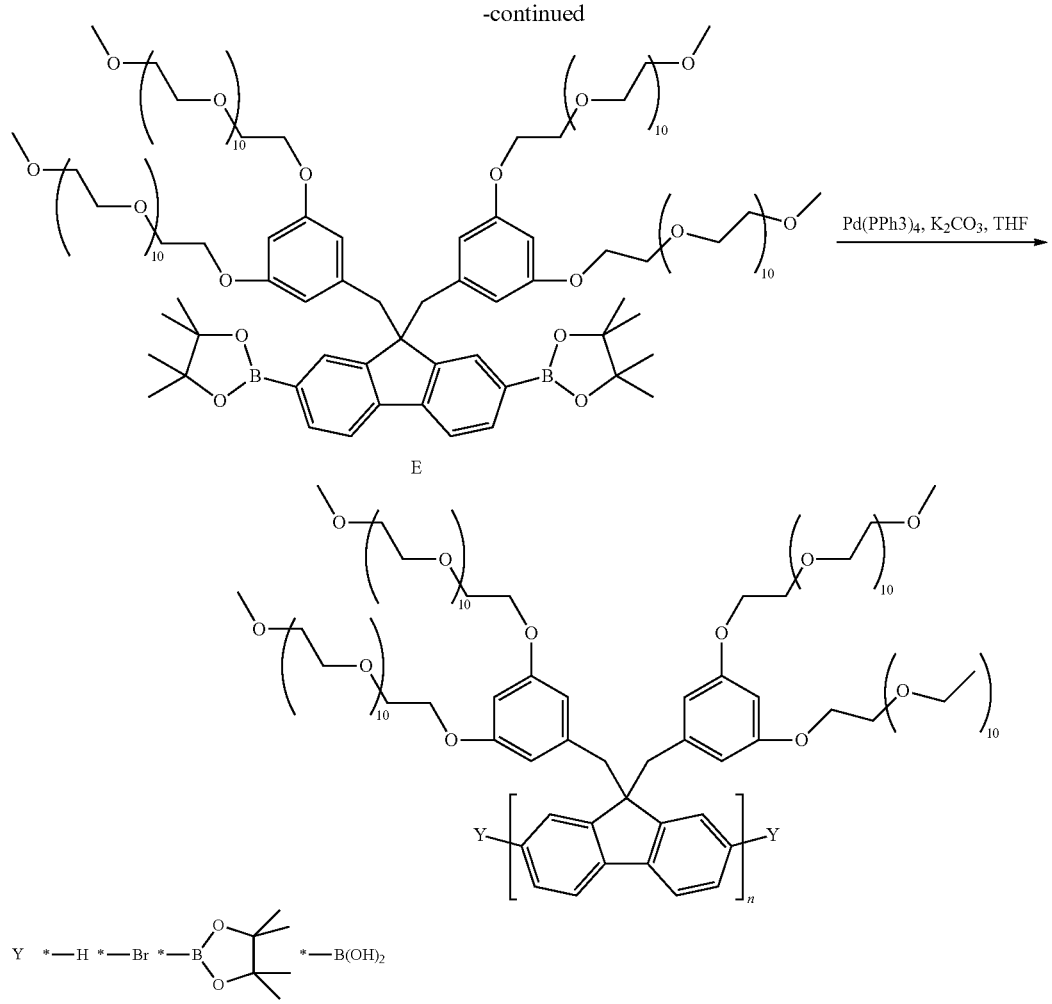
Polymerization of (D) and (E) are polymerized using conditions similar to polymerization conditions as described in Example 1b.
Example 15: Synthesis of a neutral base phenylene vinylene co-polymer
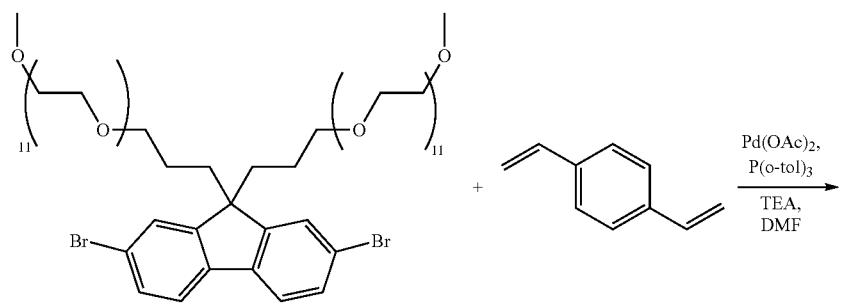

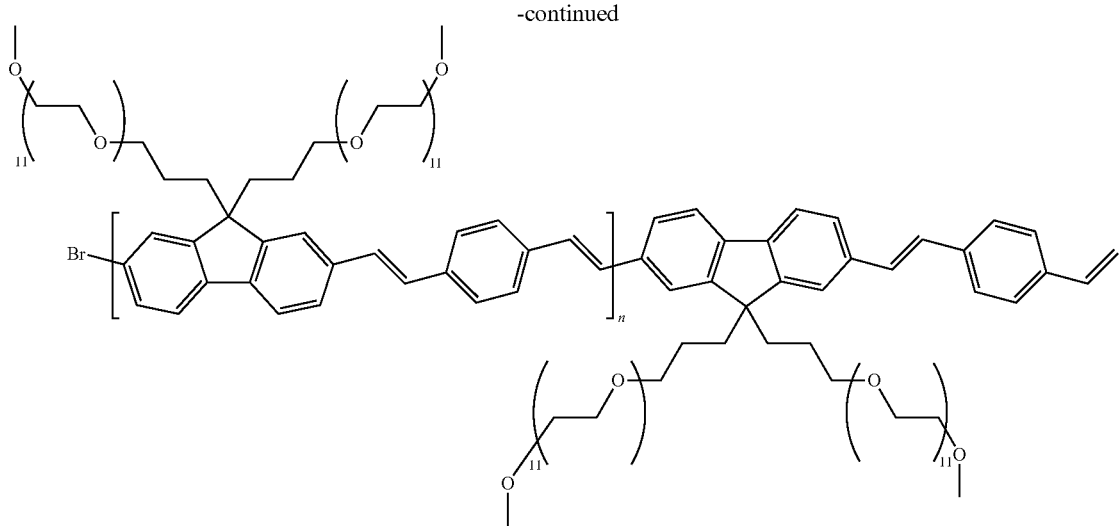

2,7-dibromo-9,9-di(2',5',8',11',14',17',23',26',29',32',35'-dodecaoxaoctatriacontan-38'-yl)fluorene (0.25 mmol), 1,4-divinylbenzene (32.3 mg, 0.25 mmol), palladium acetate (3 mg, 0.013 mmol), tri-ortho-tolylphosphine, (10 mg, 0.033 mmol), and potassium carbonate (162 mg, 1.2 mmol) are combined with 5 mL of DMF in a small round bottom flask charged with a Teflon coated stirbar. The flask is fitted with a needle valve and put in a Schlenk line. The solution is degassed by three cycles of freezing, pumping, and thawing. The mixture is then heated to 100° C. overnight. The polymer can be subsequently reacted with terminal linkers or capping units using similar (in situ) protocols to those provided in the previous examples (9, 10 and 11) or by modifying them post polymerization work up as a separate set of reactions.

Example 16: Synthesis of a Branched Phenylene Vinylene Co-Polymer

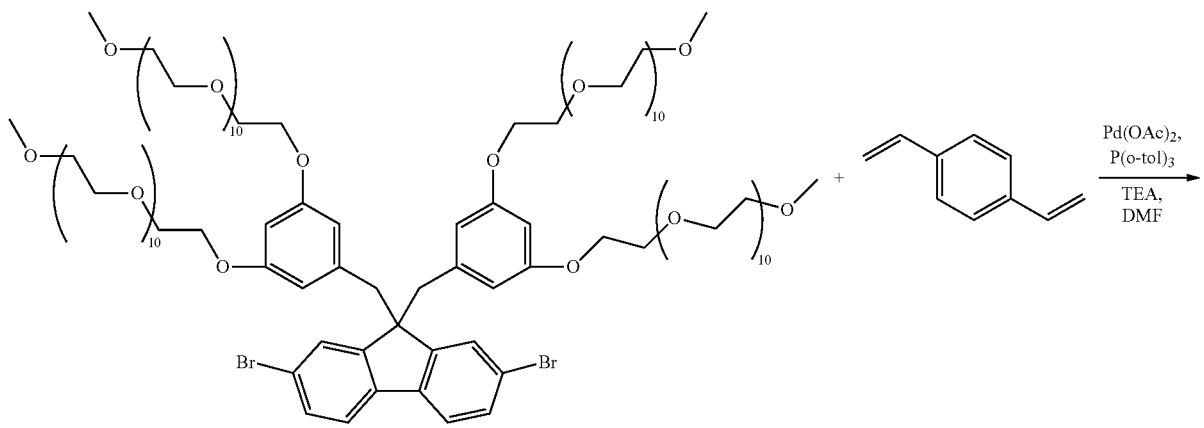

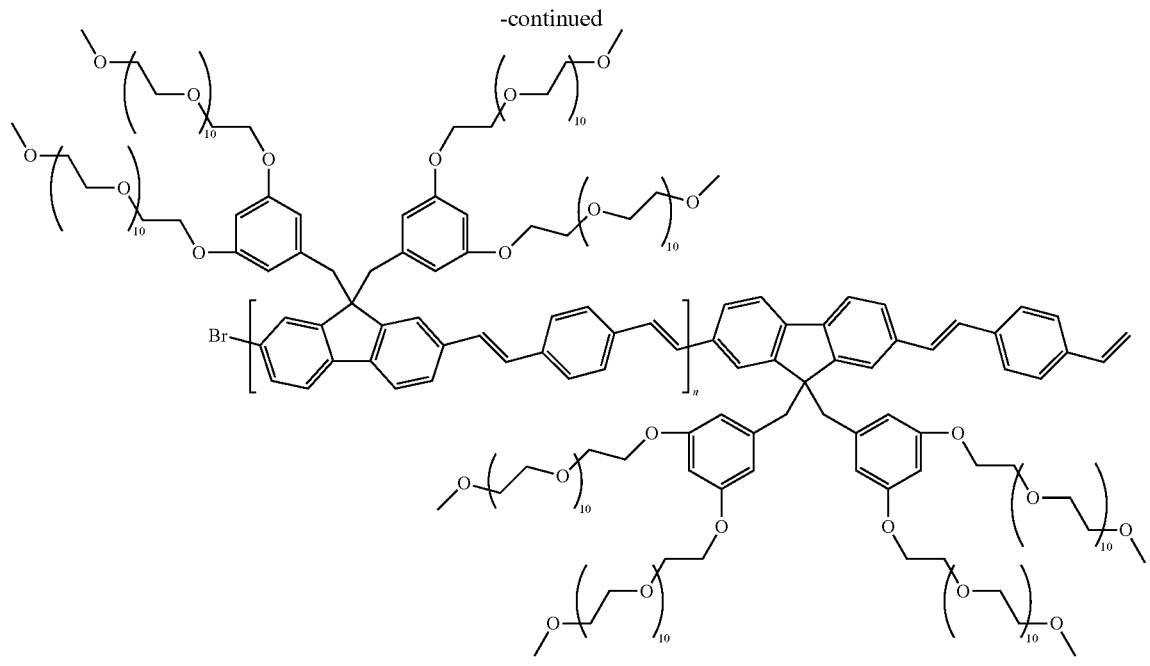

(II)

2,7-dibromo-9,9-bis(3,5-(2,5,8,11,14,17,20,23,26,29,32-undecaoxatetratriacontan-34-yl) benzyl)-9H-fluorene (636 mg, 0.25 mmol), 1,4-divinylbenzene (32.3 mg, 0.25 mmol), palladium acetate (3 mg, 0.013 mmol), tri-ortho-tolylphosphine, (10 mg, 0.033 mmol), and potassium carbonate (162 mg, 1.2 mmol) were combined with 5 mL of DMF in a small round bottom flask charged with a Teflon coated stirbar. The flask was fitted with a needle valve and put in a Schlenk line. The solution was degassed by three cycles of freezing, pumping, and thawing. The mixture was then heated to 100° C. overnight. The polymer can be subsequently reacted with terminal linkers or capping units using similar (in situ) protocols to those provided in Example 5 or by modifying them post polymerization work up as a separate set of reactions.

Example 17: Synthesis of a branched phenylene vinylene co-polymer with functional amines for covalent conjugation. Poly [2,7-divinyl{9,9-bis(3,5-(2,5,8,11,14,17,20,23,26,29,32-undecaoxatetratria-contan-34-yl)benzyl)-9H-fluorene}-alt-1,4-benzene-co-4-phenoxybutyl-N-t-butylcarbamate]

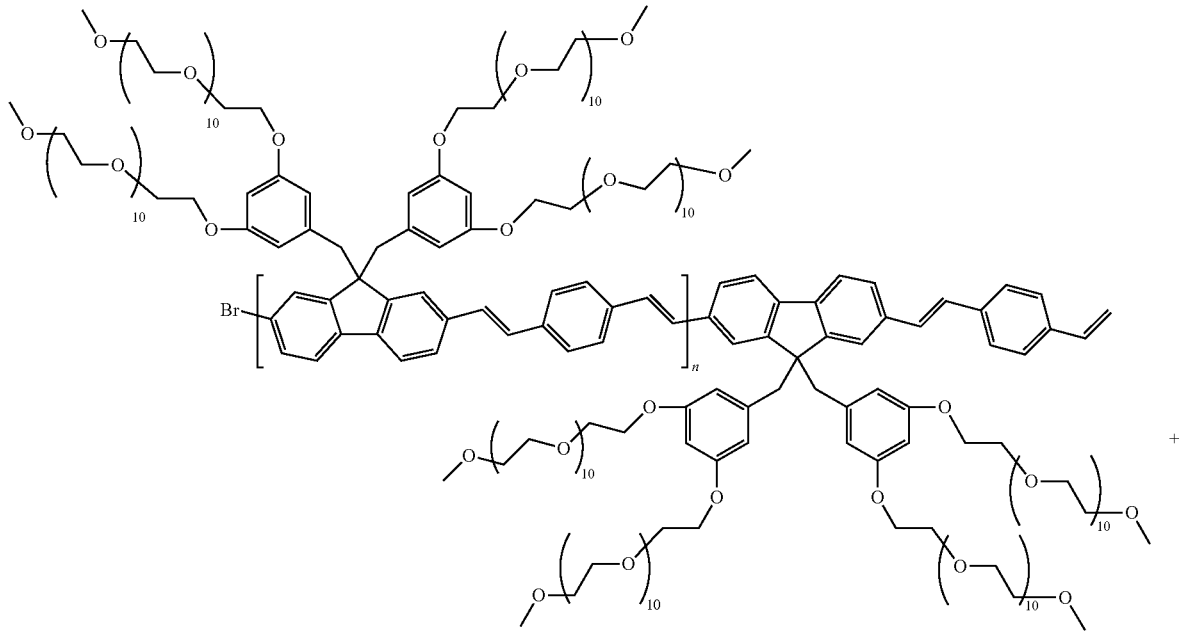

+

-continued
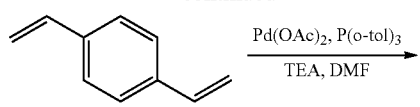
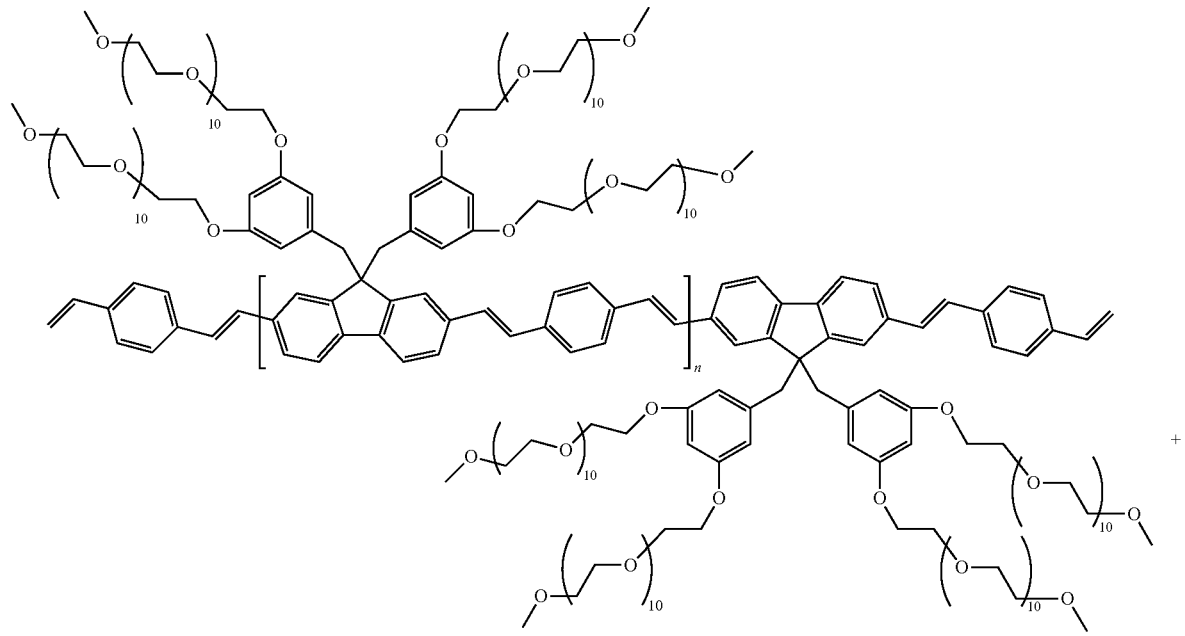
+
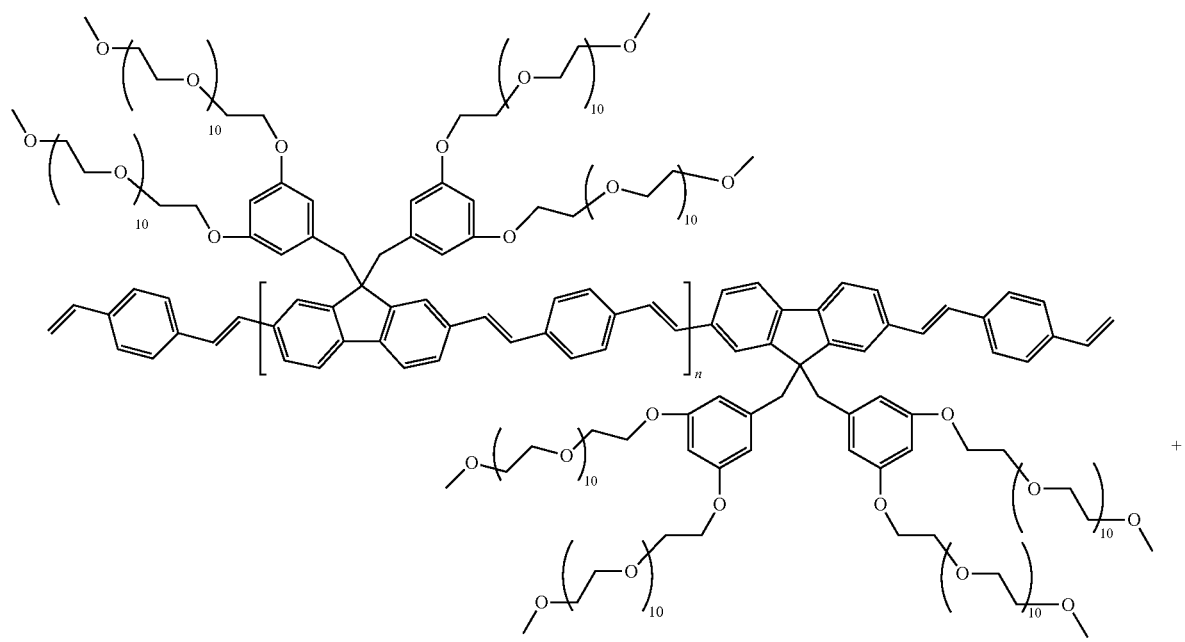
+
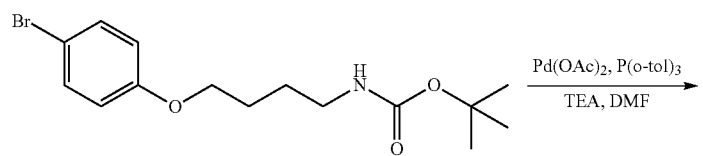

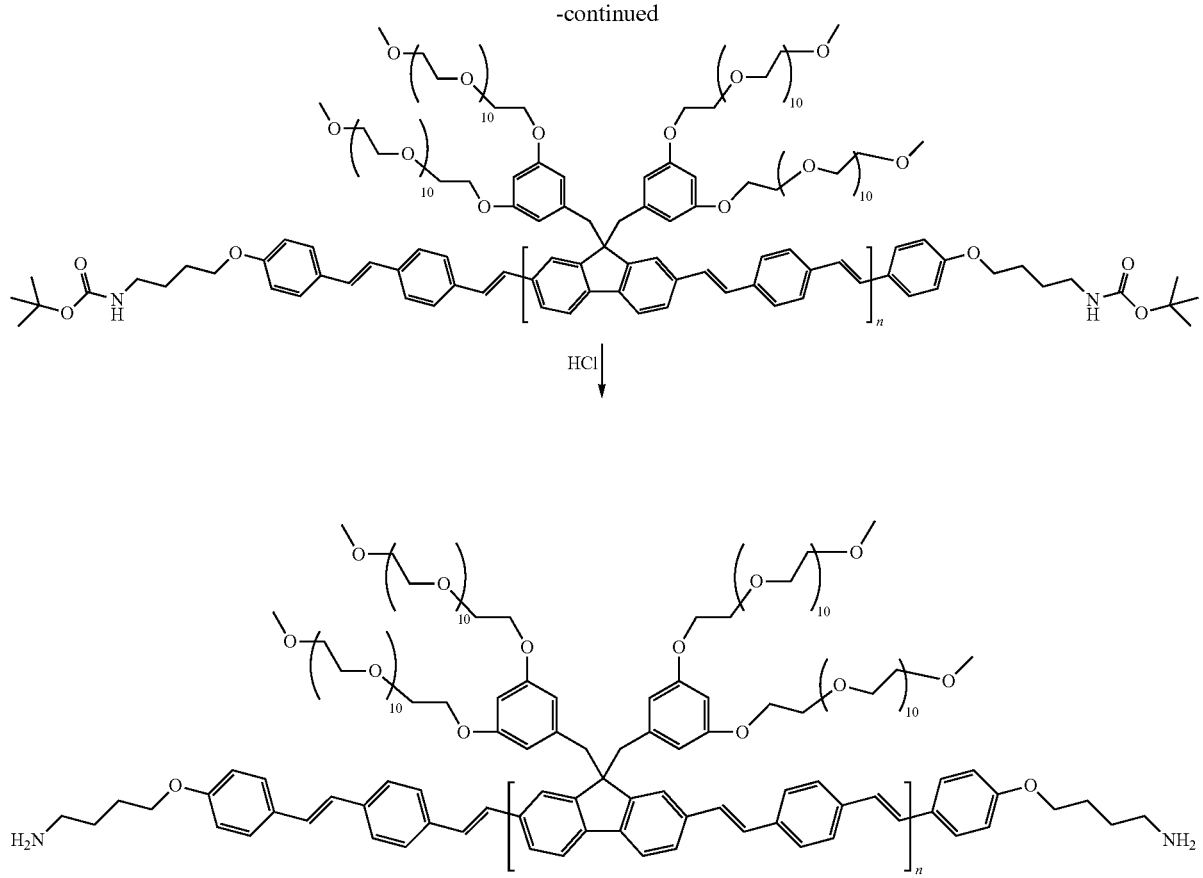

Step 1: Polymerization 2,7-dibromo-9,9-bi s(3,5-(2,5,8,11,14,17,20,23,26,29,32-undecaoxatetratriacontan-34-yl) benzyl)-9H-fluorene (636 mg, 0.25 mmol), 1,4-divinylbenzene (32.3 mg, 0.25 mmol), palladium acetate (3 mg, 0.013 mmol), tri-ortho-tolylphosphine, (10 mg, 0.033 mmol), and potassium carbonate (162 mg, 1.2 mmol) were combined with 5 mL of DMF in a small round bottom flask charged with a Teflon coated stirbar. The flask was fitted with a needle valve and put in a Schlenk line. The solution was degassed by three cycles of freezing, pumping, and thawing. The mixture was then heated to 100° C. overnight.

Step 2: Linker Addition

The next morning divinylbenzene (10 mg, 0.077 mmol) was transferred to a small round bottom flask with 1 mL of DMF. The flask was fitted with a needle valve and put in a Schlenk line. The solution was degassed by three cycles of freezing, pumping, and thawing. The solution was transferred via cannula through the needle valves and into the polymerization reaction. After this addition the reaction was allowed to continue at 100° C. overnight. The next day tert-butyl 4-(4-bromophenoxy)butylcarbamate (53 mg, 0.15 mmol) and 1 mL of DMF were transferred to a small round bottom flask. The flask was fitted with a needle valve and put in a Schlenk line. The solution was degassed by three cycles of freezing, pumping, and thawing. The solution was transferred via cannula through the needle valves and into the polymerization reaction. After this addition the reaction was allowed to continue at 100° C. overnight.

Step 3: Work Up

The reaction is then cooled and diluted with 100 mL of water. The aqueous solution was filtered twice through G-6 glass fiber filter paper. The filtrate was evaporated to dryness and re-diluted with dichloromethane. The organic layer was dried over MgSO4 and filtered. The filtrate was evaporated to yield an amber colored oil (342 mg, 56% yield).

A 4 mL portion of 4M HCl in dioxane was added to the polymer residue and stirred for a minimum of 4 hours. The solution was neutralized with 2 M potassium carbonate (aq) and then the solvent was removed under vacuum. The resulting residue was diluted to ~30 mL with 20% ethanol in water and filtered. Preparative gel permeation chromatography is performed with G-25 desalting medium to remove excess salts from the polymer. Solvent in the fractions is removed with rotary evaporation and the polymer is collected as an amber oil.

The linker or capping unit addition steps can be performed in the polymerization reaction as presented above or alternatively, in some embodiments, can be performed in a separate set of reactions after the polymerization work up. In the latter case, the polymer is reacted under the analogous conditions as those provided in the example. In other embodiments, it is also possible to react with a combination of terminal monomers to introduce polymers with bi-functionality, allowing the polymer to be conjugated to more than one entity.

Example 18: Synthesis of a Fluorene Monomer with Glycerol-Based Dendrimers

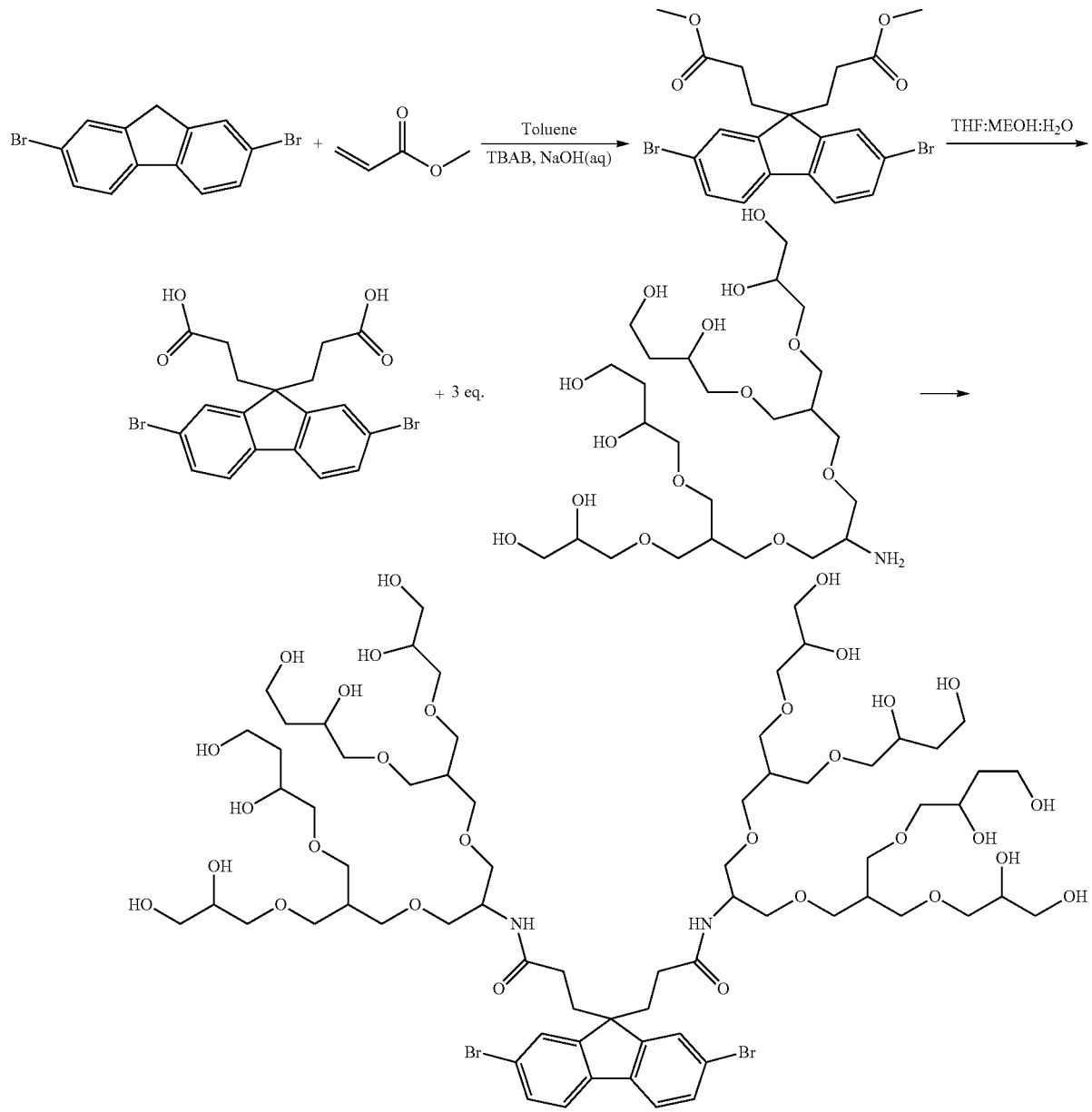

Step 1: Dimethyl 3,3'-(2,7-dibromo-9H-fluorene-9,9-diyl)dipropanoate 2,7-Dibromofluorene (1 g, 3.1 mmol), methyl acrylate (861 mg, 10 mmol) tetrabutylammonium bromide (100 mg, 0.3 mmol) and toluene (5 mL) were added to a small round bottom flask with a Teflon-coated stirbar. Next 2 mL of 50% NaOH (aq) is added while stirring. The reaction is allowed to proceed overnight. The next day the toluene layer is transferred to a flask and the aqueous layer extracted with two portions of toluene. The organic layers are combined, dried with Mg2SO4, and filtered. Silica (2 g) is added to the filtrate and the solution is evaporated. The product is obtained as a white solid (1.23 g, 80% yield) after purification by column chromatography.

Step 2: 3,3'-(2,7-dibromo-9H-fluorene-9,9-diyl) dipropanoic acid

Dimethyl 3,3'-(2,7-dibromo-9H-fluorene-9,9-diyl)dipropanoate (1.23 g, 2.5 mmol) is transferred to a small round bottom flask equipped with a Teflon-coated stirbar. A mixture of THF:MeOH:H2O, 3:2:1, (10 mL) is added and the mixture is stirred for 1 hr. Then a 1 mL portion of 1M NaOH (aq) is added and the mixture is stirred overnight. The next day the water layer is isolated and extracted with 20 mL portions diethyl ether three times. Next the water layer is acidified to ~pH 2. The water layer is extracted three times with 20 mL portions of dichloromethane. The organic layers are combined and dried with Mg2SO4. The organic solution is filtered and the solvent evaporated to obtain the product as an off-white solid (948 mg, 90% yield).

Step 3: 3,3'-(2,7-Dibromo-9H-fluorene-9,9-diyl)bis (N-(7,15-bis((2,3-dihydroxypropoxy)methyl)-1,3,19, 21-tetrahydroxy-5,9,13,17-tetraoxahenicosan-11-yl) propanamide)

3,3'-(2,7-Dibromo-9H-fluorene-9,9-diyl)dipropanoic acid (500 mg, 1.1 mmol), 11-amino-7,15-bis((2,3-dihydroxy-propoxy)methyl)-5,9,13,17-tetraoxahenicosane-1,3,19,21-tetraol (1.954, 3.3 mmol) (prepared as per ref. Heek, T.; Fasting, C.; Rest, C.; Zhang, X.; Wurthner, F.; Haag, R. Chem. Commun., 2010, 46, 1884-1886), and N,N'-dimethylaminopyridine (61 mg, 0.5 mmol) are combined in a round bottom flask equipped with a Teflon-coated stirbar and sealed with a rubber septum. The flask was flushed with N2 and 10 mL of anhydrous dichloromethane was added via syringe. The mixture is stirred to dissolve the solids. In another round bottom flask equipped with a Teflon-coated stirbar, dicyclohexylcarbodiimide (DCC, 910 mg 4.4 mmol) transferred and the flask is sealed with a rubber septum. Next, 5 mL of anhydrous dichloromethane is transferred to the flask via syringe. The DCC solution is transferred to the fluorene reaction mixture via a syringe dropwise. The reaction is allowed to react overnight. The next day the reaction mixture is filtered. The filtrate is purified by column chromatography to afford a clear oil (1.24 g, 70% yield).

Example 19: Synthesis of a Fluorene Monomer PAMAM-Based Dendritic Side Chain Capped with methylPEG Chains

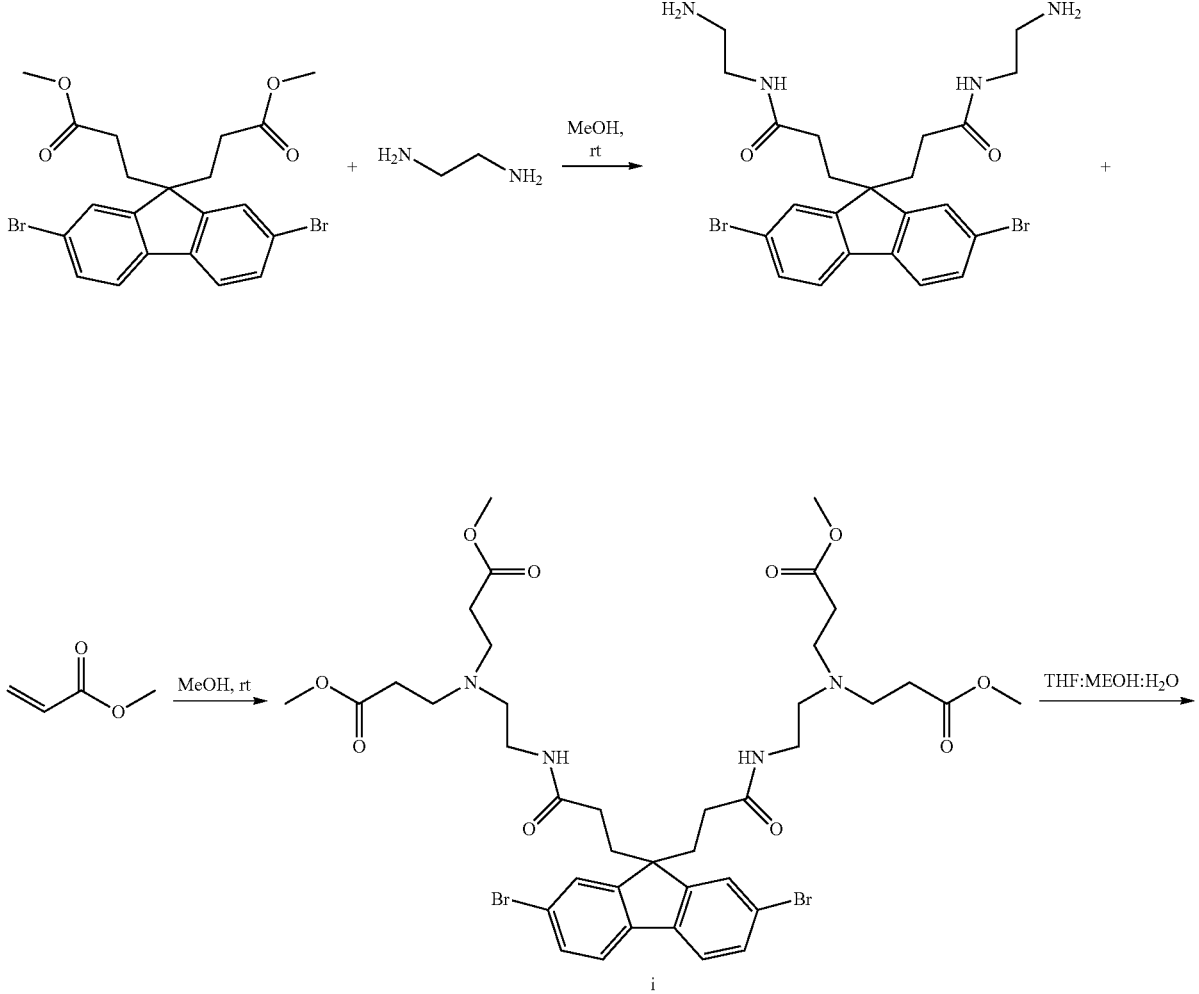

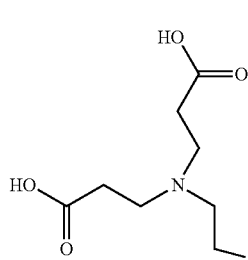
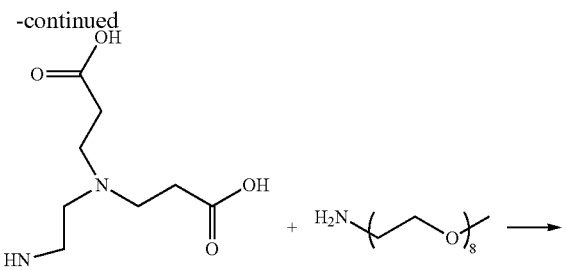

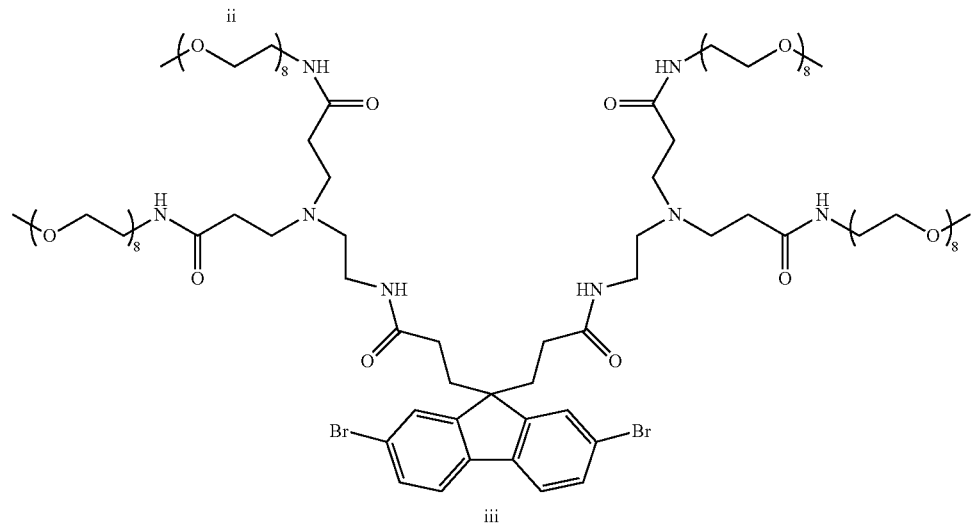

ii iii

Step 1: 9,9'-(3,3'-Diamido(tetramethyl PAMAM G[2])-2,7-dibromofluorene (i)

Dimethyl 3,3'-(2,7-dibromo-9H-fluorene-9,9-diyl)dipropanoate (1 g, 2.0 mmol) is transferred to a round bottom flask equipped with a stirbar and sealed with a rubber septum. The flask is flushed with nitrogen and 10 mL of dry methanol is transferred to the flask via syringe and the solid is dissolved by stirring. Ethylenediamine (5.5 mL, 82 mmol) is added via syringe slowly and the mixture is allowed to stir for 2 hours. The septum is removed and the methanol and unreacted ethylenediamine is removed under vacuum. Another 10 mL portion of methanol is added and stirred and then was evaporated to remove any remaining ethylenediamine. The residue remaining in the flask was then sealed again with a septum, flushed with nitrogen, and dry methanol (10 mL) was added and stirred. Methyl acrylate (7.2 mL, 80 mmol) is added slowly via syringe and the mixture is allowed to stir for 2 hours. The septum is again removed and the methanol and methyl acrylate are removed under vacuum. A 10 mL portion of toluene is added, the mixture stirred, and the solvent removed under vacuum affording an off-white solid (1.79 g, quantitative yield).

Step 2: 9,9'-(3,3'-Diamido(PAMAM G[2] tetraacid)-2,7-dibromofluorene (ii)

9,9'-(3,3'-Diamido(tetramethyl PAMAM G[2])-2,7-dibromofluorene (i) (1.79 g, 2 mmol) is transferred to a small round bottom flask equipped with a Teflon-coated stirbar. A mixture of THF:MeOH:H$_2$O, 3:2:1, (10 mL) is added and the mixture is stirred for 1 hr. Then a 1 mL portion of 1M NaOH (aq) is added and the mixture is stirred overnight. The next day the water layer is isolated and extracted with 20 mL portions diethyl ether three times. Next the water layer is acidified to ~pH 2. The water layer is extracted three times with 20 mL portions of dichloromethane. The organic layers are combined and dried with Mg$_2$SO$_4$. The organic solution is filtered and the solvent evaporated to obtain the product as an off-white solid (1.51 g, 90% yield). Step 3: 9,9'-(3,3'-Diamido(PAMAM G[2] N-(2,5,8,11,14,17,20,23-octaoxapentacosane-25-yl)propionamidyl)-2,7-dibromofluorene (iii).

9,9'-(3,3'-Diamido(PAMAM G[2] tetraacid)-2,7-dibromofluorene (ii) (500 mg, 0.6 mmol), 2,5,8,11,14,17,20,23-octaoxapentacosan-25-amine (1.15 g, 3 mmol)), and N,N'-dimethylaminopyridine (12 mg, 0.1 mmol) are combined in a round bottom flask equipped with a Teflon-coated stirbar and sealed with a rubber septum. The flask was flushed with N$_2$ and 10 mL of anhydrous dichloromethane was added via syringe. The mixture is stirred to dissolve the solids. In another round bottom flask equipped with a Teflon-coated stirbar, dicyclohexylcarbodiimide (DCC, 825 mg 4.0 mmol) transferred and the flask is sealed with a rubber septum. Next, 5 mL of anhydrous dichloromethane is transferred to the flask via syringe. The DCC solution is transferred to the fluorene reaction mixture via a syringe dropwise. The reaction is allowed to react overnight. The next day the reaction mixture is filtered. The filtrate is purified by column chromatography to afford a clear oil (967 g, 70% yield).

Example 20: Synthesis of a Fluorene Monomer with Highly Branched PEGylated Side Chains Based on a Trihydroxybenzene Linkage evaporated. After purification by column chromatography, a clear oil is obtained (887 mg, 48% yield).

Step 2: 3,4,5-Tris(2,5,8,11,14,17,20,23,26,29,32-undecaoxatetratriacontan-34-yloxy)-N-(2-aminoethyl)benzamide (v)

Methyl 3,4,5-tris(2,5,8,11,14,17,20,23,26,29,32-undecaoxatetratriacontan-34-yloxy)benzoate (iv) (887 mg, 0.52 mmol) flask is transferred to a round bottom flask equipped with a stirbar and sealed with a rubber septum. The flask is flushed with nitrogen and 10 mL of dry methanol is transferred to the flask via syringe and the solid is dissolved by stirring. Ethylenediamine (0.7 mL, 10.4 mmol) is added via

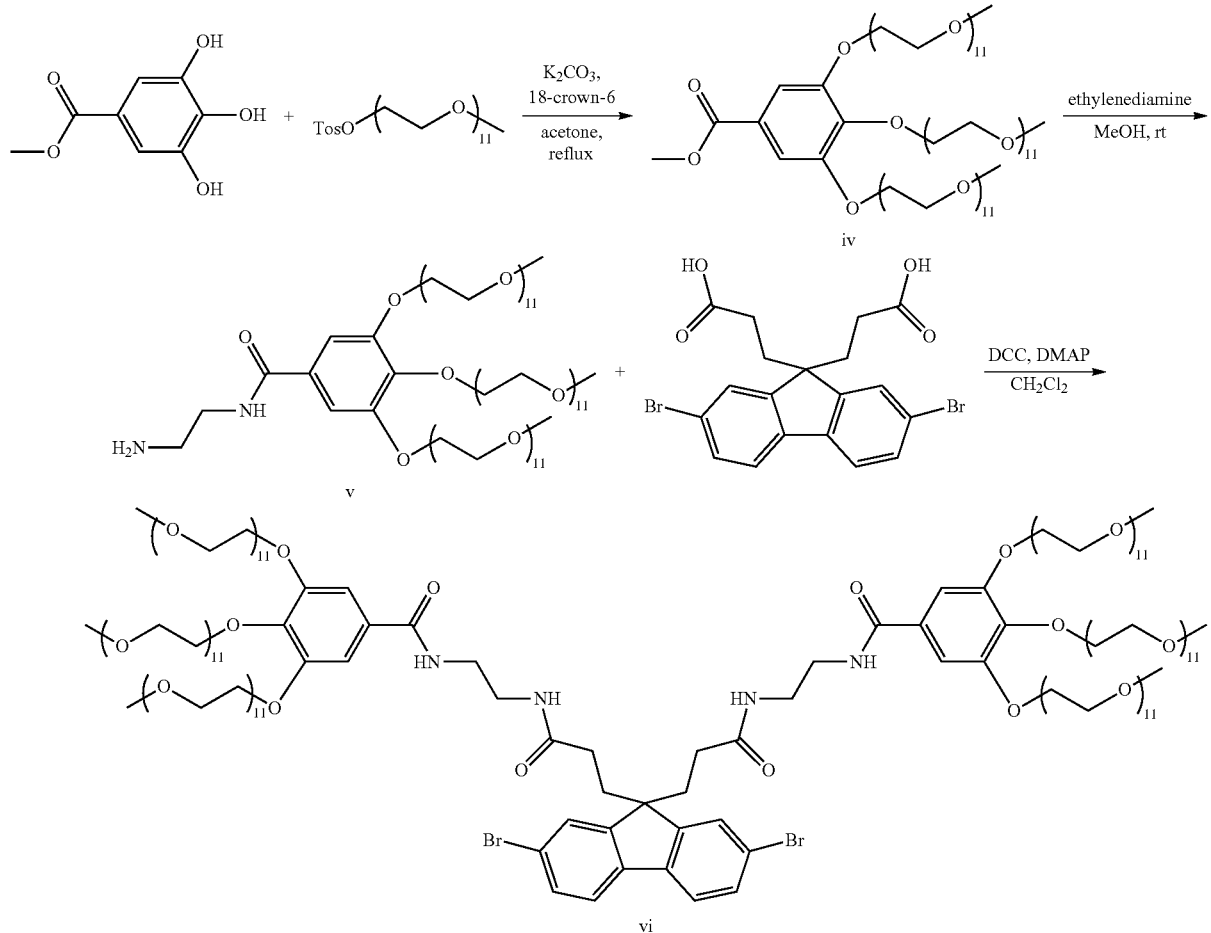

Step 1: Methyl 3,4,5-tris(2,5,8,11,14,17,20,23,26,29,32-undecaoxatetratriacontan-34-yloxy)benzoate (iv)

Methyl 3,4,5-trihydroxybenzoate (200 mg, 1.1 mmol), 2,5,8,11,14,17,20,23,26,29,32-undecaoxatetratriacontan-34-yl 4-methylbenzenesulfonate (2.58 g, 3.85 mmol), and 18-crown-6 (100 mg, 0.38 mmol) are transferred to a round bottom flask equipped with a Teflon-coated stirbar. Acetone (10 mL) is added and the flask is equipped with a reflux condenser. The mixture is refluxed with constant stirring overnight. The next day silica (4 g) is added and the solvent syringe slowly and the mixture is allowed to stir for 2 hours. The septum is removed and the methanol and unreacted ethylenediamine is removed under vacuum. The product is obtained as an oil (886 mg, quantitative yield).

Step 3:] 3,3'-(2,7-Dibromo-9H-fluorene-9,9-diyl)bis (N-(2-3,4,5-tris(2,5,8,11,14,17,20,23,26,29,32-undecaoxatetratriacontan-34-yloxy)-benzamidyl-N amidoethyl)propanamide) (vi)

3,4,5-Tris(2,5,8,11,14,17,20,23,26,29,32-undecaoxatetratriacontan-34-yloxy)-N-(2-aminoethyl)benzamide (v) (886 mg, 0.52 mmol), 3,3'-(2,7-Dibromo-9H-fluorene-9,9-diyl) dipropanoic acid (112 mg, 0.24 mmol), and N,N'-dimethylaminopyridine (12 mg, 0.1 mmol) are combined in a round bottom flask equipped with a Teflon-coated stirbar and sealed with a rubber septum. The flask was flushed with N$_2$ and 10 mL of anhydrous dichloromethane was added via syringe. The mixture is stirred to dissolve the solids. In another round bottom flask equipped with a Teflon-coated stirbar, dicyclohexylcarbodiimide (DCC, 148 mg 0.72 mmol) transferred and the flask is sealed with a rubber septum. Next, 5 mL of anhydrous dichloromethane is transferred to the flask via syringe. The DCC solution is transferred to the fluorene reaction mixture via a syringe dropwise. The reaction is allowed to react overnight. The next day the reaction mixture is filtered. The filtrate is purified by column chromatography to afford a clear oil (924 mg, 70% yield).

Example 21. Dual End Capped Polymer Used to Create a Polymer-Dye Label for Biomolecule or Substrate Conjugation

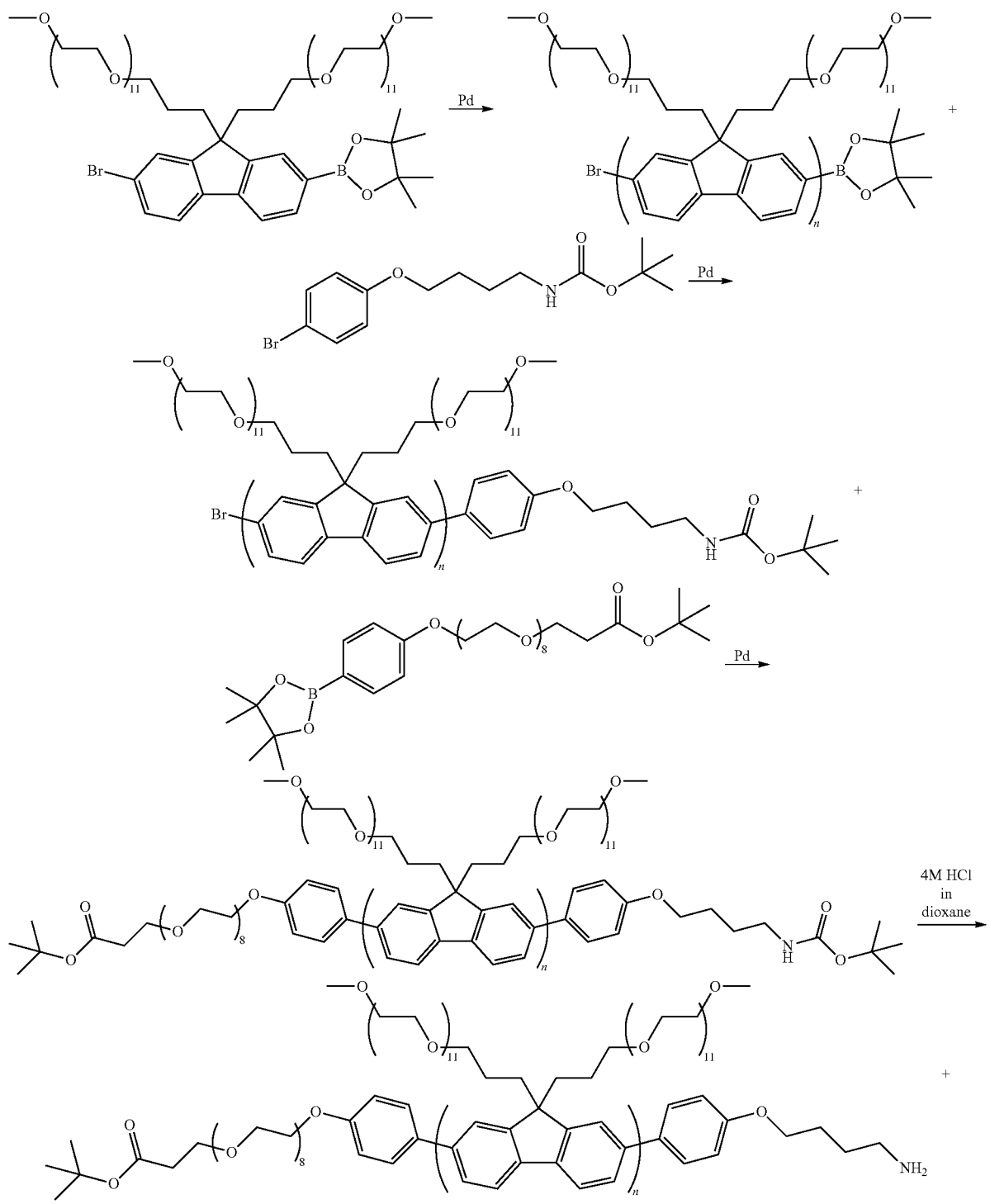

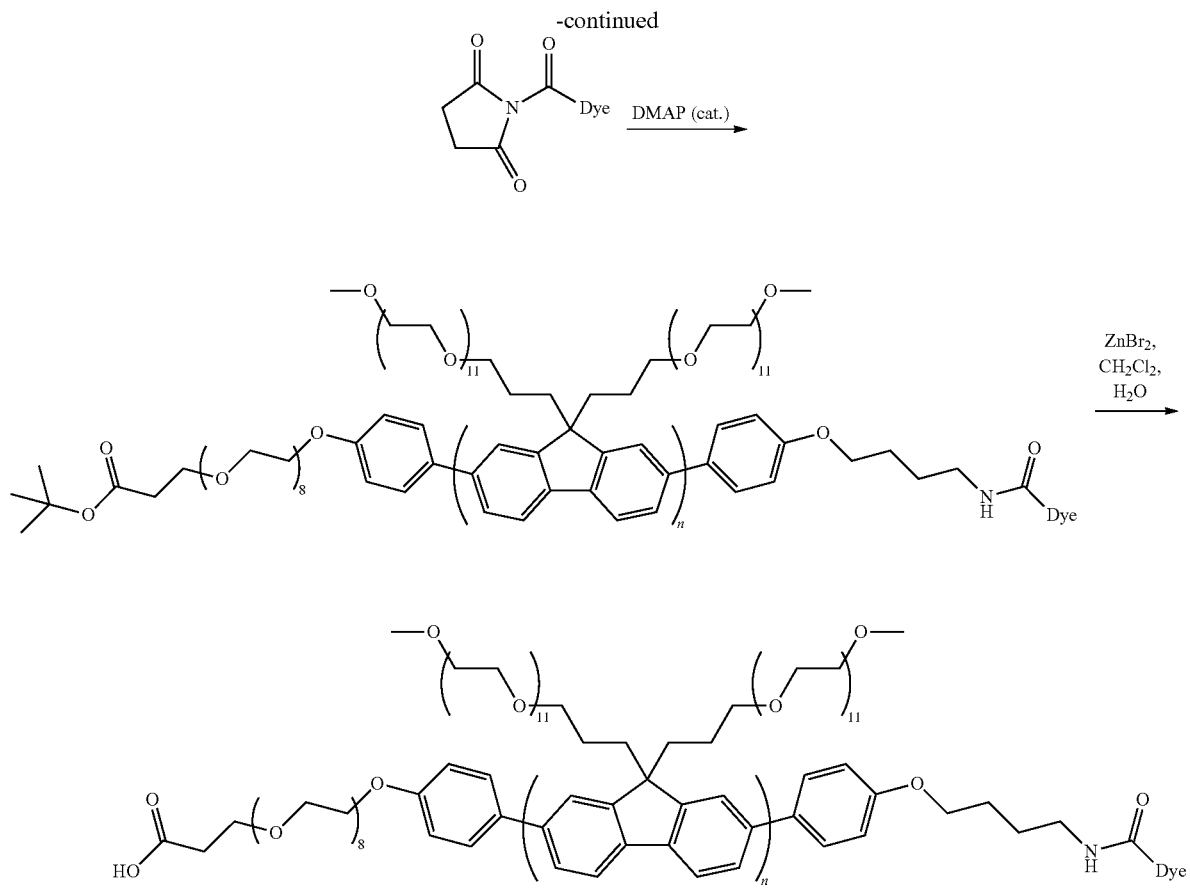

Step 1: Synthesis of an Asymmetric Neutral Water-Soluble Polymer with a t-BOC Protected Amine Pendant Group at One Terminus of the Polymer 2-bromo-7-(4"-phenoxybutyl-1-tert-butyl carbamate)-poly-2,7{9,9-bis(2,5,8,11,14,17,20,23,26,29,32,35-dodecaoxaoctatriacontane)fluorene.

2-bromo-9,9-di(2',5',8',11',14',17',20',23',26',29',32',35'-dodecaoxaoctatriacontan-38'-yl)-7-(4",4",5",5"-tetramethyl-1",3",2"-dioxaborolan-2-yl)fluorene (1.0 g, 0.674 mmol), 3 mL of tetrahydrofuran, and 2 mL of 2M potassium carbonate (aqueous) were transferred to a small round bottom flask charged with a Teflon stirbar. The flask was fitted with a septum and the solution is degassed by sparging with Ar for 15 minutes. Palladium tetra(triphenylphoshine) (15.6 mg, 0.013 mmol) was added through the neck of the flask and the flask was transferred to a reflux condenser equipped with a needle valve and fixed to a Schlenk line. The solution was quickly frozen solid with liquid nitrogen and was further degassed using freeze-pump-thaw technique. Once degassed the reaction was heated to 80° C. with constant stirring. The reaction was allowed to proceed overnight. The next day tert-butyl 4-(4-bromophenoxy)butylcarbamate (35 mg, 0.10 mmol) in 1 mL of THF was degassed with three freeze-pump-thaw cycles and then added to the polymerization reaction via cannula under excess nitrogen pressure. The reaction continued overnight at 80° C. The next day the reaction mixture was cooled and the bulk of the solvent was removed under vacuum. The remaining material was transferred to a small Erlenmeyer flask with a total of ~50 mL of dichloromethane. The solution was stirred for 30 minutes. Approximately 1 g of MgSO₄(anhydrous) was added to the solution and the mixture was filtered through a fluted paper filter. The filtrate was evaporated and 410 mg (47% yield) of an amber oil was collected.

Step 2: Synthesis to Append a Terminal Linking Monomer with a t-Butyl Ester at the Terminus Opposite the Protected Amine Pendant 2-(4-(tert-butyl 1-phenoxy-3,6,9,12,15,18,21,24-octaoxa-heptacosan-27-oate))-7-(4"-phenoxybutyl-1-tert-butyl carbamate)-poly-2,7{9,9-bis(2,5,8,11,14,17,20,23,26,29,32,35-dodecaoxaoctatriacontane)fluorene.

2-Bromo-7-(4"-phenoxybutyl-1-tert-butyl carbamate)-poly-2,7{9,9-bis(2,5,8,11,14,17,20,23,26,29,32,35-dodecaoxaoctatriacontane)fluorene (410 mg, 0.32 mmol of repeat unit), tert-butyl 1-(4-(4,4,5,5-tetramethyl-1,3,2-dioxaborolan-2-yl)phenoxy)-3,6,9,12,15,18,21-heptaoxatetracosan-24-oate (33 mg, 0.048 mmol), 2 mL of tetrahydrofuran, and 1.5 mL of 2M potassium carbonate (aqueous) were transferred to a small round bottom flask charged with a Teflon stirbar. The flask was fitted with a septum and the solution is degassed by sparging with Ar for 15 minutes. Palladium tetra(triphenylphoshine) (15 mg, 0.013 mmol) was added through the neck of the flask and the flask was transferred to a reflux condenser equipped with a needle valve and fixed to a Schlenk line. The solution was quickly frozen solid with liquid nitrogen and was further degassed using freeze-pump-thaw technique. Once degassed the reaction was heated to 80° C. with constant stirring. The reaction was allowed to proceed overnight. The remaining material was transferred to a small Erlenmeyer flask with a total of ~50 mL of dichloromethane. The solution was stirred for 30 minutes. Approximately 1 g of MgSO$_4$(anhydrous) was added to the solution and the mixture was filtered through a fluted paper filter. The filtrate was evaporated and 351 mg (78% yield) of an amber oil was collected.

Step 3: Synthesis of a Neutral Water-Soluble Polymer with Primary Amine at One Terminus and a t-Butyl Ester Pendant on the Other 2-(4-(tert-butyl 1-phenoxy-3,6,9,12,15,18,21,24-octaoxa-heptacosan-27-oate))-7-(4"-phenoxybutyl-1-amino)-poly-2,7{9,9-bis(2,5,8,11,14,17,20,23,26,29,32,35-dodecaoxaoctatriacontane)fluorene.

2-(4-(tert-butyl 1-phenoxy-3,6,9,12,15,18,21,24-octaoxa-heptacosan-27-oate))-7-(4"-phenoxybutyl-1-tert-butyl carbamate)-poly-2,7{9,9-bis(2,5,8,11,14,17,20,23,26,29,32,35-dodecaoxaoctatriacontane)fluorene (23 mg, 0.018 mmol) and 0.5 mL of 4M HCl in dioxane were combined in a 1 dram vial with a Teflon-coated stirbar. The mixture was stirred for 4 hours. The mixture was neutralized with 2M potassium carbonate (aqueous). The solution was then diluted to 50 mL of roughly 20% ethanol in water and filtered through G-6glass fiber filter paper. The filtrate was desalted by centrifugation in a 4 mL 10 KDa cutoff centrifuge filter. The retentate was evaporated under vacuum and two 1 mL portions of toluene were added and removed under vacuum to remove any remaining water. A thick amber liquid was recovered from the desalting (21 mg, 85% yield).

Step 4: Attachment of an NHS-Functionalized Dye to a Primary Amine Pendant on a Neutral Water-Soluble Polymer 2-(4-(tert-butyl 1-phenoxy-3,6,9,12,15,18,21,24-octaoxa-heptacosan-27-oate))-7-(4"-phenoxybutyl-1-amido-DYE)-poly-2,7{9,9-bis(2,5,8,11,14,17,20,23,26,29,32,35-dodecaoxaoctatriacontane)fluorene.

2-(4-(tert-butyl 1-phenoxy-3,6,9,12,15,18,21,24-octaoxa-heptacosan-27-oate))-7-(4"-phenoxybutyl-1-amino)-poly-2,7{9,9-bis(2,5,8,11,14,17,20,23,26,29,32,35-dodecaoxaoctatriacontane)fluorene (518 ug, 0.4 µM) was dissolved in 100 µL of dry dichloromethane in a glass vial. A small crystal of 4-N,N'-dimethylaminopyridine was added. In another vial 65 µg (0.06 □uM) of NHS-functionalized DyLight 594 (Pierce) was dissolved in 50 of dry dichloromethane. The two solutions were combined and allowed to stir in a sealed vial for 4 hours covered in foil. The solvent was then evaporated and the remaining material was dissolved in 95% ethanol and injected onto a Sepharose 6 column. The remaining dye was separated from the polymer. A solution of dye-labeled polymer was obtained from combining fractions (100 µg, 20% yield).

Step 5: Hydrolysis of the t-Butyl Ester Pendant on the Dye-Labeled Neutral Water-Soluble Polymer to Form the Carboxylic Acid Pendant on One of the Termini 2-(4-(1-phenoxy-3,6,9,12,15,18,21,24-octaoxaheptacosane-27-acid))-7-(4"-phenoxybutyl-1-amido-DYE)-poly-2,7{9,9-bis(2,5,8,11,14,17,20,23,26,29,32,35-dodecaoxaoctatriacontane)fluorene.

The polymer was combined with ZnBr$_2$ in dichloromethane and stirred overnight. The next day a portion of water was added and the mixture was stirred for 1 hour. The solvent was evaporated and the residue was dissolved in 20% ethanol in water. The filtrate was then desalted by centrifugation in a 4 mL 10 KDa cutoff centrifuge filter. The retentate was evaporated under vacuum and two 1 mL portions of toluene were added and removed under vacuum to remove any remaining water.

Activation (for subsequent conjugation) of the second functional group in this example (carboxylic acid) can be achieved using a number of different methods including those described in Examples 29 and other examples with carboxylic acid to amine to maleimide. One such method is given below in Step 6, by way of example only.

Step 6: NHS Activation of the Carboxylic Acid Penant of a Dye-Labeled Neutral Water-Soluble Polymer 2-(4-(1-phenoxy-3,6,9,12,15,18,21,24-octaoxaheptacosane-27-N-hydroxysuccinimidyl ester))-7-(4"-phenoxybutyl-1-amido-DYE)-poly-2,7{9,9-bis(2,5,8,11,14,17,20, 23,26,29,32,35-dodecaoxaoctatriacontane)fluorene. 2-(4-(1-phenoxy-3,6,9,12,15,18,21,24-octaoxaheptacosane-27-acid))-7-(4"-phenoxybutyl-1-amido-DYE)-poly-2,7{9,9-bis (2,5,8,11,14,17,20,23,26,29,32,35-dodecaoxaoctatriacontane)fluorene and O—(N-Succinimidyl)-1,1,3,3-tetramethyluronium tetrafluoroborate and DIPEA are combined in dry acetonitrile and allowed to react under nitrogen for 30 min. The solution is evaporated and the solid is resuspended in dry dichloromethane. Solids are filtered off and the filtrate is evaporated to afford the NHS ester.

In further embodiments, various commonly used protecting groups can be used with those functional groups provided (amine and carboxylic acid). Additionally different capping monomers and protecting group combinations can be used to produce polymers with different functional groups for conjugation. Eliminating or substituting the dye labeling step for another entity will result in a polymer with two different functional groups for conjugation. The dye attachment via NHS/amine chemistry can be performed under a variety of commonly used conditions. Dye attachment can also be performed with other functional chemistries.

Example 22. Asymmetric Polyfluorene Synthesis Using Non-Regulated Suzuki Conditions
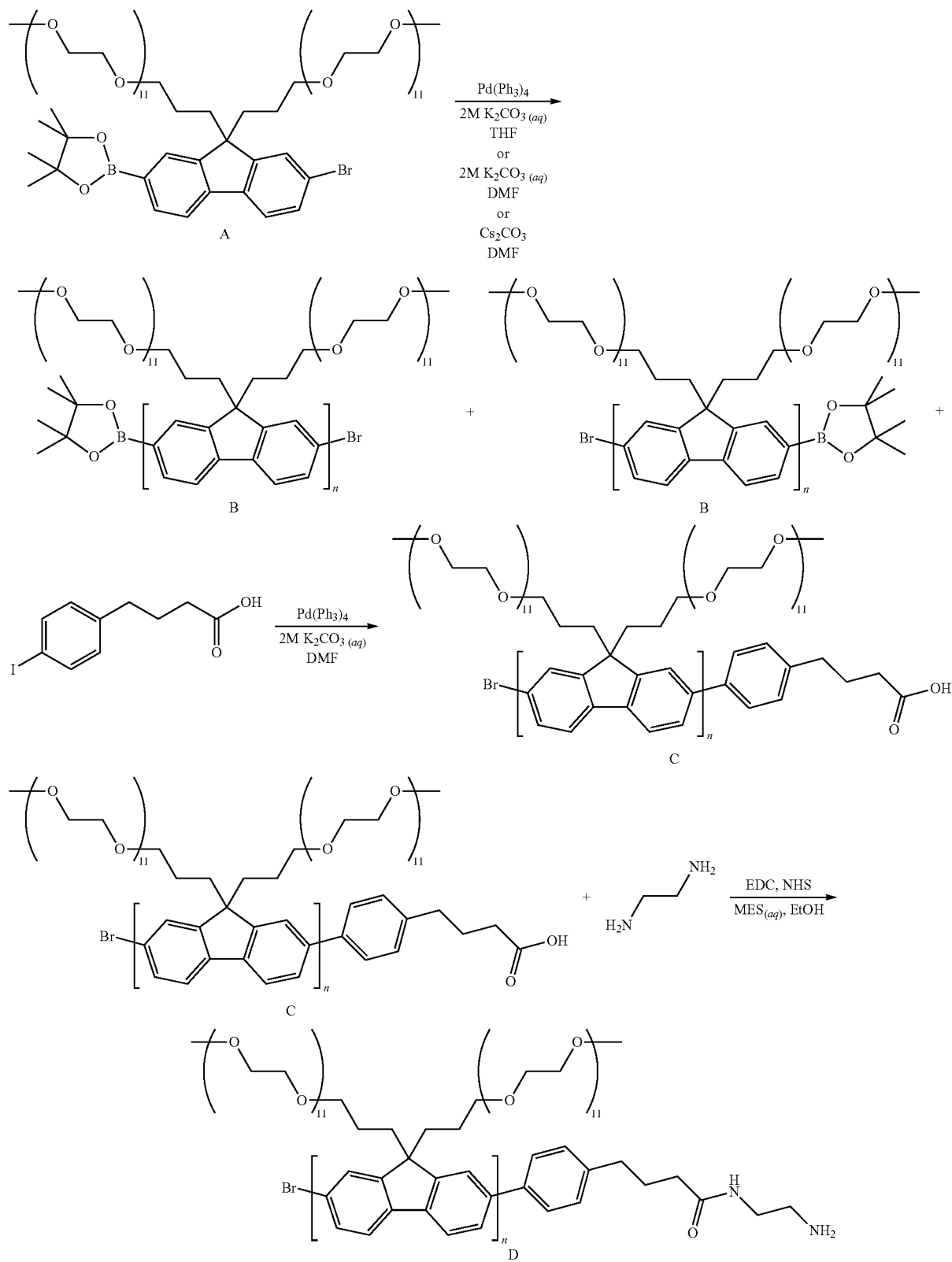

Step 1: Polymerization

Method A:

A solution of $K_2CO_3$ in water (2M, 4 mL) was added to a stirred mixture of 2-bromo-9,9-di(2',5',8',11',14',17',20', 23',26',29',32',35'-dodecaoxaoctatriacontan-38'-yl)-7-(4",4", 5",5"-tetramethyl-1",3",2"-dioxaborolan-2-yl)fluorene (A) (2.3 g, 1.5 mmol) and THF (6 mL) in a round bottom flask. This mixture was degassed with argon for 15 min. Palladium tetrakis(triphenylphosphine) (38.5 mg, 0.03 mmol) was added to the mixture and the flask was attached to a reflux condenser. The reaction vessel was degassed via 3 freeze-pump-thaw cycles and then heated to 80° C. for 12 h.

The reaction mixture was cooled to 23° C. and solvent removed by rotary evaporation. The resulting residue was transferred to an Erlenmeyer flask and diluted with 20% EtOH/H2O (75 mL). EDTA (300 mg, 1.0 mmol) was added to the mixture and stirred at 23° C. for 1 h. The mixture was filtered through a glass fiber filter paper and the filter paper rinsed with 20% EtOH/$H_2O$. The resulting filtrate was then filtered through a 0.45 um cup filter.

The filtered reaction mixture was purified using tangential flow filtration (TFF) and was diafiltered into 20% ethanol using a 10,000 molecular weight cutoff membrane (regenerated cellulose Prep/Scale TFF cartridge system, Millipore, Billerica, Mass.) until conductivity of the filtrate measured less than 0.01 mS/cm. The solvent was then removed under vacuum to give poly [2,7{9,9-bis(2,5,8,11,14,17,20,23,26, 29,32,35-dodecaoxaoctatriacontane)fluorene] (B) as a gel-like product (1.41 g, 71%) Molecular weight determined by GPC analysis relative to polystyrene standards (Mn=51,000, Mw=108,000, Mp=90,000, D=2.1). The extent of end linker incorporation was determined by first converting the acid to an NHS ester (similar protocol to that provided in Example 29) then reacting with an amine functional dye. After purification of free dye the ratio of dye to polymer was determined from absorbance measurements, factoring in the difference in extinction coefficients and polymer molecular weight.

Method B:

A solution of $K_2CO_3$ in water (2M, 4 mL) was added to a stirred mixture of 2-bromo-9,9-di(2',5',8',11',14',17',20', 23',26',29',32',35'-dodecaoxaoctatriacontan-38'-yl)-7-(4",4", 5",5"-tetramethyl-1",3",2"-dioxaborolan-2-yl)fluorene (A) (2.3 g, 1.5 mmol) and DMF (6 mL) in a round bottom flask. This mixture was degassed with argon for 15 min. Palladium tetrakis(triphenylphosphine) (38.5 mg, 0.03 mmol) was added to the mixture and the flask was attached to a reflux condenser. The reaction vessel was degassed via 3 freeze-pump-thaw cycles and then heated to 80° C. for 12 h. Work-up and purification was performed in a manner similar to previously described Method A. Molecular weight determined by GPC analysis relative to polystyrene standards (Mn=96,000, Mw=231,000, Mp=185,000, D=2.4).

Method C:

$Cs_2CO_3$ (2.08 g, 6.4 mmol) was added to a stirred mixture of 2-bromo-9,9-di(2',5',8',11',14',17',20',23',26',29',32',35'-dodecaoxaoctatriacontan-38'-yl)-7-(4",4",5",5"-tetramethyl-1",3",2"-dioxaborolan-2-yl)fluorene (A) (200 mg, 0.135 mmol) and DMF (7 mL) in a round bottom flask. This mixture was degassed with argon for 15 min. Palladium tetrakis(triphenylphosphine) (15.6 mg, 10 mol %) was added to the mixture and the flask was attached to a reflux condenser. The reaction vessel was degassed via 3 freeze-pump-thaw cycles and then heated to 80° C. for 12 h. Work-up and purification was performed in a manner similar to previously described Method A. Molecular weight determined by GPC analysis relative to polystyrene standards (Mn=95,000, Mw=218,000, Mp=206,000, D=2.3).

Step 2: End Capping

-(4-iodophenyl)butanoic acid (227 mg, 0.783 mmol) was washed into a flask containing poly [2,7{9,9-bis(2,5,8,11, 14,17,20,23,26,29,32,35-dodecaoxaoctatriacontane)fluorene] (B) (1.00 g, 0.783 mmol) using THF (3.5 mL). A solution of $K_2CO_3$ in water (2M, 2.3 mL) was added to the flask and this mixture was degassed with argon for 15 min. Palladium tetrakis(triphenylphosphine) (36 mg, 4 mol %) was added to the mixture and the flask was attached to a reflux condenser. The reaction vessel was degassed via 3 freeze-pump-thaw cycles and then heated to 80° C. for 12 h.

The reaction mixture was cooled to 23° C. and the solvent removed with rotary evaporation. The resulting residue was transferred to an Erlenmeyer flask and diluted with 20% EtOH/H2O (150 mL). EDTA (500 mg) was added to the mixture and stirred at 23° C. for 1 h. The mixture was filtered through a glass fiber filter paper and the filter paper rinsed with 20% EtOH/$H_2O$. The resulting filtrate was then filtered through a 0.45 um cup filter.

The filtered reaction mixture was purified using tangential flow filtration (TFF) and was diafiltered into 20% ethanol using a 10,000 molecular weight cutoff membrane (regenerated cellulose Prep/Scale TFF cartridge system, Millipore, Billerica, Mass.) until conductivity of the filtrate measured less than 0.01 mS/cm. The solvent was then removed under vacuum to give 4-(Poly [2,7{9,9-bis(2,5,8,11,14,17,20,23, 26,29,32,35-dodecaoxaoctatriacontane)fluorene]yl)phenyl) butanoic acid (C) as a gel-like product (388 mg, 39%) Molecular weight determined by GPC analysis relative to polystyrene standards (Mn=89,000, Mw=196,000, Mp=124, 000, D=2.2). The extent of end linker incorporation was determined by first converting the acid to an NHS ester (similar protocol to that provided in Example 29) then reacting with an amine functional dye. After purification of free dye the ratio of dye to polymer was determined from absorbance measurements, factoring in the difference in extinction coefficients and polymer molecular weight.

Step 3: Amine Activation 4-(Poly [2,7{9,9-bis(2,5,8,11,14,17,20,23,26,29,32,35-dodecaoxaoctatriacontane)fluorene]yl)phenyl)butanoic acid (C) (200 mg, 0.156 mmol) was dissolved in 2 mL ethanol, then added drop-wise to 23 mL of MES buffer (50 mM, pH 5) at 4° C. while stirring. N-(3-dimethylaminopropyl)-N'-ethylcarbodiimide hydrochloride (576 mg, 3.00 mmol) was added in portions, followed by N-hydroxy succinimide (115 mg, 1.00 mmol) in one portion. The solution was stirred for 30 minutes, ethylene diamine (0.501 mL, 7.50 mmol) was added drop-wise and the reaction mixture was stirred overnight at room temperature. The reaction mixture was then desalted over a G25 desalting column and the solvent removed via rotary evaporation to give N-(2-aminoethyl)-4-(Poly [2,7{9,9-bis(2,5,8,11,14,17,20,23,26,29,32,35-dodecaoxaoctatriacontane)fluorene]yl)butanamide as a clear yellow oil (190 mg, 95%). Molecular weight determined by GPC analysis relative to polystyrene standards (Mn=89,000, Mw=196,000, Mp=124,000, D=2.2). Extent of amine conversion was determined by reacting the amine polymer with an NHS active dye in similar fashion as that described in Example 38.

Example 23. Asymmetric Polyfluorene Synthesis Using Linker Modified End Caps to Regulate the Suzuki Polymerization

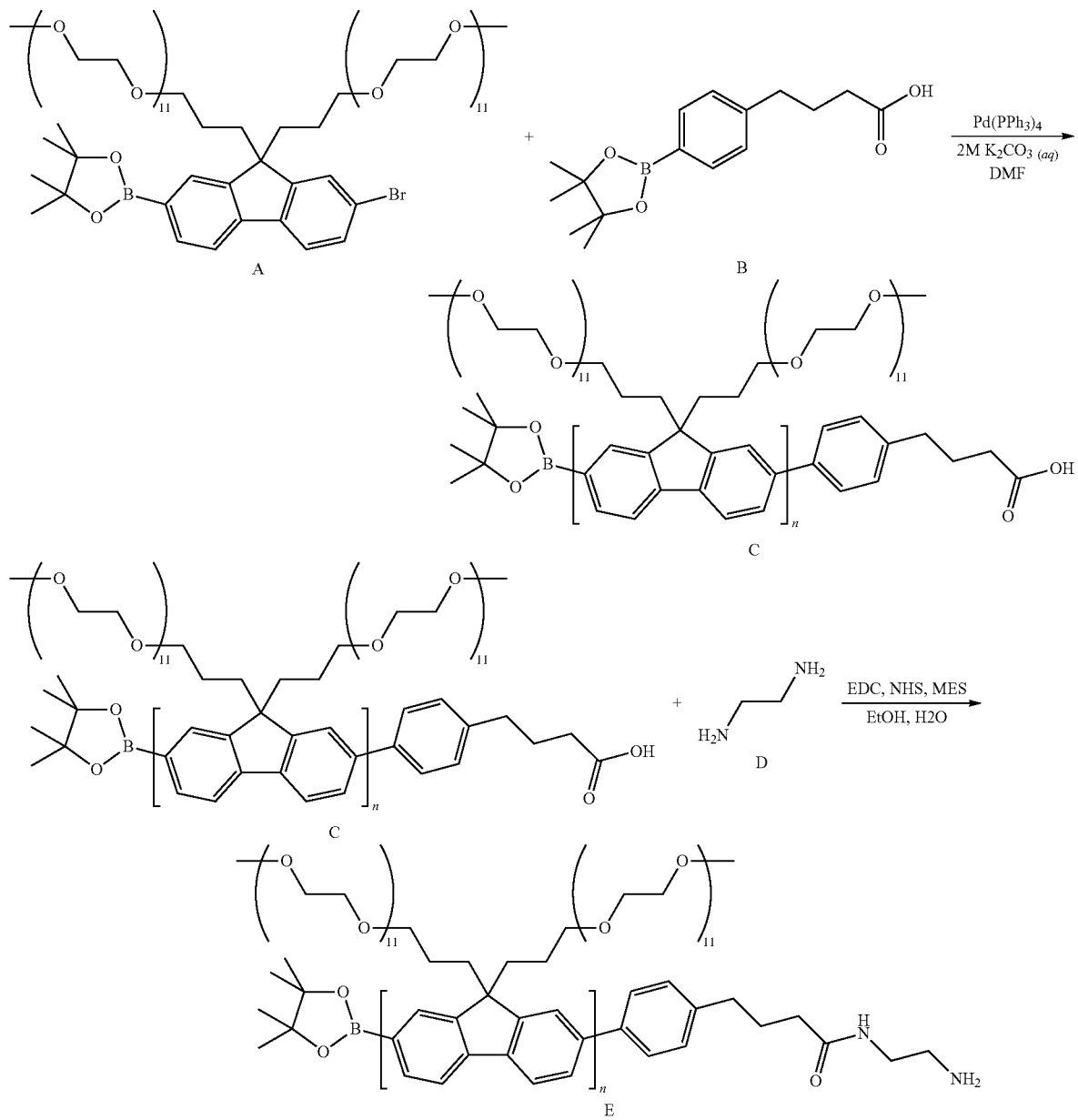

Step 1: Polymerization/End Capping/Work-Up

A solution of K$_2$CO$_3$ in water (2M, 4 mL) was added to a stirred mixture of 2-bromo-9,9-di(2',5',8',11',14',17',20', 23',26',29',32',35'-dodecaoxaoctatriacontan-38'-yl)-7-(4'',4'', 5'',5''-tetramethyl-1'',3'',2''-dioxaborolan-2-yl)fluorene (A) (2.3 g, 1.55 mmol), 4-(4-(4,4,5,5-tetramethyl-1,3,2-dioxaborolan-2-yl)phenyl)butanoic acid (B) (6.7 mg, 2 mol %), and DMF (6 mL) in a round bottom flask equipped with a side-arm stopcock. This mixture was degassed with argon for 25 min. Palladium tetrakis(triphenylphosphine) (38.5 mg, 2 mol %) was then added to the mixture and the flask was attached to a reflux condenser. The reaction vessel was further degassed via 3 freeze-pump-thaw cycles and then heated to 80° C.

Separately, 4-(4-(4,4,5,5-tetramethyl-1,3,2-dioxaborolan-2-yl)phenyl)butanoic acid (B) (230 mg, 0.793 mmol) was dissolved in DMF (3 mL) in a found bottom flask equipped with a side arm stopcock. This solution was sparged with argon for 15 minutes, attached to a reflux condenser, and degassed via three freeze-pump-thaw cycles. Upon thawing the solution was added to the reaction mixture after two hours of reaction time using an argon flushed syringe. The reaction mixture was stirred for an additional 12 h at 80° C.

The reaction mixture was cooled to 23° C. and solvent removed with rotary evaporation. The resulting residue was transferred to an Erlenmeyer flask and diluted with 20% EtOH/H$_2$O (75 mL). EDTA (300 mg, 1.00 mmol) was added to the mixture and stirred at 23° C. for 1 h. The mixture was filtered through a glass fiber filter paper and the filter paper rinsed with 20% EtOH/H$_2$O. The resulting filtrate was then filtered through a 0.45 um cup filter.

The filtered reaction mixture was purified and size fractionated using tangential flow filtration (TFF) and was diafiltered into 20% ethanol using a 30,000 molecular weight cutoff membrane (polyethersulfone Prep/Scale TFF cartridge system, Millipore, Billerica, Mass.) until conductivity of the filtrate measured less than 0.01 mS/cm and M$_n$ of the retentate measured more than 70,000 by GPC. The solvent was then removed under vacuum to give 4-(Poly [2,7{9,9-bis(2,5,8,11,14,17,20,23,26,29,32,35-dodecaoxaoctatriacontane)fluorene]yl)phenyl)butanoic acid as a gel-like product (1.41 g, 71%). Molecular weight determined by GPC analysis relative to polystyrene standards (Mn=68,000, Mw=134,000, Mp=122,000, D=1.9). The extent of end linker incorporation was determined by first converting the acid to an NHS ester (similar protocol to that provided in Example 29) then reacting with an amine functional dye. After purification of free dye the ratio of dye to polymer was determined from absorbance measurements, factoring in the difference in extinction coefficients and polymer molecular weight.

Despite having a molecular weight in excess of 50,000 g/mole the polymer is soluble in both water and phosphate buffered saline solutions at concentrations easily greater than 10 mg/mL. In many conjugation experiments the polymer provided (and other described herein with similar structure) was concentrated to 50 mg/mL or higher which is remarkable for a neutral conjugated polymer. The moderate molecular weight also provides extinction coefficients greater than 2,500,000 M$^{-1}$ cm$^{-1}$. The large extinction coefficient and quantum yield of 60% (PBS) provide for exceptionally bright fluorescent reporters for use in biological assays including their use in flow cytometry.

Step 2: Amine Activation 4-(Poly [2,7{9,9-bis(2,5,8,11,14,17,20,23,26,29,32,35-dodecaoxaoctatriacontane)fluorene]yl)phenyl)butanoic acid (C) (500 mg, 0.13 mmol) was dissolved in 2 mL ethanol, then added drop-wise to 23 mL of MES buffer (50 mM, pH 5) at 4° C. while stirring. N-(3-dimethylaminopropyl)-N'-ethylcarbodiimide hydrochloride was added in portions, followed by N-hydroxy succinimide (0.52 g) in one portion. The solution was stirred for 30 minutes, ethylene diamine (2.8 mL) was added drop-wise and the reaction mixture was stirred overnight at room temperature. The reaction mixture was then desalted over a G25 desalting column and the solvent removed via rotary evaporation to give N-(2-aminoethyl)-4-(Poly [2,7{9,9-bis(2,5,8,11,14,17,20,23,26,29,32,35-dodecaoxaoctatriacontane)fluorene]yl)butanamide as a yellow oil (450 mg, 90%). Extent of amine conversion was determined by reacting the amine polymer with an NHS active dye in similar fashion as that described in Example 38.

Example 24. Yamamoto polymerization of PEG modified polyfluorene

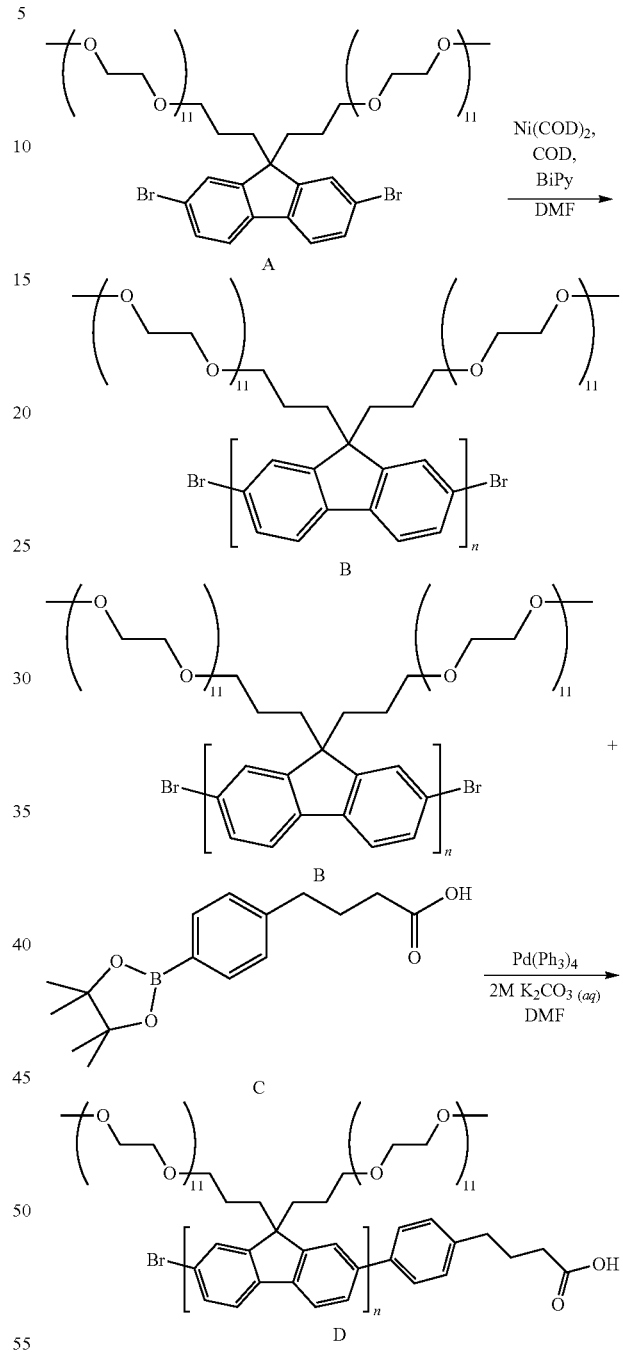

Step 1: Yamamoto Polymerization/Work-Up

In a dry box, Ni(COD)$_2$ (0.387 g, 1.41 mmol), 2,2'-bipyridyl (0.220 g, 1.41 mmol), COD (0.152 g, 1.41 mmol) and anhydrous DMF (16 ml) were added to a long-neck round bottom flask. 2,7-dibromo-9,9-di(2',5',8',11',14',17', 23',26',29',32',35'-dodecaoxaoctatriacontan-38'-yl)fluorene (A) (1.00, 0.696) was weighed into a 40 ml vial and dissolved in anhydrous DMF (8 ml). The flask was sealed with a septum and the vial was closed with a septum screw cap. The catalyst mixture and the monomer solution were transferred out of the dry box and were placed under static argon. The reaction flask was heated to 70° C. for 45 min. The monomer solution was then was quickly transferred from the vial to the catalyst mixture flask with an argon flushed syringe. The reaction mixture was then heated to 70° C. for 6 h.

The reaction mixture was cooled and solvent removed by rotary evaporation. The resultant black residue was re-dissolved in 20% EtOH (80 mL) and centrifuged at 2400 rpm for 12 hours. The supernatant was then decanted and filtered through a 0.45 um cup filter.

The filtered reaction mixture was purified using tangential flow filtration (TFF) and was diafiltered into 20% ethanol using a 10,000 molecular weight cutoff membrane (polyethersulfone Prep/Scale TFF cartridge system, Millipore, Billerica, Mass.) until GPC analysis of retentate indicated the absence of low molecular weight material. The solvent was then removed under vacuum to give poly [2,7{9,9-bis(2,5,8,11,14,17,20,23,26,29,32,35-dodecaoxaoctatriacontane)fluorene] (B) as a viscous oil (0.700 g, 79%) Molecular weight determined by GPC analysis relative to polystyrene standards (Mn=62,000, Mw=127,000, Mp=93,000, D=2.0).

Step 2: End Capping: End Capping is Performed in a Manner Similar to Example 22, Step 2

Step 3: Amine Activation: Amine Activation is Performed in a Manner Similar to Example 22, Step 3

Example 25. Synthesis of a Tandem Polymer with Two Different Linkers

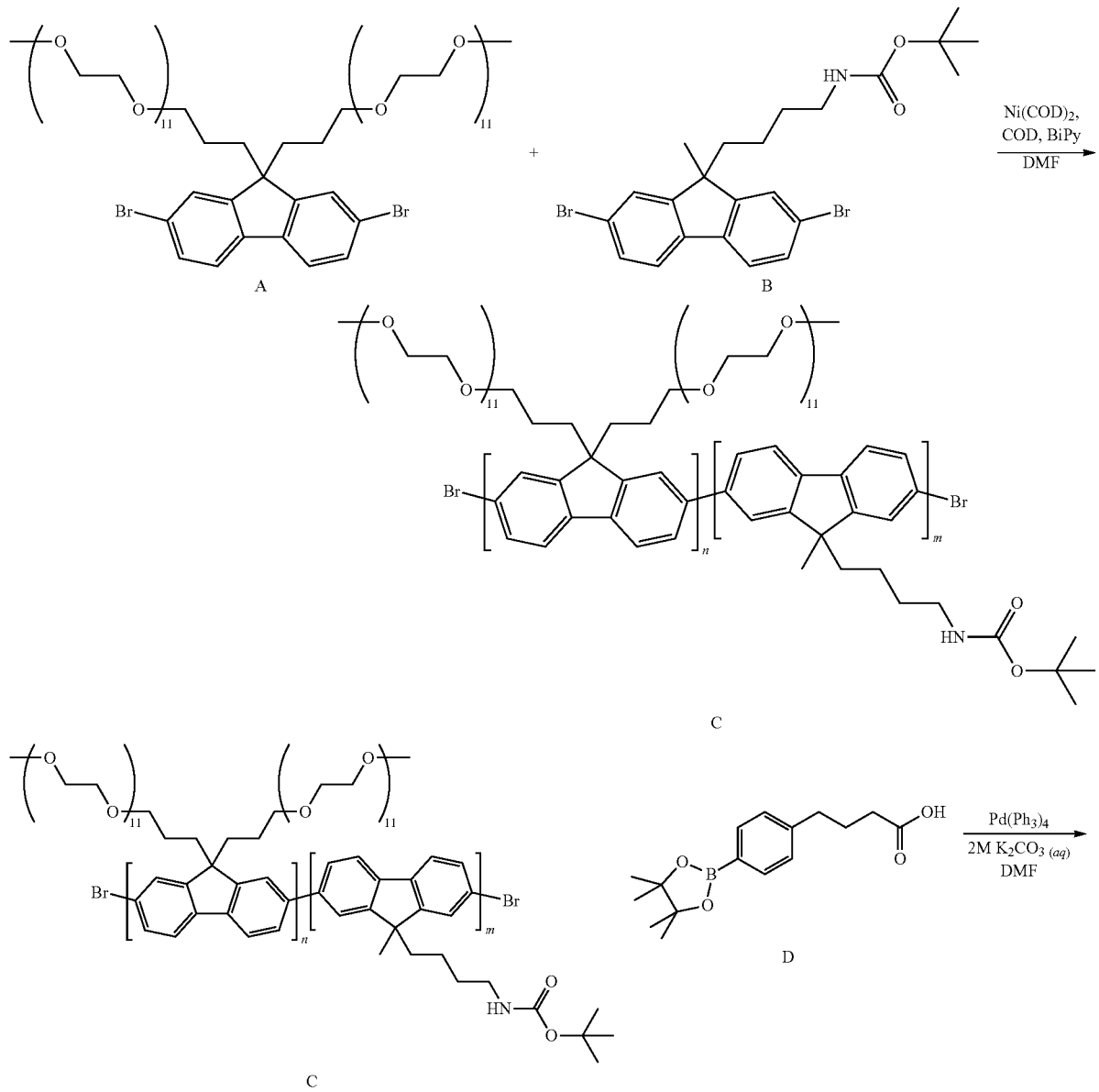

-continued

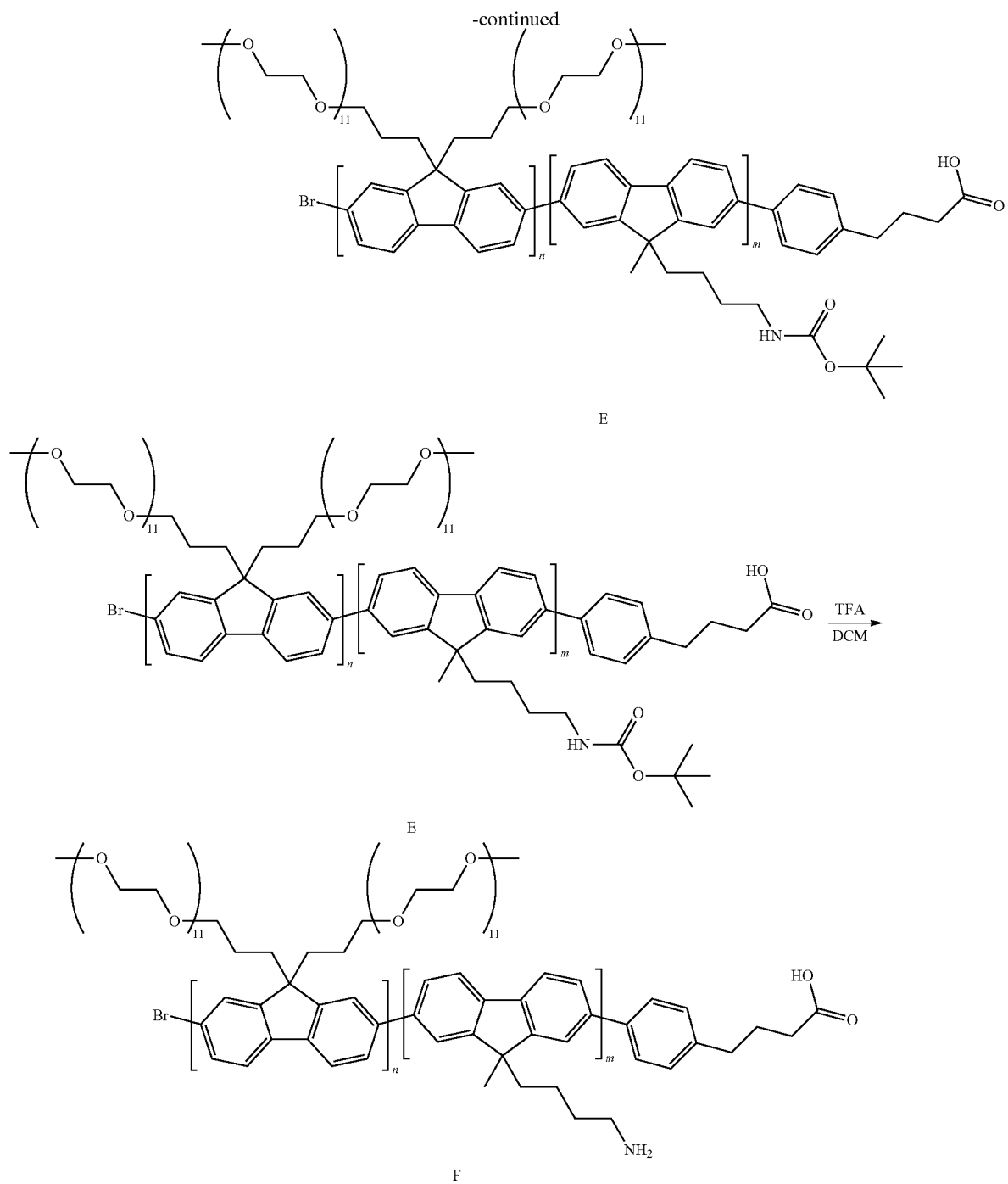

Step 1: Polymerization

In a dry box, Ni(COD)₂ (0.765 g, 2.78 mmol), 2,2'-bipyridyl (0.435 g, 2.78 mmol), COD (0.301 g, 2.78 mmol) and anhydrous DMF (20 ml) were added to a long-neck round bottom flask. 2,7-dibromo-9,9-di(2',5',8',11',14',17',23',26',29',32',35'-dodecaoxaoctatriacontan-38'-yl)fluorene (A) (1.80, 1.26 mmol) and tert-butyl 4-(2,7-dibromo-9-methyl-9H-fluoren-9-yl)butylcarbamate (B) (0.071 g, 0.126 mmol) were added to a 40 ml vial and dissolved in anhydrous DMF (30 ml). The flask was sealed with a septum and the vial was closed with a septum screw cap. The catalyst mixture and the monomer solution were transferred out of the dry box and were placed under static argon. The reaction flask was heated to 70° C. for 45 min. The monomer solution was then was quickly transferred from the vial to the catalyst mixture flask with an argon flushed syringe. The reaction mixture was then heated to 70° C. for 6 h.

The reaction mixture was cooled and solvent removed by rotary evaporation. The resultant black residue was re-dissolved in 20% EtOH (80 mL) and centrifuged at 2400 rpm for 12 hours. The supernatant was then decanted and filtered through a 0.45 um cup filter.

The filtered reaction mixture was purified using tangential flow filtration (TFF) and was diafiltered into 20% ethanol using a 10,000 molecular weight cutoff membrane (polyethersulfone Prep/Scale TFF cartridge system, Millipore, Billerica, Mass.) until GPC analysis of retentate indicated the absence of low molecular weight material. The solvent was then removed under vacuum to give 2,7-dibromo-poly-[2,7{9,9-bis(2,5,8,11,14,17,20,23,26,29,32,35-dodecaoxaoctatriacontane)fluorene-co-2,7-(9-methyl-9'-(butyl-4-t-butylcarbamate)fluorene)] (C) as a viscous oil (1.3 g, 45%) Molecular weight determined by GPC analysis relative to polystyrene standards (Mn=72,000, Mw=156,000, Mp=138,000, D=2.1).

Step 2: End Capping

A solution of $K_2CO_3$ in water (2M, 4 mL) was added to a stirred mixture of 2,7-dibromo-poly-[2,7{9,9-bis(2,5,8,11,14,17,20,23,26,29,32,35-dodecaoxaoctatriacontane)fluorene-co-2,7-(9-methyl-9'-(butyl-4-t-butylcarbamate)fluorene)] (C) (800 mg, 0.67 mmol), 4-(4-(4,4,5,5-tetramethyl-1,3,2-dioxaborolan-2-yl)phenyl)butanoic acid (D) (120 mg, 0.41 mmol), and DMF (6 mL) in a round bottom flask. This mixture was degassed with argon for 15 min. Palladium tetrakis(triphenylphosphine) (50 mg, 6 mol %) was added to the mixture and the flask was attached to a reflux condenser. The reaction vessel was degassed via 3 freeze-pump-thaw cycles and then heated to 80° C. for 12 h.

The reaction mixture was cooled to 23° C. and concentrated in vacuo to a volume of 2 mL. The crude reaction mixture was transferred to an Erlenmeyer flask and diluted with 20% EtOH/H2O (75 mL). EDTA (300 mg, 2.00 mmol) was added to the mixture and stirred at 23° C. for 1 h. The mixture was filtered through a glass fiber filter paper and the filter paper rinsed with 20% EtOH/H2O. The resulting filtrate was then filtered through a 0.45 um cup filter.

The filtered reaction mixture was purified and size fractionated using tangential flow filtration (TFF) and was diafiltered into 20% ethanol using a 10,000 molecular weight cutoff membrane (polyethersulfone Prep/Scale TFF cartridge system, Millipore, Billerica, Mass.) until conductivity of the filtrate measured less than 0.01 mS/cm. The solvent was then removed under vacuum to give 4-(4-(2-bromo-poly-[2,7{9,9-bis(2,5,8,11,14,17,20,23,26,29,32,35-dodecaoxaoctatriacontane)fluorene-co-2,7-(9-methyl-9'-(butyl-4-t-butylcarbamate)fluorene)])phenyl)butanoic acid (E) as a yellow oil (660 mg, 82%).

Step 3: Linker Deprotection

Trifluoroacetic acid (4 mL) was added dropwise to a stirred solution of 4-(4-(2-bromo-poly-[2,7{9,9-bis(2,5,8,11,14,17,20,23,26,29,32,35-dodecaoxaoctatriacontane)fluorene-co-2,7-(9-methyl-9'-(butyl-4-t-butylcarbamate)fluorene)])phenyl)butanoic acid (E) (200 mg, 0.169 mmol) and dichloromethane (16 mL) in a round bottom flask. The reaction mixture was stirred at room temperature for 2 hours and then concentrated in vacuo. The residue was redissolved in minimal 20% EtOH and 1M HCl was added to the solution until pH=7. The neutralized solution was then desalted over G25 gel and the resultant material was concentrated to dryness to yield a clear pale yellow oil (F).

Examples of dye incorporation, linker activation and bioconjugation are contained in further Example 38 and related examples.

Example 26: Synthesis of a Tandem Polymer with Two Different Linkers Using End Capping Units to Regulate the Polymerization Reaction

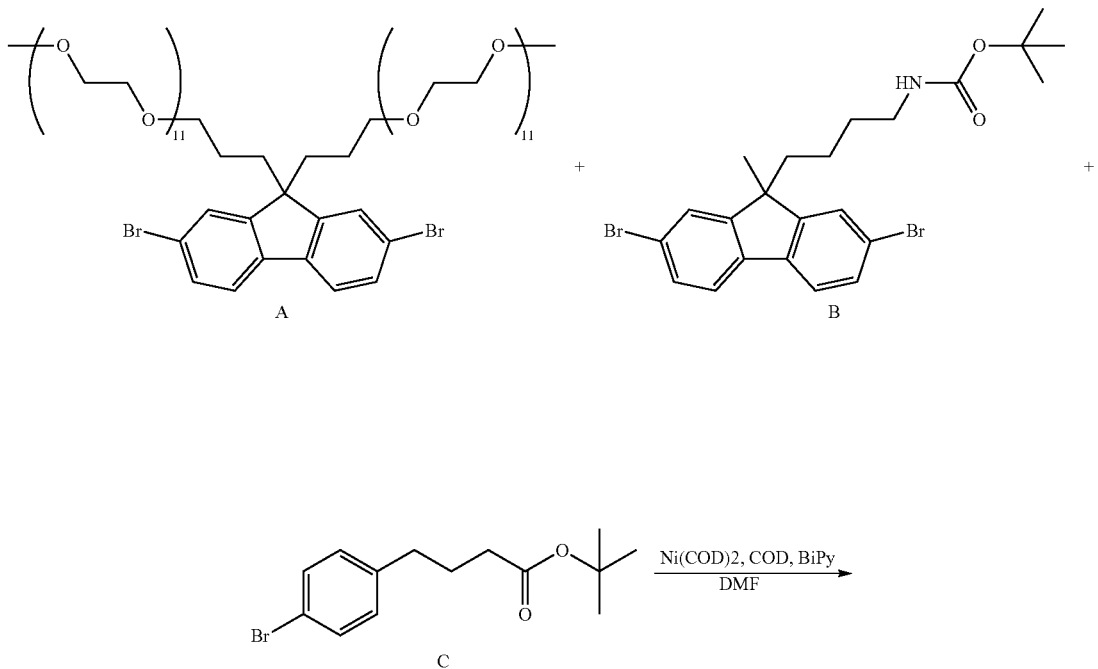

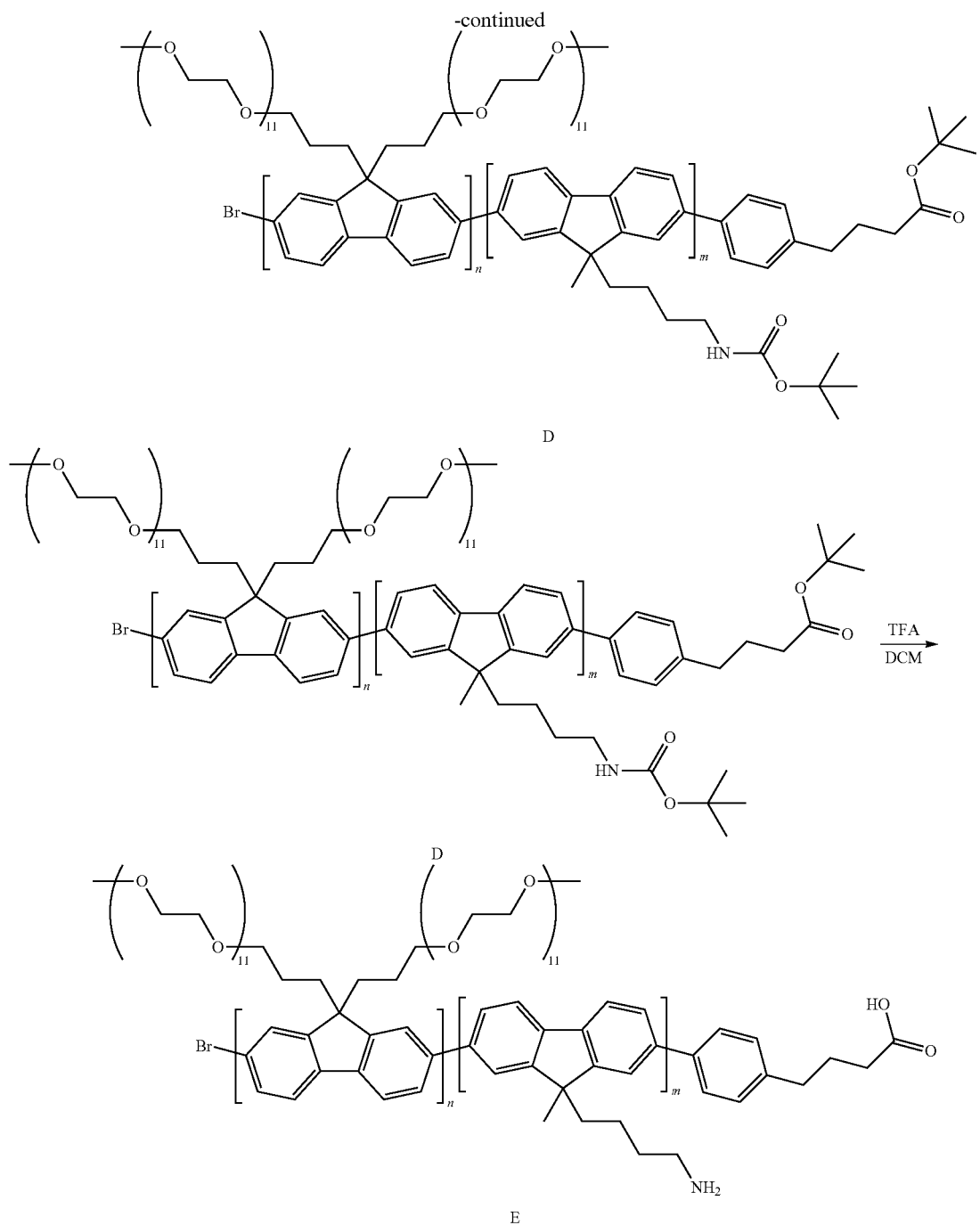

D

E

Step 1: Yamamoto Polymerization

In a dry box, Ni(COD)$_2$ (0.433 g, 8.40 mmol), 2,2'-bipyridyl (0.246 g, 8.40 mmol), COD (0.170 g, 8.40 mmol) and anhydrous DMF (15 ml) were added to a long-neck round bottom flask. 2,7-dibromo-9,9-di(2',5',8',11',14',17',23',26',29',32',35'-dodecaoxaoctatriacontan-38'-yl)fluorene (A) (1.00, 0.696 mmol), tert-butyl 4-(2,7-dibromo-9-methyl-9H-fluoren-9-yl)butylcarbamate (B) (0.037 g, 0.069 mmol), and tert-butyl 4-(4-bromophenyl)butanoate (C) (0.004 g, 0.007 mmol) were added to a 40 ml vial and dissolved in anhydrous DMF (10 ml). The flask was sealed with a septum and the vial was closed with a septum screw cap. The catalyst mixture and the monomer solution were transferred out of the dry box and were placed under static argon. The reaction flask was heated to 70° C. for 45 min. The monomer solution was then was quickly transferred from the vial to the catalyst mixture flask with an argon flushed syringe. The reaction mixture was then heated to 70° C. for 6 h.

The reaction mixture was cooled and solvent removed by rotary evaporation. The resultant black residue was redissolved in 20% EtOH (80 mL) and centrifuged at 2400 rpm for 12 hours. The supernatant was then decanted and filtered through a 0.45 um cup filter.

The filtered reaction mixture was purified using tangential flow filtration (TFF) and was diafiltered into 20% ethanol using a 10,000 molecular weight cutoff membrane (polyethersulfone Prep/Scale TFF cartridge system, Millipore, Billerica, Mass.) until GPC analysis of retentate indicated the absence of low molecular weight material. The solvent was then removed under vacuum to give tert-butyl 4-(4-(2-bromo-poly-[2,7{9,9-bis(2,5,8,11,14,17,20,23,26,29,32,35-dodecaoxaoctatriacontane)fluorene-co-2,7-(9-methyl-9'-(butyl-4-t-butylcarbamate)fluorene)])phenyl)butanoate (D) as a viscous oil (664 g, 80%). Molecular weight determined by GPC analysis relative to polystyrene standards (Mn=50,000, Mw=88,000, Mp=174,000, D=1.8).

Step 2: Linker Deprotection

Trifluoroacetic acid (6 mL) was added dropwise to a stirred solution of Polymer (300 mg, X mmol) and dichloromethane (24 mL) in a round bottom flask. The reaction mixture was stirred at room temperature for 2 hours and then concentrated in vacuo. The residue was redissolved in minimal 20% EtOH and 1M HCl was added to the solution until pH=7. The neutralized solution was then desalted over G25 gel and the resultant material was concentrated to dryness to yield a clear pale orange oil (261 mg, 87%).

Examples of dye incorporation, linker activation and bioconjugation are contained in further Example 38 and related examples.

Example 27. Dual Functional Asymmetric Polymer with Both Internal and Terminal Conjugation Sites Used to Create a Polymer-Dye Label for Biomolecule or Substrate Conjugation

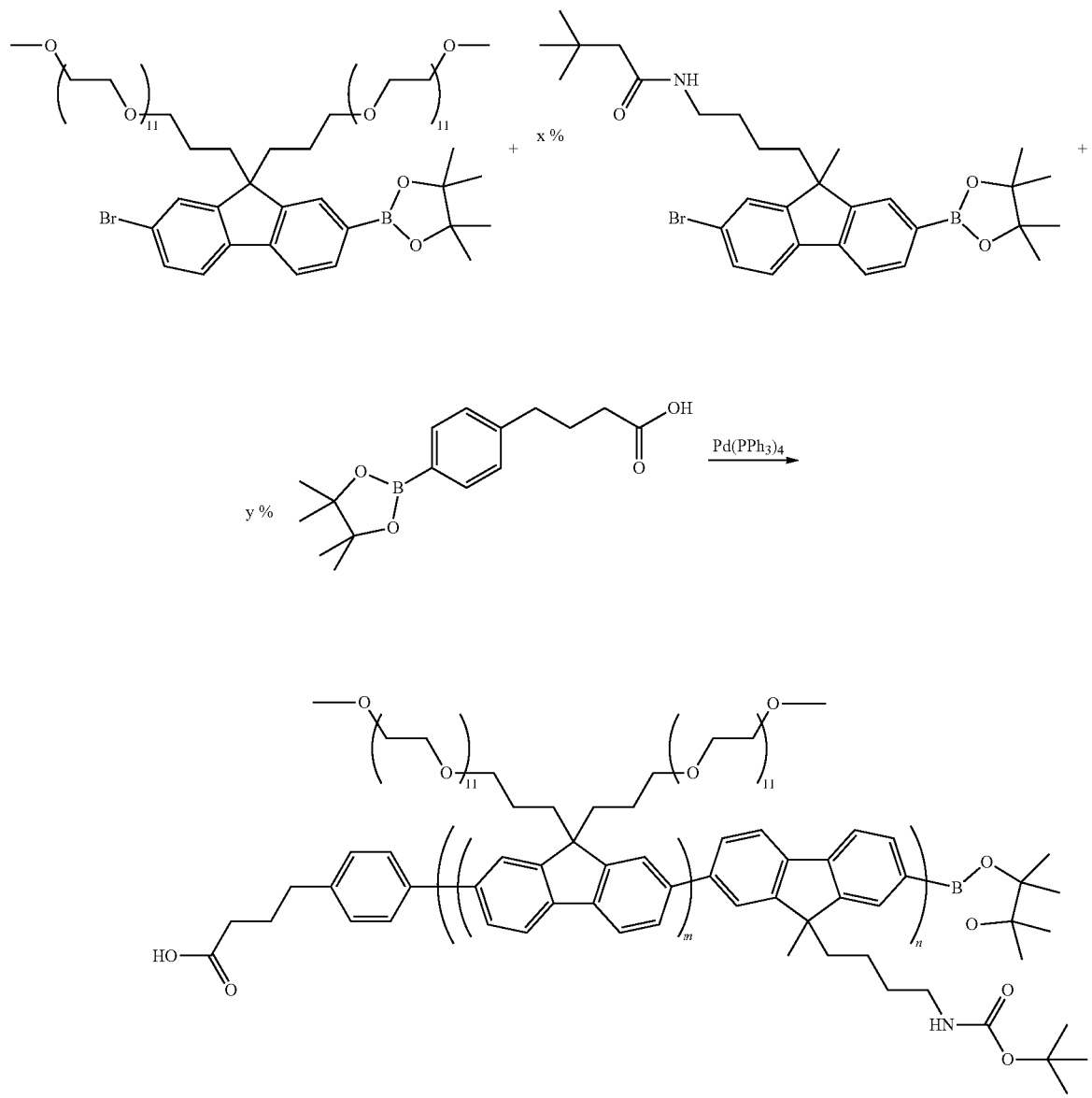

-continued

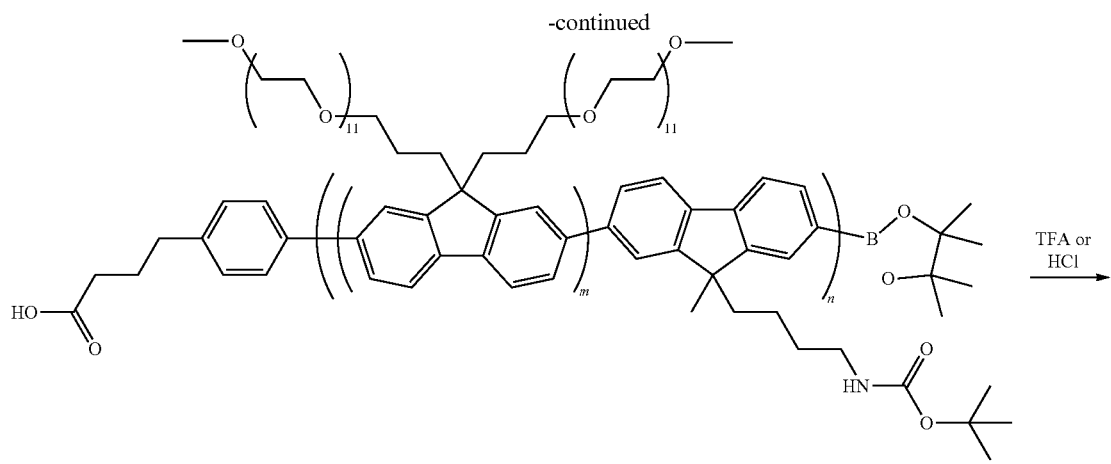

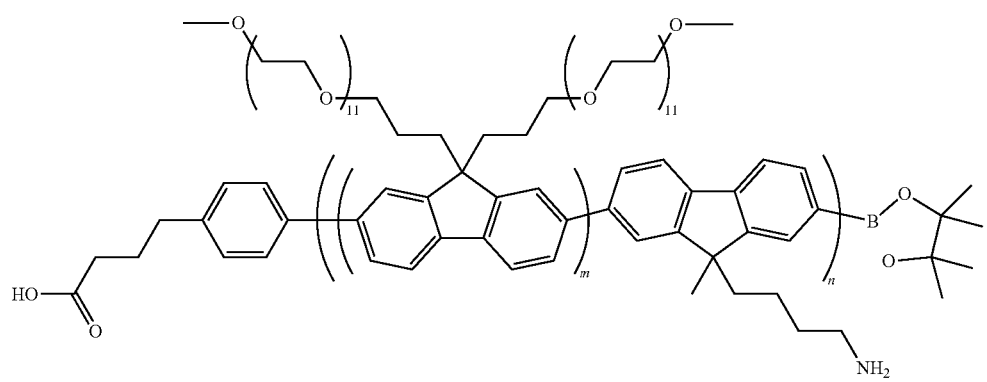

Suzuki polymerization of 2-bromo-9,9-di(2',5',8',11',14', 17',20',23',26',29',32',35'-dodecaoxaoctatriacontan-38'-yl)-7-(4'',4'',5'',5''-tetramethyl-1'',3'',238-dioxaborolan-2-yl) fluorene is performed under those conditions described in Example 23 where y % is the mol % of the end linker used to regulate the polymerization and ensure high incorporation of linker. The linker in this example is 4-(4-(4,4,5,5-tetramethyl-1,3,2-dioxaborolan-2-yl)phenyl)butanoic acid. In this example, x mol % of the internal linker is also added to the polymerization to incorporate the second linking site into the polymer. This method for incorporating the internal linker is generally described in Examples 21, 25 and 26. The internal linker must be incorporated during the polymerization as indicated, however, it is expected that it would be possible to add the terminal linker as a separate step as described in Examples 9, 10, 11 and 21.

Example 28: Enrichment of Linker-Functionalized Polymers

The synthesis of linker-functionalized polymers can yield a mixture of chains with and without linker functionalities. Because conjugation efficiency is expected to improve with higher purity polymers for conjugation, the methods described in this example address this by enriching for chains containing linker.

For a polymer batch containing a mixture of a COOH-modified and unmodified polymer: Dissolve polymer in 95% EtOH, then dilute with water to a final EtOH concentration of 20%. Desalt the polymer using 10 kDa MWCO filter until conductance is <0.1 mS/cm. Inject onto Q-Sepharose column, ensuring that the polymer load is suitable for the column capacity. Pass 20% EtOH in water over column to wash out unbound polymer. Release bound material by changing the eluting buffer to 1M NaCl in 20% EtOH in water for two column volumes to trigger the release of the bound polymeric material. Collect enriched material.

The polymer is passed over a strong anion exchanger such as a Q-Sepharose column. Polymer chains bearing a functional carboxylic acid group will bind the strong anion exchanger, and polymer that is not functionalized will not bind and instead will wash through. After the non-functionalized polymer has passed through the column, the column is washed with 1M NaCl, which triggers the release of the acid-functionalized polymer by screening the acid group from the media. By using this method, the percent functional polymer has been shown to increase from 25% of polymer chains bearing a carboxylic acid group to >80% of polymer chains bearing a carboxylic acid group. This increase in functional chains has been shown by analyzing the absorbance ratios of polymer-dye conjugates pre- and post-enrichment. This procedure is also described in Example 38. A similar process has been validated for the enrichment of amine containing polymers. In that case an anionic exchange resin, SP Sephrose (or similar), is loaded at reduced conductivity (below 0.01 mS/cm).

Example 29: Preparation of Polymer-Streptavidin Conjugates Via NHS/Amine Coupling

Example 29a: Polymer Modifications

Polymer Modification—Carboxylic Acid to Amine Conversion

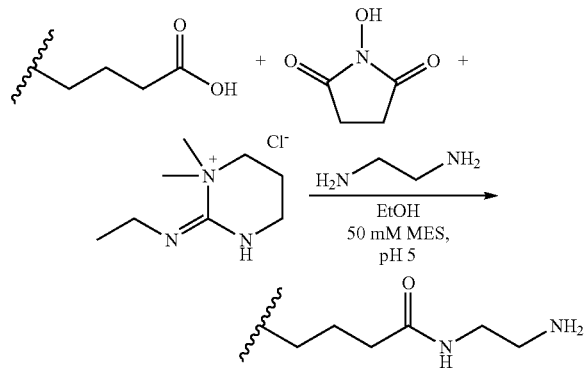

1.35 g of a carboxylic acid terminated polymer was dissolved at in 9 mL ethanol, then added dropwise to 80 mL of 4° C. 50 mM MES, pH 5 while stirring. 0.52 g N-hydroxy succinimide was added in one portion. Once the N-hydroxy succinimide had dissolved, 2.3 g N-(3-dimethylaminopropyl)-N'-ethylcarbodiimide hydrochloride was added in portions. After stirring the solution for 30 minutes, 2.8 mL of ethylene diamine was added dropwise. The solution was stirred overnight at room temperature and purified by tangential flow filtration (MWCO=10 kDa). 1.22 g yield (90%).

Polymer Modification—Amine to Carboxylic Acid Conversion

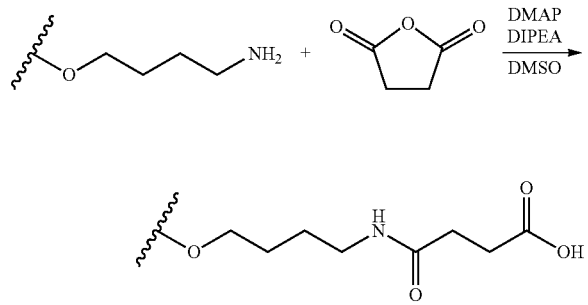 [SMILES: *OCCCCN ; O=C1CCC(=O)O1 ; *OCCCCNC(=O)CCC(=O)O]

70 mg of an amine-terminated polymer was dissolved in 7 mL DMSO. 2.3 mg DIPEA was added to the polymer solution. 2.2 mg DMAP was dissolved in 220 µL DMSO and added to the resulting polymer solution. 5.5 mg succinic anhydride was dissolved in 550 µL DMSO and added to the resulting polymer solution. The solution was agitated at room temperature overnight. The reaction was then purified over Amicon Ultra centrifugal filtration units (MWCO=10 kDa) with 25 mM MES pH 5 buffer. 62 mg yield (89%).

Polymer Modification—Carboxylic Acid to NETS-Ester Conversion

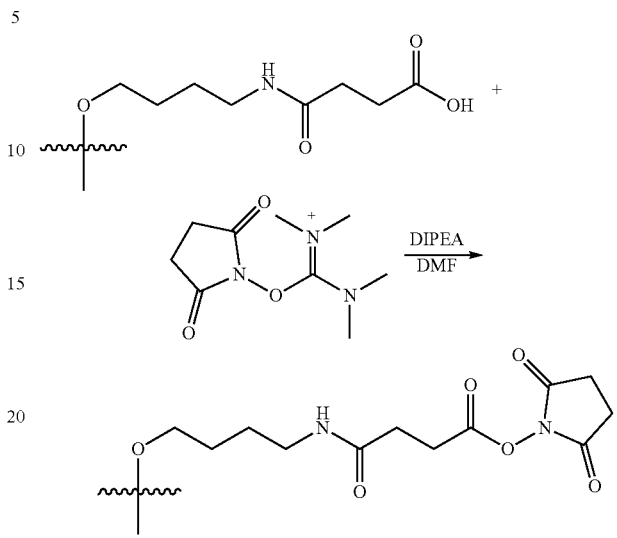

60 mg of a carboxylic acid-terminated polymer was dissolved in 600 µL acetonitrile. 1.2 µg DIPEA was added to the polymer solution. 2.8 mg N,N,N',N'-Tetramethyl-O—(N-succinimidyl)uronium was dissolved in 370 µL acetonitrile and added to the polymer solution. The solution was agitated at room temperature for 15 minutes. After the reaction is complete, the solvent was evaporated under reduced pressure. 50 mg yield (83%).

Example 29b: Protein-Polymer Conjugation

Streptavidin protein is dissolved in 50 mM NaHCO$_3$ pH 8.2 buffer to make a 1 mg/mL solution. Crude activated polymer (10-15 eq or as required) solution from Step 2 is added to the aqueous streptavidin protein solution; the protein concentration is adjust with buffer to ensure that the volume of organic solvent added is <10% of the total volume, if necessary. The solution is agitated at room temperature for 3 hr and the reaction transferred to a Amicon Ultra filter (MWCO=10 kDa) to remove DMF. The protein is recovered into the initial volume with 25 mM PO$_4$ pH 6.5 buffer.

Purification of the Protein-Polymer Conjugate

A 1 mL HiTrap SP Sepharose FF column is equilibrated with 20 mM Na Citrate pH 3 buffer. 1 mL (0.3-1 mg/mL) of Streptavidin-polymer conjugate is loaded in 25 mM NaHPO$_4$ pH 6.5. The sample is wash through column with 20 mM Na Citrate pH 3 buffer until a stable baseline is obtained. Multiple 1 mL aliquots of sample may subsequently be loaded and washed. The column is washed with a minimum of 10 column volumes of 20 mM Na Citrate pH 3 buffer. The conjugate is eluted with 10 column volumes of 20 mM Na Citrate in 0.6 M NaCl pH 7.6 buffer and the column is stripped with 10 column volumes of 20% ethanol in the elution buffer. The elution peak is concentrated with an Amicon Ultra filter (MWCO=10 kDa) to reduce the volume to ~200 µl. A 10×300 mm Superose 12 column is equilibrated with 20 mM Na Citrate in 0.6 M NaCl pH 7.6 buffer. 200 µL of concentrated Streptavidin-polymer conjugate is loaded and eluted with 20 mM Na Citrate in 0.6 M NaCl pH 7.6 buffer. Fractions are pooled and buffer exchanged into PBS+0.05% NaN$_3$ using Amicon Ultra Centrifugation filters (10 kD MWCO). Elutions are concentrated to desired concentration for testing; at around 2 µM Streptavidin.

Characterization of a Purified Protein-Polymer Conjugate

Figure 29:
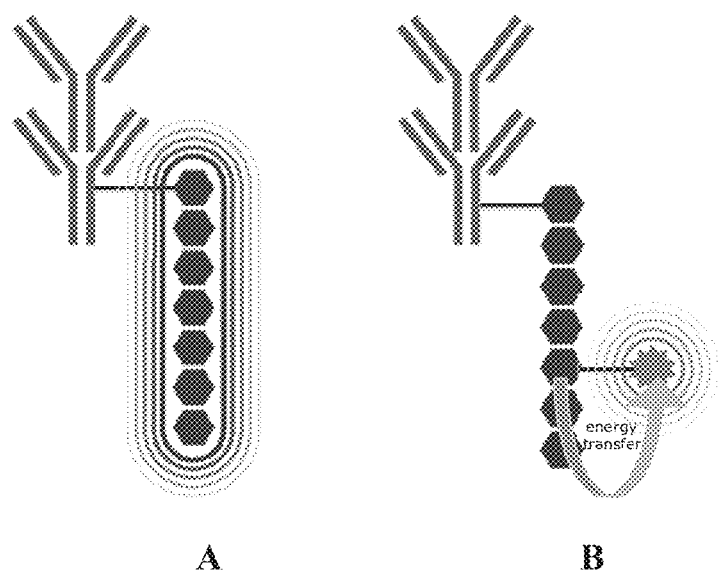
FIGS. 29. (A) and (B) Schematic of covalent linkage of conjugated polymer to 2° antibody.

A 4-20% acrylamide Tris-HCl Ready Gel (BioRad) is prepared and the gel is loaded with the conjugate along with free streptavidin and free polymer in separate lanes. Gel electrophoresis is performed in 25 mM Tris 192 mM, Glycine pH 8.3 and stained with Coomassie to visualize the protein. The gel is stained for 30 minutes then destained with commercial destain overnight. Agarose gel conditions were also used to characterize polymer-streptavidin conjugates, an example which is shown in FIG. 29.

In alternative embodiments, the above example can be adapted to allow for conjugation of the polymer to biomolecules or dyes, including but not limited to, antibodies and nucleic acids. The amine on the polymer is converted to a maleimide and a carboxylic acid (further activated to form the NHS ester) using alternative crosslinkers or modifiers. In certain embodiments, conjugation of the same polymer to other biomolecules (streptavidin, antibody fragments, nucleic acids) is facilitated using maleimide-thiol chemistry (using SATA linkers to convert free amines on the biomolecule or TCEP (or DPP) reduction of an antibody to create free thiols).

Example 30: Preparation of Polymer-Streptavidin Conjugates Via Hydrazide/Benzaldehyde Coupling Step 1: Streptavidin-4FB Modification Streptavidin protein is reconstituted at 1.7 mg/mL and exchange into reaction buffer, 50 mM NaHCO$_3$, pH 8. 15 molar equivalents of bifunctional benzaldehyde/succinimidyl linker, S-4FB (Solulink, San Diego, Calif.) 20 mg/mL in anhydrous DMSO is added to streptavidin, ensuring that the organic phase is less than 10% of the total volume. Reaction is mixed on shaker for 4 hours at room temperature and unreacted linker is subsequently filtered away via Amicon Ultra filter, 10 kD MWCO with 50 mM MES buffer, pH 5; centrifuged at 2400 rpm and a repeated wash ×3. Streptavidin protein is recovered in its initial volume, targeting 1.7 mg/mL in conjugation buffer, 50 mM NaPO$_4$, pH 6.5.

Step 2: Polymer Modification

Polymer with terminal amine group (1 molar eq) is dissolved with DMF to make a 10 mg/mL solution. 20 molar equivalents of a bifunctional hydrazine/succinimidyl linker, SHTH (Solulink, San Diego, Calif.) at 80 mg/mL in anhydrous DMSO is added to the polymer solution. 1 drop of DIPEA is added to the reaction by a syringe and 22 g needle. The solution is agitated at room temperature for 4 hr and the reaction transferred to a Amicon Ultra filter (MWCO=10 kDa) filled with 25 mM MES pH 5 buffer. The solution is then centrifuged. The filter is refilled and washed with the following wash buffers:

1×DI H2O+1 drop 1 M HCl
1×DI H2O+1 drop 1M NaOH
3×50 mM MES, pH 5

Step 3: Protein-Polymer Conjugation 15 equivalents of modified polymer from Step 2 are added with desired amount of modified protein from Step 1. Aniline is added to the reaction for a final concentration of 10 mM and allowed to mix for 12 hours. The reaction is purified with Amicon Ultra filter (MWCO=10 kDa) to remove DMF and recovered with 25 mM PO$_4$ pH 6.5 buffer.

Step 4: Purification of the Protein-Polymer Conjugate

A 1 mL HiTrap SP Sepharose FF column is equilibrated with 20 mM Na Citrate pH 3 buffer. 1 mL (0.3-1 mg/mL) of Streptavidin-polymer conjugate is loaded in 25 mM NaHPO$_4$ pH 6.5. The sample is wash through column with 20 mM Na Citrate pH 3 buffer until a stable baseline is obtained. Multiple 1 mL aliquots of sample may subsequently be loaded and washed. The column is washed with a minimum of 10 column volumes of 20 mM Na Citrate pH 3 buffer. The conjugate is eluted with 10 column volumes of 20 mM Na Citrate in 0.6 M NaCl pH 7.6 buffer and the column is stripped with 10 column volumes of 20% ethanol in the elution buffer. The elution peak is concentrated with an Amicon Ultra filter (MWCO=10 kDa) to reduce the volume to ~200 µl. A 10×300 mm Superose 12 column is equilibrated with 20 mM Na Citrate in 0.6 M NaCl pH 7.6 buffer. 200 µL of concentrated Streptavidin-polymer conjugate is loaded and eluted with 20 mM Na Citrate in 0.6 M NaCl pH 7.6 buffer. Fractions are pooled and buffer exchanged into PBS+0.05% NaN$_3$ using Amicon Ultra Centrifugation filters (10 kD MWCO). Elutions are concentrated to desired concentration for testing; at around 2 µM Streptavidin.

Step 5: Characterization of a Purified Protein-Polymer Conjugate

A 4-20% acrylamide Tris-HCl Ready Gel (BioRad) is prepared and the gel is loaded with the conjugate along with free streptavidin and free polymer in separate lanes. Gel electrophoresis is performed in 25 mM Tris 192 mM, Glycine pH 8.3 and stained with Coomassie to visualize the protein. The gel is stained for 30 minutes then destained with commercial destain overnight.

FIG. 14 top, depicts conjugation of streptavidin to a polymer of formula (Vb) in cartoon format. FIG. 14, bottom, is a Coomassie stain of acrylamide gel which depicts the mobility of the conjugate is retarded relative to the free protein indicating an increase in mass. A neutral polymer alone shows no evidence of staining and without a formal charge, the polymer is not mobile in the electrophoretic field.

In alternative embodiments, the above example can be adapted to allow for conjugation of the polymer to biomolecules or dyes, including but not limited to, antibodies and nucleic acids. The amine on the polymer is converted to a maleimide and a carboxylic acid (further activated to form the NHS ester) using alternative crosslinkers or modifiers. In certain embodiments, conjugation of the same polymer to other biomolecules (streptavidin, antibody fragments, nucleic acids) is facilitated using maleimide-thiol chemistry (using SATA linkers to convert free amines on the biomolecule or TCEP reduction of an antibody to create free thiols) and NETS-amine chemistry (reacting the NETS polymer directly with lysines on the protein or nucleic acid).

Example 31: Preparation of Biotin-Labeled Polymers

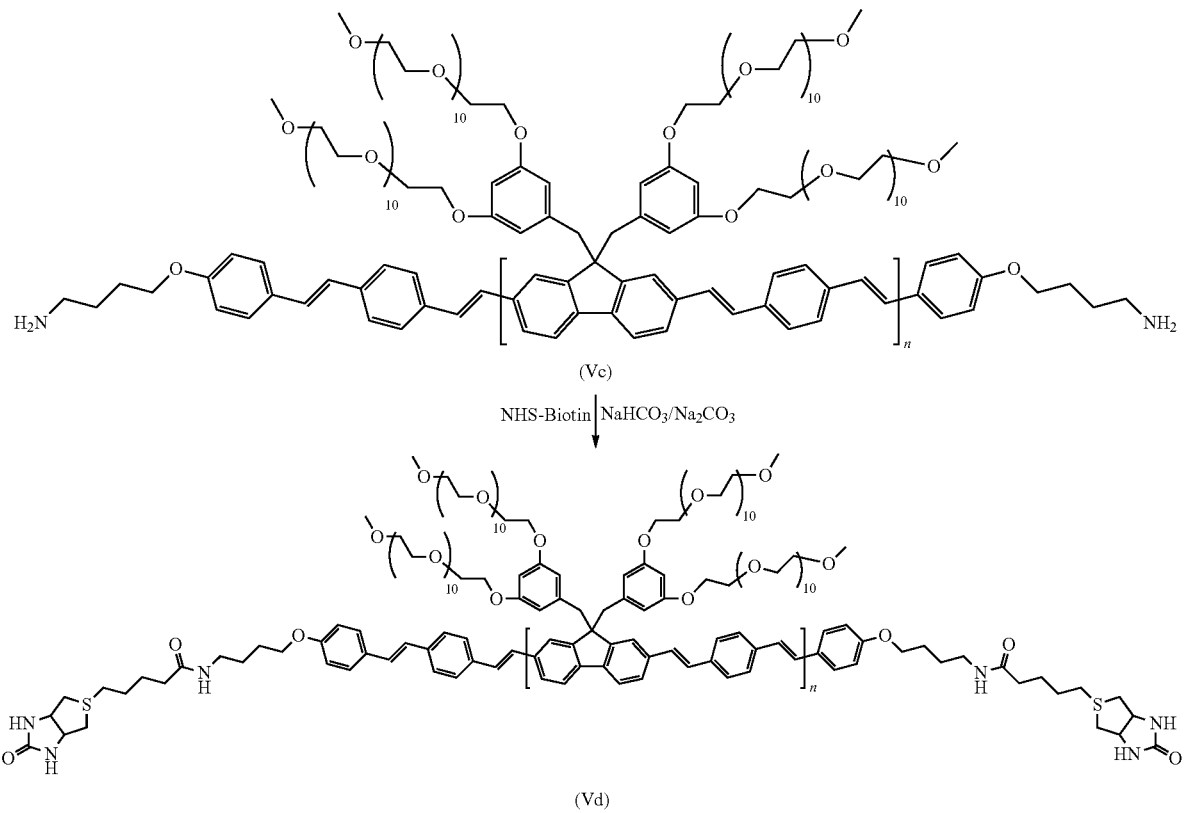

Amine functionalized polymer of formula (Vc) is dissolved at 10 mg/mL in anhydrous DMF and divided into two portions. NHS-biotin (0.9 mg in 90 µL, 88 equivalents) (Pierce, 20217) and NHS-LC-LC-biotin (Pierce, 21343) at 10 mg/mL (1.5 mg in 150 µL, 88 equivalents) are dissolved in anhydrous DMF. The NHS-biotin and NHS-LC-LC-biotin solutions are immediately added to the two portions of polymer solution and allowed to mix on a shaker overnight in the dark. Excess reactant is removed by washing the solution using Amicon Ultra-4 mL 10 kD MWCO filter cartridges in a series of wash steps: First, the cartridge is first filled approximately halfway with water, and the reaction solution (by pipet) subsequently added directly into the water. Next, the cartridge is filled with water until it is full. The solution is mixed by pipetting up and down. Then, the cartridge is centrifuged at 2400 rpm for 30 minutes, or until the volume is reduced to 250 µL. The cartridge is then refilled with water 1 drop of 1M HCl is added; the solution is mixed, and centrifuged at 2400 rpm for 30 minutes, or until the volume was reduced to 250 µL. Next, the cartridge is refilled with water, 1 drop of 1M NaOH is added; the solution is mixed, and centrifuged at 2400 rpm for 30 minutes, or until the volume is reduced to 250 µL. The cartridge is then refilled with water, mixed and centrifuged at 2400 rpm for 30 minutes, or until the volume is reduced to 250 µL. This final step is repeated for a total of 5 washes.

Characterization of a Purified Biotin-Labeled Polymer

Figure 15:
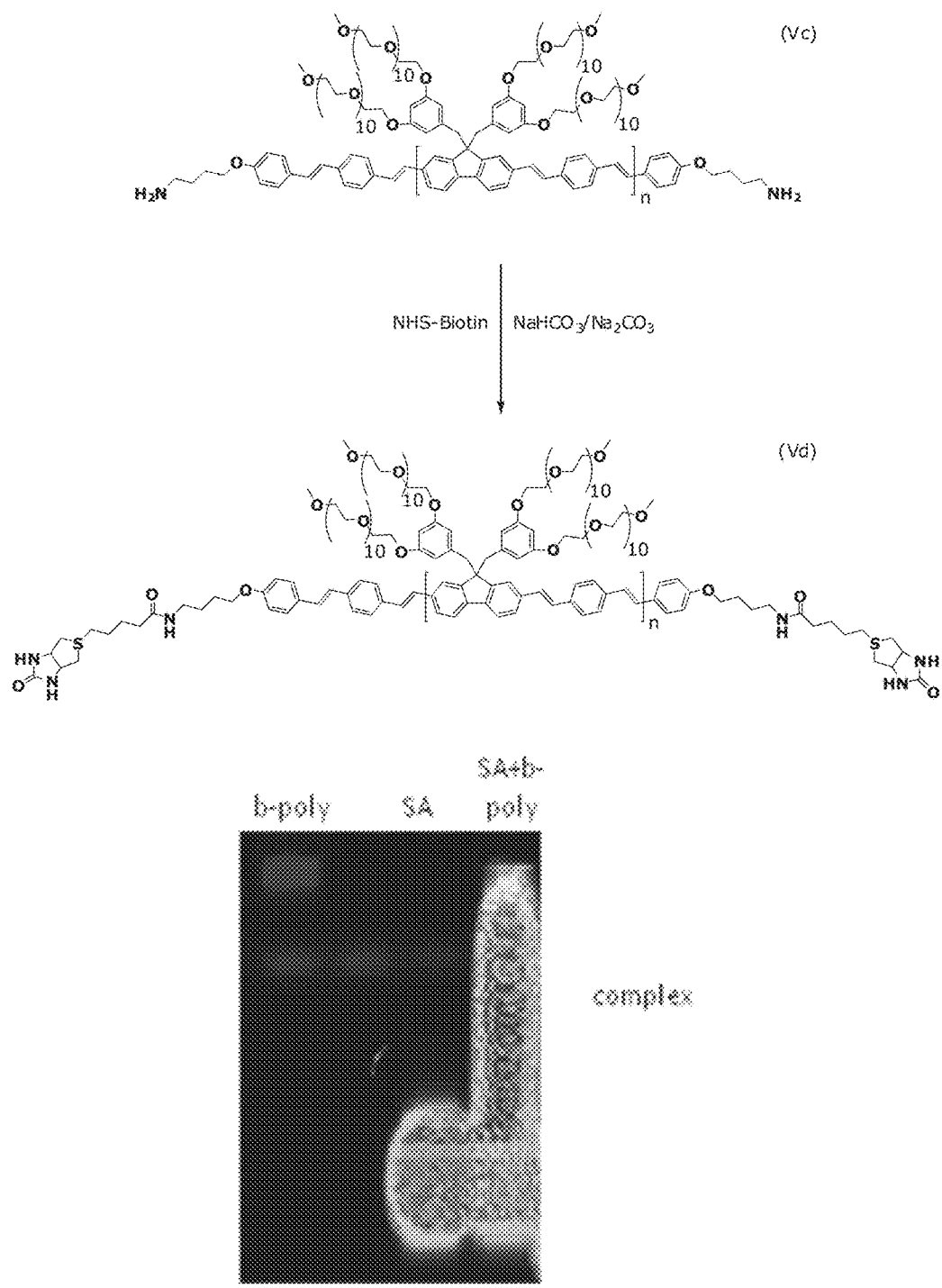
FIG. 15. Representative acrylamide gel depiction of biotinylated polymer alone or bound to Cy5-labeled streptavidin.

Excess biotin-labeled polymer is incubated with a Cy5-labeled streptavidin in DPBS buffer plus 0.2% BSA and 0.05% $NaN_3$. A 0.8% agarose gel is prepared and the gel is loaded with the conjugate along with free Cy5-streptavidin and free biotinylated polymer in separate lanes. Gel electrophoresis is performed in 10 mM $NaHCO_3$ pH10 and visualized using a Typhoon gel imager with 457 nm and 635 nm laser excitation. FIG. 15 (bottom) depicts retardation of mobility of the polymer-streptavidin complex relative to the free protein indicating an increase in mass. The polymer alone shows little mobility on its own due to a lack of formal charge.

This protocol is adapted to successfully biotin-modify a range of conjugated polymers containing both internal and terminal amine linkers.

Example 32: Functional Testing of Covalent Polymer Streptavidin Conjugates by Selective Binding to Biotinylated Microspheres Materials Required:
1×TBST: 50 mM Tris-HCl, 150 mM NaCl, 0.1% Tween20, pH 7.5; Biotin microspheres (10 mg/mL in TBST); BSA (1 mg/mL); AvDN (220 µM); and Polymer-Strepavidin (SA) conjugate: (1 µM with regard to SA, provided at 5 µM).

Preparation of Master Mixes:

Prepare in labelled 1.5 mL microfuge tubes:

| Experimental master mix | Negative control master mix |
|---|---|
| 14 µl TBST | 9 µl TBST |
| 6 µl BSA stock | 6 µl BSA stock |
| 5 µl bead stock | 5 µl avidin stock |
|  | 5 µl bead stock |

Briefly vortex both tubes and allow 20-30 minutes to pre-incubate the negative control beads with excess avidin before proceeding. A variable speed orbital mixer at 800 RPM for incubation is suggested to keep beads from settling.

Bead Hybridization:

Pipette 10 µL of each master mix into separate labelled 1.5 ml microfuge tubes. Add 2 µL of polymer-SA conjugate to each. Prepare additional tube containing 10 µL master mix and no polymer to be used as a blank. Briefly vortex and pulse spin all tubes. Transfer to variable speed orbital mixer and incubate for 30 mins at 800 RPM.

Bead Processing/Washing:

Add 0.5 ml TBST to all samples and controls and vortex briefly. Centrifuge at 1200 g for 2 min and remove 480 µl supernatant being diligent not to disturb bead pellet. Add 0.5 ml TBST to all samples and controls and vortex briefly. Centrifuge at 1200 g for 2 min and remove 500 µl supernatant being diligent not to disturb bead pellet. Repeat steps 3 and 4. Remove as much of remaining supernatant as possible using P200 pipette without disturbing bead pellet. Add 100 µL TBST and vortex briefly to re-suspend beads.

Bead Measurement:

Transfer 100 µL of positive, negative and blank beads to a BLACK 96 well plate. Excite wells at 430 nm and collect emission in the range 450-650 nm using required slit widths and/or sensitivity setting to achieve measurable signals above background. Compare emission of positive and negative control beads.

Figure 16:
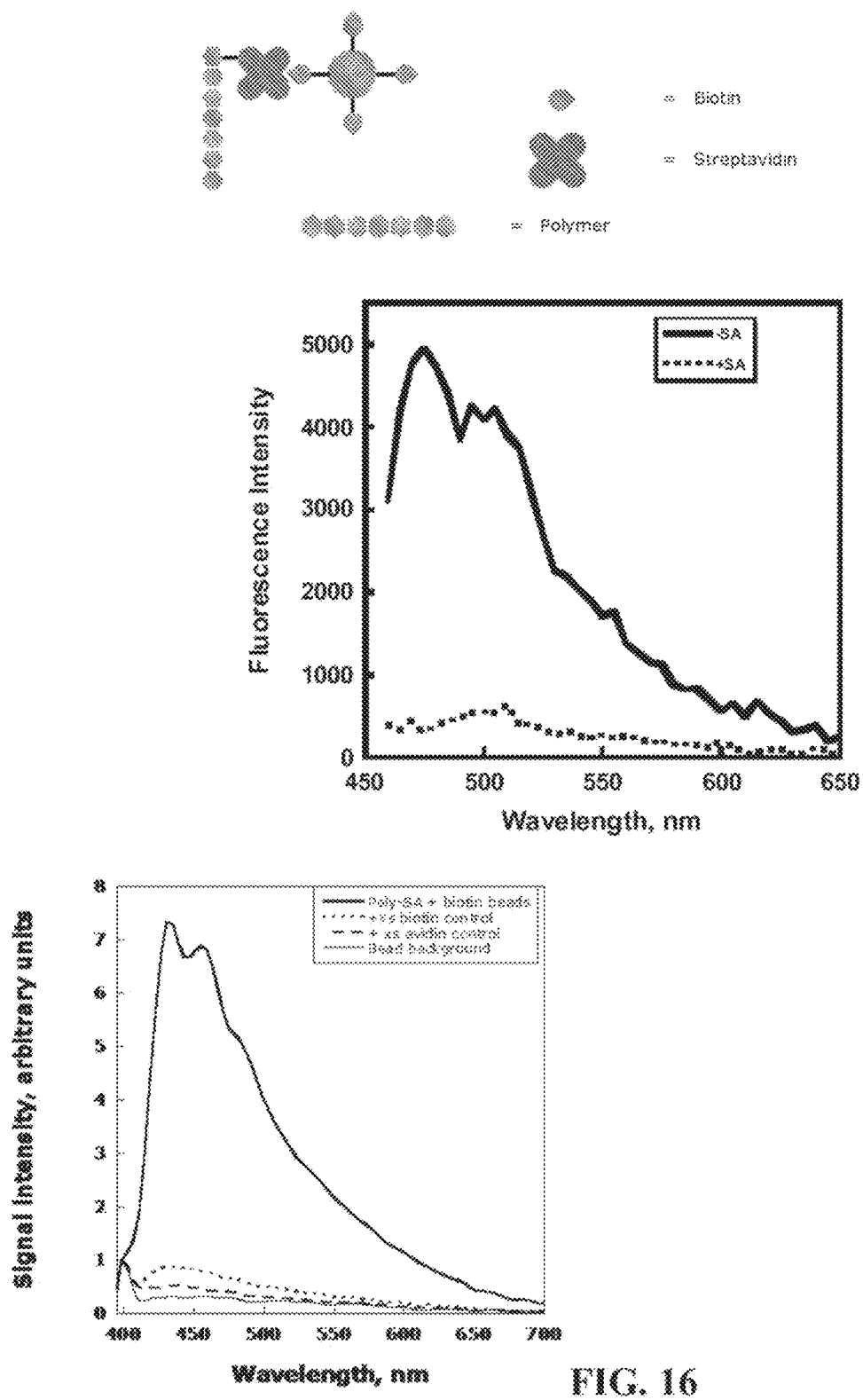
FIG. 16. Schematic of streptavidin-attached conjugated polymer of FIG. 14 binding to biotinylated microspheres (top) and plot of fluorescence excitation of control biotinylated microspheres and microspheres bound to streptavidin conjugated polymer.

FIG. 16 shows the polymer streptavidin conjugate was bound to a biotinylated microsphere. Excitation at 440 nm in a fluorometer resulted in emission from the polymer as indicated by the solid curve. The dashed curve represents the negative control where the biotin bead was first treated with excess avidin to block the biotin binding sites prior to treatment with the polymer streptavidin conjugate.

Example 33: Functional Testing of Covalent Polymer Streptavidin Conjugates by Selective Binding to Biotinylated Microspheres and FRET to Dye Acceptors on Co-Localized Streptavidin-Dye Conjugates Materials Required:

1×TBST: 50 mM Tris-HCl, 150 mM NaCl, 0.1% Tween20, pH 7.5. Biotin microspheres (10 mg/mL in TBST). Cy3-SA (1 µM or 50 µg/mL). Polymer-Strepavidin (SA) conjugate: (1 µM with regard to SA, provided at 5 µM).

Bead Preparation and Hybridization:

Prepare in labelled 1.5 mL microfuge tubes:

| Blank control | Cy3-SA control | FRET-SA Control |
|---|---|---|
| 16 µl TBST | 14 µl TBST | 14 µl TBST |
| 4 µl bead stock | 2 µl Cy3-SA stock | 2 µl Cy3-SA stock |
|  | 4 µl bead stock | 2 µl polymer-SA stock |
|  |  | 4 µl bead stock |

Briefly vortex all tubes and transfer to variable speed orbital mixer for incubation of at least 30 mins at 800 RPM.

Bead Processing/Washing:

Add 0.5 ml TBST to all samples and controls and vortex briefly. Centrifuge at 1200 g for 2 min and remove 48 µl supernatant being diligent not to disturb bead pellet. Add 0.5 ml TBST to all samples and controls and vortex briefly. Centrifuge at 1200 g for 2 min and remove 500 µL supernatant being diligent not to disturb bead pellet. Repeat steps 3 and 4. Remove as much of remaining supernatant as possible using P200 pipette without disturbing bead pellet. Add 100 TBST and vortex briefly to re-suspend beads.

Bead Measurement:

Transfer 100 µL of all samples to a BLACK 96 well plate. Excite wells at 430 nm and collect emission in the range 450-650 nm using required slit widths and/or sensitivity setting to achieve measurable signals above background. Detect and record polymer emission in the range of 480-500 nm and Cy3 emission at the expected 570 nm.

Figure 17:
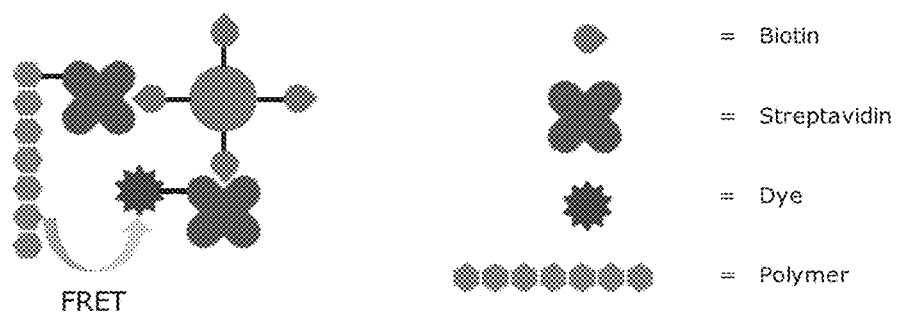
FIG. 17. Schematic of streptavidin-attached conjugated polymer of FIG. 14 selectively bound to biotinylated microspheres and energy transfer to dye acceptors on co-localized streptavidin-dye conjugates (top) and plot of energy transfer from streptavidin-attached conjugated polymer to dye acceptor (bottom).
Figure 17:
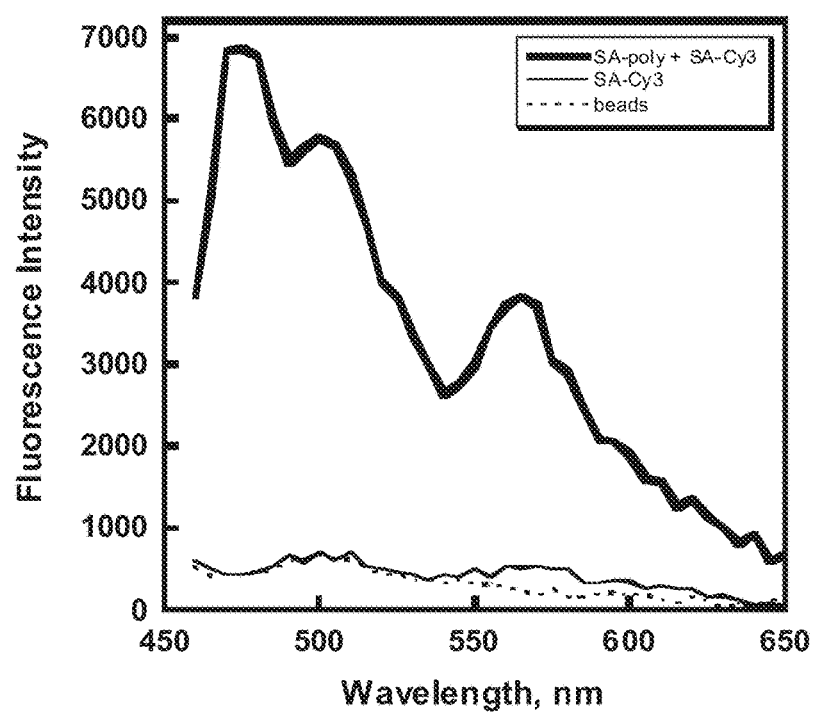

FIG. 17 shows the polymer streptavidin conjugate was bound to a biotinylated microsphere. Excitation at 440 nm in a fluorometer resulted in energy transfer between the polymer and a Cy3 dye conjugated to a different streptavidin protein as indicated by the solid upper curve. The dashed curve shows beads alone and the lower solid curve direct excitation of the Cy3-streptavidin conjugate at 440 nm.

Example 34: Functional Testing of Biotin-Labeled Polymers by Selective Binding to Avidin Coated Microspheres Materials Required:

1×TBST: 50 mM Tris-HCl, 150 mM NaCl, 0.1% Tween20, pH 7. SA microspheres (10 mg/mL in TBST). Biotin (1 mM). 440 nm biotin-polymer conjugate: (46 µM).

Bead Preparation and Hybridization:

Prepare in labelled 1.5 mL microfuge tubes:

| Blank control | Negative control | Positive Control |
|---|---|---|
| 16 µl TBST | 11 µl TBST | 15 µl TBST |
| 4 µl bead stock | 4 µl biotin stock | 4 µl bead stock |
|  | 4 µl bead stock |  |

Briefly vortex all tubes and transfer to variable speed orbital mixer for incubation of 20-30 mins at 800 RPM to ensure biotin has blocked all SA sites on negative control beads. Add 1 uL of polymer-biotin stock to both positive and negative control tubes. Vortex briefly and transfer to variable speed orbital mixer and incubate for 30 mins at 800 RPM.

Bead Processing/Washing:

Add 0.5 ml TBST to all samples and controls and vortex briefly. Centrifuge at 1200 g for 2 min and remove 480 µL supernatant being diligent not to disturb bead pellet. Add 0.5 ml TBST to all samples and controls and vortex briefly. Centrifuge at 1200 g for 2 min and remove 500 µl supernatant being diligent not to disturb bead pellet. Repeat steps 3 and 4. Remove as much of remaining supernatant as possible using P200 pipette without disturbing bead pellet. Add 100 µL TBST and vortex briefly to re-suspend beads.
Bead Measurement:
Transfer 100 µL of all samples to a BLACK 96 well plate. Excite wells at 430 nm and collect emission in the range 450-650 nm using required slit widths and/or sensitivity setting to achieve measurable signals above background. Compare emission of positive and negative control beads.

Figure 18:
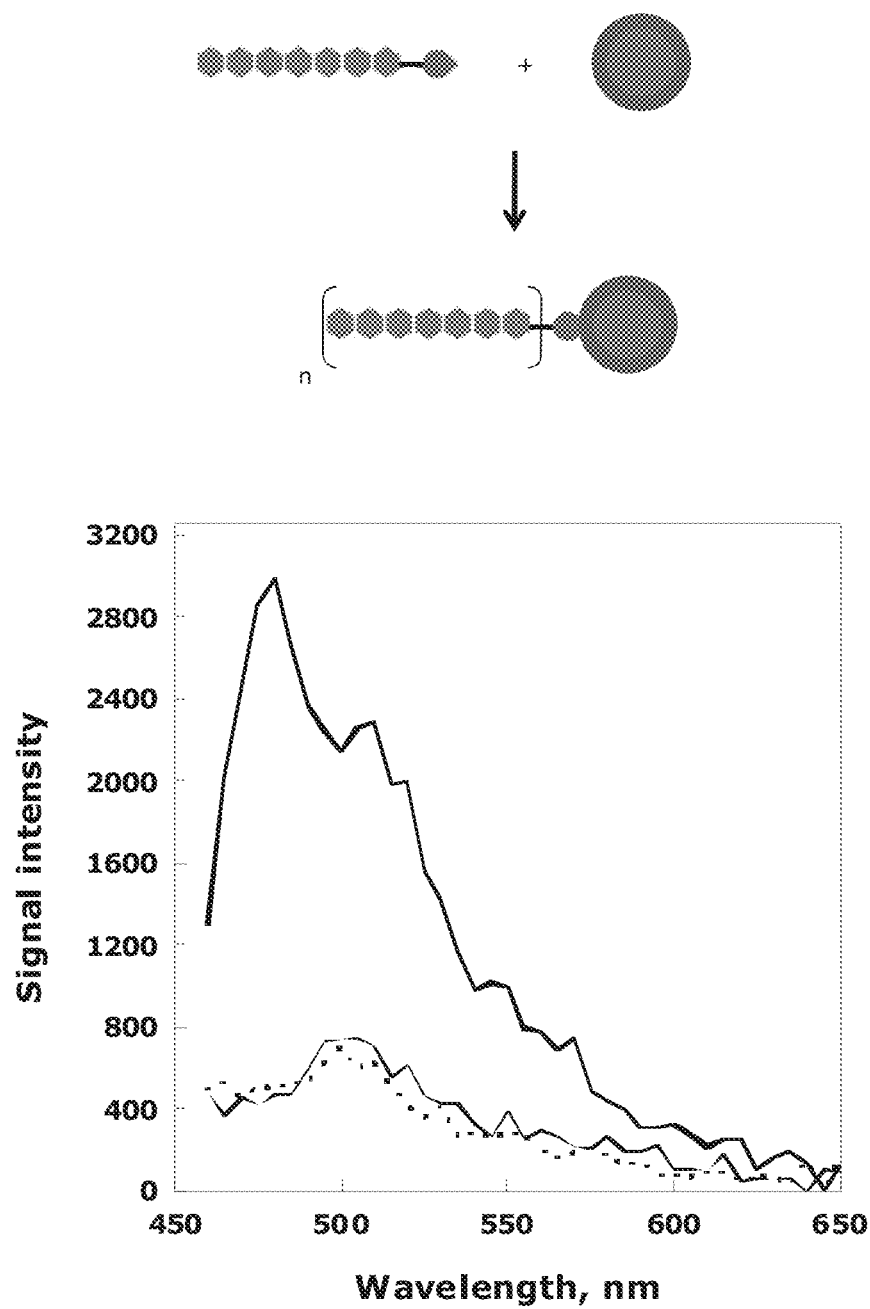
FIG. 18. Schematic of biotinylated polymer of FIG. 14 binding to streptavidin coated microspheres (top) and plot of fluorescence excitation of control streptavidin coated microspheres and microspheres bound to biotinylated polymer.

FIG. 18 shows the biotin modified polymer was bound to a streptavidin microsphere (top). In FIG. 18 (bottom), excitation at 440 nm in a fluorometer resulted in emission from the polymer as indicated by the solid upper curve. The lower solid curve represents the negative control where the streptavidin bead was first treated with excess biotin to block the binding sites prior to treatment with the biotinylated polymer. The lower solid curve represents beads alone.

Example 35: Selective Binding of Biotin-Labeled Polymer to Dye-Labeled SA Conjugates to Validate FRET Properties and Functional Activity of the Polymer Modification Materials Required:
Biotin-Polymer Conjugate: (46 Cy3-SA conjugate (1 mg/mL or 18.9 µM). BLACK 96-well plate.
Forming the Biotin-Streptavidin Complex:
In a 1.5 mL microfuge tube, combine 9.4 µL of the biotin-polymer conjugate and 2.9 µL of the Cy3-SA. Vortex to mix, then incubate on a shaker (under foil) for 0.5 h. Longer incubation times are also suitable.
Instrument Settings:
Model experiments were conducted on a BioTek Synergy 4 in the Fluorescence mode with the following settings: Emission: 400-750 nm in 5 nm steps and Sensitivity level: 50.
Plate Layout:
Prepare solutions in a BLACK 96-well plate as in the below table. Take care to add the A+B solution last, after all other materials have been added:

| Material | Well 1 | Well 2 | Well 3 |
|---|---|---|---|
| Polymer-biotin | 9.4 µL* | 9.4 µL | — |
| Cy3-SA | 2.9 µL* | — | 2.9 µL |
| Buffer | 100 µL | 100 µL | 100 µL |

*Pre-incubated in the first step, Forming the Biotin-Streptavidin Complex.

Figure 19:
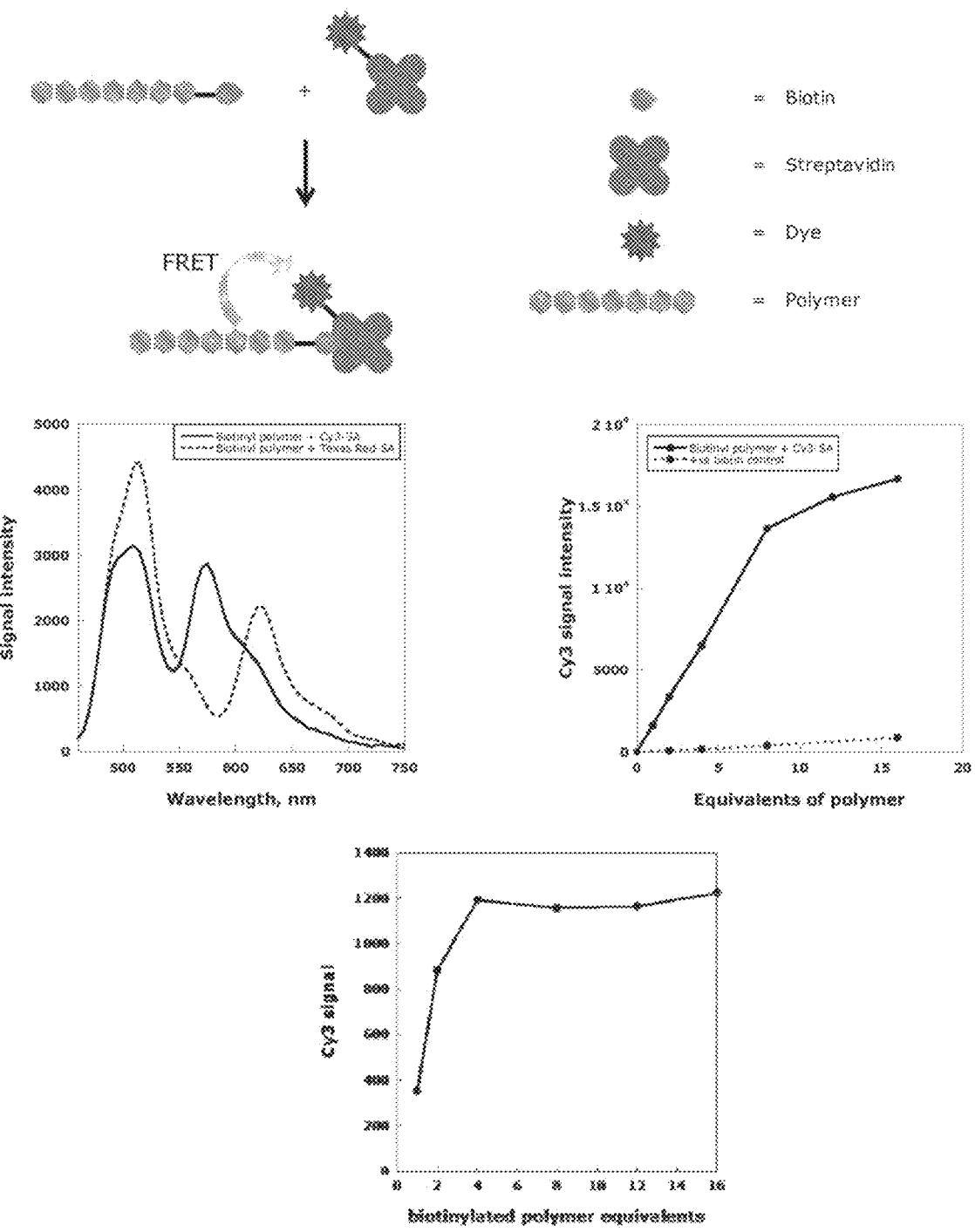
FIG. 19. Schematic of biotinylated polymer of FIG. 14 binding to dye-labeled streptavidin conjugates and FRET (top); plot of energy transfer from biotinylated polymer to two different dye acceptors (bottom left) and titration plot of polymer saturation (bottom right).

FIG. 19 shows the biotin modified polymer was bound to a dye labeled streptavidin (Cy3 or Texas Red—top). Excitation at 440 nm in a fluorometer resulted in emission from the dye acceptors at their respective emission wavelength (approximately 570 nm and 620 nm respectively—bottom left) as well as some residual emission from the polymer (approximately 520 nm). A titration was also performed to saturate the binding of polymer to the streptavidin (bottom right). The solid curve indicates the emission from the Cy3 label on the streptavidin via energy transfer from the polymer at 440 nm excitation. The dotted curve represents the negative control where the streptavidin was first treated with excess biotin to block the binding sites prior to treatment with the biotinylated polymer.

Example 36: Polymer-Streptavidin Conjugates for Use in Flow Cytometry

Polymer bioconjugates are evaluated by Stain Index, as defined by Becton Dickinson (BD) Biosciences on a flow cytometer. See, e.g., H. Maeker and J. Trotter, BD Biosciences Application Note: "Selecting Reagents for Multicolour Flow Cytometry", September 2009. The stain index reports a measure of the polymer's brightness, nonspecific binding and can also be related by the Resolution Index on a flow cytometer. Flow cytometry provides a method through which to measure cells of a specific phenotype or analytes of interest on specific microspheres. This can be done with direct labeling of a primary antibody or, if signal amplification is desired, through a secondary antibody or the avidin-biotin complexation with avidin-polymer conjugates.
Procedure for Cell Staining
Cells of interest are taken up in sufficient quantity, at least $10^5$ per test condition. Cells are then spun down at 250 rcf for 3 minutes, washed in DPBS+0.2% BSA and 0.05% $NaN_3$ (staining buffer), then resuspended in staining buffer at $1 \times 10^7$ cells/mL.

For primary incubation, cells are incubated with a primary conjugate (reporter labeled antibody) specific to an antigen of interest, negative cells serve as a negative non-specific binding reference. A control population or an established commercial conjugate is used as a positive control. Primary polymer conjugates are incubated at 4° C. with $4 \times 10^5$ cell aliquots at concentrations with volume dilutions from 10-330 nM for 30 minutes. Following primary incubation, cells are rinsed with 5 volumes staining buffer and spun down at 250 rcf for 3 minutes; this rinse is repeated three times. Cells are resuspended for testing at $8 \times 10^5$ cells/mL in DPBS+0.2% BSA, 0.05% $NaN_3$.

For secondary antibody labeling, an unlabeled primary antibody to the antigen of interest is incubated at 0.4 ug/uL, or other titrated amount, at 4° C. with $4 \times 10^5$ cells per test condition for 30 min. Following primary incubation, cells are rinsed with 5 volumes staining buffer and spun down at 250 rcf for 3 minutes; this rinse is repeated three times. Species reactive secondary polymer conjugates are incubated at 4° C. with $4 \times 10^5$ cell aliquots at concentrations with volume dilutions from 10-330 nM for 30 minutes. Following secondary incubation, cells are rinsed with 5 volumes staining buffer and spun down at 250 rcf for 3 minutes; this rinse is repeated three times. Cells are resuspended for testing at $8 \times 10^5$ cells/mL in DPBS+0.2% BSA, 0.05% $NaN_3$.

For streptavidin-polymer conjugate labeling, cells are incubated with a biotinylated primary antibody to the marker of interest, as detailed above for the secondary antibody labeling, instead of an unlabeled primary. Following the primary washing, cells are resuspended and divided in $4 \times 10^5$ cell aliquots and incubated with streptavidin-polymer conjugates at 1-100 nM volume dilutions for 30 minutes at 4° C. Following secondary incubation, cells are rinsed with 5 volumes staining buffer and spun down at 250 rcf for 3 minutes; this rinse is repeated three times. Cells are resuspended for testing at $8 \times 10^5$ cells/mL in DPBS+0.2% BSA, 0.05% $NaN_3$. If further signal amplification is desired, cells and be incubated with an unlabeled primary antibody and then subsequently follow with a species reactive biotinylated secondary antibody prior to incubation with streptavidin conjugates. The incubation steps, washing protocol and testing protocol should follow as previously detailed.

These flow testing procedures have been developed specific to CD4 markers on Cyto-trol cells. Cell preparation and incubation protocols may vary with cell type and an optimal staining, washing and handling protocol should be developed specific to cell type. Working concentration ranges of antibodies have been identified as optimal for both CD4 (35-50% population) and CD45 (85% population) markers on Cyto-trol control lymphocytes as well as on Whole Lysed Blood (for primary antibody only). Markers which have populations significantly different than these ranges may fall outside of the suggested titration ranges.

Testing was also done on a Jurkat cell line grown in culture following similar protocols. In these tests a CD45 marker was used. As there are no negative cell populations a different negative control procedure was used. In the negative control samples the primary antibody was omitted from the primary incubation step. This step and all subsequent steps were performed according to the standard protocol. Again a commercially dye-antibody or dye-strepatvidin conjugate were used as a positive control.

Procedure for Flow Cytometry Analysis

Flow testing was done in test tubes, at 0.5 mL volumes on a BD LSR II Flow Cytometer. Flow testing is performed using the voltage settings determined from daily calibration of the cytometer with calibration particles by flow facility staff. Lymphocyte specific gating by forward scatter vs. side scatter is performed on unstained cell samples as a background control. Standard doublet gating is performed for both forward scatter and side scatter area vs. width profiles. With only a single color, no compensation is required. Data are collected for all forward and side scatter parameters and fluorescence measurements are made using BD's standard Pacific Blue channel. Pacific Blue data utilizes excitation with the 408 nm Violet lasers and a 450/50 BP filter. Samples are collected for 30,000 events within the stated gating parameters.

Representative Experiments:

CD4 marking was measured on Cyto-trol cells, lyophilized human lymphocytes for analysis of polymer performance in flow. Cyto-trol cells (Beckman Coulter) were reconstituted in the provided reconstitution buffer and allowed to swell for 15 minutes at room temperature. Cells were then spun down at 250 rcf for 3 minutes, washed in DPBS+0.2% BSA and 0.05% $NaN_3$ (staining/testing buffer), then resuspended in staining buffer at $1\times10^7$ cells/mL. Cell suspension was divided in two; half the cells were incubated with biotinylated anti-CD4 at 0.4 ug/uL, the other half of the cells were incubated with staining buffer as a negative control for 30 min. Following primary incubation, cells were rinsed with 5 volumes staining buffer and spun down at 250 rcf for 3 minutes; this rinse was repeated three times. Cells were resuspended at prior volume in staining buffer. $4\times10^5$ cells were measured per test and divided out accordingly, streptavidin-fluorophore conjugates prepared in Example 19 were incubated at 100 nM with each aliquot of cells for 30 min, allowing the avidin-biotin complex to form. Following the secondary incubation, cells were rinsed and detailed previously. Final cell suspensions were made for testing at $8\times10^5$ cells/mL.

Flow analysis was performed on a BD LSR II flow cytometer at The Scripps Research Institute (TSRI), San Diego, Calif. Routine calibration with Rainbow fluorescent particles for aligning fluorescent channels on the cytometer was performed by staff at TSRI, all calibrated voltages were used, per staff recommendation. All samples were excited with a 408 nm Violet laser, the polymer conjugate was measured in the AmCyan channel with a 525/50 filter. All samples were initially referenced to unstained cells. The polymer streptavidin conjugate from FIG. 14 showed specific secondary labeling of the primary identified CD4 positive cells, with the positive cells as 44% of the population. The polymer streptavidin conjugate demonstrated a positive stain index showed low non-specific binding with reference to unstained cells and its respective negative control (FIG. 20. (A)). This provides evidence that the polymer, although its peak absorbance is a 440 nm, is a viable fluorescent material for use in flow cytometry with Violet laser excitation. Secondary Antibody polymer conjugate on Cyto-trol cells Amine-functionalized 405 polymer was conjugated to goat anti-mouse IgG κ1 purified antibody by route of maleimide-thiol conjugation and TCEP partial reduction of the antibody. The polymer and conjugation procedure are provided specifically in Example 46.

Conjugates were tested on Cyto-trol cells (Beckman Coulter), a fixed and lyophilized lymphocyte cell population for control testing of specific human antigens. Cell staining followed secondary cell staining protocol. Cells were incubated with and without (negative control) unlabeled anti-CD4 (RPA-T4 clone, BD Biosciences) raised in mouse against the human antigen. After complete washing of primary antibody incubation, cells were incubated with polymer labeled goat anti-mouse conjugates for specific labeling of primary identified CD4 positive cells. Secondary labeling occurs by Fc recognition and binding of the mouse primary antibody by the secondary goat IgG, raised against murine species. A positive control was used by incubation with commercially available Pacific Blue goat anti-mouse IgG (Invitrogen) as the secondary labeling species.

Figure 20:
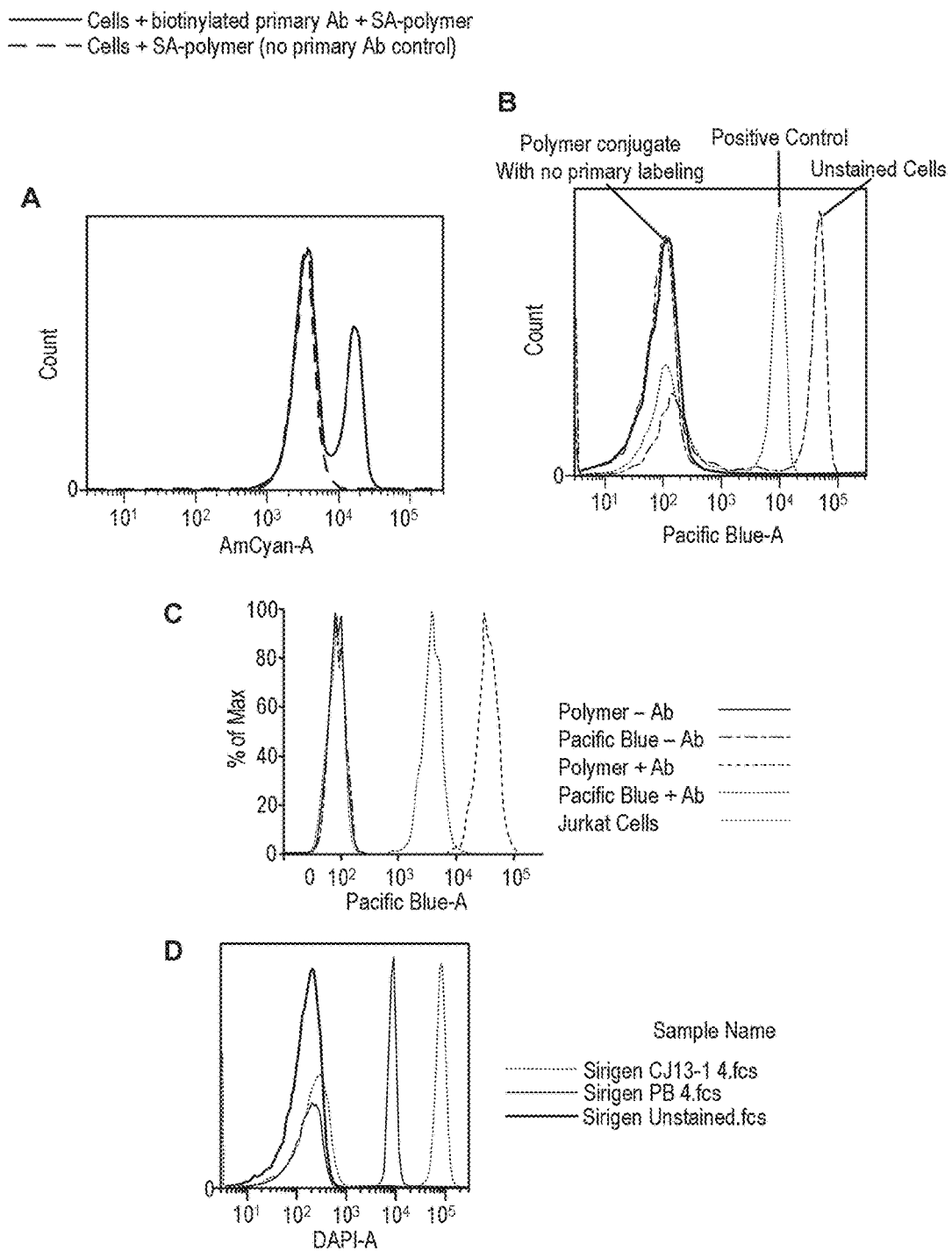
FIG. 20. Flow cytometry analysis of CD4 marking of Cyto-trol cells with 440 nm polymer-streptavidin-conjugates.

FIG. 20 (B) depicts the specific recognition of CD4 specific cells by the secondary fluorescent conjugates. Unstained cells show a negative control and natural autofluorescence of the cells, and incubation of polymer conjugate on cells with no primary labeling show minimal non-specific binding of the conjugate to unlabeled cells. Positive control, Pacific Blue goat anti-mouse shows the commercially available standard for CD4 labeling by secondary antibody with Violet excitation. 405 polymer-goat anti-mouse conjugate (red) shows positive identification of CD4 positive cells, a minimal shift in the negative cell population and great fluorescent signal and resolution that Pacific Blue standard.

FIG. 20 (C) depicts Streptavidin polymer conjugates on Jurkat cells. Conjugates were produced with the polymer provided in Example 11 using the protocol defined in Example 29. The stain index for the polymer streptavidin conjugate was over 10 fold higher than that obtained for the commercially available Pacific Blue streptavidin control conjugate.

FIG. 20 (D) depicts a primary monoclonal antibody polymer (antiCD4, RPA-T4) conjugate evaluated on Cyto-trol cells using the protocols defined above. The conjugate was prepared using the polymers and protocols defined in Example 46. Additional details on the conjugation can also be found in Example 39.

Example 37: Preparation of Polymer Conjugated to —COOH Beads Via EDC Coupling Materials (Per 100 μL of Beads)

LodeStars —COOH functionalized magnetic beads (Varian, Inc. PL6727-0001) (100 μL of suspension at spec'd 30 mg/mL). Polymer with amine terminal ends from Example 17 (125 μL at 1.6 μM in 25 mM MES pH 5, for a 10-fold excess over theoretical bead capacity). 10 mM NaOH (2 mL). DI H2O (3 mL). 25 mM cold MES, pH 5. EDC at 50 mg/mL in 25 mM cold MES, pH 5 (100 μL). NHS at 50 mg/mL in 25 mM cold MES, pH 5 (100 μL). 100 mM Tris/HCl pH 7.4 (1 mL). Centrifuge and black flat-bottom 96-well plate.

Antibody capacity was given at 10 ug/mg bead, giving an amine coupling capacity of 2 nmol polymer/mL bead (at 30 mg/mL). A 10 fold-excess of polymer over the suggested capacity was used to target the antibody concentration given in Varian's protocol.

Bead Washing

Beads were washed collectively as 600 μL and then split into 6×100 μL samples for coupling. Beads were washed 2× with 1 mL 10 mM NaOH, then 3× with 1 mL DI H2O; in between washes, the tube was centrifuged 1 min at 3000 rpm to recollect the beads as a pellet, supernatant was discarded and beads were resuspended in the next wash. After the final wash, beads were resuspended in 600 μL cold 25 mM MES, pH 5 and aliquoted into 6×100 μL volumes in microcentrifuge tubes. Beads were centrifuged again 1 min at 3000 rpm and supernatant was discarded.

EDC Activation

100 μL of the EDC solution was added to each reaction set. 100 μL of the NHS solution was added to each reaction set. Beads were resuspended by vortexing and then allowed to mix on a rotator for 30 minutes. Beads were washed 2× in cold 25 mM MES pH 5, pelleted by centrifuging for 1 min at 3000 rpm and the supernatant was discarded. Beads were resuspended in 125 μL cold 25 mM MES, pH 5.

Polymer Coupling

125 μL of polymer at 1.6 μM was added. Samples were vortexed to mix thoroughly and then reacted at RT on a mixer for 3 hours. Beads were pelleted by centrifuging for 1 min at 3000 rpm; supernatant was discarded. Beads were resuspended in 1 mL 100 mM Tris/HCl to block unreacted —COOH sites, vortexed and mixed for 1 hour.

Beads were recollected by centrifugation and resuspended in 100 μL 25 mM MES. At this point, the supernatant of several tubes were yellow in color and had significant absorbance at 440 nm; the beads were washed 6 times until absorbance was at baseline. Beads sat for an additional 2 days prior to fluorescence measurement, after sitting in solution for 2 days, the supernatant was again yellow in color and had measurable absorbance. Beads were washed 3 more times with 30 minute mixes in between until no absorbance was measurable. At 2 days following fluorescence measurements, the supernatant remained clear and free of measurable absorbance.

Example 38: Preparation of Polymer-Dye Conjugates

Example 38a: Preparation of Polymer-Dye Conjugate at Polymer Terminal

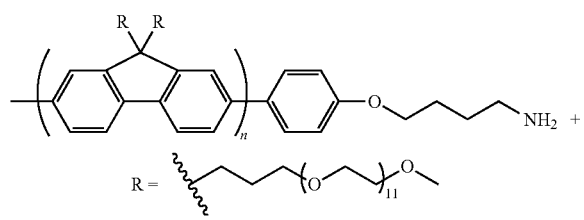

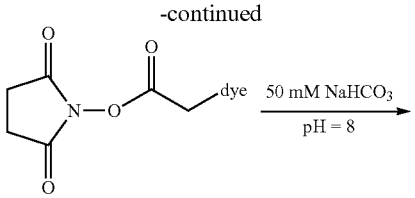

-continued

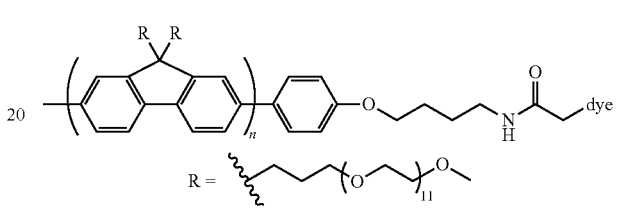

0.5 mg amine-terminated polymer was dissolved in 15 μL DMSO. The polymer solution was then exchanged into 50 mM NaHCO3/Na2CO3, pH 8 buffer and recovered in buffer at ~5 mg/mL as determined by UV-VIS absorbance. 50 μg NETS-ester dye (DyLight 594) was dissolved at 10 mg/mL in anhydrous DMSO, which was then immediately added to 120 μg of polymer. The tube was mixed on shaker (600-800 rpm) for 1 h and subsequently diluted to 100 μL with 20% EtOH in water. The mixture was added to a 30 cm Superdex 200 SEC column in 0.6M NaCl and 20% EtOH to separate polymer-dye conjugate from unreacted dye. The addition of dye can be used to estimate the incorporation of linker on the polymer structure by measuring an absorbance ratio based on the relative extinction coefficients of the polymer and dye. Using the molecular weight of the polymer it is possible to estimate the number of polymer chains which contain a linker.

In additional embodiments, polymers with a carboxylic acid side chain are modified with amine functional dyes using standard EDC conjugation procedures or by first converting to the NETS ester using the protocol similar to that described in Example 29. Thiol dyes conjugated to maleimide terminated polymers have also been demonstrated. Any range of chemistry pairs would be expected to work in similar fashion to conjugate a polymer and dye.

Example 38b: Preparation of Polymer-Dye
Conjugate at Internal Position

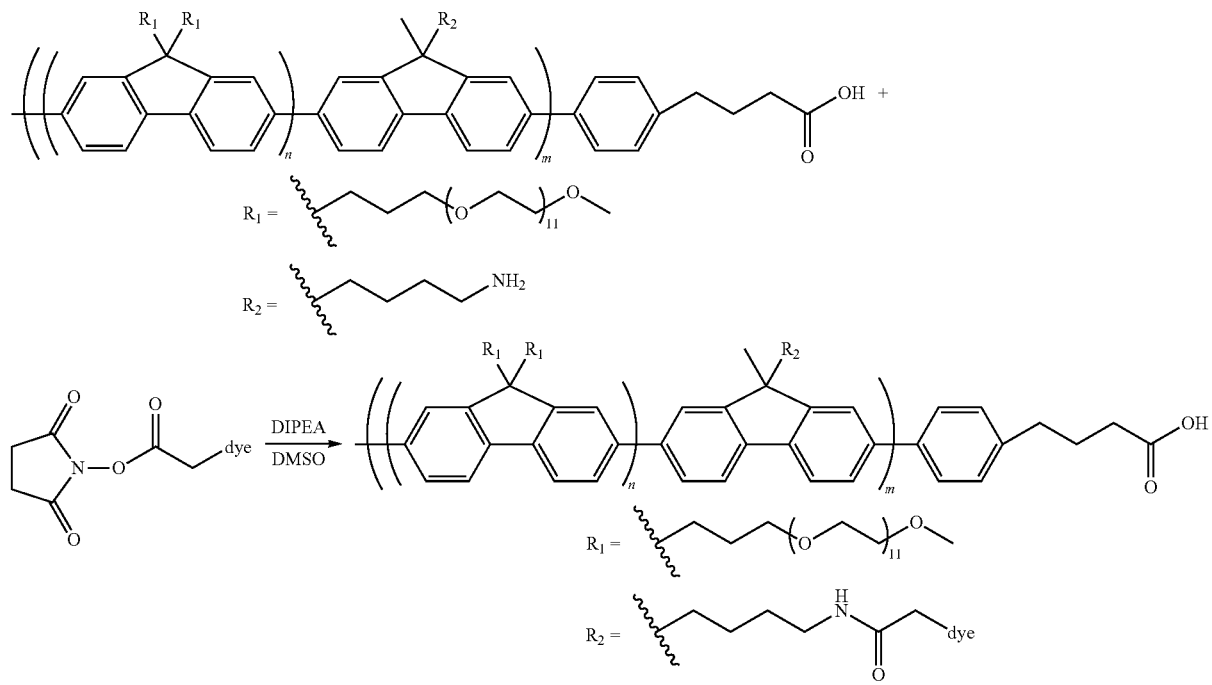

In a glovebox, 100 mg polymer with internal amine functionalities was dissolved in 10 mL anhydrous DMSO in a 20 mL amber scintillation vial. 0.32 mL DIPEA was added to the polymer solution. 24 mg of NETS-ester dye (Cy3) was dissolved in 2.4 mL in anhydrous DMSO and added to the polymer solution. The vial was tightly sealed, then removed from the glovebox and stirred at room temperature for 48 hours. The reaction was then purified over Amicon Ultra centrifugal filtration units (MWCO=30 kDa) with 20% ethanol in water until all free dye was removed. Purity was verified by running a 0.15 mg sample over a 30 cm Superdex 200 SEC column in 0.6M NaCl and 20% ethanol. 90 mg yield (90%).

The addition of dye can be used to estimate the incorporation of linker monomers in the polymer structure by measuring an absorbance ratio based on the relative extinction coefficients of the polymer and dye. For polymers described above, the ratio of linker monomers (or dye attachments) per fluorene monomer in the final polymer are in general agreement with the molar feed ratio of monomers used in the polymerization reaction.

Polymers with a carboxylic acid side chain can also be modified with amine functional dyes using standard EDC conjugation procedures or by first converting to the NHS ester using the protocol similar to that described in Example 29.

Analogous procedures can be used to conjugate a range of dyes including Cy3, DyLight 549, DyLight 633, FAM, FITC, Alexa633, Alexa647 and several others. Polymers with a carboxylic acid side chain can also be modified with amine functional dyes using standard EDC conjugation procedures.

FIG. 21 (A) shows the polymer structure above conjugated to (from left to right) FITC, Cy3, DyLight 594 and DyLight633. The polymer alone is show for reference (far left). Note in each case the amount of residual donor (polymer) emission is minimal. The data highlight the capability of generating several diagnostic signals at different wavelengths for multiplex applications. In this embodiment a single light source is capable of generating five distinct emission wavelengths.

Example 38c: Energy Transfer Evaluation for
Polymer-Dye Conjugates Based on Polymer
Excitation for Use in Polymer Tandem Conjugates FIG. 21 (B) depicts a comparison of the fluorescence of the dye (DyLight594) excited near its absorbance maximum (lower curve) and polymer-dye conjugate excited at 405 nm (upper curve). Dye emission around 620 nm was over 5 fold brighter from the polymer-dye conjugate at the same molar concentration of dye versus direct dye excitation. Such embodiments highlight the signal amplification afforded by the disclosed polymer donors in energy transfer processes. The picture in the upper left corner highlights the visual color change in the emission of the complex based on dye conjugation. The polymer solution emits blue in the absence of dye and red upon dye conjugation (post purification).

FIG. 21 (C) compares the fluorescent signal of the base polymer (no dye, peak emission near 420 nm) to that of the polymer-dye conjugate (peak emission near 620 nm). The DyLight594 dye quenches >98% of the polymer emission when conjugated to the polymer above (Example 38b). This is a feature of the polymer materials as any remaining donor emission could manifest as background signal in multiplex assay formats. The ability to conjugate the dye directly to the polymer structure and vary the number of attachment sites provides for efficient transfer that can be regulated by chemical design.

Example 39: Flow Testing of Monoclonal Antibody (antiCD4) Conjugates on Whole Lysed Blood Samples Polymer conjugates of primary antiCD4 antibody (RPA-T4 clone) were produced using 3 different conjugation routes as provided in Examples 45, 46 and 49. 1) Amine modified polymer converted to a maleimide reactive group using SMCC (maleimide/NHS crosslinker) reacted with thiol groups on the antibody introduced by reacting SATA (thiol/NHS cross linker) with lysine (amine) groups (CJ11-2, FIG. 22). 2) Same polymer modified with SMCC (malemide) but with thiol groups introduced on antibody using TCEP to partially reduce the disulfide linkages in the antibody (CJ13-2, FIG. 22 and FIG. 20D). 3) A carboxylic acid terminated polymer activated with TSTU to form the NHS ester was reacted directly with the lysine (amine) groups on the antibody (CJ04-2 FIG. 22). All conjugates were made from the same polymer structure and batch. The polymer was synthesized using the protocol depicted in Example 12 with an amine end capping unit in place of the carboxylic acid capping unit shown. The NHS/amine conjugation was done with the protocol described in Example 45. The maleimide/thiol conjugation reactions were done in lines with those protocols described in Examples 46 and 49.

Figure 22:
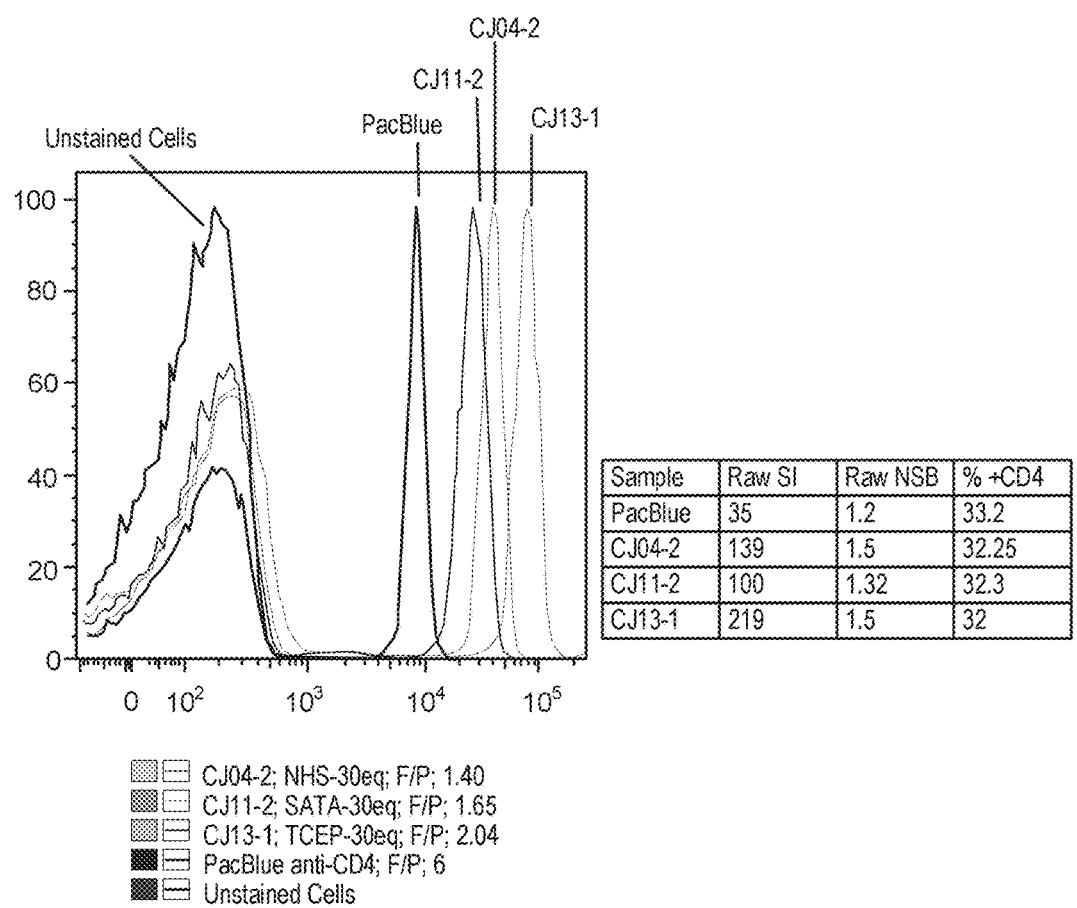
FIG. 22. Plot of flow testing of monoclonal antibody (antiCD4) conjugates on whole lysed blood samples.

FIG. 22 depicts the performance of these conjugates in flow cytometry conduced as follows. 100 µl whole human blood from a healthy volunteer was aliquoted into FACS tubes (duplicates for each sample). Antibody conjugates were diluted in wash buffer (PBS with 0.5% BSA and 0.1% Sodium Azide) and added to the blood at specified concentrations. Samples were vortexed vigorously then incubated for 15-30 mins in the dark at room temperature. 2 ml of 1×BD FACS Lyse solution was added to each sample and mixed in by vigorous vortexing prior to a further 10 mins incubation in the dark at room temperature. Samples were centrifuged for 5 min at 500 g and the supernatant tipped off and discarded. Samples were vortexed and 3 ml of wash buffer (PBS with 0.5% BSA and 0.1% Sodium Azide) added. Centrifugation was repeated at 500 g for a further 5 min. The resulting supernatant was tipped off and discarded and the remaining cell pellet vortexed. Samples were run on a BD LSRII flow cytometer acquiring all violet channels equipped with a violet laser and 450/50 nm filter that had been set up and precalibrated against BD CST beads. All polymer conjugate samples (CJ04-2, CJ11-2 and CJ13-1 lines) showed minimal non specific binding compared to unstained cells. Further, all polymer conjugates produced significantly higher positive signals than a commercially available Pacific Blue control conjugate of the same antibody clone which is commonly used for flow cytometry at compatible wavelengths. The best performing conjugates from this set provided over 6 fold high stain index than the commercially available Pacific Blue control antibody.

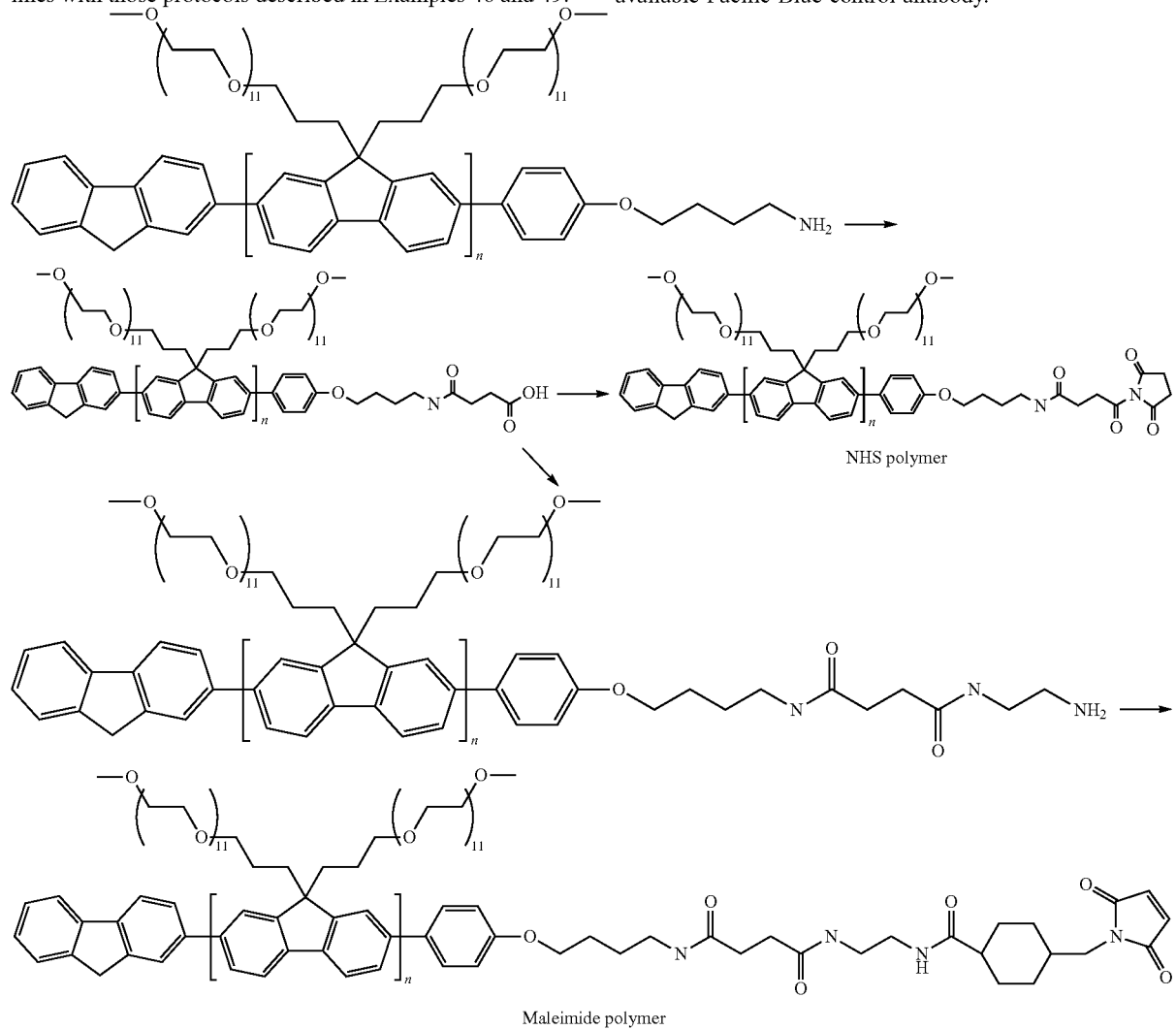

NHS polymer

Maleimide polymer

Example 40: Preparation of Polymer-Dye Conjugate
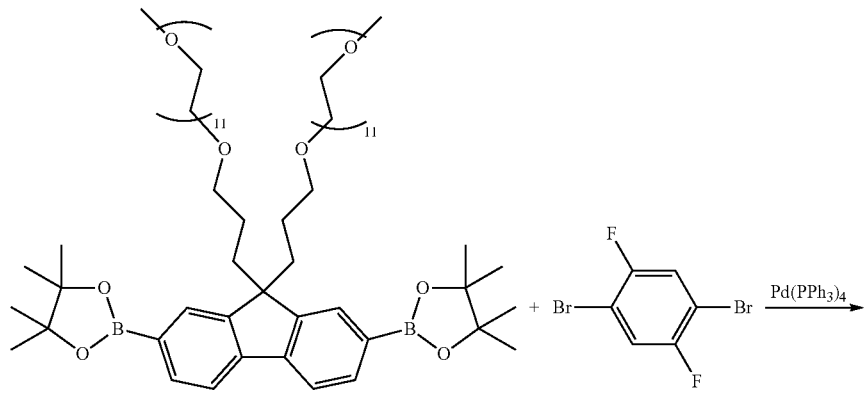
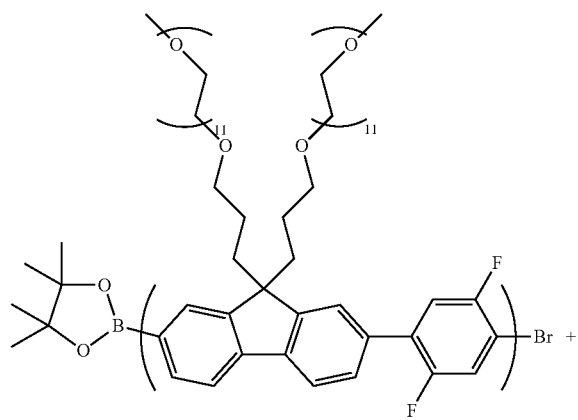
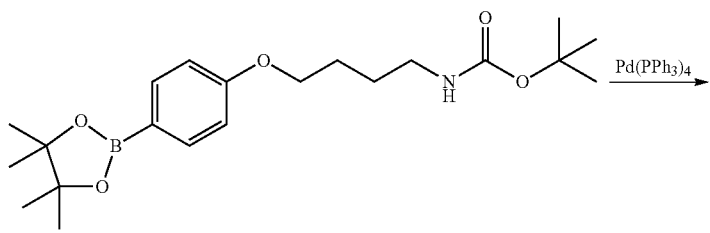
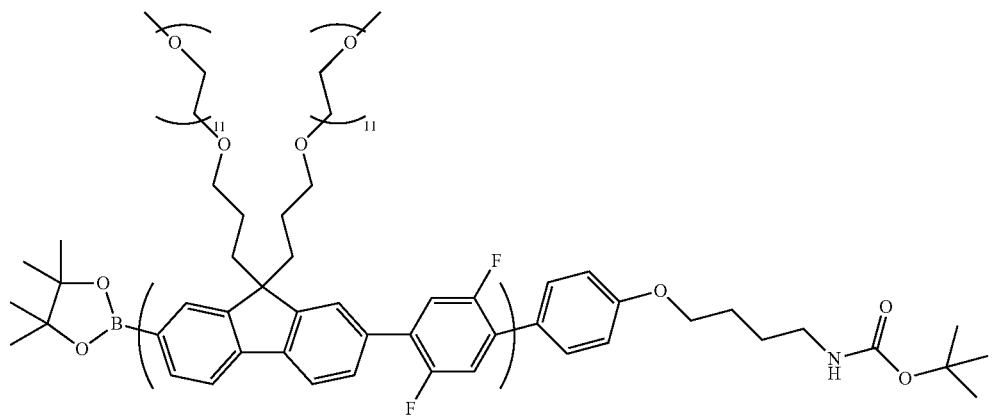

-continued
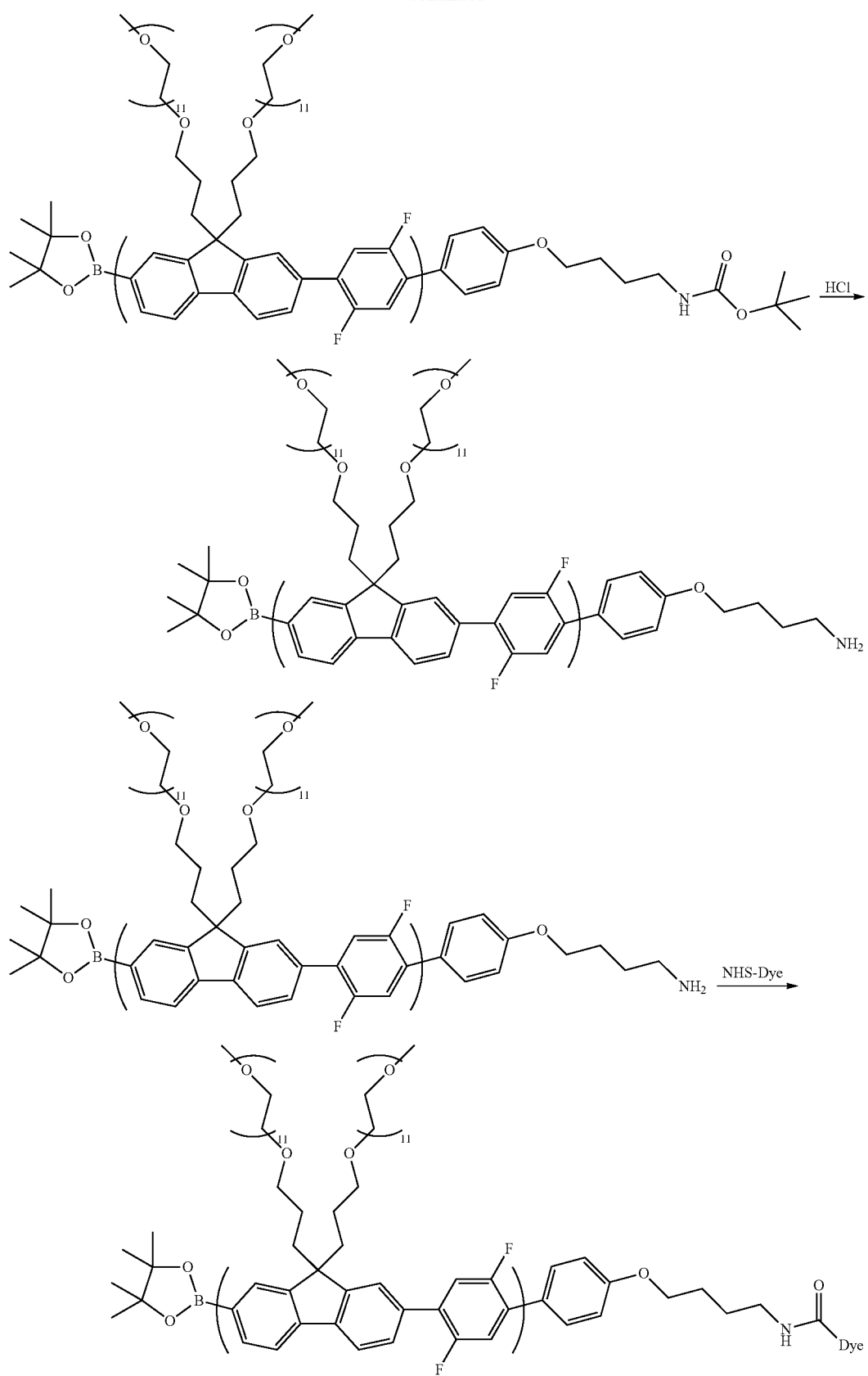

Figure 23:
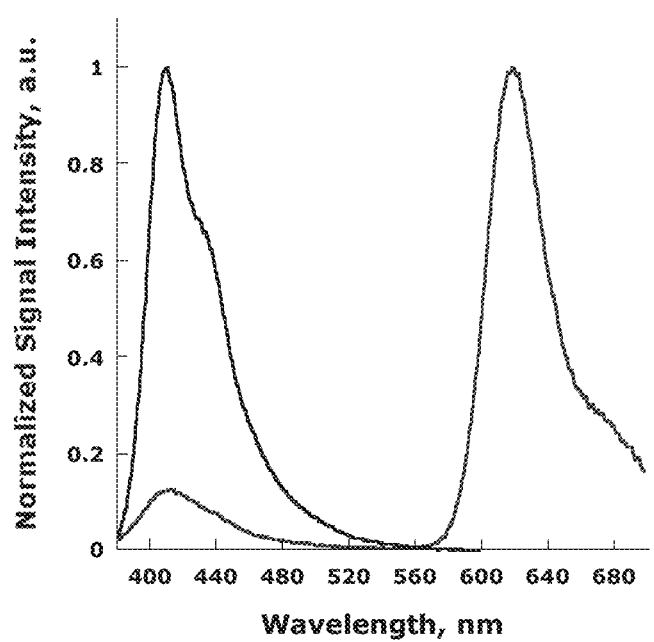
FIG. 23. Plot of florescence of a dye (DyLight594) and a polymer-dye conjugate by excitation of dye at 594 nm and the polymer-dye conjugate at 380 nm.

The polymer is conjugated to a dye, Dylight 594, and purified in a manner similar to the methods as described in Example 36. FIG. 23 depicts a comparison of the florescence of the dye (DyLight594) and polymer-dye conjugate. The dye was excited at 594 nm and the polymer-dye conjugate at 380 nm.

Example 41: Fluorescent Immunoassay (ELISA) with Streptavidin-Conjugated Polymer An immunoassay for human IgG was developed as a demonstrative system in 96 well plate format. In further embodiments, similar functionality would be equally applicable in other formats including suspended microspheres and protein chip microarrays.

Step 1: Preparation of Reagents

Wash concentrate was prepared by dissolving 79.2 g Tris base pre-set crystals (pH 7.7), 225 g sodium chloride and 0.5 g Thimerosol in 1000 mL deionised water. Wash solution was prepared by adding 100 mL wash concentrate to 2400 mL deionised water. Subsequently, 10 mL 10% Triton X-100 was added. The basic assay buffer was prepared by dissolving 14.8 g Tris base pre-set crystals (pH 7.7), 18 g sodium chloride and 0.5 g Thimerosol in 2000 mL Milli-Q water (conductivity 18.2 mΩcm). Subsequently, 2 mL 10% Tween 20 and 10 g Bovine Serum Albumin Fraction V, essentially gamma globulin free were added. The solution was filtered and stored at 4° C.

Step 2: Preparation of Capture Antibody Coated Plates

Capture antibody was coated onto the surface of Nunc white Maxisorp 96 well plates at a concentration of approximately 1 microgramme per well. The plates were sealed and stored overnight at 4° C. Subsequently, the plates were washed once with wash solution and tapped dry on absorbent paper. Unless otherwise stated all plate washing in this example was performed on an automated microtitre plate washer. Two hundred and fifty (250) microliters of blocking buffer (0.1M PBS containing 2% BSA) were added to each well, the plates re-sealed and stored at 4° C. until use.

Step 3: Immunoassay

Figure 24:
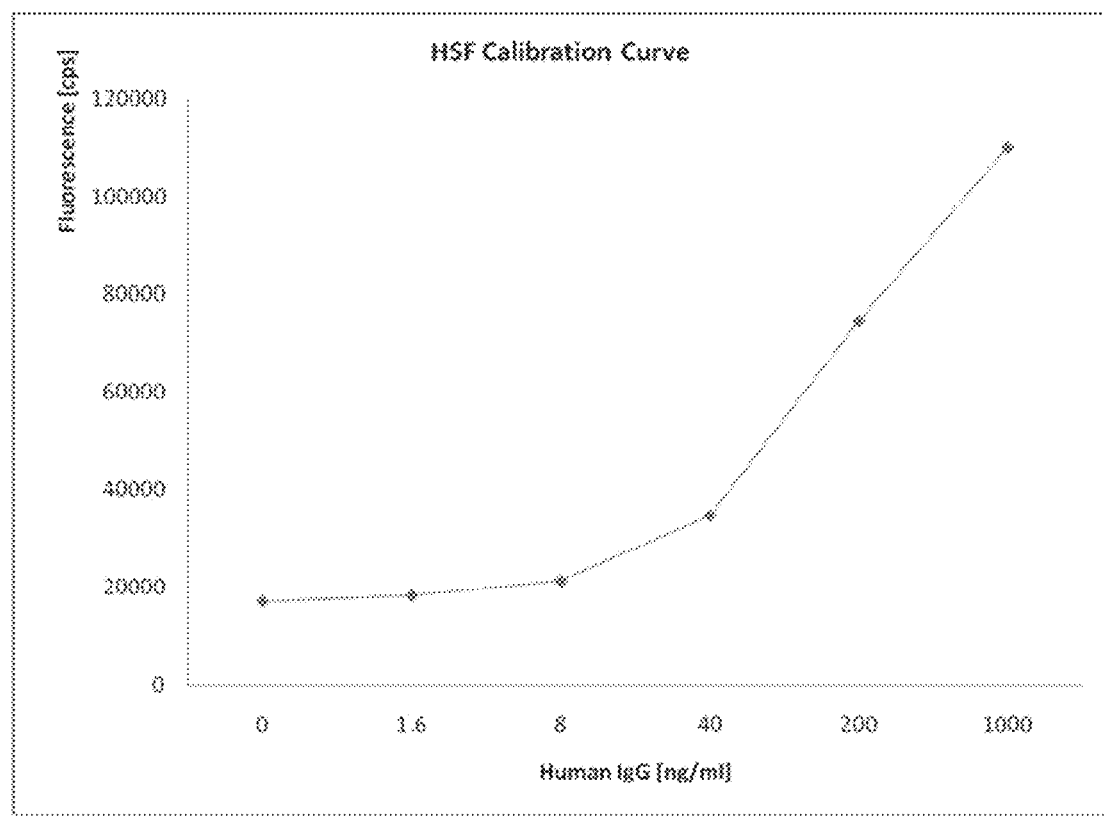
FIG. 24. Plot of fluorescent immunoassay (ELISA) with streptavidin-attached conjugated polymer.

Capture antibody-coated microtitre plates were washed twice with wash solution and tapped dry on absorbent paper. Two hundred (200) μL of either assay standard or experimental unknown sample were added in quadruplicate to appropriate wells of the coated plate. The plates were incubated on a shaker for 2 hours at 18° C. Subsequently, the plates were washed three times with wash solution, tapped dry on absorbent paper, and 200 μL of biotinylated detection antibody at a previously determined optimal concentration (diluted in assay buffer and filtered before use) were added to each well. The plates were incubated on an orbital shaker at ambient temperature for a further 60 minutes. The plates were then washed three times and tapped dry on absorbent paper. Two hundred (200) μL of 0.2 micron syringe filtered Streptavidin-polymer conjugate as prepared in Example 30 diluted to a concentration previously determined as suitable in assay buffer. The polymer was a fluorene polymer with neutral PEG11 side chains and an amine conjugation site. The plates were incubated on an orbital shaker at ambient temperature for a further 2 hours. The plates were then washed six times, tapped dry, turned around 180°, and re-washed a further six times. The plates were again tapped dry on absorbent paper. Two hundred (200) μL of filtered release reagent (0.1M sodium hydroxide, 2% Triton X-100) were added using a multi-channel pipette, the plates shaken for 60 minutes at ambient temperature and the fluorescence measured with a Victor Fluorometer. The plate was then sealed, stored overnight at 4° C. and re-read in the Victor Fluorimeter the following morning. Fluorescence counts were analysed using the Multicalc Software from Perkin Elmer to determine lower limit of assay detection and assorted similar parameters. Alternative conditions were also evaluated to release the conjugate from the well plate surface to improve the fluorescent readout. A representative data set is shown in FIG. 24. Comparisons were also made to commercially available SA-dye conjugates. The polymer conjugates demonstrated superior detection limits relative to the dye conjugates as was expected due to the collective optical properties.

Example 42: Synthesis, Conjugation and Application of Para-Phenylene Vinylene Co-Polymer with Active Functional Linker for Bioconjugation

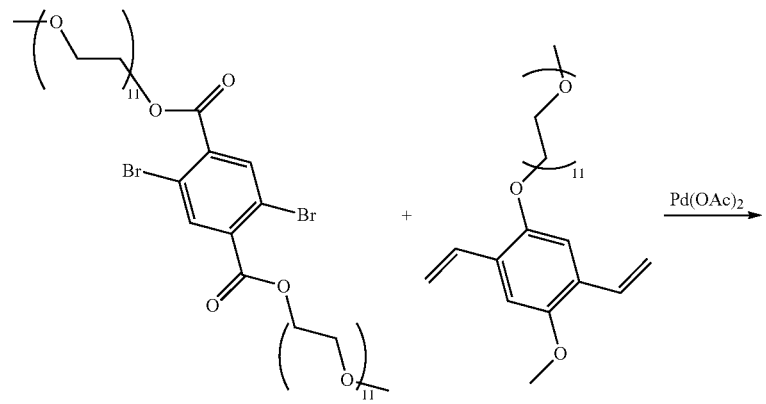

-continued
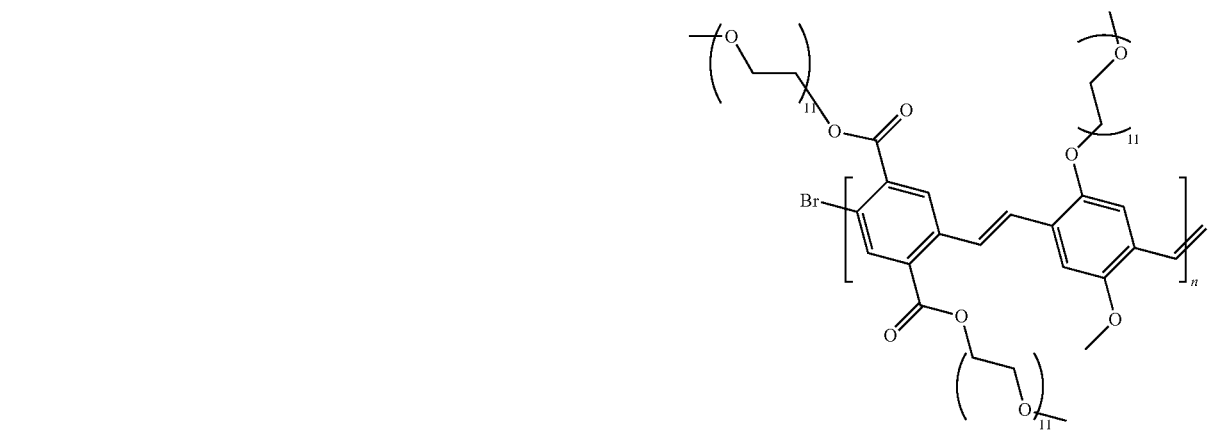
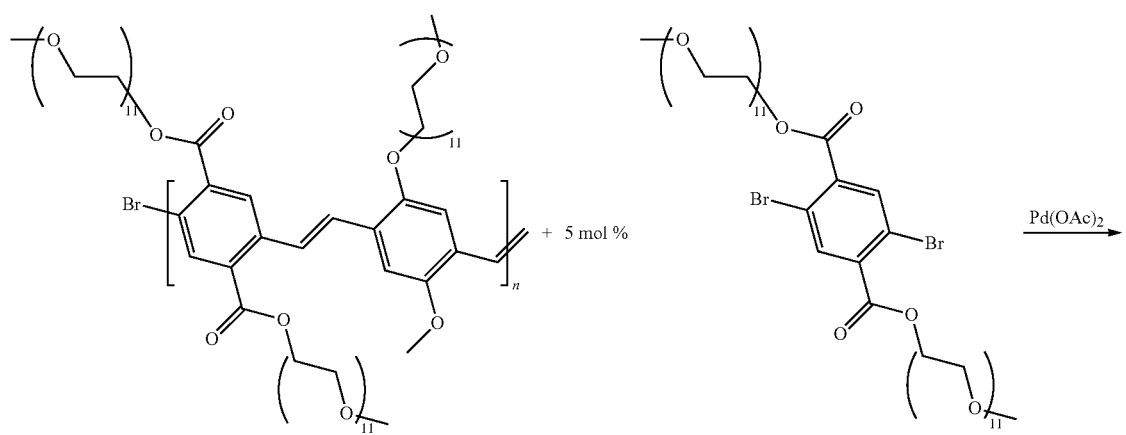
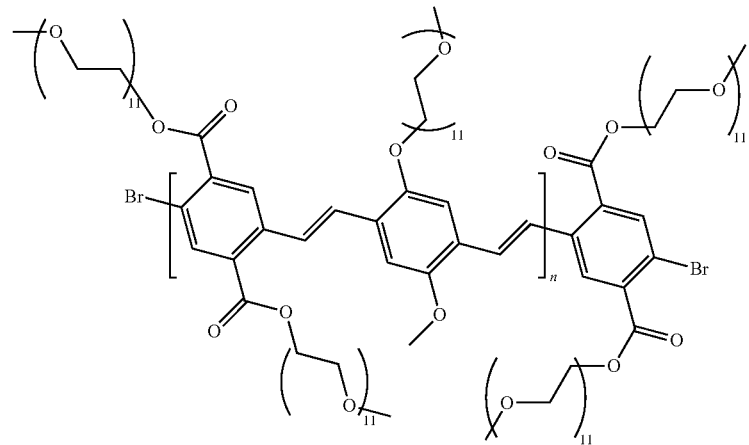

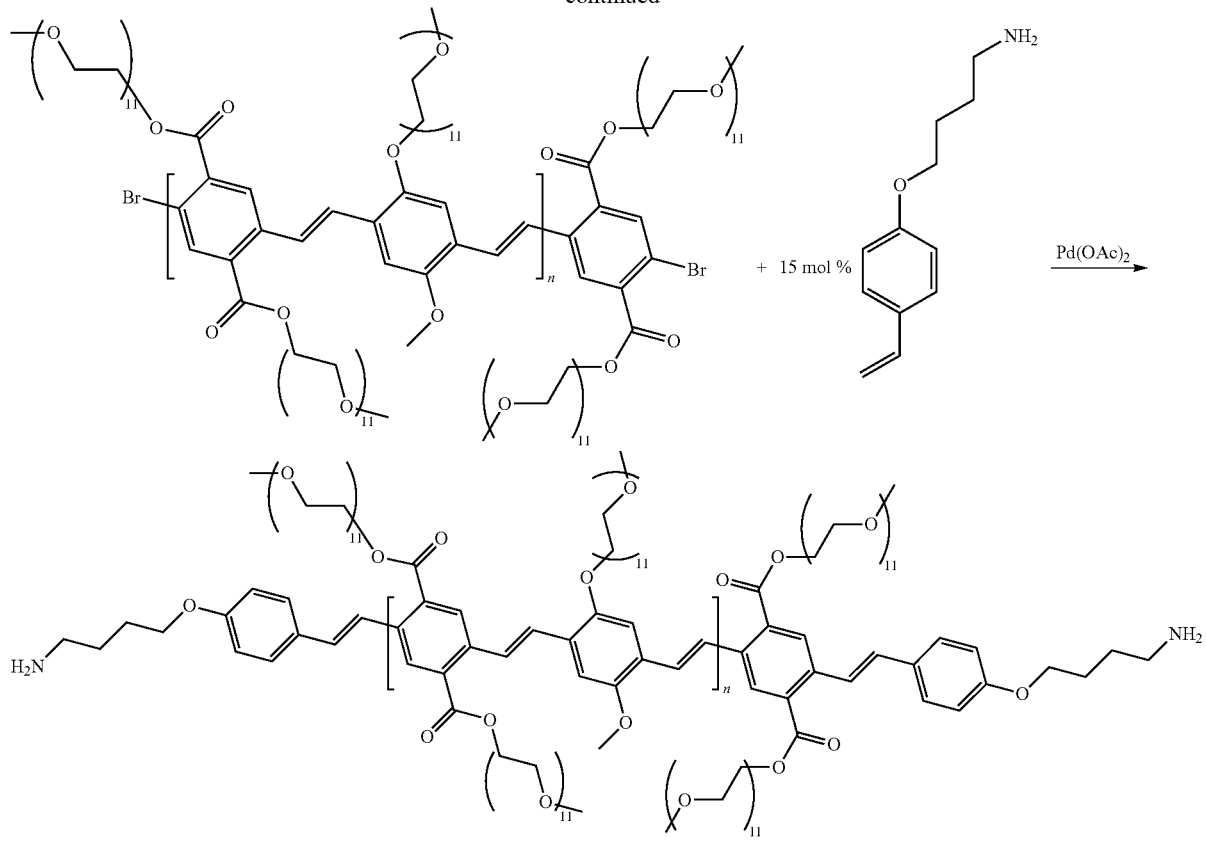

Poly(1,4-(di2,5,8,11,14,17,20,23,26,29,32-undecaoxatetratriacontan-34-yl 2,5-dibromoterephthalate)-vinyl-alt-para (2-methoxy-5-2,5,8,11,14,17,20,23,26,29,32-undecaoxatetratriacontan-34-yl benzene)-vinylene) with phenylbutoxyamino termini.

Di-2,5,8,11,14,17,20,23,26,29,32-undecaoxatetratriacontan-34-yl 2,5-dibromoterephthalate (2.0 g, 1.52 mmol), 34-(4-methoxy-2,5-divinylphenoxy)-2,5,8,11,14,17,20,23,26,29,32-undecaoxatetratriacontane (1.11 g, 1.52 mmol), palladium acetate (13.6 mg, 0.061 mmol), tri-o-tolylphosphine (37 mg, 0.121 mmol), triethylamine (1 mL, 7.6 mmol) and 4 mL of DMF were combined in a small round bottom flask, equipped with a Teflon stribar, fitted with a needle valve and transferred to a Schlenk line. The solution was degassed via three freeze-pump-thaw cycles, put under nitrogen and heated to 100 C with constant stirring overnight. Next di-2,5,8,11,14,17,20,23,26,29,32-undecaoxatetratriacontan-34-yl 2,5-dibromoterephthalate (2.0 g, 1.52 mmol) (100 mg, 5 mol %), palladium acetate (5 mg), and tri-o-tolylphosphine and 0.5 mL DMF were combined in a small round bottom flask which is fitted with a needle valve and transferred to the Schlenk line. The solution was degassed via three cycles of freeze-pump-thaw and once warmed to room temperature was transferred to the polymerization reaction via cannula to exclude air and moisture. Allowed the mixture to react overnight. Next 4-(4-bromophenoxy)butan-1-amine (43 mg, 15 mol %) and 0.5 mL of DMF were combined in a small round bottom flask, equipped with a Teflon stribar, fitted with a needle valve and transferred to a Schlenk line. Once warmed to room temperature the solution was transferred to the polymerization reaction via cannula to exclude air and moisture. Allowed the mixture to react overnight. The next day the reaction was cooled to room temperature and the bulk of triethylamine was removed under vacuum. The reaction mixture was diluted with ~30 mL of water and filtered through G 6 glass fiber filter paper. The filtrate was transferred to several Amicon filters (10 kDa cutoff) to concentrate the polymer and remove DMF. The remaining water is removed under vacuum and the residue is extracted into methylene chloride. The methylene chloride solution is dried over magnesium sulfate and filtered. The solvent is removed leaving behind a dark red thick oil, approximately 900 mg.

The polymer was found to have a Mn of 20,400 g/mol as determined by GPC analysis relative to polystyrene standards. Incorporation of the amine linker was verified by conjugating a dye to the final polymer as described in Example 38.

The polymer was then conjugated to streptavidin protein as follows: Amine polymer was dissolved at 50 mg/ml and desalted and buffer exchanged into 100 mM phosphate buffer pH 7.5. Polymer concentration was assessed by absorbance and 25 molar equivalents of SMCC (10 mg/ml in anhydrous DMSO) added. The reaction was mixed for 60 mins at room temperature and then desalted and buffer exchanged into PBS pH7.0+5 mM EDTA prior to repeat polymer concentration determination and confirmation of malemide functionality by SAMSA-fluorescein dye test. Streptavidin (5 mg/ml in 100 mM phosphate buffer pH7.5) was activated by addition of 20 molar equivalents of SATA (5 mg/ml in anhydrous DMSO). The reaction was mixed at room temperature for 60 mins prior to quenching (>15 mins room temp) with 10% (v/v) 50 mM EDTA, 2.5M hydroxylamine pH7.0. The activated protein was desalted and buffer exchanged into the same buffer as the activated polymer prior to an performance of an Ellman's assay to confirm and quantify thiol incorporation. Both the activated polymer and streptavidin were used as follows without delay. A greater than order of magnitude molar excess of SMCC activated polymer was added to the SATA activated streptavidin and the two mixed for 2 hours at room temperature prior to quenching with 20 molar equivalents of N-ethylmaleimide which was mixed in for 15 minutes at room temperature. Ion exchange and size exclusion chromatography were used to purify the bioconjugate of unreacted polymer and streptavidin. Appropriate fractions were pooled to maximize yield and performance and then concentrated by ultrafiltration.

Figure 27:
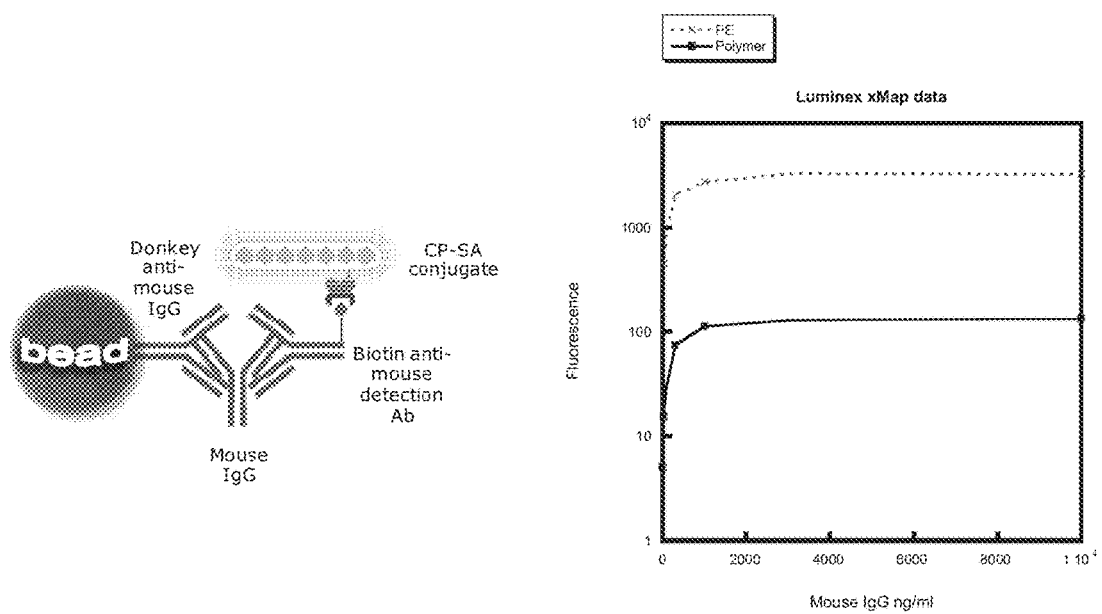
FIG. 27. Sandwich immunoassay on Luminex assay (left) and corresponding results on the Luminex system using 532 nm excitation of both the conjugated polymer and PE streptavidin detection conjugates.

The conjugate was tested and its performance compared to a commercially available streptavidin-phycoerythrin (SA-PE) conjugate designed for purpose in a model Luminex xMap assay (FIG. 27, left). Donkey anti-mouse IgG antibody was covalently conjugated to xMap beads. A standard curve titration of Mouse IgG was then performed under standard Luminex xMap assay conditions (FIG. 27, right).

Replicate samples were detected using either 4 μg/mL streptavidin-phycoerythrin or streptavidin conjugated polymer conjugate prepared as above (concentration not rigorously controlled). Samples were then read on a Luminex instrument. Absolute signals were found to be lower using the conjugated polymer. This is partially attributed to a non-ideal match between the polymer spectra and the excitation and emission optics in the instrument as well as the putative lower concentration of detection reagent used compared with the commercially available phycoerythrin product. However, the proportional background (non specific signal) from the polymer was also markedly lower resulting in a very comparable lower limit of detection for both detection formats (Fluorescence highest point in standard curve/fluorescence zero concentration of analyte (MFI/zero): 21.8 PE, 26.6 Polymer).

Example 43: Synthesis of a Fluorene Co-Polymer with a DPP Band Gap Modifying Unit

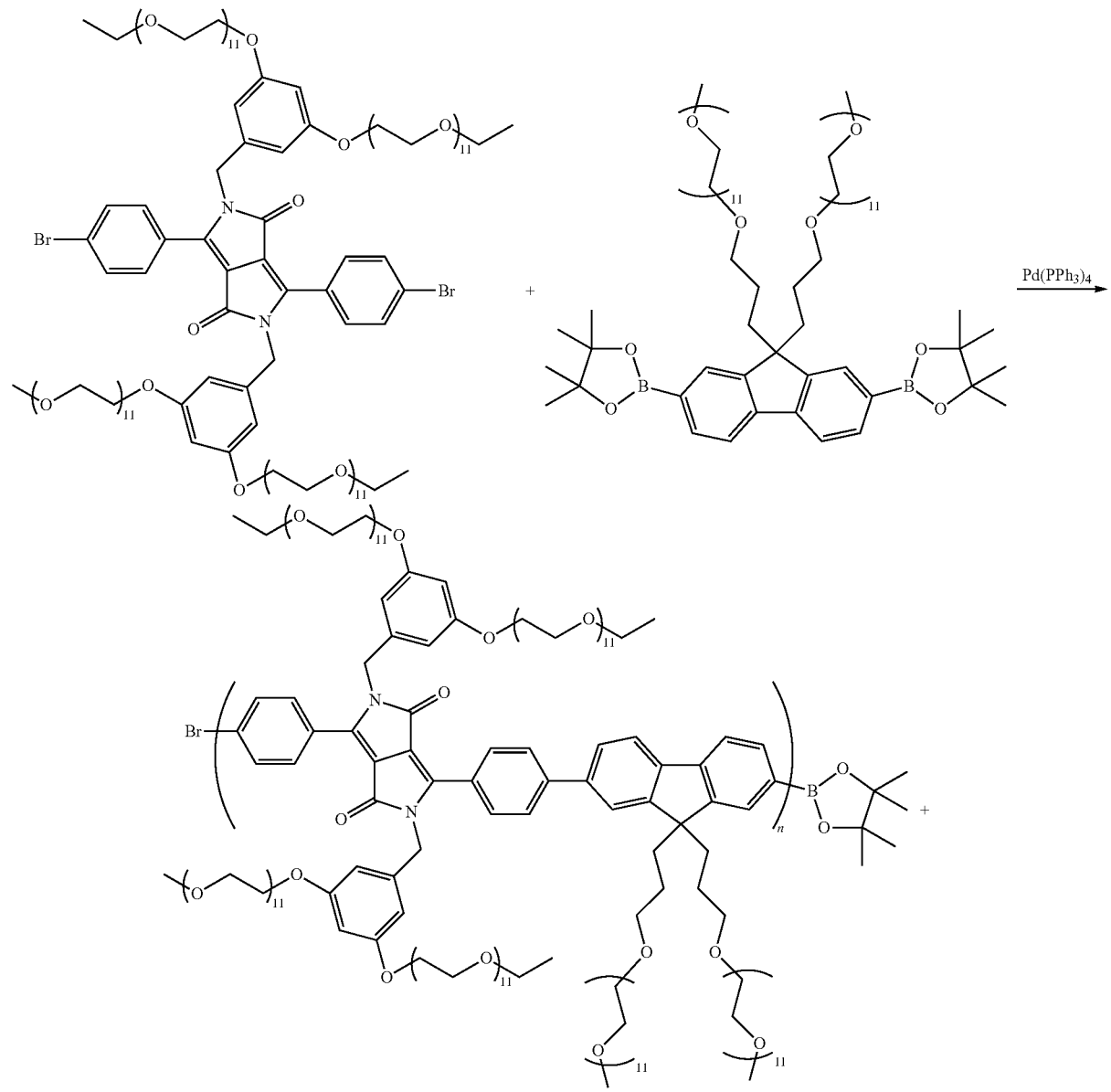

-continued

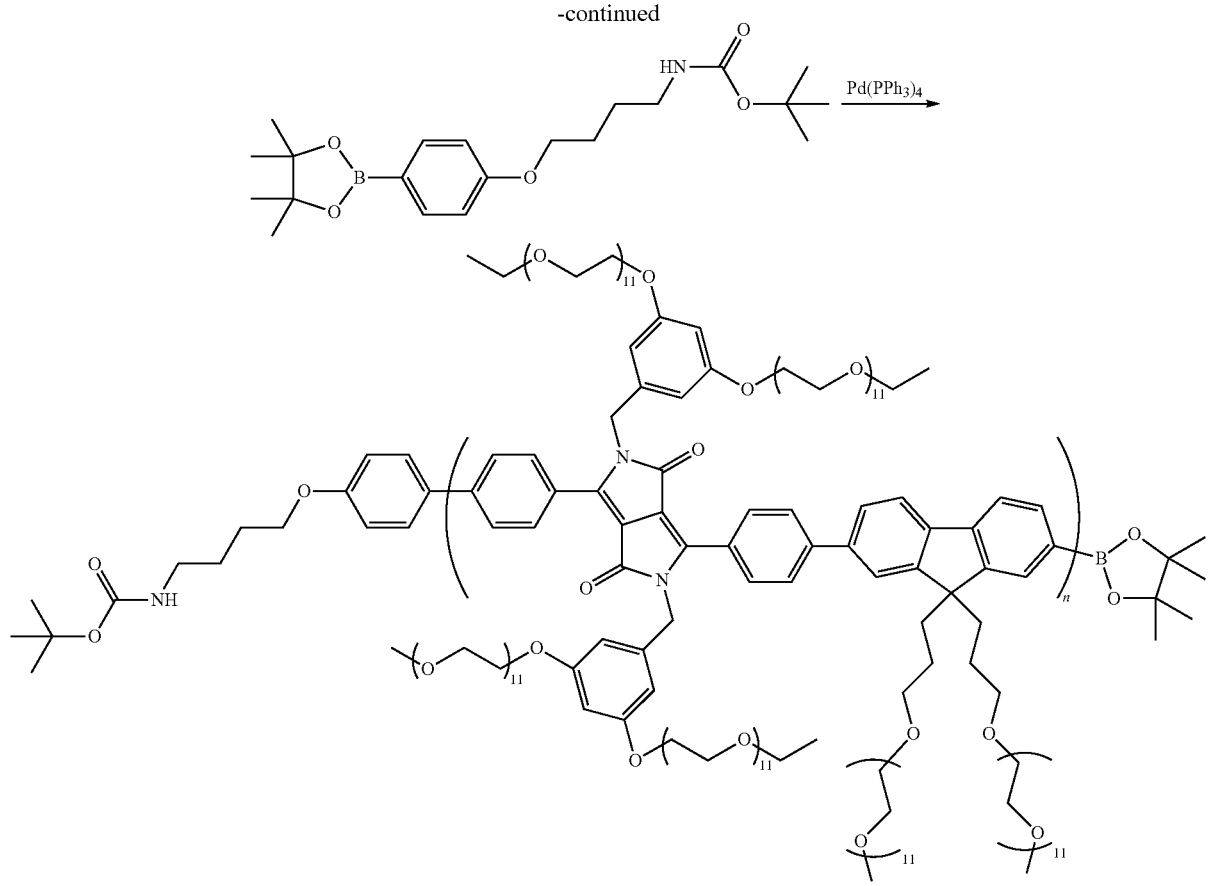

To a 25 mL round-bottomed flask were added: PEGylated dibromo-DPP monomer (110 mmol), PEGylated fluorene diboronicester (110 mmol), THF (2.4 mL) solvent, 2M $K_2CO_3$ (1.6 mL) and tetrakis(triphenylphosphine)palladium (3.3 mmol) catalyst. The mixture was degassed by three freeze-pump-thaw cycles and then stirred under argon at 80 C over night. The resulting mixture was allowed to r.t. and diluted with water. Polymer was collected after dichloromethane extraction.

The resulting polymer was found to have an absorption maxima at 520 nm and emission maxima at 590 nm with quantum yield of 6% in water. The polymer had a MW estimated at 16,000 by GPC analysis relative to polystyrene standards and was soluble in water, methanol and dichloromethane.

End linker incorporation can be performed using methods similar to those described above and including methods described in Examples 9, 10 and 11.

Example 44: Synthesis of a Substituted Divinylbenzene Polymer

Methods used to prepare the polymer above were similar to those provided in Example 38. General methods for the preparation of divinylbenzene polymers as disclosed herein may be derived from known reactions in the field as well as methods found herein, and the reactions may be modified by the use of appropriate reagents and conditions, as would be recognized by the skilled person, for the introduction of the various moieties found in the formulae as provided herein.

Example 45: Conjugation of Polymer to an Amine on a Primary Antibody

Procedure for Production of NHS Ester Polymer-Antibody Conjugate

Primary monoclonal antibody, anti-CD4 (RPA-T4 clone) was desalted, and exchanged into 50 mM $NaHCO_3$ buffer, pH 8.2 at 1 mg/mL. Enriched NHS functionalized polymer was dissolved into anhydrous dimethyl sulfoxide (DMSO) at 100 mg/mL. Polymer solution was added at 30 fold molar excess of antibody into the antibody solution and allowed to mix by agitation for 3 hours at RT. Protein concentration was adjusted with buffer prior to incubation to ensure the volume of organic solvent was <10% the total volume. Following ultrafiltration over a 10 KDa MWCO filter device, ion exchange and size exclusion chromatographic techniques were then used to purify the bioconjugate of unreacted polymer and antibody, respectively. Appropriate fractions were pooled to maximize yield and buffer exchanged into PBS+0.05% $NaN_3$ and simultaneously concentrated by ultrafiltration as above. Degree of labeling (indicated as p above) was determined via absorbance at 405 nm and a corrected 280 nm value. The polymer conjugate (CJ04-02) provided in Example 39 (FIG. 22) had an F/P (# of polymers per antibody) of approximately 2.04. This conjugate demonstrated flow performance as determined by stain index measurements which were greater than 3 fold higher than a Pacific Blue control conjugate of the same antibody.

Example 46: Conjugation of Polymer to an Antibody Using Malemide/Thiol Chemistry
Malemide/Thiol Conjugation of Polymers to Partially Reduced Antibodies Secondary antibody, goat anti-mouse IgG (H+L) was reconstituted in PBS+10 mM acetic acid and desalted/exchanged into 50 mM Tris-HCl buffer, pH7.4 at 1.0 mg/mL. TCEP (tris(2-carboxyethyl)phosphine) was dissolved in 50 mM Tris-HCl buffer, pH7.4, added at 6 molar excess with a final TCEP concentration of 10 mM and mixed for 30 minutes at room temperature. The modified protein was purified over a PD-10 desalting column to remove excess TCEP and exchanged into reaction buffer, 100 mM NaPO4, pH 6.5 reaction buffer with 10 mM EDTA. Amine-activated polymer was dissolved in anyhydrous DMSO at 10 mg/mL and mixed with succinimidyl-4-(N-maleimidomethyl)cyclohexane-1-carboxylate (SMCC) linker. The linker was added at 50 mg/mL, 20 molar excess in DMSO to the polymer solution and activated by diisopropylethylamine (DIPEA). The reaction was purified over Amicon Ultra centrifugation filters and exchanged into reaction buffer, 100 mM NaPO4, pH 6.5 reaction buffer with 10 mM EDTA. Immediately following disulfide reduction, maleimide functionalized polymer in reaction buffer at 10 mg/mL was added in 20 molar excess of antibody and allowed to mix for 4 hours. Ion exchange and size exclusion chromatographic techniques were then used to purify the bioconjugate of unreacted polymer and antibody, respectively. Degree of labeling (indicated as p above) is determined via absorbance at 405 nm and a corrected 280 nm value. The polymer conjugate provided in Example 36 (FIG. 20B) had an F/P (# of polymers per antibody) of approximately 2. This conjugate demonstrated flow performance as determined by stain index measurements which were greater than 4 fold higher than a Pacific Blue control conjugate of the same antibody.

Malemide/Thiol Conjugation of Polymers to Thiol Modified Antibodies

Secondary antibody, goat anti-mouse IgG (H+L) was reconstituted in PBS+10 mM acetic acid and desalted/exchanged into 100 mM phosphate pH7.5 buffer. SATA (N-succinimidyl-S-acetylthioacetate) was dissolved anhydrous DMSO, added at 15 molar excess and mixed for 60 minutes at room temperature. After quenching with a hydroxylamine solution, the modified protein was desalted over a PD-10 column to remove excess SATA and exchanged into reaction buffer, 5 mM EDTA, PBS pH 7.0 buffer. Amine-activated polymer was dissolved in anhydrous DMSO at 10 mg/mL and mixed with succinimidyl-4-(N-maleimidomethyl)cyclohexane-1-carboxylate (SMCC) linker. The linker was added at 50 mg/mL, 20 molar excess in DMSO to the polymer solution and activated by diisopropylethylamine (DIPEA). The reaction was purified over Amicon Ultra centrifugation filters and exchanged into reaction buffer, 5 mM EDTA, PBS pH 7.0 buffer. Immediately following activation of the antibody, maleimide functionalized polymer in reaction buffer at 10 mg/mL was added in 20 molar excess of antibody and allowed to mix for 4 hours. Ion exchange and size exclusion chromatographic techniques were then used to purify the bioconjugate of unreacted polymer and antibody, respectively. Degree of labeling (indicated as p above) is determined by absorbance at 405 nm and a corrected 280 nm value. The resulting purified conjugates were flow tested in similar fashion as those described in Example 36 for the conjugates prepared using TCEP reduction (data not provided).

The polymer structures defined in Example 39 were used to prepare primary antiCD4 (RPA-T4) antibody conjugates in similar fashion to those described in the example above. 30 eq of polymer were reacted with the SATA modified antibody (CJ11-2, FIG. 22) and TCEP reduced antibody (CJ13-1, FIG. 20D and FIG. 22) to produce polymer conjugates for testing in flow cytometry assays after purification. SMCC modified polymers from Examples 23 and 26 were also successfully conjugated to antiCD4 (RPA-T4) and antiCD8 (RPA-T8) antibodies using the TCEP reduction method. DTT reduction was also successfully performed in place of TCEP. Performance in flow cytometry of the antiCD4 and antiCD8 conjugates were evaluated in similar fashion to those described in Example 39 (FIG. 22).

Example 47: Polymer Conjugation to a DNA Oligomer

Azide Polymer Synthesis for Click Conjugation to Alkyne Terminated DNA Oligo

A solution of azidohexanoic acid NHS ester (2.5 mg) in anhydrous DMF (100 µL) was added to a solution of the amine-functional polymer (9.9 mg) in anhydrous DMF (100 µL) under argon. Diisopropylethylamine (2 µL) was then added. The reaction was agitated at room temperature for 15 hours. Water was then added (0.8 mL) and the azide-modified polymer was purified over a NAP-10 column. The eluent was freeze dried overnight. Yield 9.4 mg, 95%.

Oligo Synthesis with Pendant Alkyne (Hexyne) for Click Conjugation to Azide Polymer The 3' propanol oligo A8885 (sequence YATTTTAC-CCTCTGAAGGCTCCP, where Y=hexynyl group and P=propanol group) was synthesized using 3' spacer SynBase™ CPG 1000 column on an Applied Biosystems 394 automated DNARNA synthesizer. A standard 1.0 limole phosphoramidite cycle of acid-catalyzed detritylation, coupling, capping and iodine oxidation was used. The coupling time for the standards monomers was 40 s, and the coupling time for the 5' alkyne monomer was 10 min.

The oligo was cleaved from the solid support and deprotected by exposure to concentrated aqueous ammonia for 60 min at room temperature, followed by heating in a sealed tube for 5 h at 55° C. The oligo was then purified by RP-HPLC under standard conditions. Yield 34 OD.

Solution Phase Click Conjugation: Probe Synthesis

A solution of degassed copper sulphate pentahydrate (0.063 mg) in aqueous sodium chloride (0.2 M, 2.5 µL) was added to a degassed solution of tris-benzo triazole ligand (0.5 mg) and sodium ascorbate (0.5 mg) in aqueous sodium chloride (0.2 M, 12.5 µL). Subsequently, a degassed solution of oligo A8885 (50 nmole) in aqueous sodium chloride (0.2 M, 30 µL) and a degassed solution of azide polymer (4.5 mg) in anhydrous DMF (50 µL) were added, respectively. The reaction was degassed once more with argon for 30 s prior to sealing the tube and incubating at 55° C. for 2 h. Water (0.9 mL) was then added and the modified oligo was purified over a NAP-10 column. The eluent was freeze-dried overnight. The conjugate was isolated as a distinct band using PAGE purification and characterized by mass spectrometry. Yield estimated at 10-20%.

Fluorescence Studies

Figure 25:
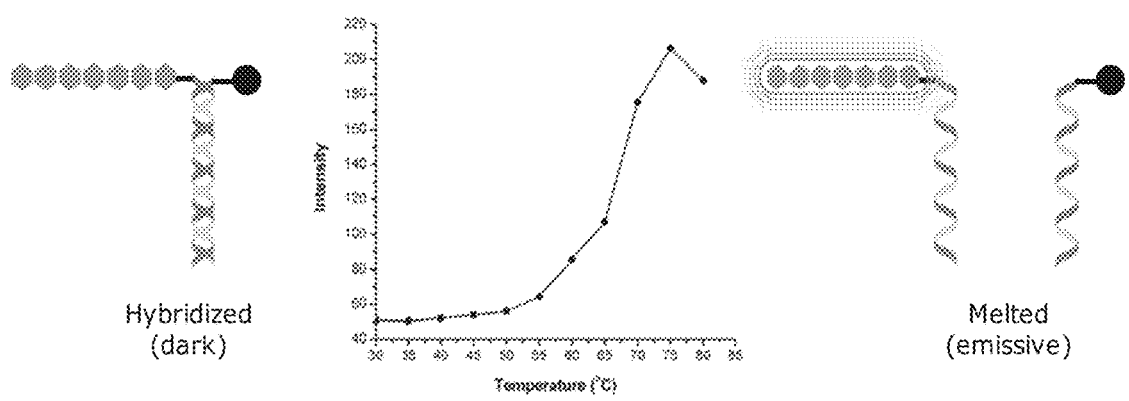
FIG. 25. Plot of fluorescent intensity vs. temperature of a DNA oligomer-polymer conjugate hybridized to a target.

The oligo-polymer conjugate was used as a probe in fluorescence studies. The probe was hybridized with the target A8090 (sequence GGAGCCTTCAGAGGG-TAAAAT-Dabcyl (SEQ ID NO: 2)), which was labeled with dabcyl at the 3' end to act as a fluorescence quencher. The target and probe were hybridized, and fluorescence monitored in a Peltier-controlled variable temperature fluorimeter. The fluorescence was scanned every 5° C. over a temperature range of 30° C. to 80° C. at a rate of 2° C./min. FIG. 25 shows increasing fluorescence intensity or emission with increasing temperature, indicating that as the probe-target pair melt, the polymer and quencher separate and fluorescence is recovered.

Polymer conjugation to nucleic acids can also be performed using methods adapted from the protocols described in Examples 14, 45 and 46.

Example 48: Purification of Polymer Antibody Conjugates

Figure 26:
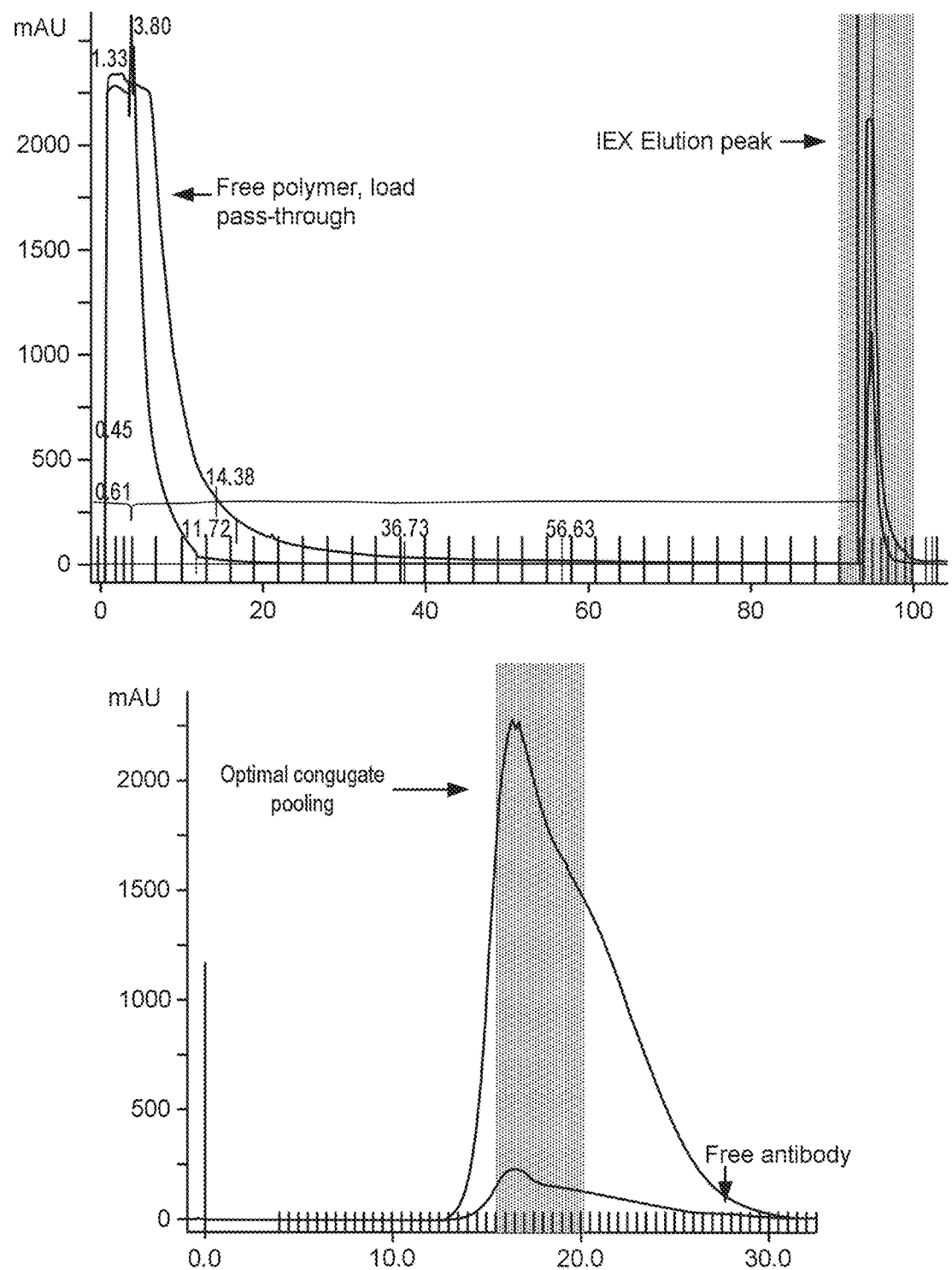
FIG. 26. Ion exchange chromatogram for a polymer antibody conjugate to remove free polymer (left) and an SEC chromatogram showing the separation of final conjugate from free antibody. In both chromatograms absorbance was monitored at 280 nm (lower curves) and 407 nm (upper curves).

Polymer antibody conjugates produced via the protocols described in Examples 45, 46 and 49 were purified using a two step method. First ion exchange is used to remove free, unreacted polymer. As the polymers described in this invention do not possess any formal charge they do not bind to the ion exchange media. Proteins (antibodies), however, do contain charged groups and are commonly bound to various ion exchange media for purification. In the examples provided the pH and conductivity of the conjugate solution (post reaction) was lowered to improve the binding of the free antibody and conjugate to the cationic exchange resin. After loading the conjugate, the resin is washed to baseline (measuring both 280 and 407 nm absorbance) to ensure all free polymer is removed. Bound antibody and polymer antibody conjugate are eluted by increasing the pH and ionic strength. A representative example of this separation is provided below in FIG. 26 (left) where the left peak represents the free polymer and the right peak the eluted conjugate and free protein. Removal of free polymer can also be achieved using affinity chromatograph methods in a similar fashion. Specific affinity resin can be used to bind the free protein and conjugate while removing polymer.

After the polymer is removed, the conjugate solution is concentrated and loaded on a size exclusion column to separate any un-reacted or free antibody from the polymer. The polymer compositions described in Examples 43 and 44 elute much earlier than then antibodies despite having a lower molecular weight. This is expected to be a result of the rigid polymer structure. The conjugates thus elute well before any free antibody providing near base line separation of the desired conjugate. Isolating fractions near the center of the distribution also ensures no free antibody is included. A representative example of this separation is provided below in FIG. 26 (right) where the left peak represents the conjugate and the small peak on the far right the free antibody. Retention times of the individual components was verified in an independent experiment.

Taken together the purification ensures that both free antibody and free polymer are removed. Purity of the resulting conjugates is reasonably estimated at >95%. Pooled samples can be concentrated and concentration measured by absorbance at 280 and 407 nm, being sure to correct for the polymer absorbance at 280 nm. Such measurements also allow for the determination of polymer to antibody labelling ratios (F/P).

Example 49: Dye Labeling and Linker Activation of Tandem Polymer

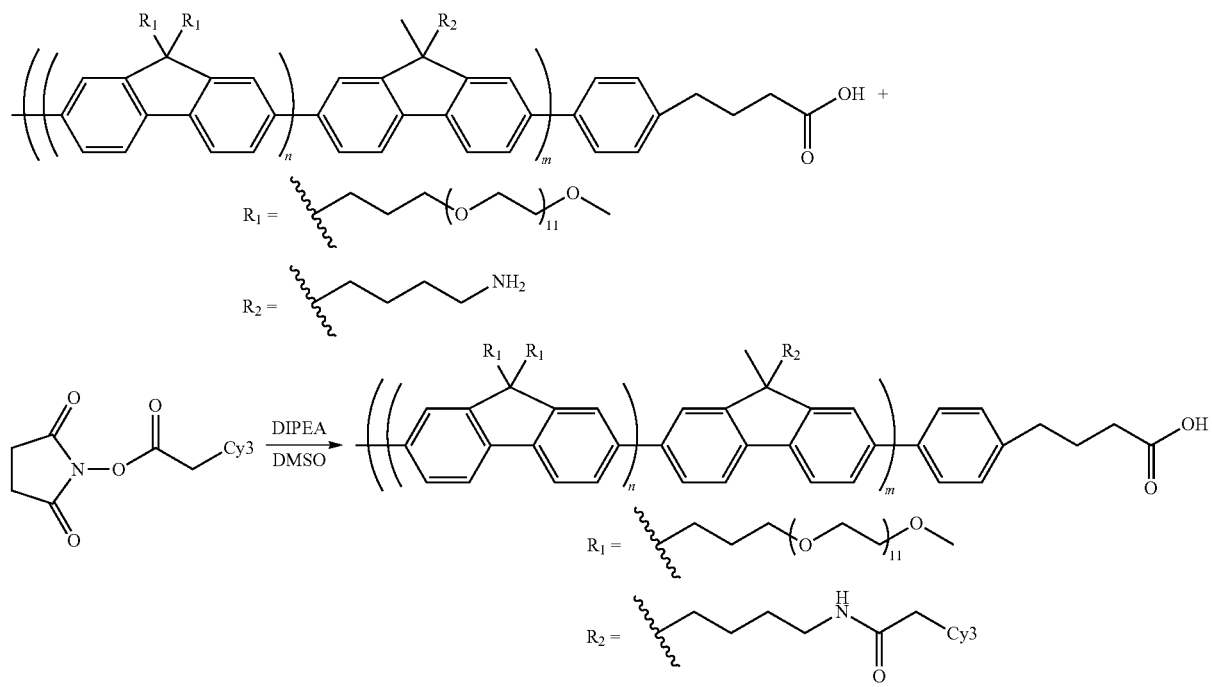

Tandem Dye Conjugation

In a glovebox, 93 mg tandem polymer (from Example 26) was dissolved at 15 mg/mL in anhydrous DMSO in a glass vial with stir bar. 22.5 mg Cy3-NHS ester was also dissolved at 15 mg/mL in anhydrous DMSO and added to the polymer solution, followed by 0.3 mL diisopropylethylamine. After stirring for 48 h at room temperature, the solution was diluted to 90 mL with 20% EtOH in water and concentrated over Amicon Ultra-15 filters. The retentate was repeatedly diluted and concentrated over the filters until excess Cy3 was removed. 90% yield. Labeling and linker content were validated by measuring and taking the ratio of polymer and dye absorbance as described in Example 38.

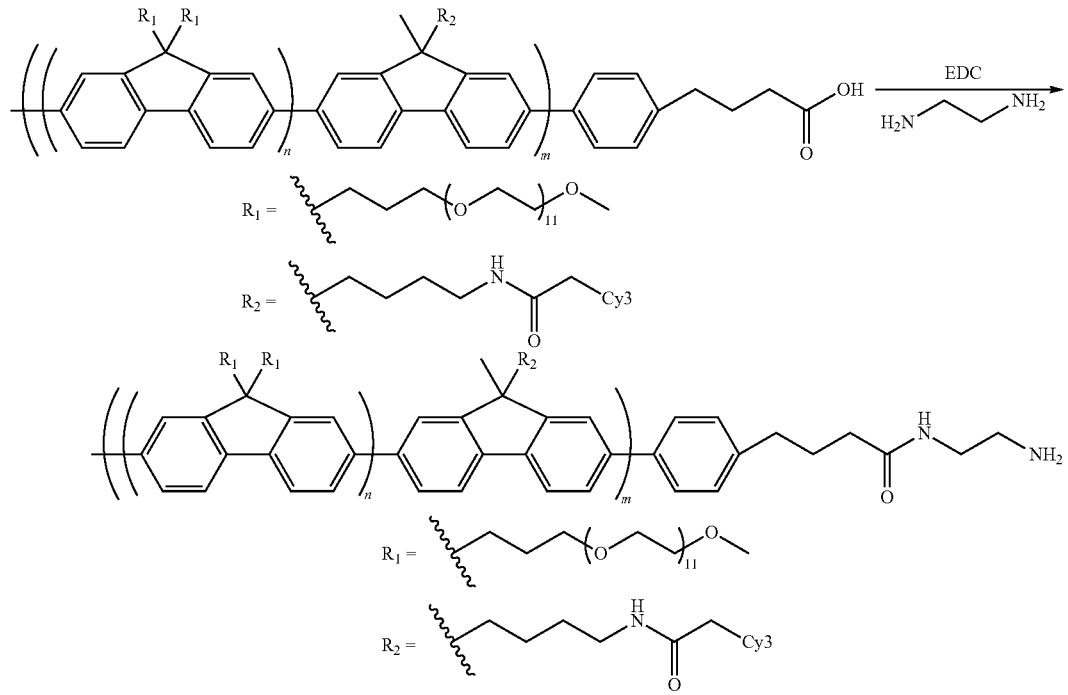

Amine Modification of Tandem (Aqueous Conditions)

100 mg of polymer-dye conjugate was dissolved at 150 mg/mL in ethanol. This was added dropwise to 6 mL 50 mM MES buffer (pH 5) at 4° C. 38 mg N-hydroxy succinimide was added in one portion, and the solution was stirred to dissolve the solids. After dissolution, 192 mg of N-(3-dimethylaminopropyl)-N'-ethylcarbodiimide hydrochloride was added in portions while stirring. After stirring the solution for 30 minutes, 33 µL of ethylene diamine was added. After stirring overnight at room temperature, the solution was diluted to 90 mL with 20% EtOH in water and concentrated over Amicon Ultra-15 filters. The retentate was repeatedly diluted and concentrated over the filters a total of four times to remove impurities. 90% yield, 60% conversion. Linker conversion was verified by conjugating a second dye to the terminal amine as described in Example 38.

Tandem Conjugation to a Primary Antibody

Primary monoclonal antibody, anti-CD8 (RPA-T8 clone) was desalted/exchanged into 5 mM EDTA, 50 mM phosphate 150 mM NaCl pH 7.0 buffer. TCEP (tris(2-carboxyethyl)phosphine) was dissolved water and added at 12 molar excess and mixed for 90 minutes at 30° C. The modified protein was purified over a PD-10 desalting column to remove excess TCEP and exchanged into 5 mM EDTA, 50 mM phosphate 150 mM NaCl pH 7.0 buffer.

Amine-activated tandem polymer was dissolved in ethanol at 50 mg/mL and this solution was mixed with two volumes of 100 mM phosphate pH 7.5 buffer. This solution was then desalted/exchanged into 100 mM phosphate pH 7.5 buffer using a PD-10 desalting column. To this solution was added 25 molar excess of succinimidyl-4-(N-maleimidomethyl)cyclohexane-1-carboxylate (SMCC) linker (prepared as a 10 mg/ml solution in anhydrous DMSO). The resulting solution was roller mixed at 20° C. for 60 minutes before being desalted/exchanged into 5 mM EDTA, 50 mM phosphate 150 mM NaCl pH 7.0 buffer using a PD-10 desalting column. Immediately following disulfide reduction, the maleimide functionalized polymer was added in 25 molar excess of antibody and allowed to mix for 2 hours at 20° C. Ion exchange and size exclusion chromatographic techniques were then used to purify the bioconjugate of unreacted polymer and antibody, respectively. Degree of labeling (indicated as p below) is determined via absorbance and a corrected 280 nm value.

Figure 28:
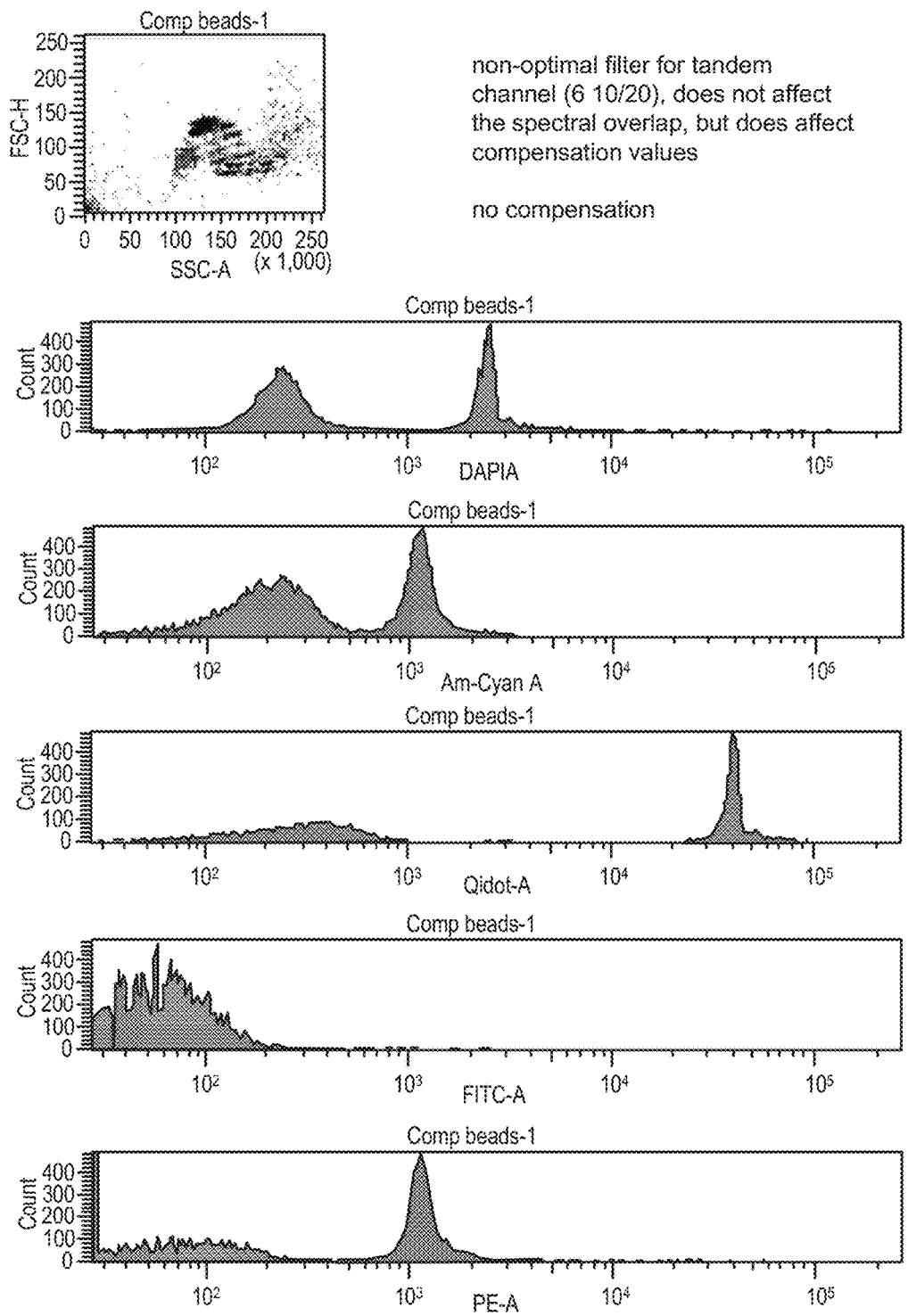
FIG. 28. Data on left show results obtained with compensation beads while the data set on the right results from a 4 color assay on human blood samples.
Figure 28:
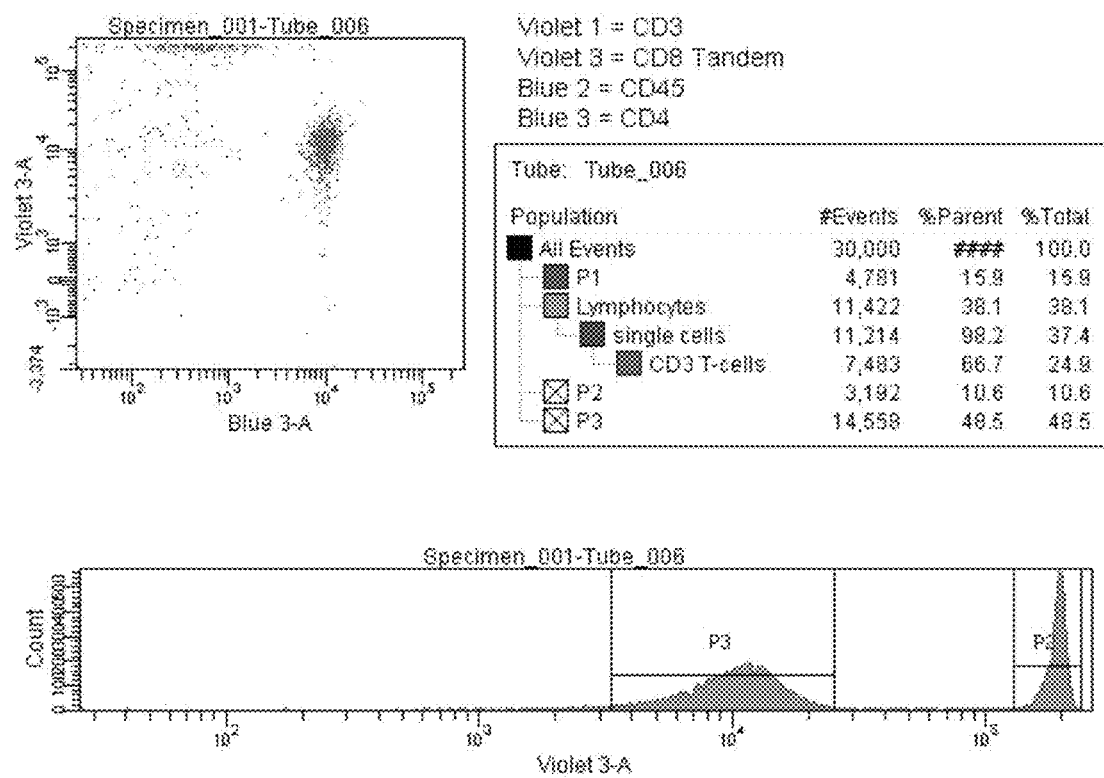

Flow Cytometry Analysis of Polymer Tandem Conjugate in Multicolor Experiment The resulting antiCD8 Tandem conjugate was evaluated on both compensation beads and whole blood samples on a flow cytometer. Anti mouse IgG compensation beads were used to capture the antibody and quantify signal spill over into detection channels (detectors with unique emission filters) other than that intended for the conjugate. FIG. 28 (left) shows the signal measured when the tandem conjugate was excited with a violet laser with emission detected using a 610 nm filter matched to the conjugates emission (labeled QDotA). Crosstalk into the flow cytometer's other channels paired with the violet excitation laser (DAPI-A and AmCyan-A) and two channels off the 488 nm laser (FITC-A and PE-A) are also shown in this panel of the figure. The data show minimal crosstalk in the 450/50 nm filter (DAPI-A) which specifically detects residual polymer (donor) emission. The significantly higher signal from the Cy3 reporter on the Tandem (610 nm filter) relative to the other channels above illustrates that minimal compensation (maximally no more than 6% in this example and case by case often much lower) is required.

The Tandem anti CD8 conjugate was subsequently evaluated in a 4 color flow assay with other labeled antibodies (anti CD3 Pacific Blue, anti CD45 Phycoerythrin and anti CD4 fluorescein) on whole human blood from a healthy volunteer using staining and analysis protocols in accord and developed from Example 39. The data in FIG. 28 (right) clearly show the compatibility of the Tandem label with common multicolour flow cytometry instrumentation, reagents and protocols. Specifically, intense and specific staining of CD8 positive lymphocytes is observed and within the CD4 positive subset ready discrimination of CD8 expressive and non expressive cells is clear Collectively the data highlight the viability of the polymer-dye Tandem conjugates in multicolor flow assays as described in the disclosed invention (See, e.g., FIG. 20 and FIG. 22).

Example 50: Validation of Non-Ionic Polymer Side Chains for Water Solubility and Flow Cytometry Application A series of different polyfluorene polymers were produced to investigate the interaction of water soluble conjugated polymers with cells. This was done by first synthesizing a range of monomers substituted with different solubilizing side chains (e.g., PEG-, sulfonate-, quaternary amine-, zwitterion-substituted) which were then polymerized using Suzuki coupling. The purpose was to determine what influence the side chains had on both non-specific cell binding and polymer solubility in typical buffers used in biological assays, particularly those used in flow cytometry (e.g. PBS and DPBS).

Figure 33:
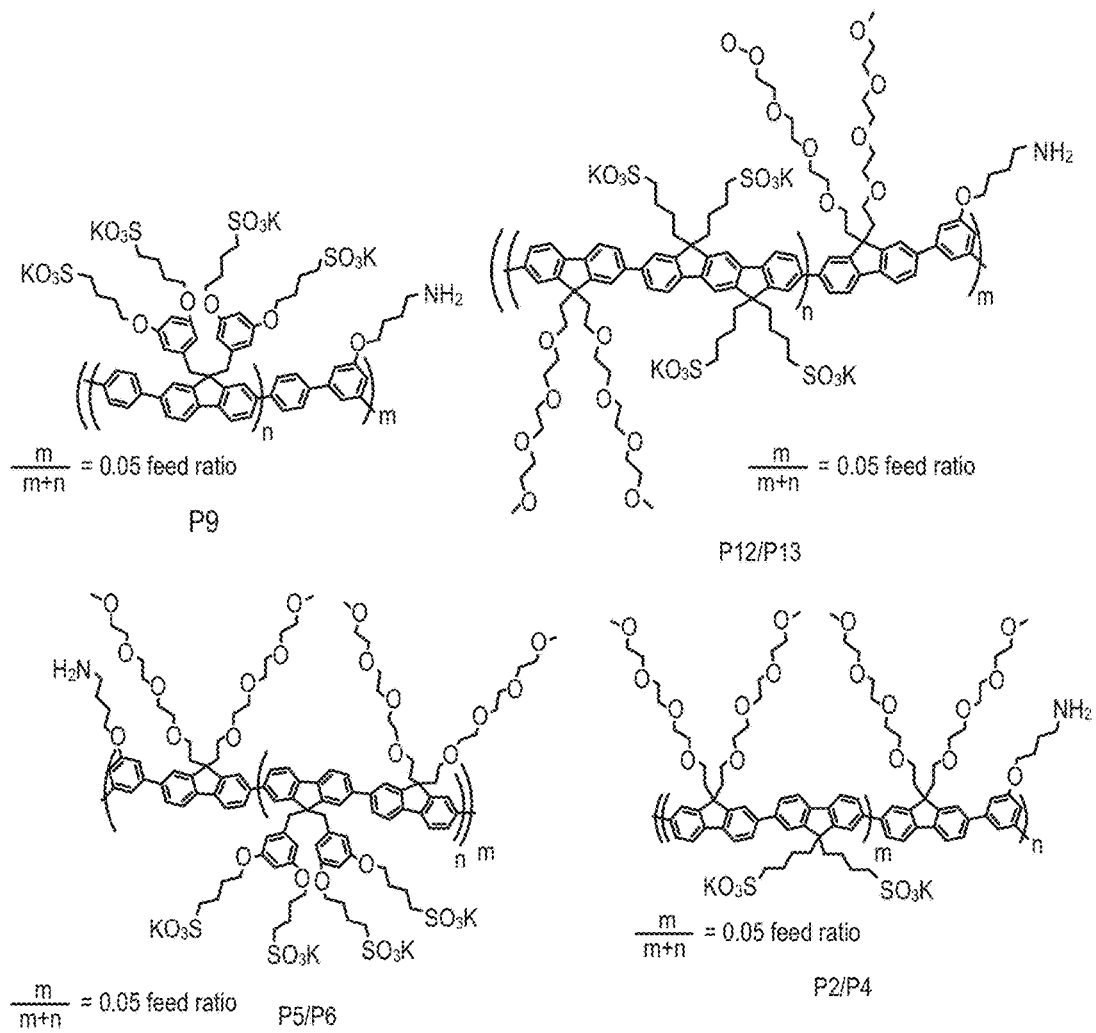
FIG. 33. Comparison of non-specific binding in various polymers (top) in a Jurkat cell (lymphocyte cell line) model; (bottom) plot ranking the polymers in terms of signal generated purely by non-specific binding (NSB).
Figure 33:
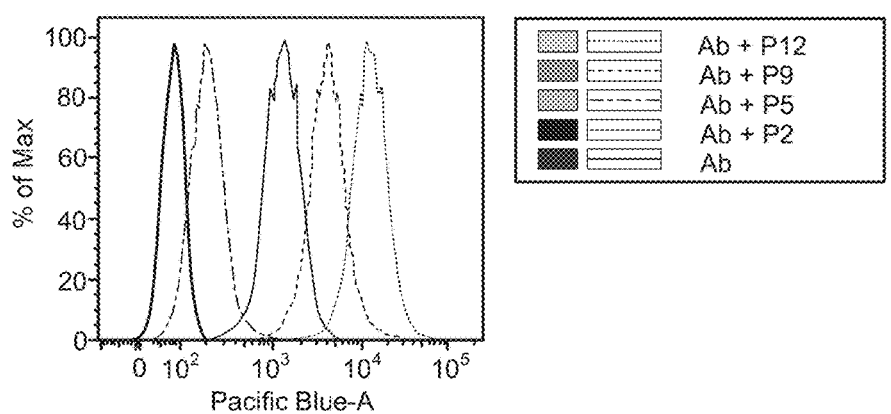

The number and property diversity of polymer candidates synthesized made it impractical to produce purified conjugates of each for flow cytometry testing. Thus, a system was developed to score each candidate polymer based on its contribution to non-specific binding to cells. Such a system enabled ranking of polymers, with predictive value on whether they would perform sufficiently once conjugated. A Non-specific Binding (NSB) "Index" was developed around a Jurkat cell model (lymphocyte cell line). In this, cells were incubated with a fixed concentration of each polymer, washed, and analyzed by flow. FIG. 33 displays the outcome following such analysis, and illustrates the wide variation in signal generated by each polymer type. The polymers in FIG. 33 were evaluated with a phthalamide protecting group on the pendant amine with the exception of P9.

The data ranks these polymers in terms of signal generated purely by NSB. More accurate assessment of relative NSB was enabled by adjusting further normalizing the flow signal by differences in fluorescence efficiency (crude assessment of quantum yield) of each form of polymer when assayed independently in stain buffer using 405 nm excitation on a fluorometer and monitoring emission in the range of 420-460 nm (to estimate a 440/40 nm filter in the cytometer). Representative polymers P5, P2, P9 and P12 showed increasing NSB relative to unstained cells (far left curve, intensity represented on x-axis).

Figure 34:
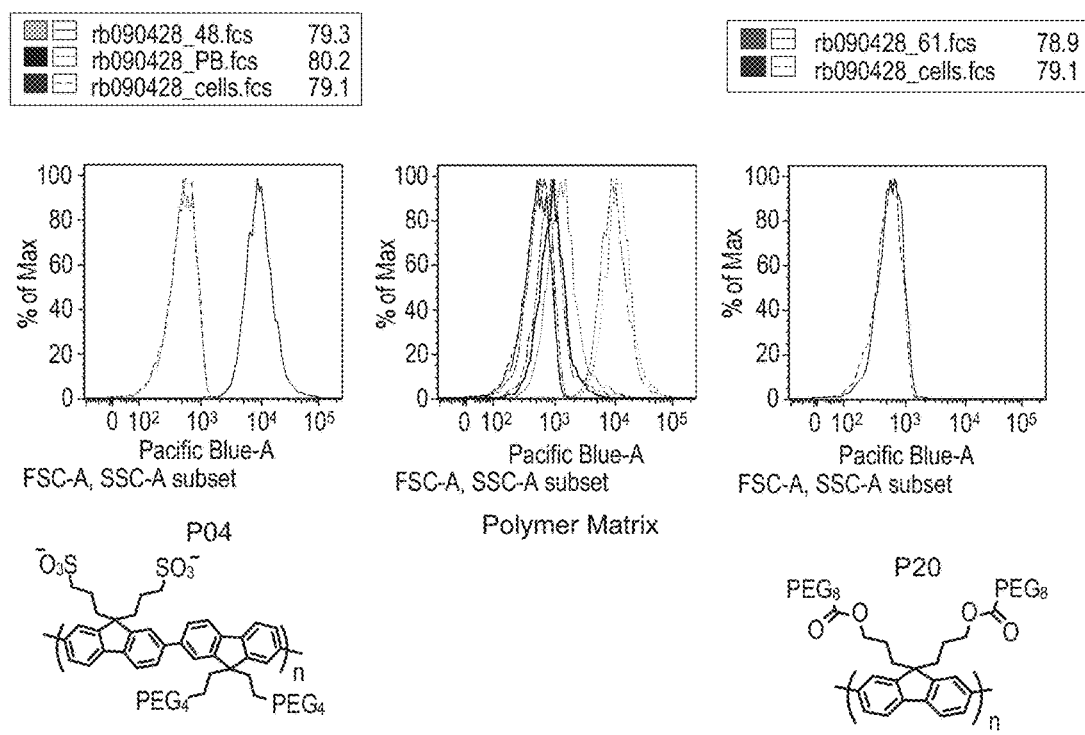
FIG. 34. Histograms collected from flow cytometry analysis (405 nm excitation in a BD LSR-II cytometer) using a Jurkat cell line; (left) unstained cells and a negative control, anionic P4 polymer; (middle) range of different polymer and polymer side chain combinations tested on the same cells; (right) neutral polymer P20 showed almost no off set from the untreated cells.

The data in FIG. 34 go on to highlight the difference in polymers produced with neutral, non-ionic PEG side chains (designated P20) verses those which also incorporate anionic side chains (designated P4). The data are histograms collected from flow cytometry analysis (405 nm excitation in a BD LSR-II cytometer) using a Jurkat cell line as in FIG. 33. The panel on the left shows unstained cells and a negative control (cells treated with a non-specific Pacific Blue labeled conjugate) which are the two curves on the far left. Little if any non-specific staining is observed for the Pacific Blue control. In this same panel, however, curve on the right represents cells treated with the anionic P4 polymer and has a clear off set in signal (x-axis) as shown. Conversely the neutral polymer P20 showed almost no off set from the untreated cells which is in line with the Pacific Blue control. The panel in the middle represents a range of different polymer and polymer side chain combinations tested on the same cells.

The data highlighted the advantage of neutral side chains. This advantage has also translated to other assay formats including plate based immunoassays and cytometric bead arrays (data not shown). The neutral side chains also unexpectedly resulted in a significant increase in the solubility of the conjugated polymers in aqueous solutions relative to those made previously with ionic side chains. This was particularly true in buffers containing even moderate ionic strength (such as those used in basic cell protocols). The solution quantum yields were also seen to increase, possibly due to the higher aqueous solubility (and less aggregation). The poor solubility in buffers also made protein conjugation more difficult and streptavidin conjugates produced from P4 showed signs of aggregation in typical assay buffers such as phosphate buffered saline (PBS). This was not true of polymers and conjugates produced in other examples disclosed herein.

Example 51: Purification and Characterization of Polymer-Avidin Conjugates

Gel Analysis of Polymer-Avidin Conjugates

Figure 35:
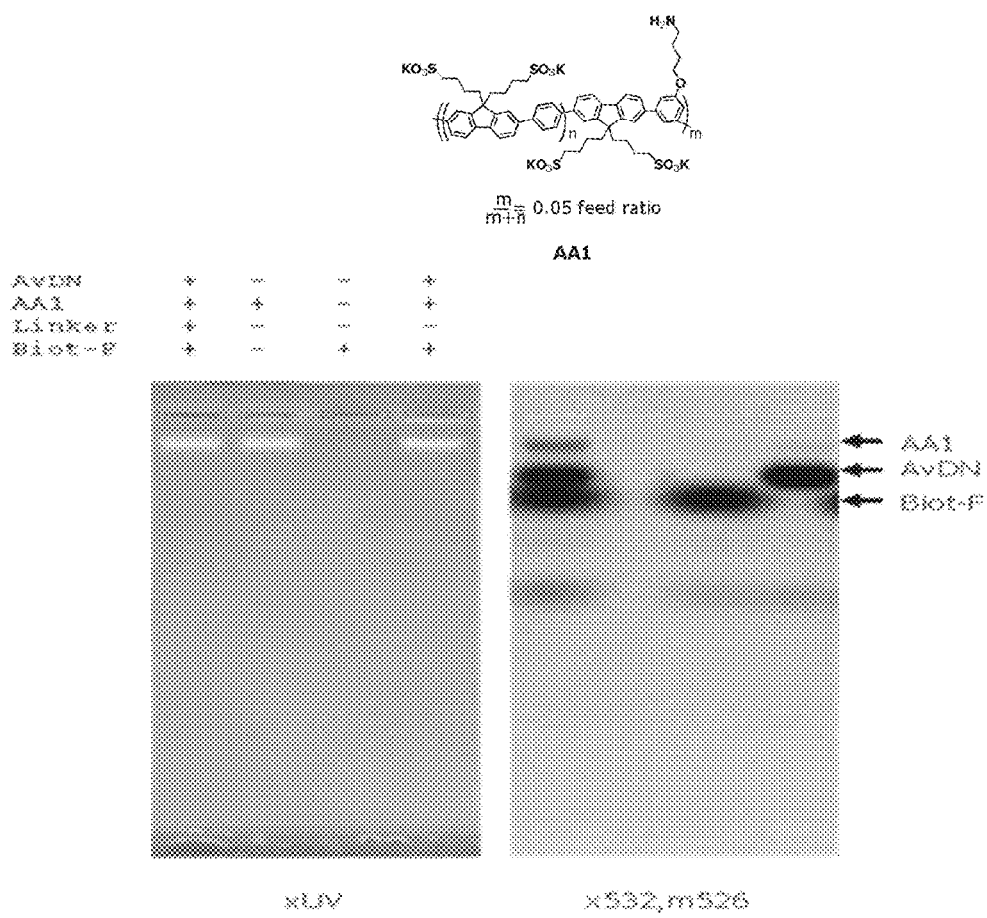
FIG. 35. Gel electrophoresis depicting relative mobility of avidin as a function of the degree of conjugation with polymer AA1.

To verify successful conjugation to avidin (AvDN), an agarose gel electrophoresis method was developed and used to assess the relative mobility of AvDN as a function of the degree of conjugation with polymer (FIG. 35). Prior to gel loading, the conjugation reaction was stained with biotinyl-fluorescein, which bound polymer-AvDN conjugate and free AvDN. Electrophoresis was performed in 0.8% agarose gels, poured and run in a buffer of 10 mM Sodium Borate, pH 11. The gel was visualized under UV illumination (to visualize the polymer) and by 532 nm excitation (to visualize fluorescein) to assess the degree of conjugation. Under UV illumination, a single band was observed for polymer. Under 532 nm excitation, bands were observed for unbound biotinyl-fluorescein, unreacted AvDN, and polymer-AvDN conjugate which coincided with the free polymer band, indicating that unreacted polymer co-eluted with polymer-AvDN conjugate (FIG. 35). Conjugation was confirmed by the intensity of the conjugate band.

The key at the top of the gel images (FIG. 35) indicates which components were included in the conjugation reaction, as well as whether the samples were pre-incubated with biotinyl fluorescein prior to loading and electrophoresis. The image on left visualizes polymer by UV-excitation, whereas the image on right captures the result of fluorescein excitation. On the right image, biotinylated fluorescein can be seen associating with polymer when conjugation was performed in the presence, but not in the absence, of hetero-bifunctional NHS-ethoxy-maleimide linkers (linkers were used to functionalize the polymer amine, while protein amines were partially converted to thiols using Traut's reagent, prior to the maleimide-thiol coupling). Abbreviations: AvDN=avidin DN, AA1=polymer, Linker=hetero-bifunctional NHS-Maleimide linker included in the reaction, Biot-F=biotinyl fluorescein pre-staining before electrophoresis.

Purification: Removal of Unreacted Avidin by SEC Chromatography

Figure 36:
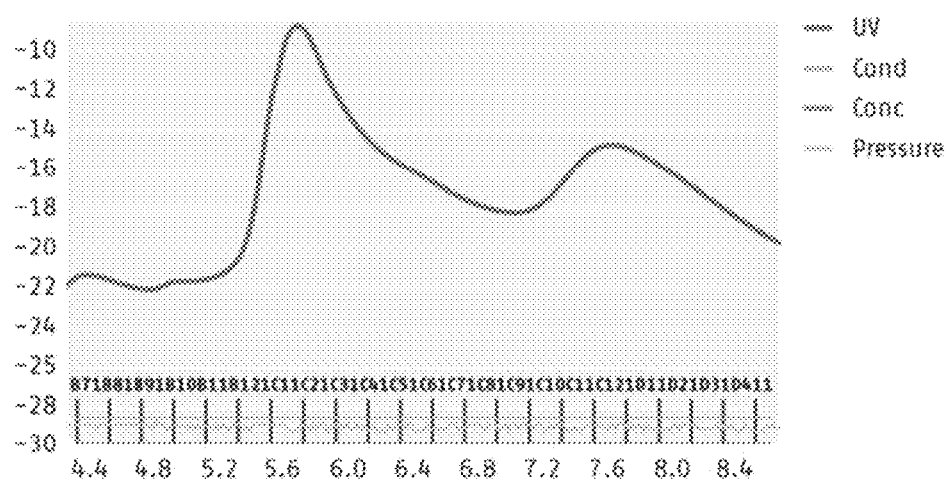
FIG. 36. Fractionation of crude polymer-avidin conjugate mixtures on a Superdex 200 size exclusion column; (top) monitoring fractions by UV absorbance; (bottom) gel electrophoresis of selected fractions to visualize the degree to which avidin was attached to polymer.
Figure 36:
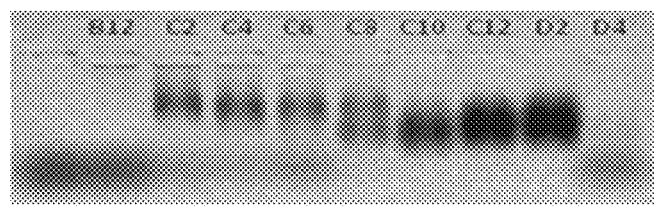

The crude conjugate mixture was fractionated on a Superdex 200 size exclusion column, while fractions were monitored by UV absorbance (FIG. 36, top). To validate the method, fractions were analyzed by agarose gel electrophoresis. As described above, this method of electrophoresis made it possible to visualize the degree to which avidin was attached to polymer, and in this case to analyze the composition of each fraction from the column. Selected fractions were incubated with biotinyl-fluorescein (1 molar equivalent relative to avidin) prior to gel loading, with biotinyl-fluorescein loaded separately as a marker (leftmost lane, FIG. 36, bottom). Electrophoresis was performed in 0.8% agarose gels, poured and run in a buffer of 10 mM Sodium Borate, pH 11. The gel was visualized by 532 nm excitation. Retardation of fluorescein-visualized bands for fractions C2-C6 indicates purified polymer-avidin conjugate, while the two bands observed for fraction C8 indicate a mixture of polymer-avidin conjugate and free avidin. Fractions C10-D2 show only free avidin.

Evaluation of Conjugation Efficiency by Gel Analysis

Figure 37:
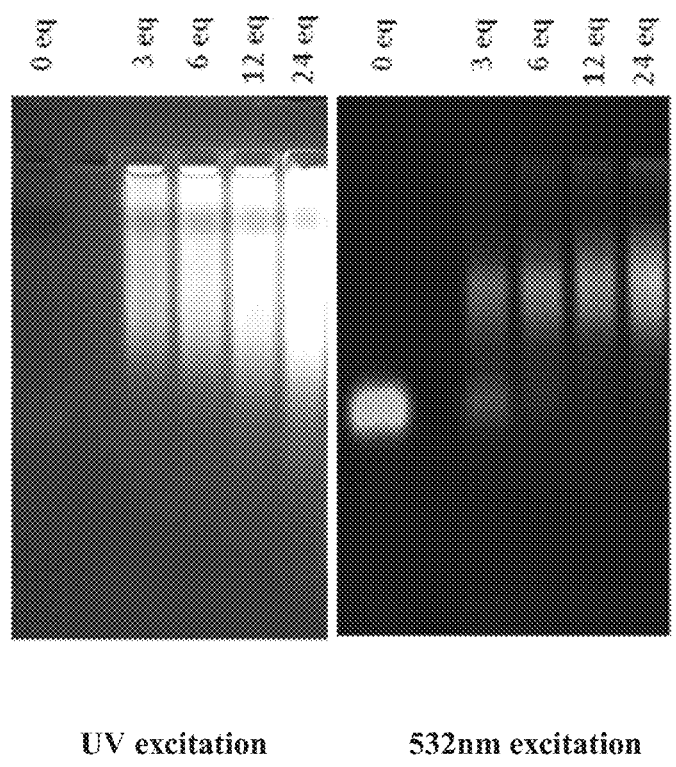
FIG. 37. Gel electrophoresis of conjugation reactions performed with polymer in varying molar excess to streptavidin; (left) UV illumination; (right) 532 nm excitation.

In order to determine the best ratio of polymer to streptavidin in conjugation reactions, the molar equivalents of polymer to streptavidin were varied from 0-24 equivalents. Post conjugation, the conjugation products were incubated with biotinyl-fluorescein prior to electrophoresis. The gel was visualized by UV illumination and 532 nm excitation (FIG. 37). At 0 molar equivalents of polymer to streptavidin, free streptavidin is observed as a band with relatively high mobility. As the molar equivalents for polymer are increased from 3 equivalents to 12 equivalents, the free streptavidin band decreases in intensity while the polymer-streptavidin conjugate band increases in intensity. At 24 equivalents of polymer, only the conjugate band is observed by 532 nm excitation.

Figure 38:
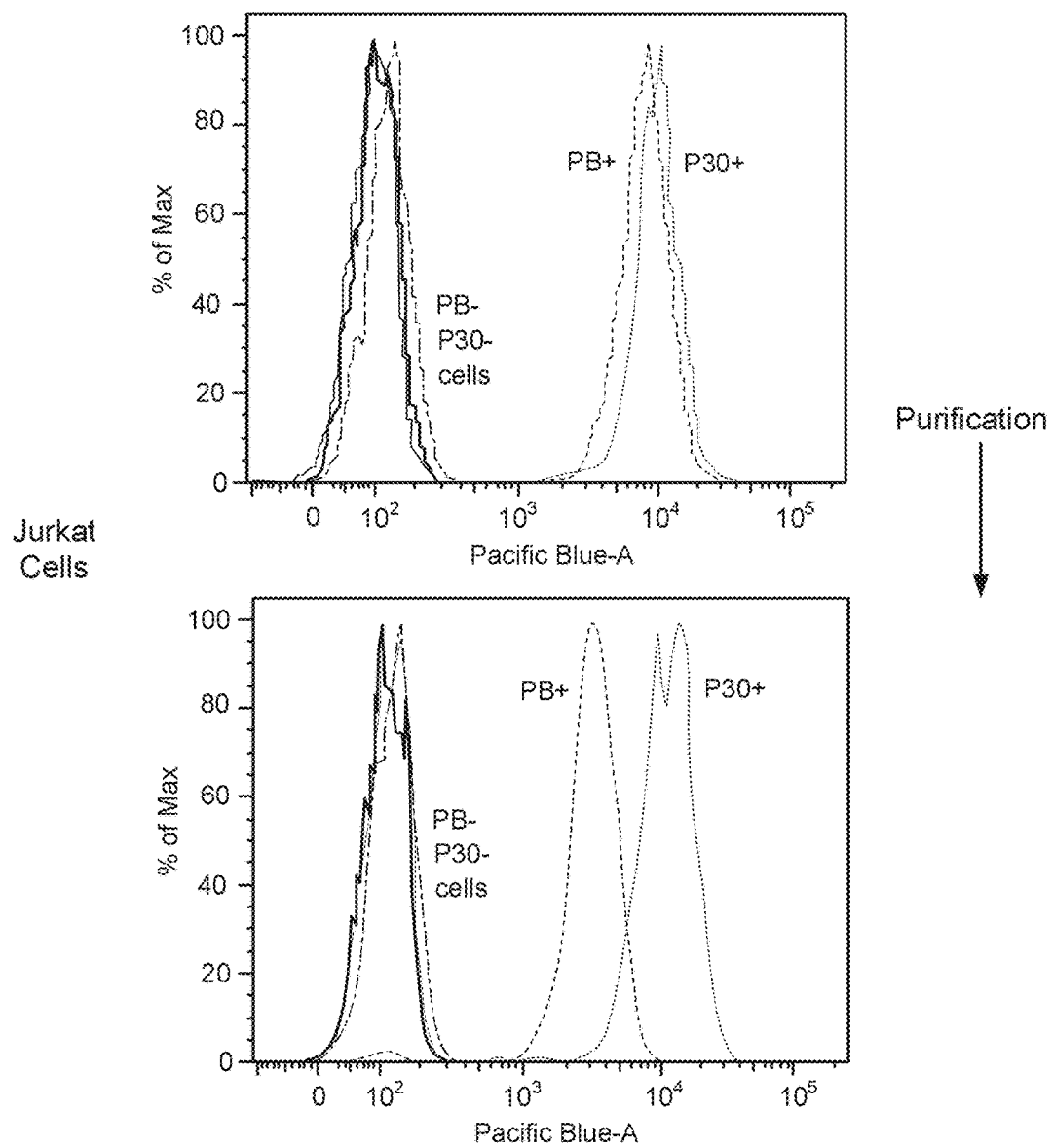
FIG. 38. Plot depicting purification of polymer streptavidin conjugates with polymers exemplified in Example 9, denoted P30, (top) crude samples; (bottom) purified conjugates).
Figure 41:
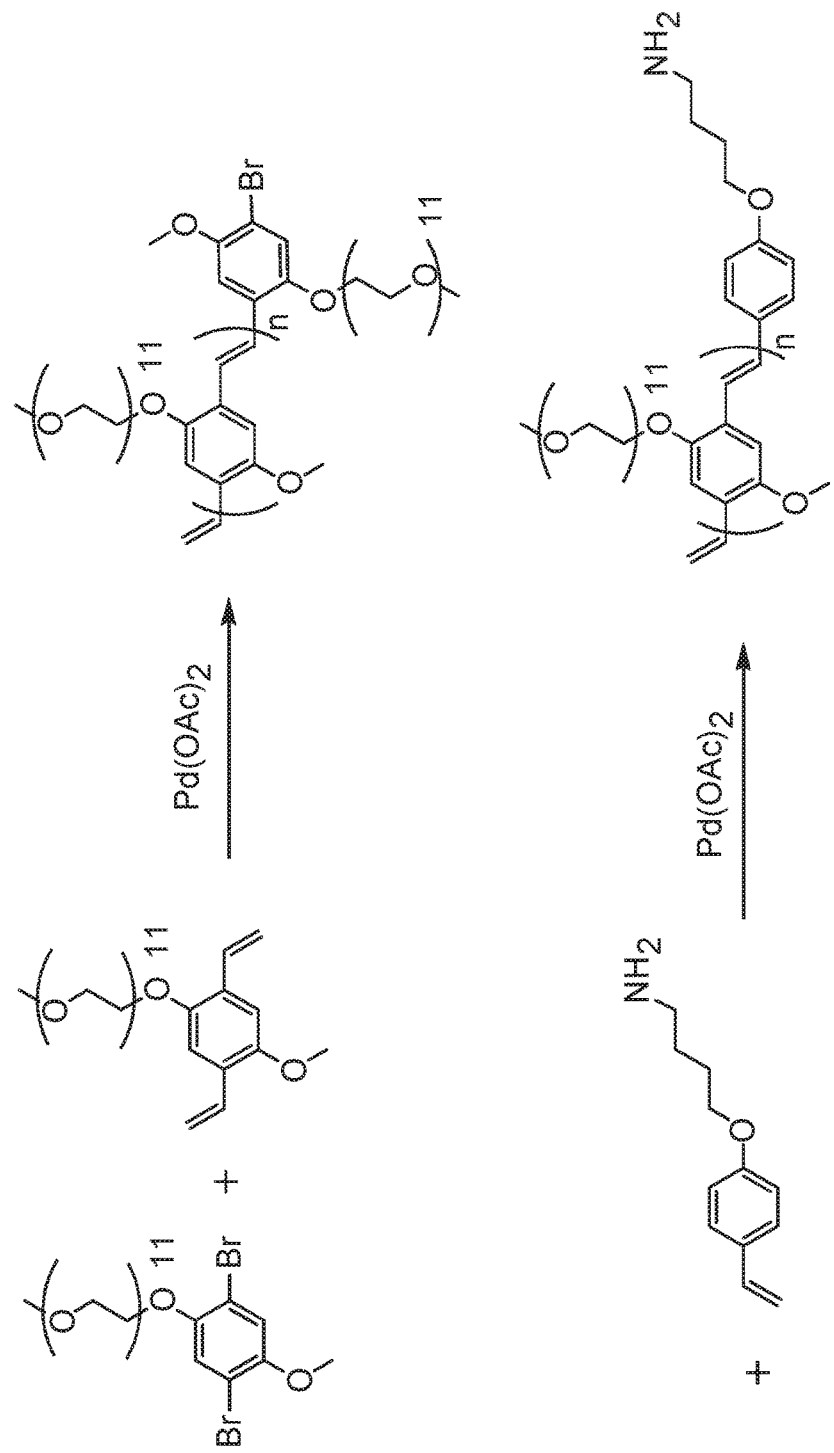
FIG. 41. Synthesis of a substituted divinylbenzene polymer and End linker incorporation.
Figure 42:
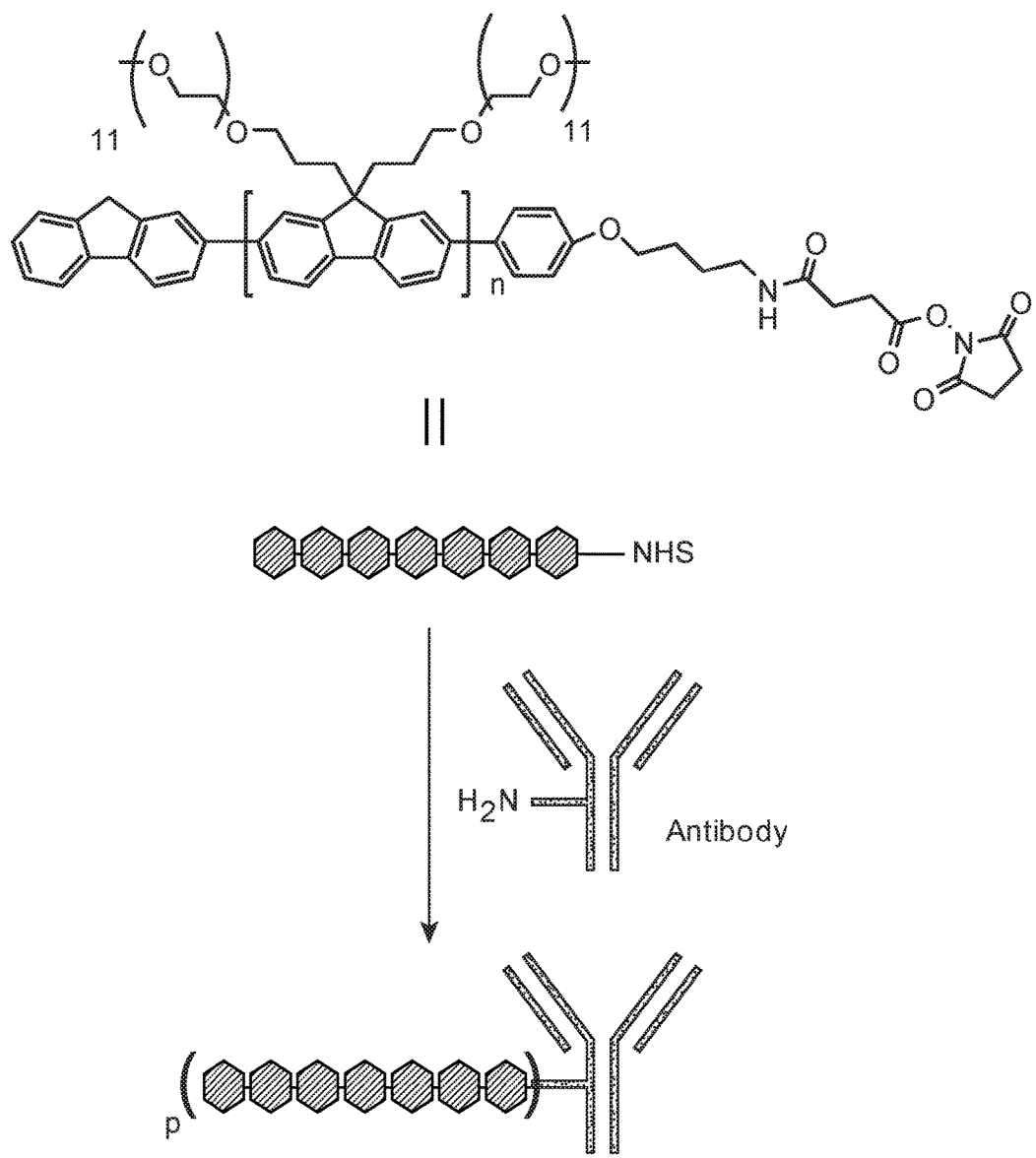
FIG. 42. Conjugation of polymer to an amine on a primary antibody.
Figure 43:
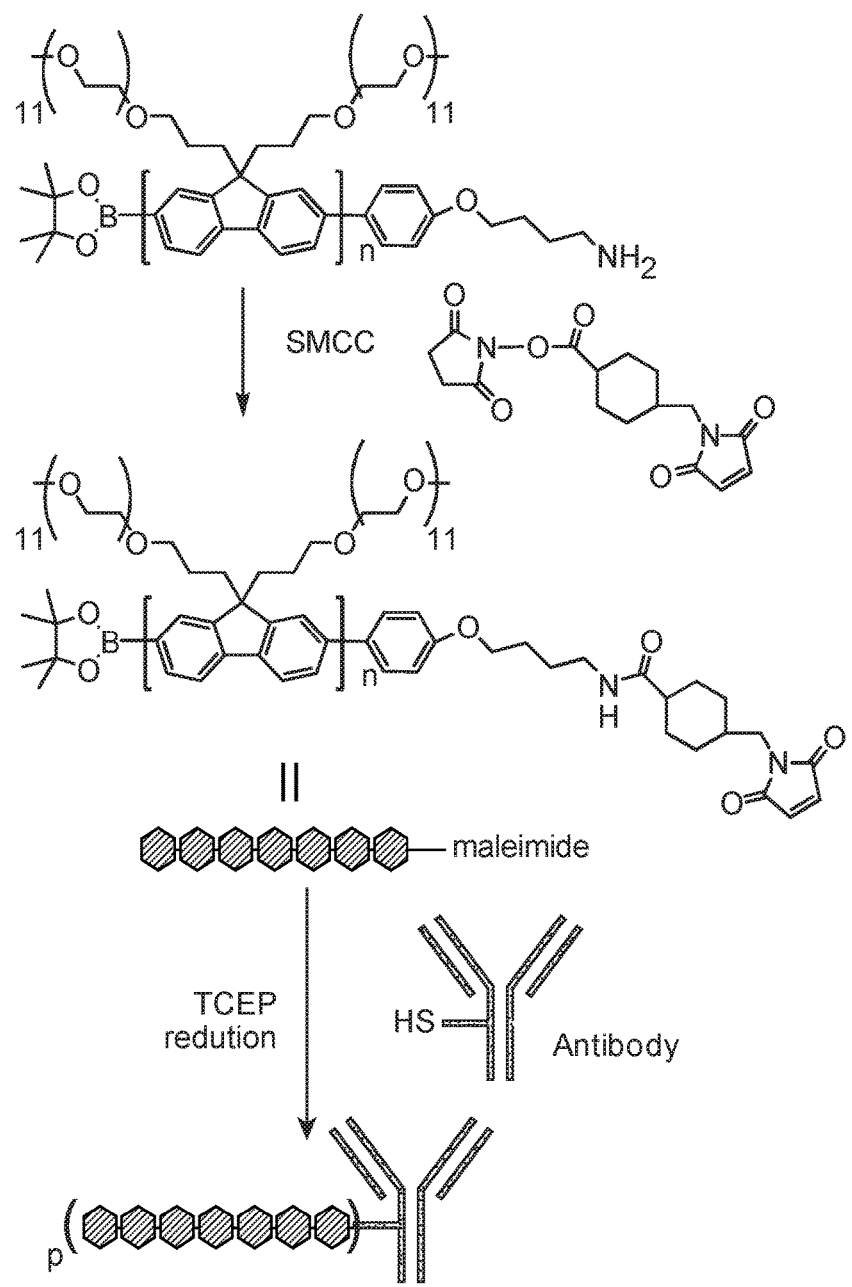
FIG. 43. Conjugation of polymer to an antibody using maleimide/thiol chemistry and partially reduced antibodies.
Figure 44:
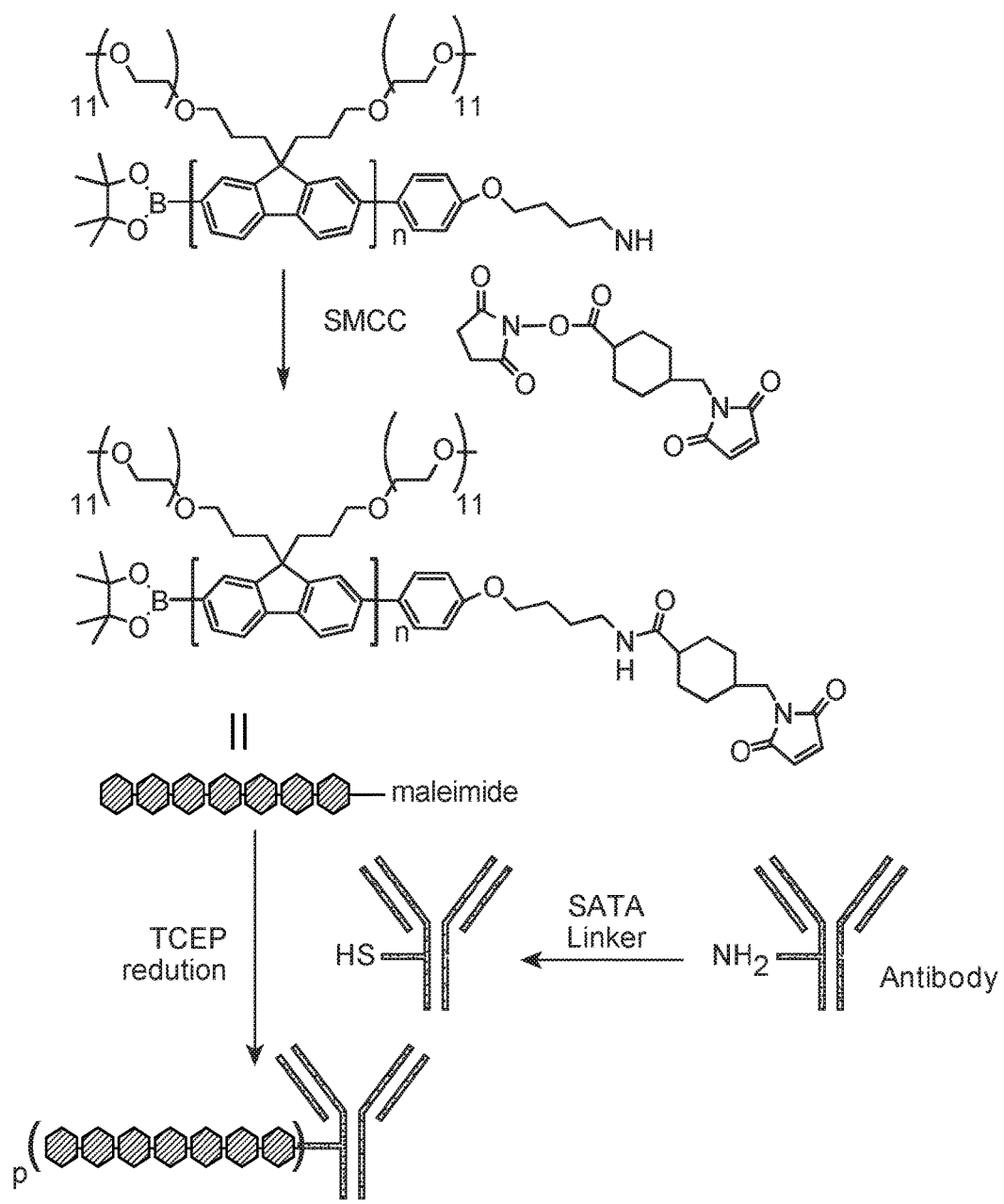
FIG. 44. Malemide/thiol conjugation of polymers to thiol modified antibodies.
Figure 45:
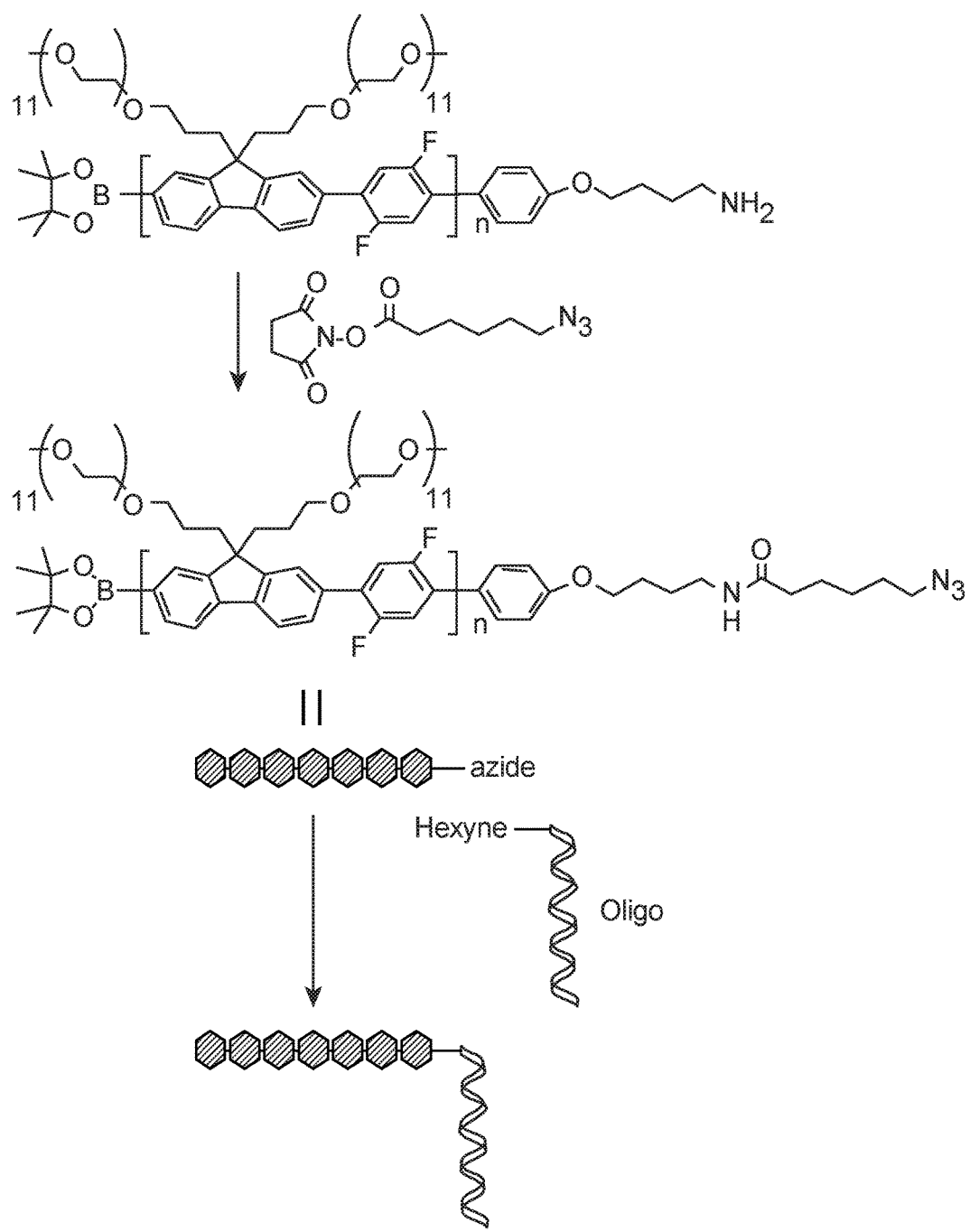
FIG. 45. Azide polymer conjugation to alkyne terminated DNA oligomer.
Figure 46:
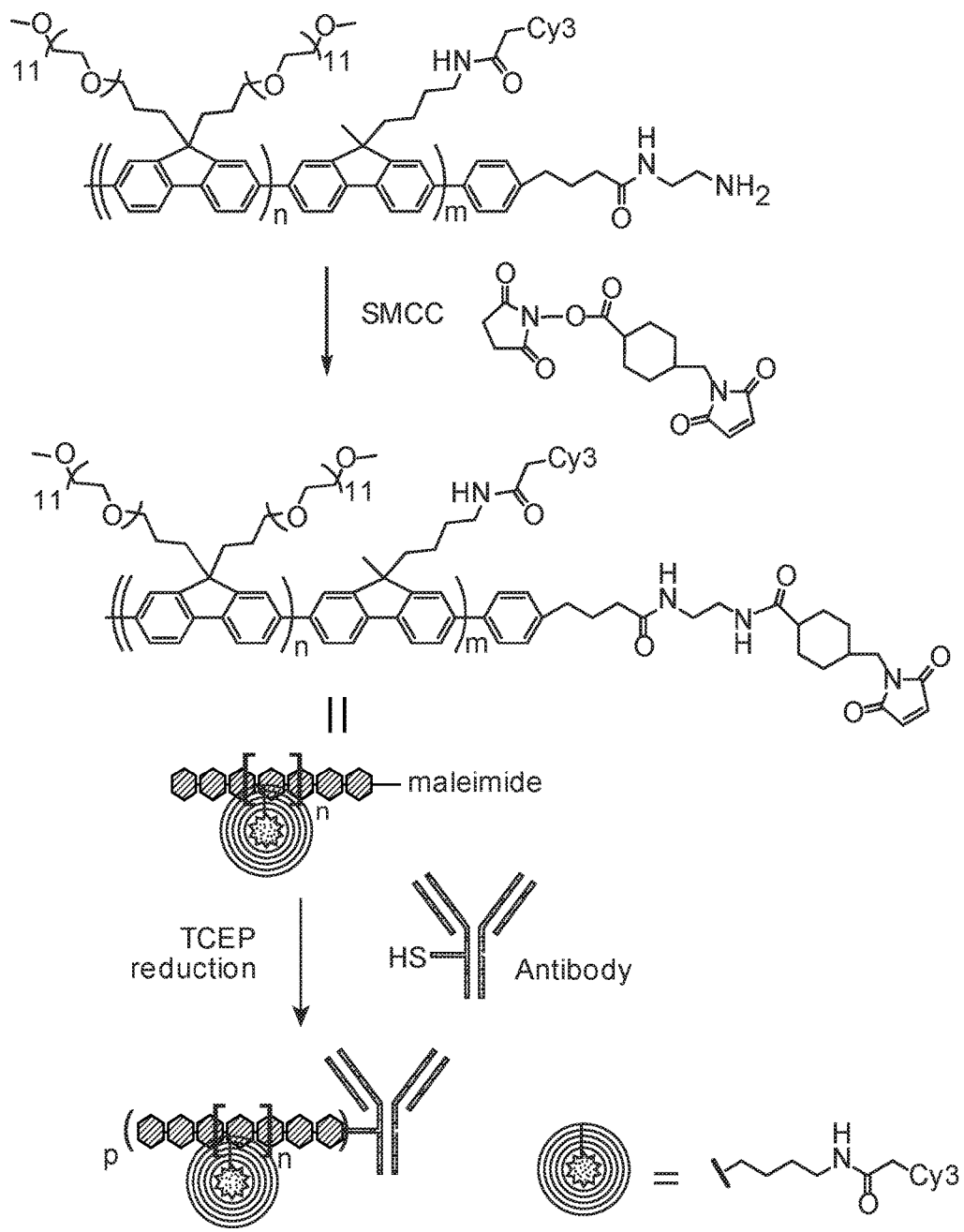
FIG. 46. Polymer tandem conjugation to a primary antibody using maleimide/thiol chemistry.

Impact of Purification on Conjugate Performance on Cell Analysis by Flow Cytometry Purification of polymer streptavidin conjugates (polymer structure exemplified in Example 9, denoted P30 in FIG. 38) was performed to determine the impact on flow cytometry performance. Cation-exchange chromatography was implemented in purification to improve removal of excess free polymer. Uncharged polymer eluted in the flow-through while protonated amines on proteins were retained by the media. Thus, streptavidin, whether conjugated to polymer or unreacted, was retained. This ion exchange phase of purification was kept simple with a step gradient, which resulted in co-elution of conjugated and unreacted SA. Further fractionation was enabled by subsequent size-exclusion chromatography, which provided better resolution of conjugate from free SA. Performance benefits in flow cytometry of this new purification method were observed using Jurkat cells incubated with polymer-streptavidin conjugate which were analyzed by flow cytometry. Comparisons were made between crude samples (FIG. 38—top) and purified conjugates (FIG. 38 bottom). Commercially available Pacific Blue-streptavidin conjugates were used as a comparator for brightness, nonspecific binding, and stain index. An improvement in overall Stain Index of approximately 3-fold was shown for Jurkat cells, with similar NSB for both Polymer conjugates and PB-SA based on the histograms shown in FIG. 38. Testing in blood (data not shown) indicated a significant reduction in NSB to levels similar to PB-SA upon conjugate purification.

In a separate experiment with a similar polymer (exemplified in Example 11), conjugates with varying polymer to streptavidin ratios were obtained by SEC. Those with the higher ratio provided flow performance relative to those with lower labeling. Ratios were determined based on a ratio of absorbance at 385 nm/280 nm. Relative performance to a Pacific Blue control showed an increase from 10.9 times higher stain index (385/280 ratio of 3.6) to a stain index 13.8 times that of Pacific Blue (A385/280 ratio of 4.7).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of determining whether a target is present in a sample, the method comprising:

contacting the sample with a conjugated polymer complex comprising a sensor for the target conjugated to a water soluble conjugated polymer having the structure of the formula:

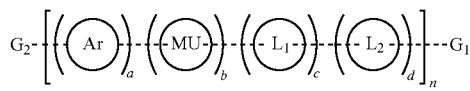

wherein:
Ar is an aryl or heteroaryl unit substituted with a non-ionic side group capable of imparting solubility in water;

MU is a polymer modifying unit or band gap modifying unit that is evenly or randomly distributed along the polymer main chain and is optionally substituted with one or more optionally substituted substituents selected from halogen, hydroxyl, $C_1$-$C_{12}$ alkyl, $C_2$-$C_{12}$ alkene, $C_2$-$C_{12}$ alkyne, $C_3$-$C_{12}$ cycloalkyl, $C_1$-$C_{12}$ haloalkyl, $C_1$-$C_{12}$ alkoxy, $C_2$-$C_{18}$ (hetero)aryloxy, $C_2$-$C_{18}$ (hetero)arylamino, a $C_2$-$C_{18}$ (hetero)aryl group and $(CH_2)_{x'}(OCH_2CH_2)_{y'}OCH_3$ where x' is independently an integer from 0-20 and y' is independently an integer from 0 to 50;

optional linkers $L_1$ and $L_2$ are each independently an aryl or a heteroaryl group evenly or randomly distributed along the polymer main chain and are substituted with one or more pendant chains terminated with: i) a functional group selected from amine, carbamate, carboxylic acid, carboxylate, maleimide, activated ester, N-hydroxysuccinimidyl, hydrazine, hydrazide, hydrazone, azide, alkyne, aldehyde, thiol, and protected groups thereof for conjugation to a molecule or biomolecule; or ii) a conjugated organic dye or biomolecule;

$G_1$ and $G_2$ are each independently selected from hydrogen, halogen, alkyne, optionally substituted aryl, optionally substituted heteroaryl, halogen substituted aryl, boronic acid substituted aryl, boronic ester substituted aryl, boronic ester, boronic acid, optionally substituted fluorene and aryl or heteroaryl substituted with one or more pendant chains terminated with: i) a functional group selected from amine, carbamate, carboxylic acid, carboxylate, maleimide, activated esters, N-hydroxysuccinimidyl, hydrazine, hydrazide, hydrazone, azide, alkyne, aldehyde, thiol, and protected groups thereof for conjugation to a molecule or biomolecule; or ii) a conjugated organic dye or biomolecule;

wherein the polymer comprises at least 1 functional group selected from amine, carbamate, carboxylic acid, carboxylate, maleimide, activated ester, N-hydroxysuccinimidyl, hydrazines, hydrazide, hydrazone, azide, alkyne, aldehyde, and thiol within $G_1$, $G_2$, $L_1$ or $L_2$, or a conjugated organic dye or biomolecule;

n is an integer from 1 to about 10,000; and a, b, c and d define the mol % of each unit within the structure which each can be evenly or randomly repeated and where a is a mol % from 10 to 100%, b is a mol % from 0 to 90%, and each c and d are mol % from 0 to 25%.

2. The method according to claim 1, wherein MU is selected from optionally substituted benzothiadiazole, benzoxidazole, benzoselenadiazole, benzotellurodiazole, naphthoselenadiazole, 4,7-di(thien-2-yl)-2,1,3-benzothiadiazole, squaraine dyes, quinoxaline, perylene, perylene diimide, diketopyrrolopyrrole, thienopyrazine low bandgap commercial dyes, olefin, and cyano-substituted olefins and isomers thereof.

3. The method according to claim 1, wherein MU is selected from the group consisting of a'-k' having the structure:

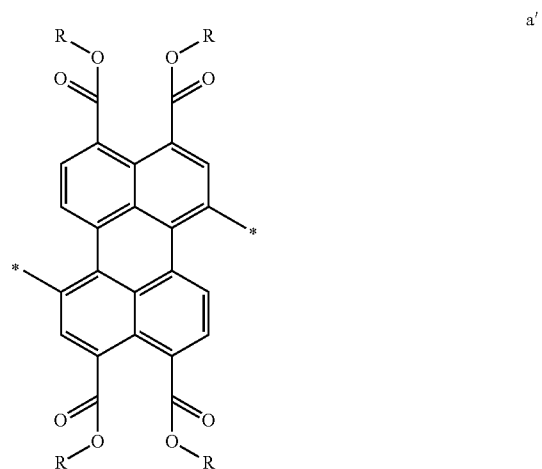

a'

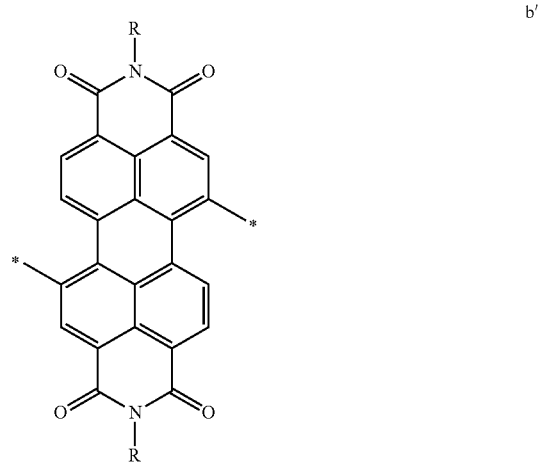

b'

219
-continued
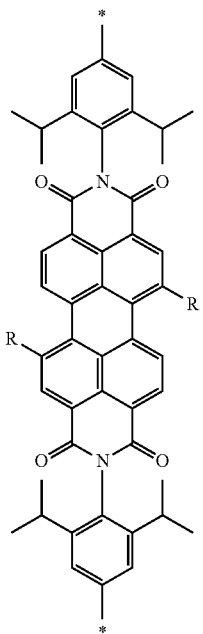
220
-continued
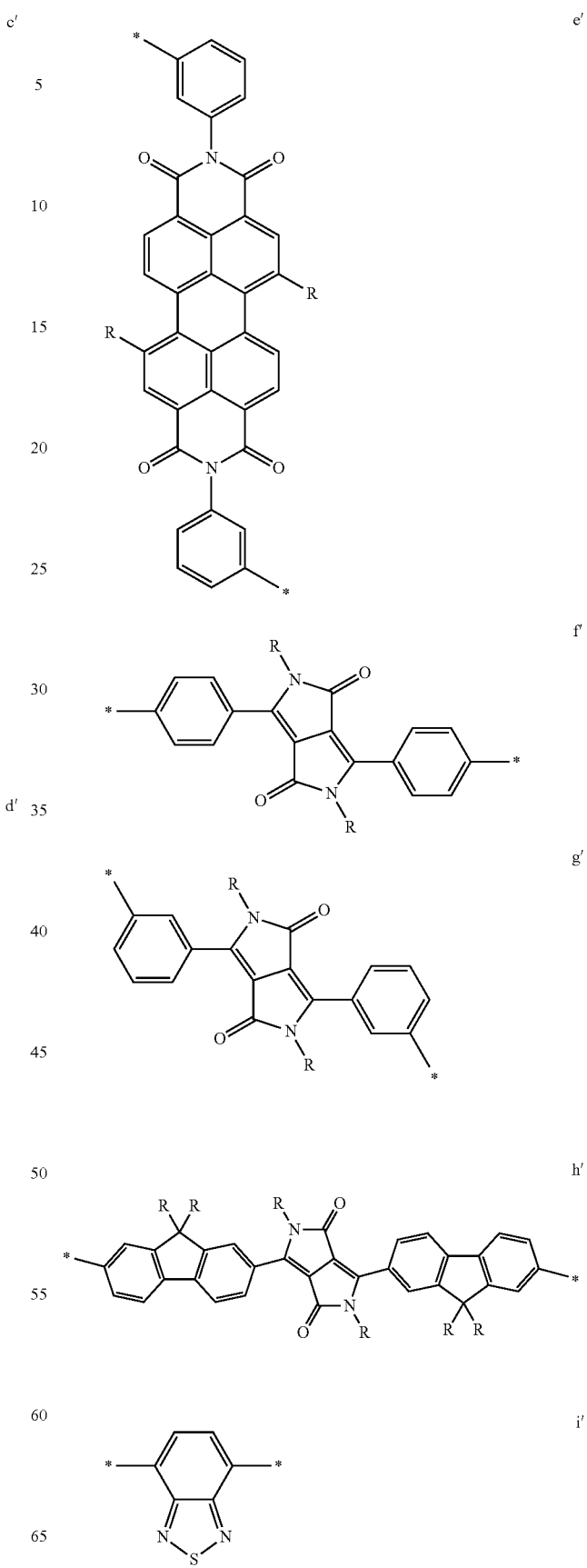

-continued

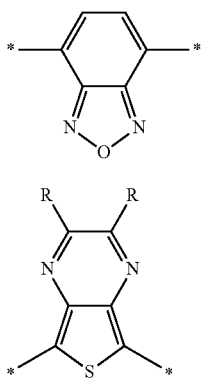

wherein * is a site for covalent attachment to unsaturated backbone and each R is a non-ionic side group capable of imparting solubility in water.

4. The method according to claim 3, wherein MU is selected from one of the following:

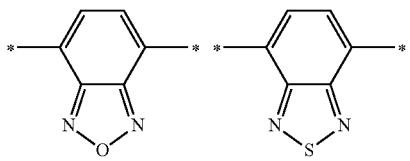

wherein * is site for covalent attachment to unsaturated backbone.

5. The method according to claim 1, wherein MU is a phenyl.

6. The method according to claim 5, wherein MU is

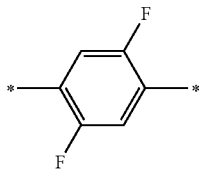

wherein *=site for covalent attachment to unsaturated backbone.

7. The method according to claim 1, wherein the non-ionic side group comprises an ethylene glycol oligomer.

8. The method according to claim 7, wherein Ar is substituted with one or more non-ionic side groups comprising mPEG5, mPEG8, mPEG11 or mPEG24.

9. The method according to claim 7, wherein Ar is substituted with one or more groups selected from $(CH_2)_{x'}$ $(OCH_2CH_2)_{y'}OCH_3$ where x' is independently an integer from 0-20 and y' is independently an integer from 0 to 50, and a benzyl substituted with one or more halogen, hydroxyl, $C_1$-$C_{12}$ alkoxy, or $(OCH_2CH_2)_zOCH_3$ where z is independently an integer from 0 to 50.

10. The method according to claim 7, wherein Ar is substituted with one or more $(CH_2)x(OCH_2CH_2)_{y'}OCH_3$ where x' is independently an integer from 0-20, y' is independently an integer from 0 to 50.

11. The method according to claim 7, wherein Ar is substituted with a dendrimer of PAMAM, PEA, PEHAM, PPI, tri-branched benzoate, or glycerol with a generation of 1 to 4 and optional terminal substitutions selected from (- - - - -)$CH_2CH_2O)_jCH_3$ and (- - - - -)$(OCH_2CH_2)_jCH_3$ where j is an integer from 0 to 25 and the dotted lines (- - - - -) are each independently selected from any one or a combination of, $C_1$-$C_{12}$ alkyl, $C_1$-$C_{12}$ alkoxy, $C_2$-$C_{12}$ alkene, amido, amino, aryl, $(CH_2)_r(OCH_2CH_2)_s(CH_2)_r$ where each r is independently an integer from 0-20, s is independently an integer from 0 to 50, carbamate, carboxylate, $C_3$-$C_{12}$ cycloalkyl, imido, phenoxy and $C_4$-$C_{18}$(hetero)aryl group.

12. The method according to claim 1, wherein Ar is a substituted fluorene unit.

13. The method according to claim 1, wherein $L_1$ and/or $L_2$ is conjugated to a signaling chromophore.

14. The method according to claim 1, wherein $L_1$ and/or $L_2$ are present and have the structure:

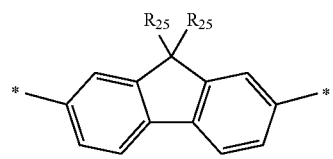

wherein:
*=site for covalent attachment to backbone;
each $R_{25}$ is independently a bond, $C_1$-$C_{20}$ alkyl, $C_1$-$C_{20}$ alkoxy, $C_2$-$C_{20}$ alkene, $C_2$-$C_{20}$ alkyne, $C_3$-$C_{20}$ cycloalkyl, $C_1$-$C_{20}$ haloalkyl; $(CH_2)_x(OCH_2CH_2)_p$ $(CH_2)_x$ where each x is independently an integer from 0-20, p is independently an integer from 0 to 50; aryl, $C_2$-$C_{18}$(hetero)aryl, phenoxy, amido, amino, carbamate, carboxylate, carbonates, sulfide, disulfide, or imido groups; and
at least one $R_{25}$ is terminated with a functional group selected from amine, carbamate, carboxylate, carboxylic acid, maleimide, activated ester, N-hydroxysuccinimidyl, hydrazine, hydrazide, hydrazone, azide, alkyne, aldehyde and thiols, or a conjugated organic dye or biomolecule.

15. The method according to claim 1, wherein at least one of $G_1$ and $G_2$ comprises a functional conjugation site.

16. The method according to claim 15, wherein at least one of $G_1$ and $G_2$ has the structure:

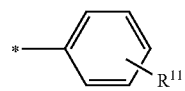

wherein:
=site for covalent attachment to backbone; and
$R^{11}$ is a bond, $C_1$-$C_{20}$ alkyl, $C_1$-$C_{20}$ alkoxy, $C_2$-$C_{20}$ alkene, $C_2$-$C_{20}$ alkyne, $C_3$-$C_{20}$ cycloalkyl, $C_1$-$C_{20}$ haloalkyl, $(CH_2)_x(OCH_2CH_2)_p(CH_2)_x$ wherein each x is independently an integer from 0-20 and p is an integer from 0 to 50, aryl, $C_2$-$C_{18}$(hetero)aryl, phenoxy, amido, amino, carbamate, carboxylate, carbonate, sulfide, disulfide, or imido groups; and is terminated with: i) a functional group selected from amine, carbamate, carboxylate, carboxylic acid, maleimide, activated esters, N-hydroxysuccinimidyl, hydrazines, hydrazids, hydrazones, azide, alkyne, aldehydes, thiols, and protected groups thereof, or ii) a conjugated organic dye or biomolecule.

17. The method according to claim 1, wherein at least one of $G_1$ and $G_2$ is selected from the group consisting of capping units 1-31 having the structures:
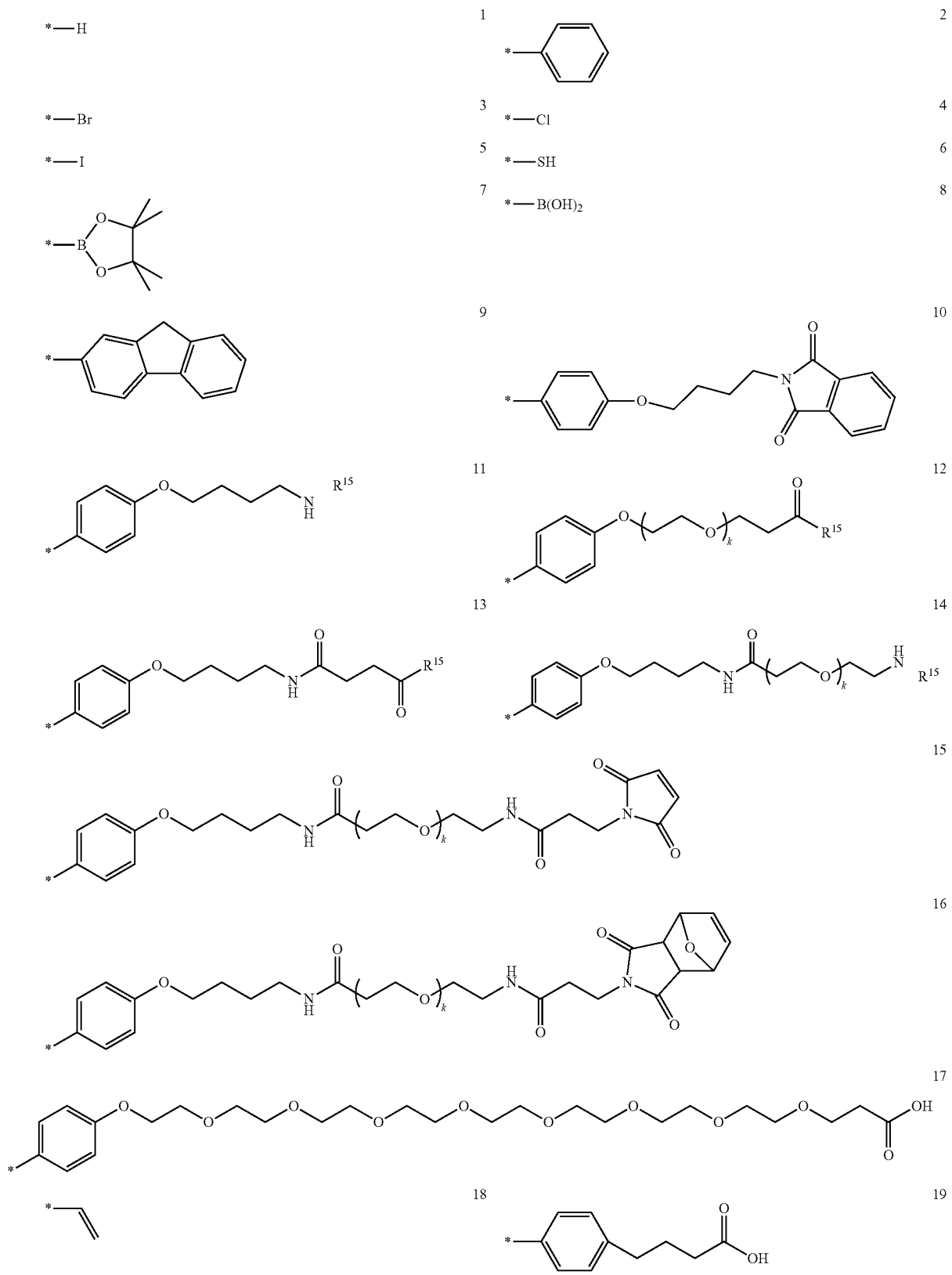

-continued
20
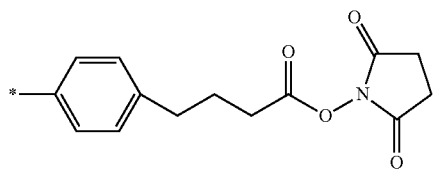
21
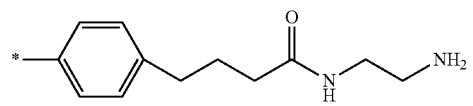
22
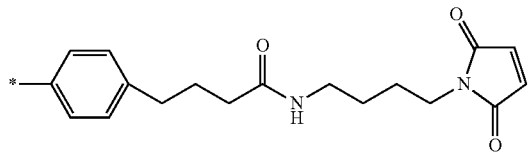
23
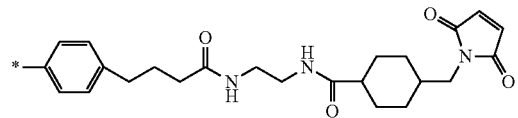
24
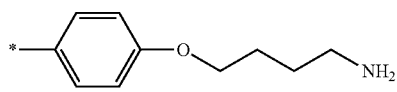
25
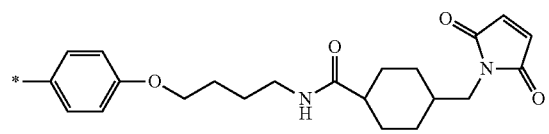
26
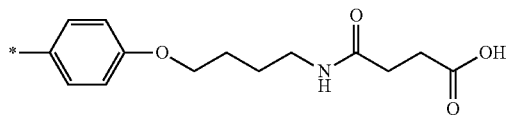
27
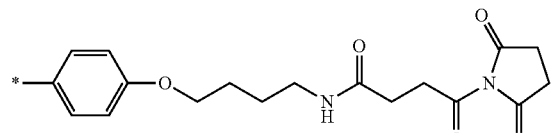
28
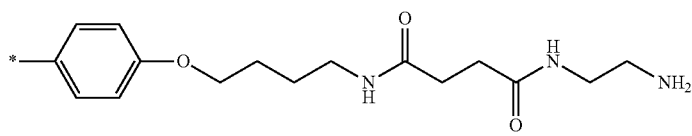
29
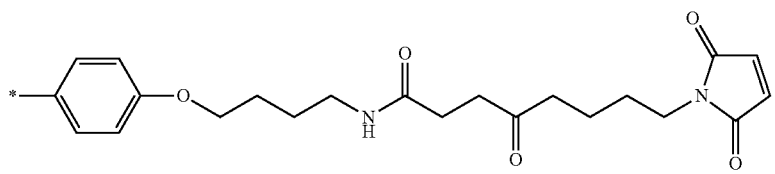
30
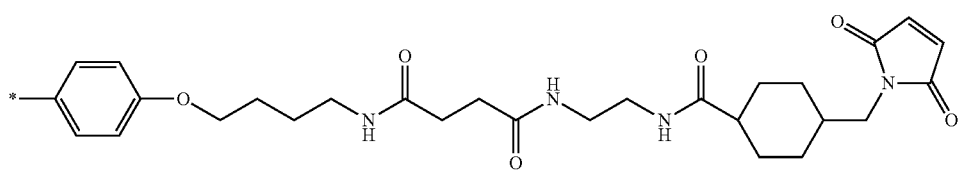
31
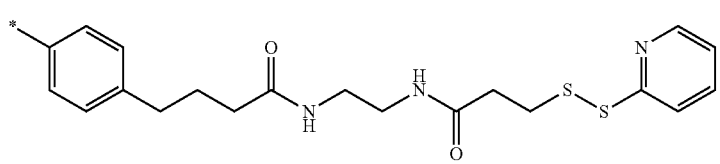
wherein:
*=site for covalent attachment to backbone;
k is 2, 4, 8, 12 or 24; and
$R^{15}$ is selected from the group consisting of 1-t having the structures:
*—OH
-continued
m
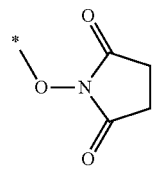

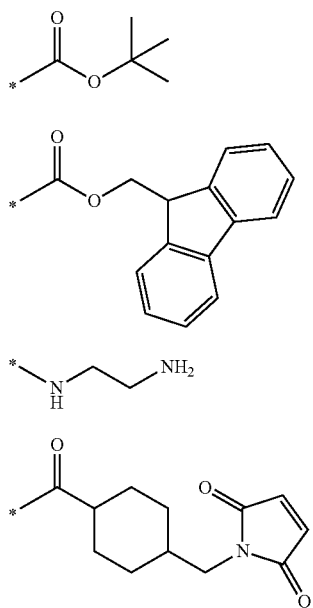
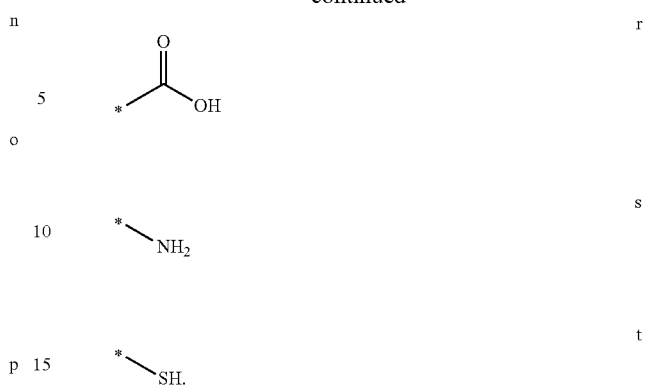
18. The method according to claim 1, wherein the sensor is an antibody.
19. The method according to claim 1, wherein the method is configured for intracellular staining.
20. The method according to claim 1, wherein the method is configured for flow cytometry.
* * * * *

(12) INTER PARTES REVIEW CERTIFICATE (3481st)

United States Patent
Gaylord et al.

(10) Number: US 10,365,285 K1
(45) Certificate Issued: Mar. 8, 2024

(54) REAGENTS FOR DIRECTED BIOMARKER SIGNAL AMPLIFICATION

(71) Applicants: Brent S. Gaylord; Russell A. Baldocchi; William H. Huisman; Glenn P. Bartholomew; Janice W. Hong; Yongchao Liang; Lan T. Tran; Adrian Charles Vernon Palmer; Trung Nguyen; Jean M. Wheeler; Frank Peter Uckert

(72) Inventors: Brent S. Gaylord; Russell A. Baldocchi; William H. Huisman; Glenn P. Bartholomew; Janice W. Hong; Yongchao Liang; Lan T. Tran; Adrian Charles Vernon Palmer; Trung Nguyen; Jean M. Wheeler; Frank Peter Uckert

(73) Assignee: SIRIGEN II LIMITED

Trial Number:

IPR2022-01204 filed Jun. 28, 2022

Inter Partes Review Certificate for:

Patent No.: 10,365,285
Issued: Jul. 30, 2019
Appl. No.: 15/717,580
Filed: Sep. 27, 2017

The results of IPR2022-01204 are reflected in this inter partes review certificate under 35 U.S.C. 318(b).

INTER PARTES REVIEW CERTIFICATE
U.S. Patent 10,365,285 K1
Trial No. IPR2022-01204
Certificate Issued Mar. 8, 2024

AS A RESULT OF THE INTER PARTES REVIEW PROCEEDING, IT HAS BEEN DETERMINED THAT:

Claims 1-10, 12, 13 and 15-20 are cancelled.

\* \* \* \* \*